US008828703B2

(12) United States Patent
Ladner

(10) Patent No.: US 8,828,703 B2
(45) Date of Patent: Sep. 9, 2014

(54) PROTEASE INHIBITION

(75) Inventor: Robert C. Ladner, Ijamsville, MD (US)

(73) Assignee: Dyax Corp., Burlington, MA (US)

( * ) Notice: Subject to any disclaimer, the term of this patent is extended or adjusted under 35 U.S.C. 154(b) by 1314 days.

(21) Appl. No.: 11/646,148

(22) Filed: Dec. 27, 2006

(65) Prior Publication Data

US 2008/0255025 A1    Oct. 16, 2008

Related U.S. Application Data

(60) Provisional application No. 60/754,903, filed on Dec. 29, 2005.

(51) Int. Cl.
C12N 9/48 (2006.01)
C12N 15/00 (2006.01)
C12P 21/06 (2006.01)
C12P 21/04 (2006.01)

(52) U.S. Cl.
USPC .......... 435/212; 435/69.1; 435/71.1; 435/440

(58) Field of Classification Search
USPC ............................... 435/212, 69.1, 71.1, 440
See application file for complete search history.

(56) References Cited

U.S. PATENT DOCUMENTS

| | | | |
|---|---|---|---|
| 4,966,852 A | 10/1990 | Wun et al. |
| 5,106,833 A | 4/1992 | Broze, Jr. et al. |
| 5,212,091 A | 5/1993 | Diaz-Collier et al. |
| 5,223,409 A | 6/1993 | Ladner et al. |
| 5,312,736 A | 5/1994 | Rasmussen et al. |
| 5,378,614 A | 1/1995 | Petersen et al. |
| 5,455,338 A | 10/1995 | Sprecher et al. |
| 5,466,783 A | 11/1995 | Wun et al. |
| 5,563,123 A | 10/1996 | Innis et al. |
| 5,589,359 A | 12/1996 | Innis et al. |
| 5,618,696 A | 4/1997 | Norris et al. |
| 5,629,176 A | 5/1997 | Bjørn et al. |
| 5,648,331 A | 7/1997 | Koudsi et al. |
| 5,663,143 A | 9/1997 | Ley et al. |
| 5,696,088 A | 12/1997 | Innis et al. |
| 5,736,364 A | 4/1998 | Kelley et al. |
| 5,780,265 A | 7/1998 | Dennis et al. |
| 5,786,328 A | 7/1998 | Dennis et al. |
| 5,795,954 A | 8/1998 | Lazarus et al. |
| 5,834,244 A | 11/1998 | Dennis et al. |
| 5,863,893 A | 1/1999 | Dennis et al. |
| 5,880,256 A | 3/1999 | Dennis et al. |
| 5,914,316 A | 6/1999 | Brown et al. |
| 6,008,196 A | 12/1999 | Curran et al. |
| 6,057,287 A | 5/2000 | Markland et al. |
| 6,063,764 A | 5/2000 | Creasey et al. |
| 6,071,723 A | 6/2000 | Markland et al. |
| 6,103,500 A | 8/2000 | Innis et al. |
| 6,171,587 B1 | 1/2001 | Wun et al. |
| 6,174,721 B1 | 1/2001 | Innis et al. |
| 6,180,607 B1 | 1/2001 | Davies et al. |
| 6,242,414 B1 | 6/2001 | Johnson et al. |
| 6,333,402 B1 | 12/2001 | Markland et al. |
| 6,423,498 B1 | 7/2002 | Markland et al. |
| 6,534,276 B1 | 3/2003 | Wun et al. |
| 6,548,262 B2 | 4/2003 | Gentz et al. |
| 6,583,108 B1 | 6/2003 | Tamburini et al. |
| 6,689,582 B1 | 2/2004 | Davies et al. |
| 6,783,960 B2 | 8/2004 | Innis et al. |
| 6,806,360 B2 | 10/2004 | Wun et al. |
| 6,914,135 B2 | 7/2005 | Sheppard et al. |
| 7,550,427 B2 | 6/2009 | Ley et al. |
| 7,704,949 B2 | 4/2010 | Ladner et al. |
| 2002/0111460 A1 | 8/2002 | Holloway |
| 2003/0114372 A1 | 6/2003 | White et al. |
| 2003/0129659 A1 | 7/2003 | Whelihan et al. |
| 2003/0175919 A1 | 9/2003 | Ley et al. |
| 2004/0152633 A1 | 8/2004 | Jorgensen et al. |
| 2004/0171794 A1 | 9/2004 | Ladner et al. |
| 2005/0004021 A1 | 1/2005 | Sprecher et al. |
| 2005/0164945 A1 | 7/2005 | Nixon et al. |
| 2005/0180977 A1 | 8/2005 | Nixon et al. |
| 2006/0264603 A1 | 11/2006 | Markland et al. |
| 2007/0020252 A1 | 1/2007 | Ladner et al. |
| 2008/0139473 A1 | 6/2008 | Ladner et al. |
| 2009/0264350 A1 | 10/2009 | Blair et al. |
| 2010/0286061 A1 | 11/2010 | Devy et al. |

FOREIGN PATENT DOCUMENTS

| | | |
|---|---|---|
| EP | 0 274 826 | 7/1988 |
| EP | 0 318 451 | 5/1989 |
| WO | 96/20278 | 7/1996 |
| WO | WO 97/33996 | 9/1997 |
| WO | WO 01/68707 | 9/2001 |
| WO | WO 2005/021557 | 3/2005 |

OTHER PUBLICATIONS

Branden et al. Introduction to Protein Structure, Garland Publishing Inc., New York, p. 247, 1991.*
Sheffield. Modification of clearance of therapeutic and potentially therapeutic proteins. Curr Drug Targets Cardiovasc Haematol Disord. Jun. 2001;1(1):1-22.*
Wriggers et al. Control of protein functional dynamics by peptide linkers Biopolymers. 2005;80(6):736-46.*
International Search Report of International Application No. PCT/US06/49322 mailed Dec. 7, 2007.
Fries et al., Inter-alpha-inhibitor, hyaluronan and inflammation, Acta Biochimica Polonica, 2003, vol. 50, No. 3, pp. 735-742.
Magklara et al., Characterization of the enzymatic activity of human kallikrein 6:Autoactivation, substrate specificity, and regulation by inhibitors, Biochem. Biophys. Res. Commun., Aug. 2003, 8;307(4):948-55, abstract only.
Scarff et al., Targeted Disruption of SP13/Serpinb6 Does Not Result in Developmental or Growth Defects, Leukocyte Dysfunction, or Susceptibility to Stroke, Molecular and Cellular Biology, May 2004, pp. 4075-4082.
Taggart et al., Inactivation of Human beta-Defensins 2 and 3 by Elastolytic Cathepsins1, The Journal of Immunology, 2003, 170:931-937.

(Continued)

Primary Examiner — Yong Pak
(74) Attorney, Agent, or Firm — Wolf, Greenfield & Sacks, P.C.

(57) ABSTRACT

Proteins including engineered sequences which inhibit proteases are disclosed, including proteins having two or more engineered Kunitz domains, and uses of such proteins.

7 Claims, No Drawings

(56) References Cited

OTHER PUBLICATIONS

Borregaard and Cowland, "Granules of the Human Neutrophilic Polymorphonuclear Leukocyte," *Blood*, 89(10):3503-3521 (1997).
Burrage et al., "Matrix Metalloproteinases: Role in Arthritis," (2006). *Frontiers in Bioscience*, 11:529-543.
Cassim et al., "Kallikrein cascade and cytokines in inflamed joints," *Pharmacology & Therapeutics*, 94:1-34 (2002).
Churg and Wright, "Proteases and emphysema," *Curr. Opin. Pulm. Med.*, 11:153-159 (2005).
Colman, Robert W., "Plasma and tissue kallikrein in arthritis and inflammatory bowel disease," *Immunopharmacology*, 43:103-108 (1999).
Cunningham et al., "Structural and functional characterization of tissue factor pathway inhibitor following degradation by matrix metalloproteinase-8," *Biochem. J.*, 367:451-458 (2002).
Dela Cadena et al., "Inhibition of plasma kallikrein prevents peptidoglycan-induced arthritis in the Lewis rat," *FASEB J.*, 9:446-452 (1995).
Devani et al., "Kallikrein-kinin system in inflammatory bowel diseases: Intestinal involvement and correlation with the degree of tissue inflammation," *Digestive and Liver Disease*, 37:665-673 (2005).
Eigenbrot et al., "Structural effects induced by removal of a disulfide-bridge: the X-ray structure of the C30A/C51A mutant of basic pancreatic trypsin inhibitor at 1.6 Å," *Protein Engineering*, 3(7):591-598 (1990).
Girard et al., "Functional significance of the Kunitz-type inhibitory domains of lipoprotein-associated coagulation inhibitor," *Nature*, 338:518-520 (1989).
Gulberg et al., "Biosynthesis, processing and sorting of neutrophil proteins: insight into neutrophil granule development," *Eur. Journal of Haematology*, 58:137-153 (1997).
Hagihara et al., "Screening for Stable Mutants with Amino Acid Pairs Substituted for the Disulfide Bond between Residues 14 and 38 of Bovine Pancreatic Trypsin Inhibitor (BPTI)," *The Journal of Biological Chemistry*, 277(52):51043-51048 (2002).
Herter et al., "Hepatocyte growth factor is a preferred in vitro substrate for human hepsin, a membrane-anchored serine protease implicated in prostate and ovarian cancers," *Biochem. J.*, 390:125-136 (2005).
Huang et al., "Kinetics of Factor Xa Inhibition by Tissue Factor Pathway Inhibitor," *The Journal of Biological Chemistry*, 268(36):26950-26955 (1993).
Huang et al., "Novel Peptide Inhibitors of Angiotensin-converting Enzyme 2*," *The Journal of Biological Chemistry*, 278(18):15532-15540 (2003).
Hynes et al., "X-ray Crystal Structure of the Protease Inhibitor Domain of Alzheimer's Amyloid β-Protein Precursor," *Biochemistry*, 29:10018-10022 (1990).
Kido et al., "Kunitz-type Protease Inhibitor Found in Rat Mast Cells," *The Journal of Biological Chemistry*, 263(34):18104-18107 (1988).
Kirchhofer et al., "Hepsin activates pro-hepatocyte growth factor and is inhibited by hepatocyte growth factor activator-1B (HAI-1B) and HAI-2," *FEBS Letters*, 579:1945-1950 (2005).
Kuno et al., "Possible involvement of neutrophil elastase in impaired mucosal repair in patients with ulcerative colitis," *Journal of Gastroenterology*, 37(Suppl XIV):22-32 (2002).
Léonetti et al., "Increasing Immunogenicity of Antigens Fused to Ig-Binding Proteins by Cell Surface Targeting," *The Journal of Immunology*, 160:3820-3827 (1998).

Mine et al., "Strutural Mechanism for Heparin-Binding of the Third Kunitz Domain of Human Tissue Factor Pathway Inhibitor," *Biochemistry*, 41:78-85 (2002).
Novotny et al., "Purification and Characterization of the Lipoprotein-associated Coagulation Inhibitor from Human Plasma," *The Journal of Biological Chemistry*, 264(31):18832-18837 (1989).
Petersen et al., "Inhibitory properties of separate recombinant Kunitz-type-protease-inhibitor domains from tissue-factor-pathway inhibitor," *Eu. J. Biochem.*, 235:310-316 (1996).
Pintigny and Dachary-Prigent, "Aprotinin can inhibit the proteolytic activity of thrombin: A fluorescence and an enzymatic study," *Eur. J. Biochem.*, 207:89-95 (1992).
Piro et al., "Role for the Kunitz-3 Domain of Tissue Factor Pathway Inhibitor-α in Cell Surface Binding," *Circulation*, 110:3567-3572 (2004).
Rahman et al., "Identification and functional importance of plasma kallikrein in the synovial fluids of patients with rheumatoid, psoriatic, and osteoarthritis," *Annals of the Rheumatic Diseases*, 54:345-350 (1995).
Sprecher et al., "Molecular Cloning, Expression, and Partial Characterization of a Second Human Tissue-Factor-Pathway Inhibitor," *Proceedings of the National Academy of Sciences of the United States of America*, 91(8):3353-3357 (1994).
Stadnicki et al., "Activation of Plasma Contact and Coagulation Systems and Neutrophils in the Active Phase of Ulcerative Colitis," *Digestive Diseases and Sciences*, 42(11):2356-2366 (1997).
Taby et al., "Inhibition of Activated Protein C by Aprotinin and the Use of the Insolubilized Inhibitor for its Purification," *Thrombosis Research*, 59:27-35 (1990).
Tremblay et al., "Anti-inflammatory activity of neutrophil elastase inhibitors," *Current Opinion in Investigational Drugs*, 4(5):556-565 (2003).
Volpe-Junior et al., "Augmented plasma and tissue kallikrein like activity in synovial fluid of patients with inflammatory articular diseases," *Inflamm. Res.*, 45:198-202 (1996).
Wun et al., "Cloning and Characterization of a cDNA Coding for the Lipoprotein-associated Coagulation Inhibitor Shows that it Consists of Three Tandem Kunitz-type Inhibitory Domains," *The Journal of Biological Chemistry*, 263(13):6001-6004 (1988).
Delgado, C., "The Uses and Properties of PEG-Linked Proteins", Critical Reviews in Therapeutic Drug Carrier Systems, 9(3,4):249-304 (1992).
Dhalluin, C., "Structural, Kinetic, and Thermodynamic Analysis of the Binding of the 40 kDa PEG-Interferon-α2a and Its Individual Positional Isomers to the Extracellular Domain of the Receptor IFNAR2", Bioconjugate Chem, 16, 518-527 (2005).
Molineux, G., "Pegylation: engineering improved pharmaceuticals for enhanced therapy", Cancer Treatment Reviews, 28(Suppl. A):13-16 (2002).
Roberts, M.J., "Chemistry for peptide and protein PEGylation", Advanced Drug Delivery Reviews, 54:459-476 (2002).
Veronese, Fm., "Peptide and protein PEGylation: a review of problems and solutions", Biomaterials, 22:405-417 (2001).
Wark, P.A.B., "DX-890", Drugs, 5(6):586-589 (2002).
U.S. Appl. No. 12/471,875, Ley et al.
Supplementary European Search Report including the European Search Opinion from corresponding European Application No. EP06848187.8, dated Dec. 7, 2009.
Delaria et al., "Characterization of placental bikunin, a novel human serine protease inhibitor.", J. Biological Chemistry, vol. 272, No. 18., pp. 12209-12214, May 2, 1997.

* cited by examiner

PROTEASE INHIBITION

CROSS-REFERENCE TO RELATED APPLICATIONS

This application claims the benefit of prior U.S. provisional application 60/754,903, filed Dec. 29, 2005.

BACKGROUND

Aspects of the pathology of many diseases include the excessive activity of proteases. Pharmaceutical agents that reduce such protease activity can be used to ameliorate disease conditions.

SUMMARY

Kunitz domains are robust protease inhibitors. Examples of Kunitz domains include non-naturally occurring Kunitz domains that inhibit human plasma kallikrein, human plasmin, human hepsin, human matriptase, human endotheliase 1 (hET-1) human endotheliase 2 (hET-2), and human neutrophil elastase (also known as human leukocyte elastase). Kunitz domains can be engineered to have very high affinity and specificity for most serine proteases.

Sometimes in a single disease state there is more than one protease whose activity is detrimental. In different patients, a given symptom may result from the aberrant activity of two different proteases, one in one patient, another in another patient. In cases such as these, it would be useful to have a single active pharmacologic agent that inhibits two or more proteases. Often, low-specificity inhibitors (e.g., small molecule inhibitors) cause serious side effects by inhibiting proteases other than the intended targets. A molecule that contains multiple domains, each having high affinity and specificity for a different protease can be used to provide inhibition of different target proteases without causing side effects due to cross reaction of the inhibitor with protease(s) other than the target(s). This allows the development of a single agent for the treatment of patients with multiple or various dysregulated proteases.

In one aspect, the disclosure features an isolated protein that includes one or more engineered protease inhibitory sequences, wherein the protein inhibits two or more human proteases. For example, the protein inhibits the two or more human proteases, each with a Ki of less than 100 nM, 10 nM, 1 nM, or 0.1 nM.

In one embodiment, the protein of the invention comprises two or more Kunitz domains, each of which inhibit the same protease and the protein has longer serum residence than would a single Kunitz domain due to increased molecular mass. The protein may or may not be glycosylated.

In one embodiment, the protein contains a single engineered Kunitz domain that inhibits two or more human proteases as the engineered protease inhibitory sequence.

The protease inhibitory sequences can be, for example, Kunitz domains, peptides (e.g., cyclic peptides or linear peptides of length less than 24 amino acids), and variable domains of antigen binding fragments. For example, the protease inhibitory sequences can include the amino acid sequence of a heavy chain variable domain that binds and inhibits a human protease in conjunction with a light chain variable domain.

In one embodiment, the protein includes at least two, three, four, five, six, seven, or eight Kunitz domains, as the engineered proteases inhibitory sequences. For example, the protein contains two, three, four, five, or six Kunitz domains. In some cases, at least one of the Kunitz domains comprises the framework of a naturally occurring human Kunitz domain (e.g., TFPI or other human protein mentioned herein), but that differs from the naturally occurring human Kunitz domain at no less than one residue in the protease binding loops.

In one embodiment, the protein has a molecular weight of at least 15 kiloDaltons and/or a beta-phase half life of at least 30 minutes in mice. Molecular weight of proteins and/or beta-phase half life may be increased by, for example, modifying the protein to include one or more PEG moieties or by covalently linking the protein to a carrier such as human serum albumin (HSA). Such covalent linkage may be accomplished by covalent cross-linking of the protein and the carrier following production of the protein or by expression of the protein as a fusion protein with the carrier.

In one embodiment, at least one of the Kunitz domains contains only two disulfide bonds. For example, the protein does not include cysteines at positions corresponding to amino-acid positions 14 and 38 in bovine pancreatic trypsin inhibitor (BPTI).

Exemplary proteins can inhibit:
two or more proteases whose excessive activity contributes to rheumatoid arthritis, multiple sclerosis, Crohn's disease, cancer, and chronic obstructive pulmonary disorder;
two or more of (e.g., all of) neutrophil elastase, proteinase 3, and cathepsin G;
two or more of (e.g., all of) human neutrophil elastase, proteinase 3, cathepsin G, and tryptase.
human plasma kallikrein and human neutrophil elastase;
two or more of (e.g., all of) human kallikrein 6 (hK6), human kallikrein 8 (hK8), and human kallikrein 10 (hK10);
hK6 and human neutrophil elastase;
human tissue kallikrein (h.K1) and human plasma kallikrein
two or more of human plasmin, human hepsin, human matriptase, human endotheliase 1, and human endotheliase 2.

For example, the protein includes at least two Kunitz domains, a first Kunitz domain specific for neutrophil elastase and a second Kunitz domain specific for proteinase 3. The first Kunitz domain can be N-terminal or C-terminal to the second Kunitz domain.

DX-88 is a Kunitz-domain inhibitor of human plasma kallikrein (hpKall) and DX-890 is a Kunitz-domain inhibitor of human neutrophil elastase (hNE). In one embodiment, the protein includes (i) DX-88, a domain at least 85, 90, 92, 95, 96, 97, 98 or 99% identical to DX-88, or a Kunitz domain that includes at least 70, 80, 85, 90, 95, or 100% of the amino acid residues in the protease binding loops of DX-88 and (ii) DX-890, a domain at least 85, 90, 92, 95, 96, 97, 98 or 99% identical to DX-890, or a Kunitz domain that includes at least 70, 80, 85, 90, 95, or 100% of the amino acid residues in the protease binding loops of DX-890.

In one embodiment, the protein includes at least two Kunitz domains, and at least two of which are identical or at least 90 or 95% identical. In one example, the protein includes at least two Kunitz domains, each of which is DX-88, a domain at least 85, 90, 92, 95, 96, 97, 98 or 99% identical to DX-88, or a Kunitz domain that includes at least 70, 80, 85, 90, 95, or 100% of the amino acid residues in the protease binding loops of DX-88. In another example, the protein includes at least two Kunitz domains, each of which is DX-890, a domain at least 85, 90, 92, 95, 96, 97, 98 or 99% identical to DX-890, or a Kunitz domain that includes at least 70, 80, 85, 90, 95, or 100% of the amino acid residues in the protease binding loops of DX-890.

In one embodiment, the protein includes at least two Kunitz domains, and the Kunitz domains differ from each other.

In one embodiment, the at least two Kunitz domains are connected by a linker, e.g., a flexible hydrophilic linker. For example, the linker is less than 35, 22, 15, 13, 11, or 9 amino acids in length. The linker can include at least two, three, or four glycine residues. In one embodiment, the at least two Kunitz domains are separated by a serum albumin moiety. In another embodiment, the at least two Kunitz domains are not separated by a serum albumin moiety. In one embodiment, the at least two Kunitz domains are connected by a linker that does not include T cell epitopes. For example, the at least two Kunitz domains are connected by a linker that lacks medium to large hydrophobic residues and charged residues. The linker may or may not include a glycosylation site. For example, the linker has fewer than three, two, or one glycosylation sites, i.e., no glycosylation sites. The linker can be devoid of N-linked glycosylation sites.

In one embodiment, the protein inhibits the human proteases in the presence of neutrophil defensins. The protein can be resistant to degradation by resident proteases, e.g., metalloproteases, e.g., MT6-MMP (Leukolysin). For example, the protein does not include cleavage sites recognized by MMP-8 or MMP-12. In one embodiment, the protein does not inhibit both of factor VII$_a$ and factor X$_a$. The protein may differ from human bikunin by at least two amino acids.

In another aspect, the disclosure features a method of treating a subject. The method includes administering, to the subject, a protein described herein, e.g., a protein that includes one or more engineered protease inhibitory sequences, wherein the protein inhibits two or more human proteases. For example, the subject is a subject in need of a reduction in the protease activity of at least two different proteases. The subject can have a disorder to which first and second human proteases contribute and the protein administered inhibits the first and second human proteases. For example, the protein includes a Kunitz domain that specifically inhibits the first human protease and a Kunitz domain that specifically inhibits the second human protease.

In another aspect, the disclosure features an isolated protein that includes (i) a Kunitz domain that inhibits a human serine protease, and (ii) a polypeptide sequence that contributes to binding and inhibition of a human protease, e.g., a metalloprotease. In one example, the protein consists of a single polypeptide chain. In another example the protein includes at least two polypeptide chains. In one embodiment, one polypeptide chain includes a heavy chain variable domain of an antigen-binding fragment and another polypeptide chain includes a light chain variable domain of an antigen-binding fragment, such that the antigen binding binds and inhibits a human protease, e.g., a metalloprotease.

In one embodiment, the Kunitz domain is a component of the same polypeptide chain as the heavy chain variable domain of the antigen-binding fragment. In another embodiment, the Kunitz domain is a component of the same polypeptide chain as the light chain variable domain of the antigen-binding fragment. For example, the Kunitz domain may be C-terminal to a constant domain of an antibody or an antigen-binding fragment thereof or N-terminal to a variable domain. In another embodiment, one Kunitz domain is N-terminal to a variable antibody domain and a second Kunitz domain is N-terminal to the final constant domain of the same chain. The two Kunitz domains may have the same inhibitory activity or different inhibitory activities.

In another aspect, the disclosure features a method of providing a protein that inhibits two or more human proteases. The method includes: providing amino acid sequences of a first Kunitz domain that inhibits a first human protease and a second Kunitz domain that inhibits a second human protease; providing the amino acid sequence of a recipient protein that includes a plurality of Kunitz domains; and preparing a polynucleotide encoding a modified amino acid sequence of the recipient protein, wherein the recipient protein is modified such that (a) amino acids of one of the Kunitz domains in the recipient protein is substituted with amino acid residues that contribute to binding or specificity of the first Kunitz domain and (b) amino acids of another of the Kunitz domains in the recipient protein is substituted with amino acid residues that contribute to binding or specificity of the second Kunitz domain.

In another aspect, the disclosure features a method of providing a protein that inhibits two or more human proteases. The method includes: providing amino acid sequences of a first Kunitz domain that inhibits a first human protease and a second Kunitz domain that inhibits a second human protease; and preparing a polynucleotide encoding a polypeptide in which sequences encoding the first and second Kunitz domains are in frame. The domains can be separated by a sequence encoding a linker sequence. In certain embodiments, (a) the linker does not include medium or large hydrophobic residues, nor charged residues, or (b) MHC I epitopes are not formed by amino acids from the first and second Kunitz domain and the linker. In one embodiment, the first and second human proteases contribute to a single human disease.

These methods can further include expressing the prepared polynucleotide in a cell, e.g., a cell in a transgenic animal (e.g., a mammary cell), or a cultured host cell. The method can further include formulating a protein encoded by the prepared polynucleotide as a pharmaceutical composition.

In another aspect, the invention features a method of treating rheumatoid arthritis. The method includes: administering, to the subject having or suspected of having rheumatoid arthritis, an effective amount of a protein that comprises one or more engineered protease inhibitory sequences. In some embodiments, the protein inhibits both human plasma kallikrein and human tissue kallikrein.

In another aspect, the disclosure features a method of treating lung inflammation. The method includes: administering, to a subject having or suspected of having lung inflammation, an effective amount of a protein that comprises one or more engineered protease inhibitory sequences. In some embodiments, the protein inhibits two or more of human neutrophil elastase, proteinase 3, cathepsin G, and tryptase.

In another aspect, the disclosure features a method of treating multiple sclerosis. The method includes: administering, to a subject having or suspected of having multiple sclerosis, an effective amount of a protein that comprises one or more engineered protease inhibitory sequences. In some embodiments, the protein inhibits two or more of human kallikrein 6 (hK6), human kallikrein 8 (hK8), and human kallikrein 10 (hK10).

In another aspect, the disclosure features a method of treating spinal chord injury. The method includes: administering, to a subject having or suspected of having spinal chord injury, an effective amount of a protein that comprises one or more engineered protease inhibitory sequences. In some embodiments, the protein inhibits both of hK6 and human neutrophil elastase.

In another aspect, the disclosure features a method of treating chronic obstructive pulmonary disorder. The method includes: administering, to a subject having or suspected of having chronic obstructive pulmonary disorder, an effective amount of a protein that comprises one or more engineered protease inhibitory sequences. In some embodiments, the protein inhibits two or more of human neutrophil elastase, PR3, and cathepsin G.

In another aspect, the disclosure features a method of treating an inflammatory bowel disease (e.g., Crohn's disease or ulcerative colitis). The method includes: administering, to a subject having or suspected of having Crohn's disease, an effective amount of a protein that comprises one or more engineered protease inhibitory sequences. In some embodiments, the protein inhibits human tissue kallikrein (hK1) and human plasma kallikrein.

In another aspect, the disclosure features a protein comprising an engineered Kunitz domain that inhibits a human protease, wherein the Kunitz domain lacks the 14-38 disulfide found in most naturally occurring Kunitz domains. In some embodiments, the protease is selected from the group consisting of plasma kallikrein, human neutrophil elastase, plasmin, or other protease described herein. In one embodiment, the binding loops of the Kunitz domain are identical to the binding loops of DX-88, DX-890, or DX-1000, or at least 80, 85, 90, or 95% identical. In one embodiment, the Kunitz domain is at least 85, 90, 95, or 100% identical to DX-88, DX-890, or DX-1000, but does not include cysteines at the positions corresponding to cysteine 14 and cysteine 38 of BPTI.

In another aspect, the disclosure features a library of polynucleotides. The library includes a plurality of polynucleotides, each of which comprises a sequence encoding a Kunitz domain that lacks cysteines at positions corresponding to position 14 and 38 of BPTI. The polynucleotides of the plurality vary such that one or more residues in the first and/or second binding loops of the Kunitz domains differs among the polynucleotides of the plurality. In one embodiment, codons encoding positions 13, 15, 16, 17, 18, 19, 31, 32, 34, 39, and 40 (numbered with respect to the sequence of BPTI) are varied.

In another aspect, the invention features a polynucleotide encoding a polypeptide that includes at least two Kunitz domains that differ by no more than 80, 85, 90, 95, 98%. The polynucleotide sequences encoding the Kunitz domains use different codons at positions corresponding to one or more residues that are identical between the at least two Kunitz domains. In one embodiment, the amino-acid sequences of the Kunitz domains are identical. For example, the amino-acid sequences of the Kunitz domains are identical, yet the polynucleotide sequences encoding the identical Kunitz domains differ at least ten or twenty codons. For example, the nucleic acid sequences encoding the Kunitz domain are less than 90, 80, 70, 60, or 50% identical.

It is possible to engineer proteins that contain multiple Kunitz domains, e.g., at least two, three, four, five, or six Kunitz domains. Each Kunitz domain is engineered to have high affinity and specificity for one or more serine proteases such that the resulting protein can inhibit one to several proteases with high affinity and specificity. In addition, the size of the engineered protein can be such that the lifetime in serum is enhanced (e.g., by including amino acid residues outside of the Kunitz domains to increase the molecular weight of the protein). Any method can be used to engineer a protein with multiple Kunitz domains. Examples including fusing different domains and selecting one or more domains from a library of varied Kunitz domains.

In one aspect of the invention, a library of Kunitz domains lacking the 14-38 disulfide is constructed and high-affinity inhibitor are selected. For example, the library includes variations at one or more positions in the first and/or second binding loops of the Kunitz domains. For example, positions 13, 14, 15, 16, 17, 18, 19, 31, 32, 34, 38, 39, and 40 with respect to the sequence of BPTI are varied. In other aspects, the invention comprises the construction of genetic diversity that encodes constant or nearly constant amino acid sequences to avoid genetic instability, e.g., recombination between nucleic acid sequences encoding different segments of the protein.

All patents, patent applications, and other references cited herein are incorporated by reference in their entireties.

DETAILED DESCRIPTION

A number of disorders involve multiple proteases (Churg and Wright, 2005, Curr Opin Pulm Med, 11:153-9), and thus proteins that inhibit at least two human proteases would be useful pharmacological agents for treating (e.g., improving and/or preventing) such disorders. Such proteins can include one or more Kunitz domains, or other sequences that inhibit proteases.

Some of these disorders are associated with the excessive protease activity of dissimilar serine proteases. In such cases, the catalytic sites of any pair of serine proteases may differ enough that no single Kunitz domain can bind both proteases with useful affinity. Accordingly, provided herein are compositions which include two or more Kunitz domains, wherein the composition includes at least two different engineered Kunitz domains (or Kunitz domains with different specificities) bound via a covalent linkage. The Kunitz domains are typically linked via a peptide bond (although it should be understood that the Kunitz domains need not be directly linked by a peptide bond in the sense that the carboxy terminus of one Kunitz domain directly linked via a peptide bond to the amino terminus of another Kunitz domain); a linker of one or more amino acids may separate the Kunitz domains). A peptide linker may be any desired length, but in some embodiments the linker is limited in size, for example, less than 35, 22, 15, 13, 11, or 9 amino acids in length. The linker can include at least two, three, or four glycine residues.

In one embodiment, the at least two Kunitz domains are not separated by a serum albumin moiety. In one embodiment, the at least two Kunitz domains are connected by a linker that does not include T cell epitopes. For example, the at least two Kunitz domains are connected by a linker that lacks medium to large hydrophobic residues and charged residues. The linker may or may not include a glycosylation site. For example, the linker has fewer than three, two, or one glycosylation sites, i.e., no glycosylation sites. The linker can be devoid of N-linked glycosylation sites.

In some embodiments, proteins comprising multiple different engineered Kunitz domains are produced by transferring the binding determinants of an engineered Kunitz domain to a recipient protein that naturally includes a plurality of Kunitz domains (e.g., modifying the naturally occurring sequences by reference to an engineered sequence so as to produce a protein comprising at least two engineered Kunitz domains (or Kunitz domains with different specificities).

If two or more serine proteases are similar, one can select for a Kunitz domain that inhibits all of the target serine proteases, e.g., inhibits each target protease with a Ki of less than 10 nM. As used herein, two serine proteases are "similar" if the approximately 20 residues that correspond to the trypsin residues that touch BPTI in the trypsin-BPTI complex are 80% identical. As will be understood, the likelihood of obtaining a single Kunitz domain that inhibits two or more target serine proteases increases with increasing identity between the target proteases. In some embodiments, proteins comprising Kunitz domains with specificity for more than one protease have a K, of less than 100 nM, 10 nM, 1 nM, or 0.1 nM for each of the target proteases.

Additionally, in some embodiments, protein comprises a Kunitz domain linked to a antibody (or antigen binding fragment or derivative thereof, such as Fab's, (Fab)$_2$, scFv, Fd, Fv) or non-Kunitz domain peptide which binds and inhibits a serine protease.

Some disorders involve not only serine proteases, but other types of proteases as well (e.g., metalloproteases, such as the matrix metalloproteases, or MMPs, or cysteine proteases). Accordingly the invention also provides proteins which comprise at least one Kunitz domain linked to at least one peptide or protein which inhibits a metalloprotease or a cysteine protease. Exemplary proteins which inhibit metalloproteases are antibodies and antigen-binding fragments or derivatives thereof (e.g., Fab's, (Fab)$_2$, scFv, Fd, Fv) which bind to and inhibit metalloproteases, particularly those that bind to and inhibit members of the matrix metalloprotease (MMP) family. Exemplary proteins which inhibit cysteine proteases are antibodies and antigen-binding fragments or derivatives thereof (Fab's, (Fab)$_2$, scFv, Fd, Fv) which bind to and inhibit cysteine proteases, particularly those that bind to and inhibit members of the cathepsin family (e.g. cathepsin L and/or cathepsin W).

Fusions between a single or multiple Kunitz domain-containing sequences and an antibody (or antigen-binding fragment or derivative thereof) may be in any configuration, such as fusion of the Kunitz domain-containing sequence to: a) the N-term of the light chain of an antigen binding fragment or full length antibody, b) the C-term of the light chain of an antigen binding fragment or full length antibody, c) the N-term of the heavy chain of an antigen binding fragment or full length antibody, or d) the C-term of heavy chain of an antigen binding fragment or full length antibody. Antibodies can be arranged as Fab's, (Fab)$_2$, scFv, Fd, Fv. For example, it is can be sufficient to use a protein that includes the light chain variable domain and the heavy chain variable domain.

Peptides which inhibit may also be incorporated into the proteins of the invention. Such inhibitory peptides may be fused to a Kunitz domain or to a protein containing multiple Kunitz domains and either antibody or albumin components that will ensure long residence in blood. Peptides that inhibit metalloproteinases could be fused to either end of a protein containing one or more therapeutic Kunitz domains. Another exemplary configuration is the insertion of an inhibitory peptide between Kunitz domains (e.g., the peptide may be used to replace a inter-Kunitz domain linker in an engineered version of human TFPI, or it may be used as a linker to connect two separate Kunitz domains).

Antibodies and/or peptides which bind proteases may be identified by selection of antibody or peptide libraries with the target protease (e.g., U.S. 2005/0180977 and Huang et al., J Biol Chem. 2003, 278:15532-40). Such selection is typically coupled with a screening step to identify those library members that inhibit the target protease as well. Such methods are similar to the selection and screening methods disclosed herein, as will be understood by practitioners in the art.

As referred to herein, an "engineered" protein sequence (e.g., an engineered Kunitz domain) is a protein that has a non-naturally occurring sequence. In some embodiments, an engineered Kunitz domain will vary from a naturally occurring Kunitz domain by at least 2, 3, 4, 5, 6, 7, 8, 9, or amino acids.

The comparison of sequences and determination of percent identity between two sequences can be performed using BLAST (Altschul et al. (1990) *J. Mol. Biol.* 215:403-410), particularly BLAST 2 Sequences as described by Tatusova and Madden (1999, *FEMS Microbiol. Lett.* 174:247-250) and as implemented by the National Center for Biotechnology Information (available via the world wide web at ncbi.nlm-.nih.gov/blast/bl2seq/wblast2.cgi). Parameters for comparison of two nucleotide sequences (e.g., BLASTN) are Reward for a match: 1; Penalty for a mismatch: −2; Open gap penalty: 5; extension penalty gap: 2; gap x_dropoff: 50; expect: 10.0; word size: 11. Parameters for comparison of two amino acid sequences (e.g., BLASTP) are Matrix: BLOSUM62; Open gap penalty: 11; extension gap penalty: 1; gap x_dropoff: 50; expect: 10.0; and word size 3.

As used herein, reference to hybridization under "low stringency," "medium stringency," "high stringency," or "very high stringency" conditions describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: (a) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); (b) medium stringency hybridization conditions in 6×SSC at about 45° C., followed by one or more washes in 0.2×SSC, 0.1% SDS at 60° C.; (c) high stringency hybridization conditions in 6×SSC at about 45° C., followed by one or more washes in 0.2×SSC, 0.1% SDS at 65° C.; and (d) very high stringency hybridization conditions are 0.5M sodium phosphate, 7% SDS at 65° C., followed by one or more washes at 0.2×SSC, 1% SDS at 65° C.

Kunitz Domains

A "Kunitz domain" is a polypeptide domain having at least 51 amino acids and containing at least two, and perhaps three, disulfides. The domain is folded such that the first and sixth cysteines, the third and fifth cysteine, and optionally the second and fourth form disulfide bonds (e.g., in a Kunitz domain having 58 amino acids, cysteines can be present at positions corresponding to amino acids 5, 14, 30, 38, 51, and 55, according to the number of the BPTI sequence provided below, and disulfides can form between the cysteines at position 5 and 55, 14 and 38, and 30 and 51), or, if two disulfides are present, they can form between 5 and 55 and 30 and 51. The spacing between respective cysteines can be within 7, 5, 4, 3, 2, or 1 amino acids of the following spacing between positions corresponding to: 5 to 55, 14 to 38, and 30 to 51, according to the numbering of the BPTI sequence provided herein (Table 7). The BPTI sequence can be used as a reference to refer to specific positions in any generic Kunitz domain. Comparison of Kunitz domains of interest to BPTI can be performed by identifying the best fit alignment in which the number of aligned cysteines is maximized.

The three dimensional structure (at high resolution) of the BPTI Kunitz domain is known. One of the X-ray structures of BPTI is deposited in the Brookhaven Protein Data Bank as "6PTI". The three dimensional structure of some BPTI homologues (Eigenbrot et al., (1990) Protein Engineering, 3(7): 591-598; Hynes et al., (1990) Biochemistry, 29:10018-10022) are likewise known. At least seventy natural Kunitz domain sequences are known. Known human homologues include three Kunitz domains of TFPI (Wun et al., (1988) J. Biol. Chem. 263(13):6001-6004; Girard et al., (1989) Nature, 338:518-20; Novotny et al, (1989) J. Biol. Chem., 264(31): 18832-18837; in some of these references, TFPI is identified as LACI (Lipoprotein Associated Coagulation Inhibitor) or EPI (Extrinsic Pathway Inhibitor)), two Kunitz domains of Inter-α-Trypsin Inhibitor, APP-I (Kido et al., (1988) J. Biol. Chem., 263(34):18104-18107), a Kunitz domain from collagen, and three Kunitz domains of TFPI-2 (Sprecher et al., (1994) PNAS USA, 91:3353-3357). TFPI is a human serum glycoprotein with a molecular weight of 39 kDa (amino acid sequence in Table 1) containing three Kunitz domains.

Kunitz domains interact with target protease using, primarily, amino acids in two loop regions ("binding loops"). The first loop region is between about residues corresponding to amino acids 11-21 of BPTI. The second loop region is between about residues corresponding to amino acids 31-42 of BPTI. An exemplary library of Kunitz domains varies one or more amino acid positions in the first and/or second loop regions. Particularly useful positions to vary include: positions 13, 15, 16, 17, 18, 19, 31, 32, 34, and 39 with respect to the sequence of BPTI. At least some of these positions are expected to be in close contact with the target protease.

The "framework region" of a Kunitz domain is defined as those residues that are a part of the Kunitz domain, but specifically excluding residues in the first and second binding loops regions, e.g., about residues corresponding to amino acids 11-21 of BPTI and 31-42 of BPTI. The framework region can be derived from a human Kunitz domain, e.g., TFPI domain 1. Exemplary frameworks can include at least one, two, or three lysines. In one embodiment, the lysines are present at positions corresponding to the positions found in the framework of LACI, or within at least three, two, or one amino acid(s) from such a position.

Conversely, residues that are not at these particular positions or which are not in the loop regions may tolerate a wider range of amino acid substitutions (e.g., conservative and/or non-conservative substitutions) than these amino acid positions.

BPTI is the prototypic Kunitz domain with 58 amino acids and cysteine residues at position 5, 14, 30, 38, 51, and 55. These form disulfides 5:55, 14:38, and 30:51.

There are phenylalanine residues at 33 and 45 in almost all Kunitz domains. There are glycine residues at positions 12 and 37 in almost all Kunitz domains. There is the possibility of an extra residue between positions 9 and 10, called 9a. If 9a is present, 12 need not be glycine. Insertion of up to three residues after position 26 is observed in some natural Kunitz domains; these inserted residues can be numbered 26a, 26b, and 26c. Insertion of up to three residues after position 42 is observed in some natural Kunitz domains (numbered 42a, 42b, and 42c). Cysteine residues other than those named are observed (e.g., as seen in bungarotoxin) and can lead to disulfides linking the Kunitz domain to other proteins.

Most Kunitz domains have 58 amino acids with Cys at positions 5, 14, 30, 38, 51, and 55. These domains are termed "canonical Kunitz domains" herein. All canonical Kunitz domains have essentially identical main-chain 3D structures. The first Kunitz domain of TFPI is a canonical Kunitz domain. We have constructed a phage-display library of TFPI-K1 Kunitz domains (see, e.g., U.S. Pat. No. 6,333,402). Moreover, it is possible to select a Kunitz domain having the TFPI-K1 framework for binding to a particular target protease. Then residues 13, 15-21, 34, 39-40 can be transferred into any other canonical Kunitz domain such that the recipient Kunitz domain obtains affinity for the particular target protease.

One class of non-canonical Kunitz domains has an extra amino acid at position 9a. In this class of Kunitz domains, residue 12 need not be glycine and the 3D structure in that region is different from that of canonical Kunitz domains. In TFPI-2, the second Kunitz domain has this non-canonical feature. To re-engineer TFPI-2 Kunitz domain2, a preferred embodiment is to build a library of TFPI-2 Kunitz domain2s and select the desired binding properties. Alternatively, one could change residues 8-12 and 39-43 to be canonical. That is, we would delete S9a and change D12 to G. At 13 and 39 we would put the amino acids needed for binding and change 40-45 to GNANNF (SEQ ID NO:203) since these are the most common amino acids at these positions.

When a Kunitz domain binds to a serine protease, only a small number of the amino acids of the Kunitz domain contact the serine protease. The exact number depends on the serine protease and the Kunitz domain, but is usually in the range 12 to 20. In the case of BPTI and trypsin, 13 residues (T11, G12, P13, C14, K15, A16, R17, I18, I19, G36, G37, C38, and R39) of BPTI have at least one atom positioned within 4 Å of an atom in trypsin. Residues 12, 14, 16, 37, and 38 are highly conserved in canonical Kunitz domains. In BPTI, residue 34 is valine which comes within 5 Å of an atom of trypsin. Charge (or lack thereof) and/or a bulky side chain at this position could influence binding, thus substitution of a large or charged residue at 34 could influence binding.

There are about 20 residues of trypsin (using chymotrypsinogen numbering) that come within 4 Å of an atom in BPTI: Y39, H40, F41, C42, H57, N97, L99, Y151, D189, S190, C191, Q192, G193, D194, S195, S214, W215, G216, G219, and G226. Of these positions, C42, H57, G193, D194, S195, S214, are absolutely conserved among trypsin-homologous serine proteases. Positions 39, 41, 97, 99, 151, and 192 are highly variable. Position 40 is often histidine but shows considerable variability. Position 189 is most often D, but S, G, A, and T occur in known serine proteases. Position 190 is often S, but G, V, T, A, I, and P are observed. Position 191 is most often C, but F and Y are observed. Position 215 is most often W, but F, Y, G, N, S, and K are observed. Position 216 is most often G, but V, S, and K are observed. Position 219 is most often G, but S, T, E, P, D, N, and T are observed, as is deletion of the residue. Position 226 is often G, but T, D, S, E, and A are observed. These residues are the ones most directly responsible for the substrate specificity of a particular serine protease because they contact the substrate. For other proteases, the number of amino acids that would contact a Kunitz domain could be more or less than 20.

BPTI and other Kunitz domains inhibit serine proteases by binding in the protease catalytic site but resisting cleavage and release. For a Kunitz domain to inhibit a serine protease, it must fit tightly into the catalytic site. In some cases, the bond between residue 15 of the Kunitz domain and residue 16 is cleaved, but the cleaved Kunitz domain does not release from the protease.

BPTI is not especially specific and inhibits a variety of serine proteases with affinity better than 10 nM. For example, its affinities for different proteases are: (human urine kallikrein (4 nM), porcine pancreatic kallikrein (0.55 nM), human plasmin (0.89 nM), activated protein C (1 µM) (Taby, et al., 1990, Thromb Res, 59:27-35) thrombin (30 µM) (Pintigny and Dachary-Prigent, 1992, Eur J Biochem, 207:89-95), and bovine trypsin (0.06 pM)).

Other Kunitz domains can be highly specific. For example, DX-88 inhibits human plasma kallikrein with $K_D \approx 30$ µM while its affinity for (human urine kallikrein (>100 µM), porcine pancreatic kallikrein (27 µM), human $C1r_{activated}$ (>20 µM), $C1s_{activated}$ (>20 µM), human plasmin (137 nM), human neutrophil elastase (>20 µM), human plasma F.XIIa (>20 µM), human plasma F.XIa (10 nM), human thrombin (>20 µM), human trypsin (>20 µM), and human chymotrypsin (>20 µM)) is less by a factor at least 250,000. The amino acid sequence of DX-88 is shown in Table 5 and DNA encoding DX-88 is shown in Table 6. Table 8 shows the DX-88 gene with restriction sites.

Engineered Kunitz domains are further disclosed in U.S. Pat. Nos. 6,333,402, 5,663,143, 6,953,674, each of which is incorporated by reference.

A Kunitz domain can be located within a larger protein, e.g., there can be sequences present N- and/or C-terminal to the Kunitz domain.

TFPI:

The sequence of tissue-factor pathway inhibitor (TFPI; also termed LACI) (GeneBank NM_006287) is shown in Table 3. The kinetics of TFPI binding to Factor $X_a$ was published in 1993 (Huang, et al., 1993, J Biol Chem, 268:26950-5). The sequences of TFPI proteins are known for *Danio rerio* (zebrafish), *Canis familiaris* (dog), *Macaca mulatta* (rhesus macaque), *Ogctolagus cuniculus* (rabbit), *Pan troglodytes* (chimpanzee), *Mus musculus* (mouse), *Gallus gallus* (chicken), and *Homo sapiens* (man). TFPI contains three Kunitz domains. The first Kunitz domain binds and inhibits factor $VII_a$ in the factor $VII_a$/tissue factor complex, Kunitz domain2 binds and inhibits factor $X_a$, and Kunitz domain-3 is involved in binding to cells (Piro and Broze, 2004, Circulation, 110:3567-72). The cell binding by Kunitz domain-3 can be reduced by changing the P1 arginine to leucine (Piro and Broze, 2004, Circulation, 110:3567-72).

Human TFPI may be modified to provide an engineered protein that inhibits at least two different human proteases (e.g., proteases other than factor $VII_a$ and factor $X_2$) and that has a plurality of Kunitz domains. Many of the modified proteins of the present invention will be very similar to human TFPI. A protein that includes TFPI or its Kunitz domains can be altered so that it does not bind to cells as binding a polypeptide to cell surfaces can increase antigenicity (Leonetti, et al., 1998, J Immunol, 160:3820-7). For example, modification of human TFPI to delete the C-terminal peptide GGLIKT-KRKRKKQRVKIAYEEIFVKNM (SEQ ID NO:145) while retaining Kunitz domain 3 reduces cell binding and other consequent cell signaling events. In a preferred embodiment, the therapeutic protein has no effect on the expression of any genes and does not bind to cells.

Mine et al. (Biochemistry (2002) 41:78-85.) have reported that three lysine residues in the third KuDom of TFPI (which correspond to K241, K260, and K268 in Table 1) form a positively-charged cluster that may bind heparin and foster binding to cells. In one embodiment of the invention, one or more of K241, K260, and K268 are changed to an amino acid that is not positively charged. At position 29, K is the most common AA type and Q is second most common, thus K241Q is a preferred mutation for removal of positive charge in KuDom 3 of TFPI. At position 48, E is the most common AA type. Thus K260E is a preferred mutation for removal of positive charge in KuDom 3 of TFPI. At position 56, G is the most common AA type. Thus K268G is a preferred mutation for removal of positive charge in KuDom 3 of TFPI. Removal of at least one of the three lysines will reduce the possibility of the TFPI variant binding to glycosaminoglycans.

TFPI is cleaved a particular sites by metalloproteinases, e.g., by MMP-8 after S174 and after K20. P18, L19, and L21 conform to substrate 3 in Table 42. In one embodiment, the protein used is based on TFPI, but includes modifications in the linker sequences to prevent MMP cleavage. For example, the sites of cleavage by MMPs are changed to avoid such cleavage. In certain cases S174 and K20 are altered, e.g., to alanine. In another embodiment, the sites are left as is. In most cases, the engineered Kunitz domains will have very high affinity for their targets, thus engineering TFPI-based proteins to reduce or eliminate sensitivity to MMP digestion may not be necessary.

TFPI itself does not have especially high affinity for factor $X_a$ and factor $VII_a$. Petersen et al. (Petersen, et al., 1996, Eur J Biochem, 235:310-6) report that Kunitz domain 1 binds factor $VII_a$/TF with $K_D$=250 nM and Kunitz domain 2 binds factor Xa with $K_D$=90 nM. Engineered Kunitz domain proteins based on TFPI will have much higher affinity for their targets (e.g., TFPI Kunitz domains may be engineered to increase affinity for factor $X_a$ and factor $VII_a$ to a $K_D$ of less than or equal to 10 nM or 1 nM). The basic C-terminal segment (Linker 4) is also involved in binding F.Xa (Cunningham, et al., 2002, Biochem J, 367:451-8). For example, a protein described herein has a $K_D$ of greater than 10 nM or 100 nM for one or both of factor $VII_a$ and factor $X_a$.

TFPI-2:

The amino acid sequence of TFPI-2 is shown in Table 11. Note that the second Kunitz domain is non-canonical, having a residue 9a and residues 42a and 42b. The linkers are shorter than in TFPI. The C-terminal linker is quite basic, but linkers 1, 2, and 3 are much shorter than the corresponding linkers in TFPI. TFPI-2 may be engineered to be a multiple protease inhibitor by remodeling Kunitz domain 1 and Kunitz domain 3 in the same way that the Kunitz domains of TFPI are remodeled in Examples 2, 3, and 5. Kunitz domain 2 could either be forced to be canonical or one could make a library of Kunitz domain 2 derivatives, select a member having the desired binding properties, and remodel Kunitz domain 2 as needed. TFPI-2, like TFPI, binds cell surfaces. Preferred derivatives of TFPI-2 are modified to abolish binding to cells and effects on gene expression.

Table 12 shows a DNA sequence that would cause display of TFPI-2 Kunitz domain 2 on the stump of M13 III on M13-derived phage. The sequence of the parental phage vector is shown in Table 13. The restriction sites that bound the display cassette of Table 12 are bold in Table 13. To generate a TFPI-2 Kunitz domain 2 library, the DNA between PstI and BspEI is synthesized with the diversity shown in Table 12. Table 14 shows oligonucleotides (ONs) that can be used for this synthesis. ON1U96 and ON71L97 are complementary at their 3' ends where underscored. ON1U21T2 and ON147L21 are identical to the 5' ends of the long oligonucleotides and can be used to prime PCR amplification of the long oligonucleotides. There are PstI and BspEI sites near the ends of the final product. The double-stranded DNA is cut with PstI and BspEI and ligated to similarly cleaved vector. The theoretical diversity of the library is $6.7 \times 10^{14}$ amino acid sequences. Actual libraries can include at least $10^9$, $10^{10}$, or $10^{11}$ transformants. One could also use codon-based mutagenesis to synthesize the mixtures shown in Table 12.

Hepatocyte Growth Factor Activator Inhibitor-1 and -2:

Additional examples of a mammalian proteins that include multiple Kunitz domains are: Hepatocyte Growth Factor Activator Inhibitor-1 (HAI-1) and Hepatocyte Growth Factor Activator Inhibitor-2 (HAI-2). Each contains two Kunitz domains.

HAI-1 and HAI-2 are cell bound proteins. Derivatives that are not associated with cells can be prepared, e.g., by producing a form of the protein that includes only the Kunitz domain and intervening sequences. The regions of HAI-1 and HAI-2 responsible for cell binding can be inactivated, e.g., by deletion.

Bikunin:

Table 39 shows four amino acid sequences for "humin bikunin" reported in U.S. Pat. No. 6,583,108 (the '108 patent). The SEQ ID NOs of '108 are shown as "SEQ ID NO:123", "SEQ ID NO:124", and "SEQ ID NO:125" have differences in the signal sequence and in amino acid sequence that follows the second Kunitz domain. Table 38 shows affinity data from the '108 patent for the two Kunitz domains of bikunin against a variety of serine proteases.

Protease Targets

Proteases are involved in a wide variety of biological processes, including inflammation and tissue injury. Serine proteases produced by inflammatory cells, including neutrophils, are implicated in various disorders, such as pulmonary emphysema. As such, multiple different proteases can contribute to a single disorder.

Examples of particular proteases include the following. Neutrophil elastase is a serine protease produced by polymorphonuclear leukocytes with activity against extracellular matrix components and pathogens. Pulmonary emphysema is characterized by alveolar destruction leading to a major impairment in lung function. Human neutrophil elastase consists of approximately 238 amino acid residues, contains 2 asparagine-linked carbohydrate side chains, and is joined together by 4 disulfide bonds (GeneBank Entry P08246). It is normally synthesized in the developing neutrophil as a proenzyme but stored in the primary granules in its active form, ready with full enzymatic activity when released from the granules, normally at sites of inflammation (Gullberg U, et al. *Eur J Haematol.* 1997; 58:137-153; Borregaard N, Cowland J B. *Blood.* 1997; 89:3503-3521).

Other exemplary protease targets include: plasmin, tissue kallikrein, plasma kallikrein, Factor VII$_a$, Factor XI$_a$, thrombin, urokinase, trypsin 1, trypsin 2, pancreatic chymotrypsin, pancreatic elastase, tryptase, and Factor II$_a$. Classes of relevant proteases include: proteases associated with blood coagulation, proteases associated with fibrinolysis, proteases associated with complement, proteases that digest extracellular matrix components, proteases that digest basement membranes, and proteases associated with endothelial cells. For example, the protease is a serine protease. Proteins described herein that inhibit one or more proteases can be engineered to inhibit one or more proteases within these classes.

Identifying Kunitz Domains and Other Protease Inhibitors

A variety of methods can be used to identify a Kunitz domain that binds to and/or inhibits a protease, e.g., a human protease. These methods can be used to identify natural and non-naturally occurring Kunitz domains that can be used as components of a protein that inhibits a plurality of proteases, e.g., a plurality of human proteases. Other protease inhibitors can be similarly identified, e.g., by varying known protease inhibitors or protease resistant proteins, by using libraries of randomized peptides or proteins, or using libraries of antibodies e.g., as described in US 2004-0071705 (including ¶ 102-112). As will be understood by those of skill in the art, while the description of methods of identifying inhibitors of proteases herein are largely directed towards Kunitz domains, the methods can be adapted for identifying peptide-based or antibody-based protease inhibitors.

For example, a Kunitz domain can be identified from a library of proteins in which each of a plurality of library members includes a varied Kunitz domain. Various amino acids can be varied in the domain. See, e.g., U.S. Pat. No. 5,223,409; U.S. Pat. No. 5,663,143, and U.S. Pat. No. 6,333,402. Kunitz domains can be varied, e.g., using DNA mutagenesis, DNA shuffling, chemical synthesis of oligonucleotides (e.g., using codons as subunits), and cloning of natural genes. See, e.g., U.S. Pat. No. 5,223,409 and U.S. 2003-0129659.

Libraries of Kunitz domains can be generated by varying one or more binding loop amino acid residues of a Kunitz domain described herein, e.g., a Kunitz domain having a framework described herein, e.g., a modified or naturally occurring framework region. In one embodiment, the residues that are varied are varied among a plurality of amino acids.

The library can be an expression library that is used to produce proteins. The proteins can be arrayed, e.g., using a protein array. U.S. Pat. No. 5,143,854; De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/98534, WO 01/83827, WO 02/12893, WO 00/63701, WO 01/40803 and WO 99/51773.

Kunitz domains can also be displayed on a replicable genetic package, e.g., in the form of a phage library such as a phage display, yeast display library, ribosome display, or nucleic acid-protein fusion library. See, e.g., U.S. Pat. No. 5,223,409; Garrard et al. (1991) *Bio/Technology* 9:1373-1377; WO 03/029456; and U.S. Pat. No. 6,207,446. Binding members of such libraries can be obtained by selection and screened in a high throughput format. See, e.g., U.S. 2003-0129659.

Selection from Display Libraries

This section describes exemplary methods of selecting members of a display library to identify a Kunitz domain that inhibits a protease. The methods disclosed herein can also be modified and used in combination with other types of libraries, e.g., an expression library or a protein array, and so forth. Kunitz domains can be displayed on phage, especially on filamentous phage (e.g., M13). In a preferred embodiment, the library contains members that have a variety of amino acid types at the positions of the Kunitz domain that are likely to contact a serine protease where they can affect the binding. Using immobilized or immobilizable (e.g., by modification with one member of a binding pair, such as avidin or streptavidin) serine protease as a target, one can select those members of the library that have high affinity for the serine protease of interest.

In an exemplary display library selection, a phage library is contacted with and allowed to bind to the target protease which may be an active or an inactivated form of the protease (e.g., mutant or chemically inactivated protein) or a fragment thereof. To facilitate separation of binders and non-binders in the selection process, it is often convenient to immobilize the protease on a solid support, although it is also possible to first permit binding to the target protease in solution and then segregate binders from non-binders by coupling the target protease to a support. By way of illustration, when incubated in the presence of the protease, phage displaying a Kunitz domain that interacts with target protease form complexes with the target protease immobilized on a solid support whereas non-binding phage remain in solution and are washed away with buffer. Bound phage may then be liberated from the protease by a number of means, such as changing the buffer to a relatively high acidic or basic pH (e.g., pH 2 or pH 10), changing the ionic strength of the buffer, adding denaturants, adding a competitor, adding host cells which can be infected (Hogan et al. (2005) *Biotechniques* 38(4):536, 538.), or other known means.

For example, to identify protease-binding peptides, protease can be adsorbed to a solid surface, such as the plastic surface of wells in a multi-well assay plate. Subsequently, an aliquot of a phage display library is added to a well under appropriate conditions that maintain the structure of the immobilized protease and the phage, such as pH 6-7. Phage that display polypeptides that bind the immobilized protease are bound to the protease and are retained in the well. Non-binding phage can be removed (e.g., by washing with buffer). It is also possible to include a blocking agent or competing agent during the binding of the phage library to the immobilized protease.

Phage bound to the immobilized protease may then be eluted by washing with a buffer solution having a relatively strong acid pH (e.g., pH 2) or an alkaline pH (e.g., pH 8-9). The solutions of recovered phage that are eluted from the protease are then neutralized and may, if desired, be pooled as an enriched mixed library population of phage displaying protease binding peptides. Alternatively the eluted phage from each library may be kept separate as a library-specific enriched population of protease binders. Enriched populations of phage displaying protease binding peptides may then be grown up by standard methods for further rounds of selection and/or for analysis of peptide displayed on the phage and/or for sequencing the DNA encoding the displayed binding peptide.

Recovered phage may then be amplified by infection of bacterial cells, and the screening process may be repeated with the new pool of phage that is now depleted in non-protease binders and enriched in protease binders. The recovery of even a few binding phage may be sufficient to carry the process to completion. After a few rounds of selection (e.g. 2 or 3), the gene sequences encoding the binding moieties derived from selected phage clones in the binding pool are determined by conventional methods, revealing the peptide sequence that imparts binding affinity of the phage to the target. An increase in the number of phage recovered after each round of selection and the recovery of closely related sequences indicate that the screening is converging on sequences of the library having a desired characteristic.

After a set of binding polypeptides is identified, the sequence information may be used to design secondary libraries. For example, the secondary libraries can explore a smaller segment of sequence space in more detail than the initial library. In some embodiments, the secondary library includes proteins that are biased for members having additional desired properties, e.g., sequences that have a high percentage identity to a human protein.

Iterative Selection.

Display library technology may be used in an iterative mode. A first display library is used to identify one or more Kunitz domains that bind to a target protease. These identified Kunitz domains are then varied using a mutagenesis method to form a second display library. Higher affinity proteins are then selected from the second library, e.g., by using higher stringency or more competitive binding and washing conditions.

In some implementations, the mutagenesis is targeted to regions known or likely to be at the binding interface. For Kunitz domains, many positions near the binding interface are known. Such positions include, for example, positions 13, 14, 15, 16, 17, 18, 19, 31, 32, 34, 38, and 39 with respect to the sequence of BPTI. Some exemplary mutagenesis techniques include: synthesis of DNA with mixed nucleotides, error-prone PCR (Leung et al. (1989) *Technique* 1:11-15), recombination, DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208:564-586) and incorporation of degenerate oligonucleotides (Griffiths et al. (1994) *EMBO J* 13:3245). The mixtures of nucleotides used in synthesis can be, for example, NNK which allows any base at the first two positions of a varied codon and G or T at the final base and allows all 20 amino-acid types to appear. Alternatively, varied codons that exclude some amino-acid types and perhaps stop codons may be used. NNK provides 32 codons, one of which is TAG, a stop. NNK also provides three codons for each of Ser, Leu, and Arg; two codons for each of Val, Ala, Pro, Thr, and Gly; the other twelve amino-acid types have a single codon. The varied codon NNT provides 15 amino-acid types and no stops. NNG provides 13 amino-acid types and one stop.

Mutagenesis may also be carried out in a more limited or targeted fashion. For example, if the parental amino-acid in a position of interest is Ser, a codon mix with (0.85 T, 0.05 C, 0.05 A, 0.05 G) at the first base, (0.85 C, 0.05 T, 0.05 A, 0.5 G) at the second base and (0.85 T, 0.05 C, 0.05 A, 0.05 G) at the third base may be employed. Most of the DNA molecules will have TCT encoding Ser, but others will have codons that differ by one, two, or three bases, providing a diversity of amino-acid types.

In one example of iterative selection, the methods described herein are used to first identify Kunitz domains from a display library that bind a target protease with at least a minimal binding specificity, e.g., an equilibrium dissociation constant for binding of less than 100 nM, 10 nM, or 1 nM. The nucleic acid sequences encoding the Kunitz domains that are initially identified are used as a template nucleic acid for the introduction of variations, e.g., to identify a second Kunitz domain that has enhanced properties (e.g., binding affinity, kinetics, or stability) relative to the initial protein Kunitz domain.

Selecting or Screening for Specificity.

The display library selection and screening methods described herein can include a selection or screening process that discards display library members that bind to a non-target molecule, e.g., a protease other than the target protease. In one embodiment, the non-target molecule is a protease that has been inactivated by treatment with an irreversibly bound inhibitor, e.g., a covalent inhibitor.

In one implementation, a so-called "negative selection" step or "depletion" is used to discriminate between the target and a related, but distinct or an unrelated non-target molecules. The display library or a pool thereof is contacted with the non-target protease. Members of the sample that do not bind the non-target protease are collected and used in subsequent selections for binding to the target molecule or even for subsequent negative selections. The negative selection step can be prior to or after selecting library members that bind to the target protease.

In another implementation, a screening step is used. After display library members are isolated for binding to the target molecule, each isolated library member is tested for its ability to bind to a non-target protease. For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to the target protease.

Single Kunitz Domains with Multiple Specificities

Single Kunitz domains with more than one specificity are obtained by alternating selection of libraries using the target serine proteases. Members of a library of Kunitz domains are first selected for binding to the first target serine protease, and those library members that bind the first target are selected and screened against the second target serine protease. This alternating selection and screening may be carried out on as many target serine proteases as desired. Additionally, the selection may be repeated, such that the library members which bind to all of the target proteases are then screened for the desired binding. Two to four rounds of repeated selections are commonly performed.

For example, alternating selection can be used to obtain a single Kunitz domain that inhibits both human kallikrein 1 (h.K1, also known as tissue kallikrein) and murine kallikrein 1 (m.K1). As described above, a library would be selected first against one of the targets (e.g., hK1), then the Kunitz domains identified in the first selection are then selected against the other target (e.g., mK1). A Kunitz domain that inhibits a human serine protease and its counterpart from another mammalian species (e.g., murine) is useful because its characteristics can be evaluated in an animal model of disease.

In another example, a Kunitz domain is selected that inhibits both human plasma kallikrein (h.pKal) and human tissue kallikrein by alternating selection with the two targets. Such an inhibitor would be advantageous in a disease, such as arthritis, where both human plasma kallikrein and human tissue kallikrein are excessively active. In one embodiment, the Kunitz domain differs from human bikunin (e.g., as described in U.S. Pat. No. 6,583,108) by at least two, three, five, or ten amino acids.

Transferring Specificity Determinants

Natural proteins that have more than one Kunitz domain can be modified to provide a protein with at least two engineered Kunitz domains that inhibit, respectively, two different human proteases, e.g., plasma kallikrein (pKal) and human neutrophil elastase (hNE). For example, residues from the protease binding loops of DX-88 can be transferred to one Kunitz domain of the recipient protein and residues from the protease binding loops of DX-890 can be transferred into another of Kunitz domains. The resulting protein inhibits plasma kallikrein and human neutrophil elastase.

In one embodiment, residues that contribute to binding and/or specificity are substituted into the Kunitz domains of a pre-existing protein, e.g., a naturally occurring protein such as a serum protein. Several serum proteins contain two or three Kunitz domains. Each of these Kunitz domains could be engineered to inhibit one target. For example, the extracellular compartment of human tissue contains tissue-factor pathway inhibitor (TFPI, also known as lipoprotein-associated coagulation inhibitor (LACI)), tissue-factor pathway inhibitor-2 (TFPI-2), hepatocyte growth factor activator inhibitor-1 (HAI-1), hepatocyte growth factor activator inhibitor-2 (HAI-2, also known as placental bikunin), and bikunin (also known as inter-alpha trypsin inhibitor). One strategy is to use one of the multi-Kunitz domain human proteins as a template and change only those residues that confer needed affinity and specificity.

The residues that confer affinity and specificity can be transferred from one Kunitz domain to another with high retention of the desired properties by substitution of a few residues. For example, DX-88 is based on Kunitz domain 1 of TFPI and has five amino acids within the Kunitz domain changed based on selection from a phage-displayed library. DX-88 is a 30 pM inhibitor of human plasma kallikrein (h.pKal) while TFPI Kunitz domain 1 has hardly any affinity for h.pKal. Table 7 shows the amino acid sequences of several Kunitz domains, some wildtype, some selected from phage libraries, some designed, and some designed, built and tested. BPTI, TFPI-K1, TFPI-K2, and TFPI-K3 are naturally occurring Kunitz domains. DX-88 and DX-1000 were selected from a library of TFPI Kunitz domain 1 derivatives and inhibit human plasma kallikrein and human plasmin respectively. TF890 is designed by comparison with DX-890 and should inhibit human neutrophil elastase with high affinity. TFPI-K2_88 is a modification of TFPI-K2 which should inhibit human plasma kallikrein. TFPI-K3_88 is a derivative of TFPI Kunitz domain 3 which should inhibit human plasma kallikrein. ITI-K2 is the second Kunitz domain of bikunin. DX-890 is a potent inhibitor of human neutrophil elastase that was designed bases on inhibitor selected from a library of BPTI derivatives for binding to human neutrophil elastase. TFPI-K2_890 is a derivative of TFPI Kunitz domain 2 that was designed to inhibit human neutrophil elastase. TFPI-K3_890 is a derivative of TFPI Kunitz domain 3 that was designed to inhibit human neutrophil elastase.

(*)New engineered Kunitz domain sequences may be selected using display library technology. The 'base', or 'scaffold' sequence can be any Kunitz domain-containing protein, but in certain embodiments, the 'base' sequence is derived from a naturally-occurring protein that contains two or more Kunitz domains (e.g., TFPI, for example, TFPI K1). Any serine protease of interest may be used as the target, including neutrophil elastase (e.g., human neutrophil elastase), proteinase 3 (e.g., human proteinase 3), cathepsin G (e.g., human cathepsin G), tryptase (e.g., human tryptase), plasma kallikrein (e.g., human plasma kallikrein), neutrophil elastase (e.g., human neutrophil elastase), kallikrein 6 (e.g., human kallikrein 6), kallikrein 8 (e.g., human kallikrein 8), kallikrein 10 (e.g., human kallikrein 10), tissue kallikrein (e.g., human tissue kallikrein), plasmin (e.g., human plasmin), hepsin (e.g., human hepsin), matriptase (e.g., human matriptase), endotheliase 1 (e.g., human endotheliase 1), and endotheliase 2 (e.g., human endotheliase 2).

In some embodiments, the recipient Kunitz domain is modified so that residues positions 13, 15, 16, 17, 18, 19, 31, 32, 34, and 39 (numbered with respect to the sequence of BPTI) are the same as the residues in the originating Kunitz domain. Alternatively, one could vary residues 11, 13, 15-19, 31, 32, 34, 39, and 40. In another embodiment, one could vary 11-19, 31, 32, 34, and 38-40; in this case one allows the 14-38 disulfide to be changed to other amino-acid types. In other embodiments, the recipient Kunitz domain is modified so that residues in the first and second binding loops are the same as the residues in the originating Kunitz domain.

Modifying and Varying Polypeptides

It is also possible to vary a Kunitz domain or other protein described herein to obtain useful variant that has similar or improved or altered properties. Typically, a number of variants are possible. A variant can be prepared and then tested, e.g., using a binding assay described herein (such as fluorescence anisotropy).

One type of variant is a truncation of a Kunitz domain or other protein described herein. In this example, the variant is prepared by removing one or more amino acid residues of the domain from the N or C terminus. In some cases, a series of such variants is prepared and tested. Information from testing the series is used to determine a region of the domain that is essential for protease binding and/or stability in serum. A series of internal deletions or insertions can be similarly constructed and tested. For Kunitz domains, it can be possible to remove, e.g., between one and five residues or one and three residues that are N-terminal to $C_5$, the first cysteine, and between one and five residues or one and three residues that are C-terminal to $C_{55}$, the final cysteine, wherein each of the cysteines corresponds to a respectively numbered cysteine in BPTI.

Another type of variant is a substitution. In one example, the Kunitz domain is subjected to alanine scanning to identify residues that contribute to binding activity and or stability. In another example, a library of substitutions at one or more positions is constructed. The library may be unbiased or, particularly if multiple positions are varied, biased towards an original residue. In some cases, the substitutions are all conservative substitutions.

In another example, each lysine is replaced by arginine and the binding affinity is measured. Thus, one may obtain a binding protein having no lysines and retaining the selected binding properties. Proteins lacking lysine residues with the polypeptide chain provide only a single site for pegylation (the amino terminus), and thus provide a more homogenous product upon pegylation.

Another type of variant includes one or more non-naturally occurring amino acids. Such variant domains can be produced by chemical synthesis or modification. One or more positions can be substituted with a non-naturally occurring amino acid. In some cases, the substituted amino acid may be chemically related to the original naturally occurring residue (e.g., aliphatic, charged, basic, acidic, aromatic, hydrophilic) or an isostere of the original residue.

It is also be possible to include non-peptide linkages and other chemical modifications. For example, part or all of the Kunitz domain or other protein may be synthesized as a peptidomimetic, e.g., a peptoid (see, e.g., Simon et al. (1992) *Proc. Natl. Acad. Sci. USA* 89:9367-71 and Horwell (1995) *Trends Biotechnol.* 13:132-4).

Protein Production

Recombinant Production of Polypeptides.

Standard recombinant nucleic acid methods can be used to express a protein described herein (e.g., a protein that includes one or more Kunitz domains). Generally, a nucleic acid sequence encoding the protein is cloned into a nucleic acid expression vector. If the protein is sufficiently small, e.g., the protein is a peptide of less than 60 amino acids, the protein can be synthesized using automated organic synthetic methods.

The expression vector for expressing the protein can include a segment encoding the protein and regulatory sequences, for example, a promoter, operably linked to the coding segment. Suitable vectors and promoters are known to those of skill in the art and are commercially available for generating the recombinant constructs of the present invention. See, for example, the techniques described in Sambrook & Russell, *Molecular Cloning: A Laboratory Manual, 3rd Edition*, Cold Spring Harbor Laboratory, N.Y. (2001) and Ausubel et al., Current Protocols in Molecular Biology (Greene Publishing Associates and Wiley Interscience, N.Y. (1989).

Expression of proteins that contain no sites for N-linked glycosylation can be carried out in bacteria, yeast, or mammalian cells. Proteins having sites for N-linked glycosylation can be expressed in bacteria to obtain non-glycosylated versions or in yeast or mammalian cells if glycosylation is desired. For use in humans, glycosylated versions are preferably produced in mammalian cells such as CHO or HEK293T cells.

Scopes (1994) *Protein Purification: Principles and Practice*, New York: Springer-Verlag and other texts provide a number of general methods for purifying recombinant (and non-recombinant) proteins.

Synthetic Production of Peptides.

A polypeptide can also be produced by synthetic means. See, e.g., Merrifield (1963) *J. Am. Chem. Soc.*, 85: 2149. For example, the molecular weight of synthetic peptides or peptide mimetics can be from about 250 to about 8,0000 Daltons. A peptide can be modified, e.g., by attachment to a moiety that increases the effective molecular weight of the peptide. If the peptide is oligomerized, dimerized and/or derivatized, e.g., with a hydrophilic polymer (e.g., to increase the affinity and/or activity of the peptides), its molecular weights can be greater and can range anywhere from about 500 to about 50,000 Daltons.

Pegylation and Other Modifications

A single Kunitz domain has low molecular mass and at least in some cases are rapidly filtered by the kidneys. Increasing molecular mass can increase serum residence.

A variety of moieties can be covalently attached to the protein to increase the molecular weight of a protein that includes a Kunitz domain. In one embodiment, the moiety is a polymer, e.g., a water soluble and/or substantially non-antigenic polymer such as a homopolymer or a non-biological polymer. Substantially non-antigenic polymers include, e.g., polyalkylene oxides or polyethylene oxides. The moiety may improve stabilization and/or retention of the Kunitz domain in circulation, e.g., in blood, serum, lymph, or other tissues, e.g., by at least 1.5, 2, 5, 10, 50, 75, or 100 fold. One or a plurality of moieties can be attached to protein that includes a Kunitz domain. For example, the protein is attached to at least three moieties of the polymer. In one embodiment, particularly if there are no lysines in the protease binding loops, each lysine of the protein can be attached to a moiety of the polymer.

Suitable polymers can vary substantially by weight. For example, it is possible to use polymers having average molecular weights ranging from about 200 Daltons to about 40 kDa, e.g., 1-20 kDa, 4-12 kDa or 3-8 kDa, e.g., about 4, 5, 6, or 7 kDa. In one embodiment, the average molecular weight of individual moieties of the polymer that are associated with the compound are less than 20, 18, 17, 15, 12, 10, 8, or 7 kDa. The final molecular weight can also depend upon the desired effective size of the conjugate, the nature (e.g. structure, such as linear or branched) of the polymer, and the degree of derivatization.

A non-limiting list of exemplary polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. The polymer can be a hydrophilic polyvinyl polymers, e.g. polyvinylalcohol and polyvinylpyrrolidone. Additional useful polymers include polyoxyalkylenes such as polyoxyethylene, polyoxypropylene, and block copolymers of polyoxyethylene and polyoxypropylene (Pluronics); polylactic acid; polyglycolic acid; polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, cellulose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. In some embodiments, the polymer includes a variety of different copolymer blocks.

Additional exemplary methods of attaching more than one polymer moiety to a protein are described in US 2005-0089515.

Another method of increasing the molecular weight of a protein is by making multimers of the protein (e.g., producing the protein such that at least two copies of the protein are fused, typically in tandem, but head to head fusions are also possible). Multimers may be produced by chemical crosslinking or by expression of a construct encoding the multimer. Because long repeats of DNA may be unstable, it is preferred that the polynucleotides encoding the different copies of the protein have different sequences.

Characterization of Binding Interactions

The binding properties of a protein (e.g., a protein that includes one or more Kunitz domains) can be readily assessed using various assay formats. For example, the binding properties can be assayed by quantitative measurement of the ability to inhibit the target and non-target proteases. Alternatively, for example, the binding property of a protein can be measured in solution by fluorescence anisotropy (Bentley et al., (1985) *J. Biol. Chem.* 260(12):7250-56; Shimada et al., (1985) *J. Biochem.* 97(6):1637-44; Terpetschnig et al., (1995) *Anal. Biochem.* 227(1):140-7; Durkop et al., (2002) *Anal. Bioanal. Chem.* 372(5-6):688-94), which provides a convenient and accurate method of determining a dissociation constant ($K_D$) or association constant (Ka) of the protein for a particular target protease. In one such procedure, the protein to be evaluated is labeled with fluorescein. The fluorescein-labeled protein is mixed in wells of a multi-well assay plate with various concentrations of the particular target protease or non-target protease. Fluorescence anisotropy measurements are carried out using a fluorescence polarization plate reader.

The binding interactions can also be analyzed using an ELISA assay. For example, the protein to be evaluated is contacted to a microtitre plate whose bottom surface has been coated with the target protease, e.g., a limiting amount of the target protease. The molecule is contacted to the plate. The plate is washed with buffer to remove non-specifically bound molecules. Then the amount of the protein bound to the plate is determined by probing the plate with an antibody that recognizes the protein. For example, the protein can include an epitope tag. The antibody can be linked to an enzyme such as alkaline phosphatase, which produces a colorimetric product when appropriate substrates are provided. In the case where a display library member includes the protein to be tested, the antibody can recognize a region that is constant among all display library members, e.g., for a phage display library member, a major phage coat protein.

A binding interaction between a protein and a particular target protease can be analyzed using surface plasmon resonance (SPR). For example, after sequencing of a display library member present in a sample, and optionally verified, e.g., by ELISA, the displayed protein can be produced in quantity and assayed for binding the target using SPR. SPR or real-time Biomolecular Interaction Analysis (BIA) detects biospecific interactions in real time, without labeling any of the interactants (e.g., BIAcore). Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander, S, and Urbaniczky, C. (1991) *Anal. Chem.* 63:2338-2345; Szabo et al. (1995) *Curr. Opin. Struct. Biol.* 5:699-705.

Information from SPR can be used to provide an accurate and quantitative measure of the equilibrium dissociation constant ($K_D$), and kinetic parameters, including $k_{on}$ and $k_{off}$, for the binding of a protein (e.g., a protein include Kunitz domains) to a target protease. Such data can be used to compare different proteins. Information from SPR can also be used to develop structure-activity relationship (SAR). For example, if the proteins are all mutated variants of a single parental antibody or a set of known parental antibodies, variant amino acids at given positions can be identified that correlate with particular binding parameters, e.g., high affinity and slow $k_{off}$.

Additional methods for measuring binding affinities include nuclear magnetic resonance (NMR), and binding titrations (e.g., using fluorescence energy transfer).

Other solution measures for studying binding properties include fluorescence resonance energy transfer (FRET), NMR, X-ray crystallography, molecular modeling, and measuring bound vs. free molecules. Measurement of bound vs. free molecules can be accomplished with a KinExA instrument from Sapidyne Instruments Inc., Boise, Id.

Characterization of Protease Inhibition

It may be useful to characterize the ability of a protein described herein to inhibit target proteases, as well as non-target proteases.

Kunitz domains can be selected for their potency and selectivity of inhibition of the target proteases. In one example, target protease and a substrate are combined under assay conditions permitting reaction of the protease with its substrate. The assay is performed in the absence of the protein being tested, and in the presence of increasing concentrations of the protein being tested. The concentration of test protein at which the protease activity is 50% inhibited is the $IC_{50}$ value (Inhibitory Concentration) or $EC_{50}$ (Effective Concentration) value for that test protein. Proteins having lower $IC_{50}$ or $EC_{50}$ values are considered more potent inhibitors of the target protease than those proteins having higher $IC_{50}$ or $EC_{50}$ values. Preferred proteins according to this aspect have an $IC_{50}$ value of 100 nM, 10 nM, 1 nM, or 0.1 nM or less as measured in an in vitro assay for inhibition of protease activity.

A test protein can also be evaluated for selectivity toward different protease(s). A test protein is assayed for its potency toward a panel of proteases and other enzymes and an $IC_{50}$ value is determined for each. A protein that demonstrates a low $IC_{50}$ value for the target protease, and a higher $IC_{50}$ value for other proteases within the test panel (e.g., trypsin, plasmin, chymotrypsin), is considered to be selective toward the target protease. Generally, a protein is deemed selective if its $IC_{50}$ value is at least one order of magnitude less than the next smallest $IC_{50}$ value measured in the panel of enzymes.

It is also possible to evaluate Kunitz domain activity in vivo or in samples (e.g., pulmonary lavages or serum) of subjects to which a compound described herein has been administered.

Pharmaceutical Compositions & Treatments

Also featured is a composition, e.g., a pharmaceutically acceptable composition, that includes a protein described herein (e.g., a protein that inhibits at least two human proteases). In one embodiment, the protein includes one or more Kunitz domains. For example, the protein inhibits a plurality of target proteases. The pharmaceutical composition can include a pharmaceutically acceptable carrier.

Exemplary carriers include any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

The pharmaceutical composition can include a pharmaceutically acceptable salt, e.g., a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical composition may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical compositions are in the form of injectable or infusible solutions, such as compositions similar to those used for administration of antibodies to humans. A common mode of administration is parenteral (e.g., intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion). In one embodiment, the compound is administered by intravenous infusion or injection. In another embodiment, the compound is administered by intramuscular or subcutaneous injection. Pharmaceutical compositions typically must be sterile and stable under the conditions of manufacture and storage.

The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The proteins described herein can be administered by a variety of methods known in the art. For many applications, the route/mode of administration is intravenous injection or infusion. For example, for therapeutic applications, the compound can be administered by intravenous infusion at a rate of less than 30, 20, 10, 5, or 1 mg/min to reach a dose of about 1 to 100 mg/m$^2$ or 7 to 25 mg/m$^2$. Alternatively, the dose could be 100 µg/Kg, 500 µg/Kg, 1 mg/Kg, 5 mg/Kg, 10 mg/Kg, or mg/Kg. The route and/or mode of administration will vary depending upon the desired results.

In certain embodiments, the protein is prepared with a carrier that protects against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978. Pharmaceutical formulation is a well-established art, and is further described in Gennaro (ed.), Remington: The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

Also within the scope of the invention are kits comprising a protein described herein (e.g., a protein that inhibits at least two human proteases) and instructions for use, e.g., treatment, prophylactic, or diagnostic use. In one embodiment, the kit includes (a) the compound, e.g., a composition that includes the compound, and, optionally, (b) informational material. The informational material can be descriptive, instructional, marketing or other material that relates to the methods described herein and/or the use of the compound for the methods described herein.

In one embodiment, the informational material can include instructions to administer the compound in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., a human having, or at risk for a disorder characterized by excessive elastase activity. The informational material can include information about production of the compound, molecular weight of the compound, concentration, date of expiration, batch or production site information, and so forth. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the compound and/or its use in the methods described herein. Of course, the informational material can also be provided in any combination of formats.

In addition to the compound, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the compound. In such embodiments, the kit can include instructions for admixing the compound and the other ingredients, or for using the compound together with the other ingredients.

The kit can include one or more containers for the composition containing the compound. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the compound. For example, the kit includes a plurality of syringes, ampules, foil packets, or blister packs, each containing a single unit dose of the compound. The containers of the kits can be air tight, waterproof (e.g., impermeable to changes in moisture or evaporation), and/or light-tight.

A protein described herein (e.g., a protein that inhibits at least two human proteases) can be administered, alone or in combination with, a second agent to a subject, e.g., a patient, e.g., a patient, who has a disorder (e.g., a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. The treatment may also delay onset, e.g., prevent onset, or prevent deterioration of a condition.

A therapeutically effective amount can be administered, typically an amount of the compound which is effective, upon single or multiple dose administration to a subject, in treating a subject, e.g., curing, alleviating, relieving or improving at least one symptom of a disorder in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects. A therapeutically effective dosage preferably modulates a measurable parameter, favorably, relative to untreated subjects. The ability of a compound to inhibit a measurable parameter can be evaluated in an animal model system predictive of efficacy in a human disorder.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

An exemplary, non-limiting range for a therapeutically or prophylactically effective amount of a compound described herein is 0.1-20 mg/Kg, more preferably 1-10 mg/Kg. The compound can be administered by parenteral (e.g., intravenous or subcutaneous) infusion at a rate of less than 20, 10, 5, or 1 mg/min to reach a dose of about 1 to 50 mg/m$^2$ or about 5 to 20 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions (e.g., the supervising physician), and that dosage ranges set forth herein are only exemplary.

Therapeutic Uses

The proteins of the invention may be used in therapies for the treatment or prophylaxis of disorders mediated by two or more proteases. Likewise, the proteins of the invention may be used for the manufacture of a medicament for the treatment of disorders mediated by two or more proteases.

Rheumatoid Arthritis (RA):

Human plasma kallikrein, human tissue kallikrein (h.K1), and human neutrophil elastase have all be implicated in RA (Volpe-Junior, et al., 1996, Inflamm Res, 45:198-202; Cassim, et al., 2002, Pharmacol Ther, 94:1-34; Colman, 1999, Immunopharmacology, 43:103-8; Dela Cadena, et al., 1995, Faseb J, 9:446-52; Rahman, et al., 1995, Ann Rheum Dis, 54:345-50; Tremblay, et al., 2003, Curr Opin Investig Drugs, 4:556-65). Thus, a method of treating rheumatoid arthritis (e.g., stabilizing or improving total Sharp score, the Sharp erosion score, or the HAQ disability index) by administering to a subject having (or suspected of having) RA an effective amount of a protein that inhibits at least two proteases from the group of human plasma kallikrein, human tissue kallikrein (h.K1), and human neutrophil elastase is provided.

MMPs 1, 2, 3, 9, and 13 have also been implicated in RA (Burrage et al. (2006) *Front Biosci.* 11:529-43). Accordingly, also provided is a method of treating RA (e.g., stabilizing or improving total Sharp score, the Sharp erosion score, or the HAQ disability index) by administering an effective amount of a protein which inhibits (a) at least two proteases from the group of human plasma kallikrein, human tissue kallikrein (h.K1), and human neutrophil elastase, (b) at least one protease from the group of MMP-1, MMP-2, MMP-3, MMP-9, and MMP-13.

RA can be assessed by a variety of clinical measures. Some exemplary indicia include the total Sharp score (TSS), Sharp erosion score, and the HAQ disability index. A protein of the invention is administered to treat RA, e.g., to improve an assessment on one or more of these clinical measures.

Pulmonary Disorders:

Lung inflammatory disorders involve a number of different proteases, including human neutrophil elastase, proteinase 3, cathepsin G, tryptase, MMP-12, and MMP-9. Accordingly, the invention provides methods for treatment and/or prophylaxis of pulmonary disorders involving inflammation (e.g., improving or stabilizing PFT scores or slowing, preventing, or reducing a deterioration in PFT scores, or for COPD patients by reducing the destructive index score by at least 10, 20, 30 or 40% or to at least within 50, 40, 30, or 20% of normal destructive index scores for the age- and gender-matched normal population) by administering to a subject having (or suspected of having) a pulmonary disorder involving inflammation an effective amount of a protein which inhibits the activity of two or more (or all) of these proteases. Exemplary pulmonary disorders involving inflammation including asthma, emphysema, cystic fibrosis, and chronic obstructive pulmonary disease (COPD), particularly acute exacerbations of COPD. In particular, human neutrophil elastase, proteinase 3, cathepsin G, and MMP-12 have been associated with COPD, and thus proteins for the treatment of COPD inhibit at least two proteases from the group: human neutrophil elastase, proteinase 3, and cathepsin G, and, in some embodiments additionally inhibit MMP-9 and/or MMP-12.

A variety of clinical measures are available to assess pulmonary diseases and the efficacy of treatment thereof. Pulmonary function tests (PFT) such as forced expiratory volume in one second (FEV), forced expiratory volume in six second (FEV), forced vital capacity (FVC), peak expiratory flow, the ratio of FEV1 to FVC, expressed as a percentage ($FEV_1/FVC$), the forced expiratory flow less the average forced expiratory flow during the mid (25-75%) portion of the FVC ($FEF_{25-75}$), and thin section computed tomography may be used to assess pulmonary diseases and the efficacy of treatment. The "destructive index," which is a measure of alveolar septal damage and emphysema, may be particularly useful in monitoring COPD and the therapeutic effect of the proteins and methods herein. See, e.g., Am Rev Respir Dis 1991 July; 144(1):156-59.

Multiple Sclerosis:

Multiple sclerosis (MS) may involve human kallikrein 6 (hK6), human kallikrein 8 (hK8), and human kallikrein 10 (hK10). Accordingly, the invention provides methods of treating multiple sclerosis (e.g., reducing or stabilizing EDSS score, reducing the intensity or frequency of exacerbations, or reducing the size, number, or rate of increase in size or number or sclerotic lesions) by administering to a subject having (or suspected of having) MS an effective amount of a protein that inhibits two or more (e.g., all three) of these proteases. Patients having MS may be identified by criteria recognized in the medical arts as establishing a diagnosis of clinically definite MS, such as the criteria defined by the workshop on the diagnosis of MS (Poser et al., Ann. Neurol. 13:227, 1983).

Efficacy of the treatment of multiple sclerosis may be examined using any method or criteria recognized in the art. Three commonly used criteria are: EDSS (extended disability status scale, Kurtzke, Neurology 33:1444, 1983), appearance of exacerbations or MRI (magnetic resonance imaging).

Spinal Cord Injury:

Spinal chord injury may be exacerbated by hK6, human neutrophil elastase, and other serine proteases. Accordingly, the invention provides methods of treating spinal cord injury (e.g., improving gross or fine motor skills, increasing the activities of daily living (ADLs) which can be performed by the patient, improvement in reflex responses, or improvement in complex locomotion behavior) by administering to a subject with a spinal cord injury an effective amount of a protein that inhibits at least the two serine proteases hK6 and human neutrophil elastase.

Behavioural assessments often fail to define the exact nature of motor deficits or to evaluate the return of motor behaviour following spinal cord injury. In addition to the assessment of gross motor behaviour, it is appropriate to use complex tests for locomotion to evaluate the masked deficits in the evaluation of functional recovery after spinal cord injury. Suresh et al. have designed sensitive quantitative tests for reflex responses and complex locomotor behaviour as a combined behavioural score (CBS) to assess the recovery of function in the Bonnet monkey (*Macaca radiata*) (J Neurol Sci. (2000) 178(2):136-52.). Since these measurements are non-invasive, they may be adapted for use on human patients.

Inflammatory Bowel Disease:

Inflammatory bowel diseases (IBD) include two distinct disorders, Crohn's disease and ulcerative colitis (UC). Ulcerative colitis occurs in the large intestine, while in Crohn's, the disease can involve the entire GI tract as well as the small and large intestines. For most patients, IBD is a chronic condition with symptoms, which include intermittent rectal bleeding, crampy abdominal pain, weight loss and diarrhea, lasting for months to years. Human tissue kallikrein (h.K1), human plasma kallikrein and human neutrophil elastase have been implicated in both Crohn's disease and ulcerative colitis (Colman, 1999, Immunopharmacology, 43:103-8; Devani et al., (2005) Dig. Liver Dis. 37(9):665-73; Kuno et al., (2002) J. Gastroenterol. 37(Suppl 14):22-32; Stadnicki et al., (1997) Dig. Dis. Sci. 42(11):2356-66). Accordingly, the invention also provides methods of treatment and/or prophylaxis of Crohn's disease and/or ulcerative colitis (e.g., reducing or eliminated rectal bleeding, abdominal pain/cramping, weight loss, or diarrhea, improving hematocrit/eliminating improving anemia, or improving Clinical Activity Index for Ulcerative Colitis scores in UC patients) by administering to a subject an effective amount of a protein which inhibits at least two (or all three) of human tissue kallikrein (h.K1), human plasma kallikrein and human neutrophil elastase. The subject has, is suspected of having, or is at risk of developing an IBD.

Many of the symptoms of IBD (e.g., rectal bleeding, abdominal pain/cramping, diarrhea, weight loss, hematocrit/anemia) can be quantitated using standard methodologies. Additionally, a clinical index such as the Clinical Activity Index for Ulcerative Colitis may be used to monitor IBD. (see also, e.g., Walmsley et al. *Gut.* 1998 July; 43(1):29-32 and Jowett et al. (2003) Scand J Gastroenterol. 38(2):164-71).

Pancreatitis

Acute pancreatitis is characterized by sudden intrapancreatic activation of pancreatic zymogens, resulting in an essentially autolytic destruction of the pancreas if unchecked. The major enzymes involved are human trypsins 1 and 2, human pancreatic chymotrypsin, and human pancreatic elastase. Accordingly, the invention provides a method for the treatment of acute pancreatitis (e.g., stabilizing or improving Ranson score, Acute Physiology and Chronic Health Evaluation (APACHE II) score, or Balthazar computed tomography severity index (CTSI)) by administering to a subject having (or suspected of having) acute pancreatitis a protein which inhibits at least two of the proteases human trypsin 1, human trypsin 2, human pancreatic chymotrypsin, and human pancreatic elastase.

Cancer

A number of serine proteases are involved in cancer and tumorigenic pathways. Hepsin and matriptase are involved in the activation of hepatocyte growth factor. Hepatocyte growth factor (HGF) is a growth factor for many tumors and blocking its release will deprive the tumor cells of a needed growth factor. In addition, matriptase can also cleave pro-uPA into uPA, the enzyme responsible for the generation of plasmin from plasminogen. Plasmin is implicated in the activation of various matrix metalloproteinases (MMPs). Upon conversion from plasminogen to active plasmin, plasmin remains associated with the surface of a variety of epithelial cancer cells. MMP activity is important in cleaving a variety of matrix proteins that allow cancer cells to escape from one site or to invade at new sites. In addition, matriptase can also cleave pro-uPA into uPA, the enzyme responsible for the generation of plasmin from plasminogen. Endotheliases 1 and 2 have also been implicated in cancer.

Accordingly, the disclosure provides methods of treating (e.g., slowing, eliminating, or reversing tumor growth, preventing or reducing, either in number or size, metastases, reducing or eliminating tumor cell invasiveness, providing an increased interval to tumor progression, or increasing disease-free survival time) cancer (e.g., breast cancer, including Her2+, Her2−, ER+, ER−, Her2+/ER+, Her2+/ER−, Her2−/ER+, and Her2−/ER− breast cancer), head and neck cancer, oral cavity cancer, laryngeal cancer, chondrosarcoma, ovarian cancer, testicular carcinoma, melanoma, brain tumors (e.g., astrocytomas, glioblastomas, gliomas)) by administering an effective amount of an engineered multi-Kunitz domain protein of the invention that inhibits at least two proteases involved in cancer, for example at least two proteases from the group of human plasmin, human hepsin, human matriptase, human endotheliase 1, and human endotheliase 2.

The disclosed methods are useful in the prevention and treatment of solid tumors, soft tissue tumors, and metastases thereof. Solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Metastases of the aforementioned cancers can also be treated or prevented in accordance with the methods described herein.

EXAMPLES

Example 1

Expression of TFPI in Eukaryotic Cells

Table 1 shows the amino acid sequence of LACI (also known as tissue-factor pathway inhibitor (TFPI)). Table 2 shows the amino acid sequence of the different Kunitz domains within LACI. The positions marked with "|" (11, 13, 15-19, 34, 39-40) are examples of residues that can be varied to change the protease specificity of the domain. Positions marked with "^" (21 and 32) may also be varied.

The positions marked "$" can contribute to the structure of the Kunitz domain. In some implementations, these positions are kept invariant. In other implementations, they are varied, but to a limited degree, e.g., to allow for conservative substitutions.

LACI contains three potential N-linked glycosylation (Nx (S/T)) sites. The Asn (N) residues are shown bold and underscored in Table 1. In Kunitz domain2, N25 (numbering from the beginning of the domain) is a potential glycosylation site. This position is distant from the residues that contact serine proteases and glycosylation at this site is unlikely to interfere with protease binding or inhibition. Glycosylatioin of a second Asn in Linker 3 is also unlikely to affect activity. The third potential site in Kunitz domain 3 is distant from the binding site and glycosylation at this site will not prevent binding to or inhibition of a protease.

Table 3 shows the cDNA that encodes TFPI. The DNA encoding the putative signal sequence runs from base 133 to base 216 (underlined). Table 32 shows the cDNA for rabbit TFPI. There a shorter signal sequence is identified. The mature protein is encoded by bases 217-1044. Table 4 shows the annotated DNA sequence of a vector, pFTFPI_V1, having a modified sequence of TFPI that it would be expressed in CHO or HEK293T cells. The modifications provide restriction sites so that parts of TFPI can be readily altered. Other vectors and other signal sequences can be used. The DNA sequence has been modified to introduce a number of restriction sites so that parts of TFPI can be removed or modified easily. Altered bases are shown as uppercase, bold, or underscored. On each line of Table 4, every character that follows an exclamation point (!) is a comment. The naked DNA sequence in this table and other tables of similar appearance can be recovered by dropping the exclamation points and all characters that follow them on that line.

The DNA sequence in Table 4 can be constructed using the human TFPI cDNA and the oligonucleotides in Table 15. First the cDNA is used as template and ONMatureT and ON1019L27 are used to amplify the coding region, a 829 base segment. This DNA can be used as a template for ten PCR reactions that use primers 1: (ONSfiT, ONSacHinL), 2: (ONSacHinU, ONMluIL), 3: (ONMluIU, ONBBBL), 4: (ONBBBU, ONXhoBamL), 5: (ONXhoBamU, ONBsmBIL), 6: (ONBsmBIU, ONApaSalL), 7: (ONApaSalU, ONSac2L), 8: (ONSac2U, ONBspE2L), 9: (ONBspE2U, ONBssH2L), and 10: (ONBssH2U, ONfinalL). The ten products (which have 20 or more bases of overlap with one other product) are mixed and amplified with the primers ONSfiT and ONfinalL to produce a 874 base product. This nucleic acid is cut with SfiI and XbaI and ligated to a similarly cut expression vector.

Example 2

A TFPI Derivative that Inhibits h.pKal and Human Neutrophil Elastase

Human neutrophil elastase and human plasma kallikrein may both be involved in the inflammatory response associated with coronary by-pass surgery (CBPS). Thus a protein that inhibits both human neutrophil elastase and human plasma kallikrein may have synergistic beneficial effects when used for treating patients, e.g., before, during or after coronary by-pass surgery.

An inhibitor that is highly potent and specific for each of human plasma kallikrein (h.pKal) and human neutrophil elastase is encoded by the gene displayed in Table 9. Altered amino acids are shown bold and mutated bases are shown bold and uppercase. Restriction sites are shown bold. Any other signal sequence functional in eukaryotic cells could be used. This protein is named TF88890. This gene can be expressed in the same vector as was used for full-length TFPI shown in Table 4 or in any suitable expression vector. One cuts the expression vector with SfiI and XbaI and ligates the DNA shown in Table 9 to the digested vector DNA. Table 10 shows the oligonucleotides that can be used to make changes in TFPI Kunitz domain 1 and Kunitz domain 2. The procedure is as follows.

PCR of pFTFPI_V1 with ON1U23 and ON718L21 gives a 522 base product, PNK1, comprising the mature sequence up to S174. Using PNK1 as template, ON1U23 and ONK1Bot give a 141 base product, PNK2, that includes changes around residues 13-20 of TFPI Kunitz domain1. Within Kunitz domain 1, the changes are K15R, R17A, I18H, I19P, and F21W. PCR of PNK1 with ONK1T and ONK2B1 gives a 265 base product, PNK3, that overlaps the first product by 57 bases. This PCR introduces changes into Kunitz domain 2: I13P, R15I, G16A, Y17F, I18F, T19P, and Y21W. PCR of PNK1 with ONK2T1 and ONK2B2 give PNK4 of length 104 which comprises an overlap of 51 bases with PNK3 and the changes in TFPI Kunitz domain2. This introduces the changes R32L, K34P, and L39Q. PCR of PNK1 with ONK2T2 and ON718L21 give PNK5 with length 165. Mix PNK2, PNK3, PNK4, and PNK5 and use ONSfiTop and BotAmp to amplify a 573 base fragment. Cut the final PCR product with SfiI and XbaI and ligate to similarly cleaved expression vector. The new vector is called pFTFPI_V2.

The molecule encoded by pFTFPI_V2, TF88890, has the following expected characteristics. The first Kunitz domain will inhibit human plasma kallikrein and the second Kunitz domain will inhibit human neutrophil elastase (hNE). The mature protein should be 174 amino acids and may be glycosylated at N117 and N167. N117 is at position 26 in Kunitz domain 2. This site is located on a different side of the protein from the protease binding site, and, accordingly, is not expected to interfere with protease binding. The N167 is in Linker 3 and is not expected to interfere with inhibition of hNE. The protein is terminated at S174. MMP-8 and MMP12 cleave wildtype TFPI at this site. Thus, the presence of a protein ending with this sequence is less likely to cause an immune response because just such a peptide results from MMP-8 or MMP12 cleavage of wildtype TFPI. The expected molecular weight of TF88890 is 19 KDa plus the glycosylation. TF88890 is not expected to bind cell surfaces unlike TFPI because the region of TFPI implicated in cell-surface binding is absent. The molecular mass of TF88890 is approximately 14 KDa and would have a short residence in serum. A short residency may be useful for treating patients undergoing coronary bypass surgery. However, increased residency time can be engineered, e.g., by attaching one or more polymer moieties (e.g., PEG moieties).

Alternative designs for TF88890 are shown below in Tables 20-25. An additional alternative design is to use the sequence shown in Table 9 wi bases 508-579 deleted. This construct would be TF88890S and would comprise 150 amino acids with two potential N-linked sites of glycosylation. TF88890S would inhibit human plasma kallikrein and human neutrophil elastase. The sequences in these tables are exemplary mature amino acid sequences. To produce a protein including these sequence by secretion, a suitable signal sequence can be added for expression in eukaryotic cells (such as mammalian (e.g., CHO or HEK293T) or yeast cells (e.g., *Pichia pastoris*), or bacterial cells (such as *E. coli* or *Caulobacter crescentus*).

The protein can be designed so that it does not include more than two glycosylation sites, e.g., the protein can be devoid of N-linked glycosylation sites.

Kunitz domains can be joined with a linker, e.g., a hydrophilic, flexible linker (e.g., by the linker: GGSGGSSSSSG (SEQ ID NO:147)). Linkers that lack T-cell epitopes are particularly useful. All ligands for MHC molecules contain at least one or two amino-acid types picked from: (a) medium to large hydrophobic (VILMFWY (SEQ ID NO:148)), or (b) charged (EDRKH (SEQ ID NO:149)). Accordingly, linkers (e.g., of twelve amino acids) that do not contain any of these amino acids avoids creation of an MHC-I neo-epitope, including epitopes that may arise from juxtaposition of residues from adjoining Kunitz domains. Where more than one linker is used (e.g., for a protein with at least three Kunitz domains), the linkers between the Kunitz domains could be different.

For example, TF88890-2 is an alternative to the design of TF88890 and is shown in Table 20. TF88890-2 contains two copies of TFPI-Kunitz domain 1, the first modified to make it into an inhibitor of human plasma kallikrein (h.pKal) and the second modified to make it an inhibitor of human neutrophil elastase.

The amino acid sequence of mature TF88890-3 is shown in Table 21. TF88890-3 contains three copies of TFPI-Kunitz domain 1, the first and third modified to make it into an inhibitor of human plasma kallikrein and the second modified to make it an inhibitor of human neutrophil elastase. The instances of TFPI-Kunitz domain 1 are joined by hydrophilic, flexible linkers (GGSGGSSSSSG (SEQ ID NO:147)) which is not expected to provide any T-cell epitope. The first or third Kunitz domain could be modified to inhibit a different protease, giving a tri-specific inhibitor. The increased molecular mass is expected to increase the residence time in serum.

The amino acid sequence of mature TF88890-4 is shown in Table 22. TF88890-4 contains four copies of TFPI-Kunitz domain 1, the first and third modified to make it into an inhibitor of h.pKal and the second and third modified to make it an inhibitor of human neutrophil elastase. The instances of TFPI-Kunitz domain 1 are joined by hydrophilic, flexible linkers (GGSGGSSSSSG) (SEQ ID NO:147) which is not expected to provide any T-cell epitope. The linkers need not all be the same. One could have all four Kunitz domains directed to different proteases.

The amino acid sequence of mature TF88890-5 is shown in Table 23. TF88890-5 contains four copies of TFPI-Kunitz domain 1, the first and third modified to make it into an inhibitor of h.pKal and the second and third modified to make it an inhibitor of human neutrophil elastase. The instances of TFPI-Kunitz domain 1 are joined by hydrophilic, flexible linkers (GGSGNGSSSSGGSGSG (SEQ ID NO:150)) which is not expected to provide any T-cell epitope. The linkers shown each contain an N-linked glycosylation site (NGS). If produced in eukaryotic cells, TF88890-5 should carry glycosylation at three sites which should increase solubility and serum residence time. The linkers need not all be the same. One could have all four Kunitz domains directed to different proteases.

Example 3

An Inhibitor of Human Plasmin, h.pKal, and Human Neutrophil Elastase Based on TFPI Table 16 shows the amino acid sequence of a protein derived from human TFPI and named PlaKalEl01. The sequence KGGLIKTKRKRKKQRVKIAYEEIFVKNM (SEQ ID NO:151) is deleted from the C-terminus of w.t. TFPI; this sequence is involved with binding to cells and the effects that TFPI has on gene expression. Removal of the sequence and changes in Kunitz domain 3 provides a protein that neither binds cells nor modulates cellular gene expression. In Kunitz domain 1, we have changed residue 15 of Kunitz domain 1 from Lys to Arg. At residue 17, we have changed Ile to Arg. At residue 18, Met is changed to Phe. At residue 19, we change Lys to Asp. At residue 21 we change Phe to Trp. These changes produce a Kunitz domain identical to DX-1000, a potent inhibitor of human plasmin.

In Kunitz domain2 we make the following changes (all denoted by position within the Kunitz domain): I13P, G16A, Y17A, I18H, T19P, Y21W, K34I, and L38E. These changes make a Kunitz domain that is very similar to DX-88 in the part of the Kunitz domain that contacts human plasma kallikrein. This domain is highly likely to be a potent and specific inhibitor of human plasma kallikrein.

In Kunitz domain 3, we make the following changes: L13P, R15I, N17F, E18F, N19P, K34P, S36G, G39Q. Thus, Kunitz domain is very similar to DX-890 which is a highly specific inhibitor of human neutrophil elastase. As reported by Piro and Broze (Circulation 2004, 110:3567-72.), removal of the highly basic C-terminal tail greatly reduces binding to cells. Piro and Broze also reported that changing R15 of Kunitz domain 3 to Leu greatly reduced cell binding.

A gene encoding PlaKalEl01 can be constructed as follows. Oligonucleotides shown in Table 17 are used as primers with the cDNA of human TFPI (shown in Table 3). The oligonucleotides Get_TFPI_top and ON937L24 are first used to amplify the coding sequence from codon 1 to codon 276, thus truncating the 3' terminal codons. The 828 base product is called PKE_P1 and is used as template for six PCR reactions: a) Get_TFPI_top and MutK1:310L43 make PKE_P2 (220 bases), b) MutK1:310U43 and MutK2:517L56 make PKF_P3 (263 bases), c) MutK2:517U56 and MutK2:577L47 make PKF_P4 (107 bases), d) MutK2:577U47 and MutK3:792L55 make PKF_P5 (270 bases), e) MutK3:792U55 and MutK3:867L31 make PKF_P6 (106 bases), and f) MutK3:867U31 and ONLowCapPKE make PKE_P7 (114 bases). PKE_P2 through PKE_P7 are mixed and PCR amplified with primers ONLowCapPKE and ONNcoI to give a 861 base product having NcoI and XbaI sites at the ends. This fragment is cut with SfiI and XbaI and ligated to similarly cleaved expression vector having an expression cassette as shown in Table 9 (e.g., pFcFuse) for expression in eukaryotic cells.

Example 4

A Modification of PlaKalEl01 that is Resistant to Cleavage by MMPs

Known substrates for MMP-8 are shown in Table 42. The preference for P at P3, G at P1, and I or L at P1' should be noted. Known substrates for MMP-12 are shown in Table 43.

TABLE 42

Substrates of MMP-8 (From MEROPS(http://merops.sanger.ac.uk/))

| Substrate | P4 | P3 | P2 | P1 | P1' | P2' | P3' | P4' | Ref | SEQ ID NO: |
|---|---|---|---|---|---|---|---|---|---|---|
| 1 | G772 | P | Q | G | I | A | G | Q | 1 | 152 |
| 2 | Dpn | P | Q | G | I | Q | G | | 1 | 153 |
| 3 | Dpn | P | L | G | L | W | A | Dr | 1 | 154 |
| 4 | G | P | Q | G | I | W | G | Q | 1 | 155 |
| 5 | Mca | P | L | G | L | Dpa | A | R | 1 | 156 |

Substrates: 1: collagen alpha 1(I) chain (*Homo sapiens*); cleavage after G775.
2: Dnp-P-Q-G-|-I-A-G-Q-dR-OH (SEQ ID NO: 201)
3: Dnp-P-L-G-|-L-W-A-dR-NH2 (SEQ ID NO: 154)
4: G-P-Q-G-|-I-W-G-Q (SEQ ID NO: 155)
5: Mca-P-L-G-|-L-Dpa-A-R-NH2 (SEQ ID NO: 156)
Ref 1 = Tschesche, H., Pieper, M. & Wenzel, H. Neutrophil collagenase. In *Handbook of Proteolytic Enzymes*, 2 edn (Barrett, A. J., Rawlings, N. D. & Woessner, J. F. eds), p. 480-486, Elsevier, London (2004)

TABLE 43

Some known substrate cleavages for MMP-12

| Substrate | P4 | P3 | P2 | P1 | P1' | P2' | P3' | P4' | SEQ ID NO: |
|---|---|---|---|---|---|---|---|---|---|
| 1 | R | P | F | Q | V | K | D | T | 157 |
| 2 | G | A | M | F | L | E | A | I | 158 |
| 3 | E | A | I | P | M | S | I | P | 159 |
| 4 | L | V | E | A | L | Y | L | V | 160 |
| 5 | E | A | L | Y | L | V | C | G | 161 |

Substrates
1: alpha1-proteinase inhibitor (*Homo sapiens*)
2: alpha1-proteinase inhibitor
3: alpha1-proteinase inhibitor
4: insulin B chain (oxidized)
5: insulin B chain (oxidized)
Reference for all: Shapiro, S. D., Hartzell, W. O. & Senior, R. M. Macrophage elastase. In Handbook of Proteolytic Enzymes, 2 edn (Barrett, A. J., Rawlings, N. D. & Woessner, J. F. eds), p. 540-544, Elsevier, London (2004)

Table 30 shows the amino acid sequence of PlaKalEl02. This protein differs from PlaKalEl01 in that codon 49 is changed from a codon encoding Leu to a codon encoding Pro, codon 112 is changed from a codon encoding Ile to a codon encoding Pro, and codon 203 is changed from a codon encoding Thr to a codon encoding Pro to prevent cleavage by MMP-8 or MMP-12. Many proteases have difficulty cleaving before Pro and none of the known substrates of MMP-8 or MMP-12 have Pro at the P1' position.

Example 5

Half Life, Metalloproteinases, and Cysteine Proteases

The half-life of a protein (by way of example, the protein PlaKalEl01) may be extended by methods including: 1) PEGylation, 2) fusion to Fc (e.g., the Fc domain of an IgG) at either the amino or carboxy terminus of Fc (e.g., as PlaKalEl01::Fc or Fc::PlaKalEl01), 3) fusion to human serum albumin (or a fragment thereof) at the amino or carboxy terminus (e.g., as PlaKalEl01::hSA or hSA::PlaKalEl01, or 4) making multimers of the protein until the molecular mass is large enough to give an acceptable half-life.

Table 18 shows the amino acid sequence of a PlaKalEl::GGSGGSGGSGGSGG (SEQ ID NO:162)::hSA fusion protein. Although the molecules are large, the half life is very likely to be on the order of weeks, similar to IgGs or hSA.

A PlaKalEl01 dimer is shown in Table 19. After Linker 5, a 13 amino acid glycine-rich hydrophilic linker avoiding known antigenic sequences is inserted. This is followed by another copy of the mature PlaKalEl01 sequence. The resulting protein has a 509 mature amino acid sequence, PKEPKE02. The increased molecular mass is expected to give the molecule a much longer half-life than PlaKalEl01. PKEPKE02 and related proteins are expected to have molecular masses in excess of 60 kDa and may have half lives of several days.

PKEPKE02 has two inhibitory sites for each of human plasmin, h.pKal, and human neutrophil elastase. The Kunitz domains of this protein may be further engineered to create a protein that specifically inhibits up to six different serine proteases. Additionally, the protein may be modified by fusion with one or more short peptide sequences that inhibit: a) other serine protease, b) metalloproteinases, or c) cysteine proteinases.

A gene encoding PKEPKE02 is inserted after a functional signal sequence in a vector suitable for expression in mammalian cells or yeast, e.g., secretory expression. For example, a DNA sequence encoding PKEPKE02 is inserted between the SfiI and XbaI sites of an mixed and the short oligonucleotides are used as primers to generate DNA that extends from NcoI to XbaI. The PCR product is cleaved with NcoI and XbaI and is ligated to a version of DY3P82 containing TFPI Kunitz domain 1 or a derivative thereof having NcoI and XbaI sites. Table 29 contains the annotated sequence of DY3P82TFPI1, a phage vector that displays TFPI Kunitz domain1 on the stump of M13 III. DY3P82TFPI1 has a wildtype M13 iii gene and a display gene regulated by $P_{Lac}$ so that a) expression of the display can be suppressed with glucose and induced with IPTG, and b) most phage display one or fewer Kunitz domain::III stump proteins. This allows distinguishing very good binders from merely adequate binders. We select binders to human neutrophil elastase from the library of phage. Since DX-890 binds human neutrophil elastase with $K_D$ of about 3 pM, very stringent washes are used. In addition, DX-890 may be used as an eluting agent.

It is expected that Kunitz domains that lack the 14-38 disulfide and that inhibit target proteases can be selected. Once an amino acid sequence is determined that gives high-affinity binding and inhibition of human neutrophil elastase, one can construct a library of multimers as given in Example 5. This approach can be applied to any Kunitz domain and to any target protease, and to plural target proteases. For example, if human plasma kallikrein is the target, it is possible to vary the sequence of DX-88 at positions 12, 13, 14, 38, and 39 excluding only Cys from the varied amino acids.

Example 7

A Derivative of Rabbit TFPI for PK and Immunogenicity Studies

Table 32 shows the amino acid sequence of rabbit TFPI. Table 33 shows the cDNA of rabbit TFPI. Table 34 shows RaTFPKE01, an engineered derivative of rabbit TFPI. In Kunitz domain 1, the mutations are Y17R, I18F, K19D, and F21W which are designed to confer human plasmin inhibitory activity on Kunitz domain 1. In Kunitz domain 2, the mutations are I13P, G16A, Y17A, I18H, T19P, and L39E which are designed to confer inhibition of h.pKal on Kunitz domain 2. In Kunitz domain 3, the mutations are L13P, Q15I, N17F, E18F, I19P, S36G, and G39Q which are designed to confer human neutrophil elastase inhibition on Kunitz domain 3. The C-terminal basic peptide has been truncated. This protein can be produced in CHO cells in the same manner as PlaKalEl01. The protein should have a molecular mass of about 30 KDa plus glycosylation. There are six possible Nx(S/T) sites but one is NPT and is unlikely to be glycosylated. Because we have altered the third Kunitz domain and removed the lysine-rich C-terminal peptide, RaTFPKE01 should have reasonable half-life and should not bind to cells.

Table 36 shows a gene that encodes RaTFPKE01. The sequence is arranged to show: a) signal sequence, b) first linker from rabbit TFPI, c) Kunitz domain 1 with cysteine codons underlined and mutations shown uppercase bold, d) the second linker, e) Kunitz domain 2, f) third linker, g) Kunitz domain 3, and g) final linker. Table 37 shows oligonucleotides that can be used to construct the gene of Table 36 from rabbit TFPI cDNA. One first uses rabbit TFPI cDNA and ONrSfi and TruncLo to produce a 776 base product, PrTF1. PrTF1 is used as a template with ONrSfi and ONrK1Bot to produce PrTF2, a 162 base oligonucleotide. PrTF1 is used as a template with ONrK1Top and ONrK2Bot1 to produce PrTF3, a 239 base oligonucleotide. PrTF1 is used as a template with ONrK2To1 and ONrK2B2 to produce PrTF4, a 103 base oligonucleotide. PrTF1 is used as a template with ONrK2T2 and ONrK3B1 to produce PrTF5, a 236 base oligonucleotide. PrTF1 is used as a template with ONrK3T1 and ONrK3B2 to produce PrTF6, a 99 base oligonucleotide. PrTF1 is used as a template with ONrK3T2 and ONrXbaIL to produce PrTF7, a 117 base oligonucleotide. PrTF2-7 are mixed and ONrSfi and ONrXbaIL are used as primers to produce PrTF8, a 790 base oligonucleotide which is cut with SfiI and XbaI and ligated to a similarly cut expression vector.

Table 40 shows the amino acid sequence of mature RaTFPKE04, a derivative of rabbit TFPI. RaTFPKE04 has all of the mutations of RaTFPKE01 and has C14G and C38V in each of the Kunitz domains. The purpose is to make a protein that is less likely to aggregate than RaTFPKE01 might be.

Table 35 shows the amino acid sequence of RaTFPKE02, a 509 AA protein formed by joining two copies of mature RaTFPKE01 with a linker=GGSGSSGSGGSGSSG (SEQ ID NO:163). The mature protein should have molecular mass of about 56 Kda plus glycosylation. RaTFPKE02 should have a long half-like in rabbits and should not be immunogenic. Table 41 shows the amino acid sequence of mature RaTFPKE05. RaTFPKE05 is similar to RaTFPKE02 but in each Kunitz domain, C14 is changed to G and C38 is changed to V. RaTFPKE05 is less likely to aggregate than is RaTFPKE02.

Example 8

An Inhibitor for hNE, hPr3, and hGatG

Neutrophils release three serine proteases when activated: neutrophil elastase (hNE, also known as leukocyte elastase), proteinase 3 (Pr3), and cathepsin G (CatG). To block the damage caused by excessive neutrophil activation, one can use an agent that inhibits two or more of these proteases, e.g., all three proteases, each with high affinity and specificity. Kunitz-domain that inhibit human neutrophil elastase are known. Inhibitors of CatG can be obtained by selection from a library of Kunitz domains (U.S. Pat. No. 5,571,698). Inhibitors to PR3 could be obtained from a Kunitz domain library in a similar manner.

In one embodiment, the amino acid resides that confer Pr3 inhibitory activity can then be transferred to another Kunitz domain, e.g., a Kunitz domain of a multi-domain protein, e.g., a protein that includes three Kunitz domains. The amino acid residues that confer CatG inhibitory activity can likewise be transferred to another Kunitz domain of the protein. The amino acid residues that confer hNE inhibitory activity can be transferred to the third domain.

In another embodiment, Kunitz domains that inhibit neutrophil elastase, proteinase 3, and cathepsin G are physically associated with each other, e.g., by forming a fusion protein that includes the different Kunitz domains.

In some embodiments, the engineered protein does not bind to cells and can have one or more of the following attributes (e.g., two, three or four of the following): (a) ability to function in the presence of neutrophil defensins, (b) ability to resist degradation by MT6-MMP (Leukolysin), (c) ability to inhibit proteases bound to anionic surfaces, (d) ability to reduce production of IL-8 from neutrophils and TNFα and IL-1β from monocytes.

Example 9

Pharmacokinetics in Animals

The following methods can be used to evaluate the pharmacokinetics (PK) of proteins such as proteins that include Kunitz domains in animals, e.g., mice and rabbits.

The protein to be tested is labeled with iodine ($^{125}$I) using the iodogen method (Pierce). The reaction tube is rinsed with reaction buffer (25 mM Tris, 0.4 M NaCl, pH 7.5). The tube is emptied and then replaced with 0.1 ml of reaction buffer and 12 μL of carrier free iodine-126, about 1.6 mCi. After six minutes, the activated iodine is transferred to a tube containing the protein to be tested. After nine minutes, the reaction is terminated with 25 μL of saturated tyrosine solution. The reaction can be purified on a 5 ml D-salt polyacrylamide 6000 column in Tris/NaCl. HSA can be used to minimize sticking to the gel.

A sufficient number of mice (about 36) are obtained. The weight of each animal is recorded. In the case of mice, the animals are injected in the tail vein with about 5 μg of the protein to be tested. Samples are recovered at each time point per animal, with four animals per time point, at approximately 0, 7, 15, 30, and 90 minutes, 4 hours, 8 hours, 16 hours, and 24 hours post injection. Samples (about 0.5 ml) are collected into anti-coagulant (0.02 ml EDTA). Cells are spun down and separated from plasma/serum. Samples can be analyzed by radiation counting and SEC peptide column on HPLC with inline radiation detection.

For rabbits, the material is injected into the ear vein. Samples can be collected at 0, 7, 15, 30, 90 minutes, 4, 8, 16, 24, 48, 72, 96, 120, and 144 hours post-injection. Samples can be collected and analyzed as for mice.

Data can be fit to a bi-exponential (equation 1) or a tri-exponential (equation 2) decay curve describing "fast", "slow", and "slowest" phases of in vivo clearance:

$$y = A\exp(-\alpha t) + B\exp(-\beta t) \quad \text{Equation 1}$$

$$y = A\exp(-\alpha t) + B\exp(-\beta t) + C\exp(-\gamma t) \quad \text{Equation 2}$$

Where:
y=Amount of label remaining in plasma at time=t post-administration
A=Total label in "fast" clearance phase
B=Total label in "slow" clearance phase
C=Total label in "slowest" clearance phase
α="Fast" clearance phase decay constant
β="Slow" clearance phase decay constant
γ="Slowest" clearance phase decay constant
t=Time post administration The α, β, and γ phase decay constants can be converted to half-lives for their respective phases as:

$$\alpha \text{ Phase Half-life} = 0.69(1/\alpha)$$

$$\beta \text{ Phase Half-life} = 0.69(1/\beta)$$

$$\gamma \text{ Phase Half-life} = 0.69(1/\gamma)$$

In the case where the data are fit using the bi-exponential equation, the percentages of the total label cleared from in vivo circulation through the α and β phases are calculated as:

$$\% \alpha \text{ Phase} = [A/(A+B)] \times 100$$

$$\% \beta \text{ Phase} = [B/(A+B)] \times 100$$

In the case where the data are fit using the tri-exponential equation, the percentages of the total label cleared from in vivo circulation through the α and β phases are calculated as:

$$\% \alpha \text{ Phase} = [A/(A+B+C)] \times 100$$

$$\% \beta \text{ Phase} = [B/(A+B+C)] \times 100$$

$$\% \gamma \text{ Phase} = [C/(A+B+C)] \times 100$$

Example 10

A Gene that Encodes TIFP Minus the Positively Charged C-Terminal Region

Table 50 shows a gene that has been optimized for expression in CHO cells and which encodes hTFPImC1. hTFPImC1 comprises: a) a signal sequence, b) a short linker to foster cleavage by signal peptidase, c) a six-his tag to facilitate purification of the encoded multi-KuDom protein, d) a thrombin cleavage site, e) codons corresponding to TFPI 2-270. This gene can be expressed in mammalian cells, such as CHO cells. Codons 271-304 have been eliminated. Residues 271-304 are involved with causing TFPI to bind to cell surfaces, to be internalized, and to alter gene expression. These effects are unwanted in a therapeutic protease inhibitor. hTFPImC1 can be purified on a copper-chelating resin via the His6 tag. The His tag is removable by treatment with thrombin, which should cleave after R38.

Table 53 shows the DNA of a vector that contains the gene of Table 50 so that it can be expressed in eukaryotic cells. Table 56 shows the amino-acid sequence of hTFPImC1, The Asn residues where N-linked glycosylation is expected are shown as bold N with a "*" above.

hTFPImC1 was expressed in HEK293T cells transformed with the vector shown in Table 53. The protein was purified by affinity chromatography, and a sample was analyzed by gel chromatography, which showed an apparent molecular mass of ~42.5 kDa.

Cell surface binding of hTFPImC1 was tested by flow cytometry, which showed no detectable (above background) cell surface binding.

Example 11

A Modified TFPI, hTFPI[PpKhNE]

Table 51 shows an annotated gene for hTFPI[PpKhNE]. hTFPI[PpKhNE] has the first KuDom of TFPI modified so that it will inhibit human plasmin (hPla), the second KuDom modified so that it will inhibit human plasma kallikrein (h.pKal), and the third KuDom modified so that it will inhibit human neutrophil elastase (hNE). To achieve these specificities, the following mutations have been made. In the first KuDom, we made the mutations K15R, I17R, M18F, K19D, and F21W to confer anti plasmin activity. In the second KuDom, we made the mutations I13P, G16A, Y17A, I18H, T19P, Y21W, K34I, and L39E to confer anti plasma kallikrein activity. In the third KuDom, we made the mutations L13P, R15I, N17F, E18F, N19P, K34P, S36G, and G39Q to confer anti human neutrophil elastase activity. Table 54 shows the DNA sequence of a vector that allows expression of the gene shown in Table 51 in eukaryotic cells such as CHO cells. Table 57 shows the amino-acid sequence of hTFPI[PpKhNE] with annotation. For each of the KuDoms, the w.t. AAs are shown below the actual AA sequence. Because the protein has been truncated and the third KuDom has been modified, it is not expected to bind to cell surfaces (see Example 10, above). It is expected that hTFPI[PpKhNE] will strongly inhibit human plasmin (h.Pla), human plasma kallikrein (h.pKal), and human neutrophil elastase (hNE).

Example 12

Pla301B, a Triple Inhibitor of Human Plasmin

Table 52 shows a gene that encodes Pla301B, a protein derived from human TFPI and having three KuDoms, each of which is designed to inhibit h.Pla. Table 55 shows the sequence of a vector that allows the expression of Pla301B in eukaryotic cells. Table 58 shows the amino-acid sequence of Pla301B. To confer anti h.Pla activity on Pla301B, we made the following mutations. In the first KuDom, we made the mutations K15R, I17R, M18F, K19D, F21W. In the second KuDom, we made the mutations I13P, G16A, Y17R, I18F, T19D, Y21W, and K34I. In the third KuDom, we made the mutations L13P, N17R, E18F, N19D, F21W, K34I, S36G, and G39E. Each KuDom should now be a potent inhibitor of h.Pla.

Human plasmin is known to be activated by urokinase-type plasminogen activator (uPA). uPA is often bound to cell surfaces by the urokinase-type plasminogen activator receptor (uPA-R). h.Pla that is activated by the uPA-uPA-R complex often binds to the plasmin receptor (Pla-R).

Pla301B was expressed in HEK293T cells with the vector shown in Table 55. The protein was assayed for plasmin inhibition and was found to be active.

Example 13

A Multiple KuDom Inhibitor that Inhibits Plasmin, Matriptase, and Hepsin

HAI-1 inhibits matriptase (Herter et al., Biochem J. 2005 390(Pt 1):125-36.) via Kunitz domain I (Kirchhofer et al., FEBS Lett. 2005 579(9):1945-50.) (the first Kunitz domain of HAI-1B is identical to the first Kunitz domain of HAI-1). HAI-2, domain 1 inhibits hepsin (Parr and Jiang, Int J Cancer. 2006 Sep. 1; 119(5):1176-83.). Table 61 shows an amino-acid sequence of PlaMatHep, a protein designed to inhibit plasmin, matriptase, and hepsin. In the first KuDom of TFPI, we have mutated K15 to R, I17 to R, M18 to F, K19 to D, and F21 to W. This corresponds to DX-1000 (a potent inhibitor of plasmin) shown in Table 7. In the second KuDom, we have mutated I13 to R, Y17 to S, I18 to F, T19 to P, Y21 to W, E31 to K, R32 to S, and K34 to V. The mutated domain is shown in Table 7 as TFPI-K2matr with w.t. AA in lower case and mutations in upper case. These changes should make the second domain of PlaMatHep be a potent inhibitor of matriptase. In the third domain of TFPI, we have made the mutations R11 to V, L13 to R, N17 to S, E18 to M, N19 to P, F21 to W, K34 to V, S36 to G, E42 to S, and K48 to E. The K48E mutation will reduce the chance of binding glycoaminoglycans. These changes are shown in Table 7 as TFPI-K3hep and should make the third domain of PlaMatHep be a potent inhibitor of hepsin. A gene to express the protein shown in Table 61 is readily constructed from the genes of other TFPI derivatives shown herein.

Tables

TABLE 1

Human LACI (TFPI) (SEQ ID NO: 1)

| AAs | Function | AA sequence |
|---|---|---|
| 1-28 | signal | 1 1 2 2<br>1 5 0 5 0 5<br>MIYTMKKVHALWASVCLLLNLAPAPLNA |
| 29-49 | Linker 1 | 3 3 4 4 4<br>0 5 0 5 9<br>DSEEDEEHTIITDTELPPLKL |
| 50-107 | KuDom 1 | 1 1<br>5 5 6 6 7 7 8 8 9 9 0 0<br>0 5 0 5 0 5 0 5 0 5 0 5<br>MHSFCAFKADDGPCKAIMKRFFFNIFTRQCEEFIYGGCEGNQNRFESLEECKKMCTRD |
| 108-120 | Linker 2 | 1 1 1<br>1 1 2<br>0 5 0<br>NANRIIKTTLQQE |
| 121-178 | KuDom 2 | 1 1 1 1 1 1 1 1 1 1 1 1<br>2 2 3 3 4 4 5 5 6 6 7 7<br>1 5 0 5 0 5 0 5 0 5 0 5<br>KPDFCFLEEDPGICRGYITRYFYNNQTKQCERFKYGGCLGNMNNFETLEECKNICEDG |
| 179-212 | Linker 3 | 1 1 1 1 2 2 2<br>8 8 9 9 0 0 1<br>0 5 0 5 0 5 0<br>PNGFQVDNYGTQLNAVNNSLTPQSTKVPSLFEFH |
| 213-270 | KuDom 3 | 2 2 2 2 2 2 2 2 2 2 2 2<br>1 2 2 3 3 4 4 5 5 6 6 7<br>5 0 5 0 5 0 5 0 5 0 5 0<br>GPSWCLTPADRGLCRANENRFYYNSVIGKCRPFKYSGCGGNENNFTSKQECLRACKKG |
| 271-304 | Linker 4 | 2 2 2 2 2 2 3 3<br>7 7 8 8 9 9 0 0<br>1 5 0 5 0 5 0 4<br>FIQRISKGGLIKTKRKRKKQRVKIAYEEIFVKNM |

TABLE 2

AA sequences of the KuDoms in human LACI (TFPI)

| AAs | Name | AA sequence | SEQ ID NO: |
|---|---|---|---|
| | |          1     1     2     2     3     3     4     4     5     5   5<br>1     5     0     5     0     5     0     5     0     5     0     5   8 | |
| 50-107 | KuDom 1 | MHSFCAFKADDGPCKAIMKRFFFNIFTRQCEEFIYGGCEGNQNRFESLEECKKMCTRD | 3 |
| 121-178 | KuDom 2 | KPDFCFLEEDPGICRGYITRYFYNNQTKQCERFKYGGCLGNMNNFETLEECKNICEDG | 4 |
| 213-270 | KuDom 3 | GPSWCLTPADRGLCRANENRFYYNSVIGKCRPFKYSGCGGNENNFTSKQECLRACKKG | 5 |
| | |    \|$\|$\|\|\|\|\|$^        ^$\|$$$$\|\| | |

TABLE 3 cDNA of human LACI (TFPI) (SEQ ID NO: 2)

```
LOCUS       NM_006287              1431 bp    mRNA    linear   PRI 08-JUN-2005
DEFINITION  Homo sapiens tissue factor pathway inhibitor
            (lipoprotein-associated coagulation inhibitor) (TFPI), mRNA.
ACCESSION   NM_006287
VERSION     NM_006287.3 GI: 40254845
sig_peptide     133..216
                /gene="TFPI"
                /note="lipoprotein-associated coagulation inhibitor signal peptide"
    mat_peptide     217..1044
                /gene="TFPI"
                /product="lipoprotein-associated coagulation inhibitor"
ORIGIN
    1 ggcgggtctg cttctaaaag aagaagtaga aagataaat cctgtcttca ataccctggaa
   61 ggaaaaacaa ataaccctca actccgtttt gaaaaaaaca ttccaagaac tttcatcaga
  121 gattttactt agatgattta cacaatgaag aaagtacatg cactttgggc ttctgtatgc
  181 ctgctgctta atcttgcccc tgccctctt aatgctgatt ctgaggaaga tgaagaacac
  241 acaattatca cagatacgga gttgccacca ctgaaactta tgcattcatt ttgtgcattc
  301 aaggcggatg atggcccatg taaagcaatc atgaaaagat ttttcttcaa tattttcact
  361 cgacagtgcg aagaatttat atatggggga tgtgaaggaa atcagaatcg atttgaaagt
  421 ctggaagagt gcaaaaaaat gtgtacaaga gataatgcaa acaggattat aaagacaaca
  481 ttgcaacaag aaaagccaga tttctgcttt ttggaagaag atcctggaat atgtcgaggt
  541 tatattacca ggtattttta taacaatcag acaaaacagt gtgaacgttt caagtatggt
  601 ggatgcctgg gcaatatgaa caattttgag acactggaag aatgcaagaa catttgtgaa
  661 gatggtccga atggtttcca ggtggataat tatggaaccc agctcaatgc tgtgaataac
  721 tccctgactc cgcaatcaac caaggttccc agccttttg aatttcacgg tccctcatgg
  781 tgtctcactc cagcagacag aggattgtgt cgtgccaatg agaacagatt ctactacaat
  841 tcagtcattg ggaaatgccg cccatttaag tacagtggat gtggggaa tgaaaacaat
  901 tttacttcca acaagaatg tctgagggca tgtaaaaaag gtttcatcca agaatatca
  961 aaaggaggcc taattaaaac caaagaaaa agaagaagc agagagtgaa aatagcatat
 1021 gaagaaattt tgttaaaaa tatgTGAatt tgttatagca atgtaacatt aattctacta
 1081 aatatttat atgaaatgtt tcactatgat tttctattt tcttctaaaa tcgttttaat
 1141 taatatgttc attaaattt ctatgcttat tgtacttgtt atcaacacgt ttgtatcaga
 1201 gttgcttttc taatcttgtt aaattgctta ttctaggtct gtaatttatt aactggctac
 1261 tgggaaatta cttatttttct ggatctatct gtattttcat ttaactacaa attatcatac
 1321 taccggctac atcaaatcag tcctttgatt ccatttggtg accatctgtt tgagaatatg
 1381 atcatgtaaa tgattatctc ctttatagcc tgtaaccaga ttaagccccc c
```

TABLE 4

The annotated DNA sequence of pFTFPI_V1

```
!pFTFPI_V1        5705              CIRCULAR
!
! Non-cutters
!AfeI AGCgct         AflII Cttaag       AgeI Accggt
!ApaLI Gtgcac        AscI GGcgcgcc      BglII Agatct
!BlpI GCtnagc        BsgI ctgcag        BsiWI Cgtacg
!BstXI CCANNNNNntgg  Bsu36I CCtnagg     EcoNI CCTNNnnnagg
 (SEQ ID NO: 164)                       (SEQ ID NO: 165)
!EcoRV GATatc        EspI GCtnagc       FseI GGCCGGcc
!HpaI GTTaac         MfeI Caattg        NheI Gctagc
!NotI GCggccgc       PacI TTAATtaa      PmeI GTTTaaac
!PpuMI RGgwccy       PshAI GACNNnngtc   PstI CTGCAg
                      (SEQ ID NO: 187)
!SbfI CCTGCAgg       SgfI GCGATcgc      SgrAI CRccggyg
!SnaBI TACgta        SpeI Actagt        Sse8387I CCTGCAgg
!SwaI ATTTaaat       XcmI CCANNNNNnnnntgg
                      (SEQ ID NO: 166)
!
! cutters
!
! Enzymes that cut more than 3 times.
!
!AatII GACGTc                    5
!BanII GRGCYc                    6
!BciVI GTATCCNNNNNN              4  (SEQ ID NO: 167)
!BglI GCCNNNNnggc                5  (SEQ ID NO: 168)
!BpmI CTGGAG                     4
!BsaAI YACgtr                    4
!BsiHKAI GWGCWc                  5
!BsmFI GGGACNNNNNNNNNNnn        10  (SEQ ID NO: 169)
!BsmI NGcattc                    4
!BsrFI Rccggy                    5
!BssSI Cacgag                    4
!EarI CTCTTCNnnn                 5  (SEQ ID NO: 170)
!Eco57I CTGAAG                   5
!FauI nNNNNNNGCGGG              11  (SEQ ID NO: 171)
!HgiAI GWGCWc                    5
!PsiI TTAtaa                     4
!StyI Ccwwgg                     4
!
! Enzymes that cut from 1 to 3 times.
!
! $ = DAM site, * = DCM site, & = both
!
!EcoRI Gaattc                    1      6
!NdeI CAtatg                     2    259   1513
!BtrI CACgtg                     1    628
!PmlI CACgtg                     1    628
!BmgBI CACgtg                    1    645
!MscI TGGcca                     2    649   2845
!BtgI Ccrygg                     2    655   1288
!DsaI Ccrygg                     2    655   1288
!NcoI Ccatgg                     1    655
!Pf1MI CCANNNNntgg               1    655   (SEQ ID NO: 172)
!NruI TCGcga                     1    688
!SfiI GGCCNNNNnggcc              1    695   (SEQ ID NO: 173)
!Eco0109I RGgnccy                1    702
!ApaI GGGCCc                     2    703   1161
!Bsp120I Gggccc                  2    703   1161
!PspOMI Gggccc                   2    703   1161
!Ec11361 GAGctc                  1    756
!SacI GAGCTc                     1    756
!HindIII Aagctt                  1    771
!NsiI ATGCAt                     3    777   2347   2419
!BspHI Tcatga                    3    826   4587   5595
!MluI Acgcgt                     1    855
!BstEII Ggtnacc                  1    894
!BspDI ATcgat                    1    904
!BsaBI GATNNnnatc                1    907   (SEQ ID NO: 174)
!BsrGI Tgtaca                    1    939
!AvaI Cycgrg                     3   1008   1785   2622
!TliI Ctcgag                     1   1008
!XhoI Ctcgag                     1   1008
!BseRI GAGGAGNNNNNNNNNN          2   1011&  2582  (SEQ ID NO: 175)
!BamHI Ggatcc                    1   1016&
!SexAI Accwggt                   2   1044*  2368*
!BsmBI Nnnnnngagacg              1   1119   (SEQ ID NO: 176)
!AccI GTmkac                     2   1179*  3735
```

TABLE 4-continued

The annotated DNA sequence of pFTFPI_V1

| | | | | |
|---|---|---|---|---|
| !HincII GTYrac | 1 | 1179* | | |
| !SalI Gtcgac | 1 | 1179* | | |
| !SacII CCGCgg | 1 | 1288 | | |
| !BspEI Tccgga | 1 | 1371 | | |
| !BssHII Gcgcgc | 1 | 1421 | | |
| !StuI AGGcct | 2 | 1463 | 2598 | |
| !XbaI Tctaga | 1 | 1548$ | | |
| !BclI Tgatca | 1 | 1561$ | | |
| !BbsI GAAGAC | 1 | 1756 | | |
| !SphI GCATGc | 3 | 1770 | 2345 | 2417 |
| !XmaI Cccggg | 2 | 1785 | 2622 | |
| !PvuII CAGctg | 2 | 1818 | 2869 | |
| !NaeI GCCggc | 3 | 1969 | 3265 | 3548 |
| !NgoMIV Gccggc | 3 | 1969 | 3265 | 3548 |
| !DraIII CACNNNgtg | 1 | 2072 | | |
| !DrdI GACNNNNnngtc | 3 | 2115 | 2786 3969 (SEQ ID NO: 177) | |
| !BstAPI GCANNNNntgc | 2 | 2340 | 2412 (SEQ ID NO: 178) | |
| !AvrII Cctagg | 2 | 2508 | 2601 | |
| !BspMI Nnnnnnnnngcaggt | 1 | 2652 | (SEQ ID NO: 179) | |
| !BspMI ACCTGCNNNNn | 2 | 3024 | (SEQ ID NO: 180) | |
| !EagI Cggccg | 1 | 2671 | | |
| !KasI Ggcgcc | 1 | 2764 | | |
| !FspI TGCgca | 2 | 2865 | 4980 | |
| !Pf1FI GACNnngtc | 1 | 2880 | | |
| !Tth111I GACNnngtc | 1 | 2880 | | |
| !SapI gaagagc | 2 | 3114 | 3324 | |
| !RsrII CGgwccg | 1 | 3280 | | |
| !BstBI TTcgaa | 1 | 3446 | | |
| !BstZ17I GTAtac | 1 | 3735 | | |
| !AlwNI CAGNNNctg | 1 | 4278 | | |
| !AhdI GACNNNnngtc | 1 | 4755 | (SEQ ID NO: 181) | |
| !Eam1105I GACNNNnngtc | 1 | 4755 | (SEQ ID NO: 181) | |
| !BsaI nnnnngagacc | 1 | 4822 | (SEQ ID NO: 182) | |
| !PvuI CGATcg | 1 | 5127$ | | |
| !ScaI AGTact | 1 | 5238 | | |
| !BcgI cgannnnnntgc | 1 | 5276 | (SEQ ID NO: 183) | |
| !Acc65I Ggtacc | 1 | 5705 | | |
| !KpnI GGTACc | 1 | 5705 | | |

```
      1   GTACCGAATT CACATTGATT ATTGAGTAGT TATTAATAGT AATCAATTAC GGGGTCATTA

61   GTTCATAGCC CATATATGGA GTTCCGCGTT ACATAACTTA CGGTAAATGG CCCGCCTGGC

121   TGACCGCCCA ACGACCCCCG CCCATTGACG TCAATAATGA CGTATGTTCC CATAGTAACG

181   CCAATAGGGA CTTTCCATTG ACGTCAATGG GTGGACTATT TACGGTAAAC TGCCCACTTG

241   GCAGTACATC AAGTGTATCA TATGCCAAGT ACGCCCCCTA TTGACGTCAA TGACGGTAAA

301   TGGCCCGCCT GGCATTATGC CCAGTACATG ACCTTATGGG ACTTTCCTAC TTGGCAGTAC

361   ATCTACGTGT TAGTCATCGC TATTACCATA GTGATGCGGT TTTGGCAGTA CATCAATGGG

421   CGTGGATAGC GGTTTGACTC ACGGGGATTT CCAAGTCTCC ACCCCATTGA CGTCAATGGG

481   AGTTTGTTTT GGCACCAAAA TCAACGGGAC TTTCCAAAAT GTCGTAACAA CTCCGCCCCA

541   TTGACGCAAA TGGGCGGTAG GCGTGTACGG TGGGAGGTCT ATATAAGCAG AGCTTTCTGG

601   CTAACTAGAG AACCCACTGC TTACTGGCAC GTGGAAATTA ATACGACGTG GCCACC
!
!             Signal sequence..............................
!             M    G    W    S    C    I    I    L    F    L    V    A
    657      aTG  Gga  tgg  agc  tgt  atc  atc  ctc  ttc  ttg  gTC  GCG
!                                                                 NruI...
!
!             Signal sequence.............     Mature TFPI.....
!                                               1    2
!             T    A    T    G    A    H    S    D    S
    693      AcG  GCC  aca  ggG  GCC  cac  tcc   gac  tct !
!            NruI.. SfiI.............
!                            Eco0109I.
!                            ApaI....(Bsp120I)
!
!             Linker 1................................................
!             3    4    5    6    7    8    9   10   11   12   13   14   15   16   17
!             E    E    D    E    E    H    T    I    I    T    D    T    E    L    P
```

TABLE 4-continued

The annotated DNA sequence of pFTFPI_V1

```
 720   gag gaa gat gaa gaa cac aca att atc aca gat acg gag CtC cca
                                                           SacI...
!
!      Linker 1........    KuDom 1....................................
!       18  19  20  21      22  23  24  25  26  27  28  29  30  31  32
!        P   L   K   L      M1   H   S   F  C5   A   F   K   A   D  D11
 765   cca ctg aaG ctt     atg cat tca ttt tgt gca ttc aag gcg gat gat
!               HindIII(1/1)NsiI...(1/3)
!                         |
! Secondary cleavage site of MMP-8
!   Cleavage site of MMP-12 (Belaaouaj, et al.,
!     2000, J Biol Chem, 275:27123-8)
!
!          KuDom 1.................................................
!           33  34  35  36  37  38  39  40  41  42  43  44  45  46  47
!            G   P  C14  K   A   I   M   K  R20  F   F   F   N   I   F
 810       ggc cca tgt aaa gca atc atg aaa aga ttt ttc ttc aat att ttc
!                        BspHI...
!
!          KuDom 1.................................................
!           48  49  50  51  52  53  54  55  56  57  58  59  60  61  62
!            T   R   Q  C30  E   E   F   I   Y   G   G  C38  E   G   N
 855       acG cgT cag tgc gaa gaa ttt ata tat ggg gga tgt gaa ggT aaC
!          MluI...                                          BstEII...
!
!          KuDom 1.................................................
!           63  64  65  66  67  68  69  70  71  72  73  74  75  76  77
!            Q   N   R  F45  E   S   L   E  E50  C   K   K   M  C55  T
 900       cag aat cga ttt gaa TCt ctg gaa gag tgc aaa aaa atg tgt aca
! BstEII..    BspDI...                                      BsrGI..
!            BsaBI........
!
!      KuDom 1     Linker 2.........................................
!       78  79      80  81  82  83  84  85  86  87  88  89  90  91  92
!        R  D58      N   A   N   R   I   I   K   T   T   L   Q   Q   E
 945   aga gat     aat gca aac agg att ata aag aca aca ttg caa caa gaa
!
! Cleavage site of MMP-12 (Belaaouaj, et al., 2000,
! J Biol Chem, 275:27123-8)
!
!         Kudom 2.....................................................
!           93  94  95  96  97  98  99 100 101 102 103 104 105 106 107
!            K   P   D   F  C5   F   L   E   E   D   P   G   I  C14  R
 990       aag cca gat ttc tgc ttt CtC gaG gaG gat cct gga ata tgt cga
!                                  XhoI... BamHI...
!
!         Kudom 2.....................................................
!          108 109 110 111 112 113 114 115 116 117 118 119 120 121 122
!            G   Y   I   T  R20  Y   F   Y   N  N*   Q   T   K   Q  C30
1035       ggt tat att acc agg tat ttt tat aac aat cag aca aaa cag tgt
!                         SexAI....(not U)
!
!         Kudom 2.....................................................
!          123 124 125 126 127 128 129 130 131 132 133 134 135 136 137
!            E   R   F   K   Y   G   G  C38  L   G   N   M   N   N  F45
1080       gaa cgt ttc aag tat ggt gga tgc ctg ggc aat atg aac aat ttt
!
!         Kudom 2..........................................  Linker 3
!          138 139 140 141 142 143 144 145 146 147 148 149 150   151 152
!            E   T   L   E   E  C51  K   N   I  C55  E   D  G58    P   N
1125       gag acG ctg gaa gaa tgc aag aac att tgt gaa gat ggG    ccC aat
!          BsmBI....-----                                   ApaI.......
!                                                           Bsp120I....
!
!          Linker 3................................................
!          153 154 155 156 157 158 159 160 161 162 163 164 165 166 167
!            G   F   Q   V   D   N   Y   G   T   Q   L   N   A   V  N*
1170       ggt ttc cag gtC gaC aat tat gga acc cag ctc aat gct gtg aat
!                        SalI...
!
!          Linker 3................................................
!          168 169 170 171 172 173 174 175 176 177 178 179 180 181 182
!            N   S   L   T   P   Q   S   T   K   V   P   S   L   F   E
1215       aac tcc ctg act ccg caa tca act aag gtt ccc agc ctt ttt gaa
!                                     |
!                                     Cleavage site of MMP8
!      Cleavage site of MMP-12 (Belaaouaj, et al., 2000, J Biol Chem,
!        275:27123-8)
```

TABLE 4-continued

The annotated DNA sequence of pFTFPI_V1

```
!      Linker 3      KuDom 3.........................................
!       183 184      185 186 187 188 189 190 191 192 193 194 195 196 197
!        F   H        G   P   S   W   C5  L   T   P   A   D   R   G   L
1260    ttt cac      ggt ccc tca tgg tgt ctc act ccC gcG gac aga gga ttg
!                                                        SacII..
!
!          KuDom 3...................................................
!          198 199 200 201 202 203 204 205 206 207 208 209 210 211 212
!          C14  R   A   N   E   N  R20  F   Y   Y   N   S   V   I  G28
1305       tgt cgt gcc aat gag aac aga ttc tac tac aat tca gtc att ggg
!
!          KuDom 3...................................................
!          213 214 215 216 217 218 219 220 221 222 223 224 225 226 227
!           K  C30  R   P   F   K   Y   S   G  C38  G   G   N   E   N
1350       aaa tgc cgc cca ttt aag taT TCC gga tgt ggg gga aat gaa aac
!                                      BspEI..
!
!          KuDom 3...................................................
!          228 229 230 231 232 233 234 235 236 237 238 239 340 241 242
!           N*  F   T   S   K   Q   E  C51  L   R   A  C55  K   K  G58
1395       aat ttt act tcc aaa caa gaa tgt ctg CgC gca tgt aaa aaa ggt
!                                              BssHII..
!
!          Linker 4.................................................
!          243 244 245 246 247 248 249 250 251 252 253 254 255 256 257
!           F   I   Q   R   I   S   K   G   G   L   I   K   T   K   R
1440       ttc atc caa aga ata tca aaa gga ggc cta att aaa acc aaa aga
!
!          Linker 4.................................................
!          258 259 260 261 262 263 264 265 266 267 268 269 270 271 272
!           K   R   K   K   Q   R   V   K   I   A   Y   E   E   I   F
1485       aaa aga aag aag cag aga gtg aaa ata gca tat gaa gaa att ttt
!
!          Linker 4.......
!          273 274 275 276
!           V   K   N   M    . (SEQ ID NO: 7).
1530       gtt aaa aat atg taa tga TCTAGA
!                                  XbaI..
1554           AGCTC GCTGATCAGC CTCGACTGTG CCTTCTAGTT GCCAGCCATC TGTTGTTTGC

1609    CCCTCCCCCG TGCCTTCCTT GACCCTGGAA GGTGCCACTC CCACTGTCCT TTCCTAATAA

1669    AATGAGGAAA TTGCATCGCA TTGTCTGAGT AGGTGTCATT CTATTCTGGG GGGTGGGGTG

1729    GGGCAGGACA GCAAGGGGGA GGATTGGGAA GACAATAGCA GGCATGCTGG GGATGGCCCG

1789    GGCTCTATGG CTTCTGAGGC GGAAAGAACC AGCTGGGGCT CTAGGGGGTA TCCCCACGCG

1849    CCCTGTAGCG GCGCATTAAG CGCGGCGGGT GTGGTGGTTA CGCGCAGCGT GACCGCTACA

1909    CTTGCCAGCG CCCTAGCGCC CGCTCCTTTC GCTTTCTTCC CTTCCTTTCT CGCCACGTTC

1969    GCCGGCTTTC CCCGTCAAGC TCTAAATCGG GCATCCCTT TAGGGTTCCG ATTTAGTGCT

2029    TTACGGCACC TCGACCCCAA AAAACTTGAT TAGGGTGATG GTTCACGTAG TGGGCCATCG

2089    CCCTGATAGA CGGTTTTTCG CCCTTTGACG TTGGAGTCCA CGTTCTTTAA TAGTGGACTC

2149    TTGTTCCAAA CTGGAACAAC ACTCAACCCT ATCTCGGTCT ATTCTTTTGA TTTATAAGGG

2209    ATTTTGGGGA TTTCGGCCTA TTGGTTAAAA AATGAGCTGA TTTAACAAAA ATTTAACGCG

2269    AATTAATTCT GTGGAATGTG TGTCAGTTAG GGTGTGGAAA GTCCCCAGGC TCCCCAGGCA

2329    GGCAGAAGTA TGCAAAGCAT GCATCTCAAT TAGTCAGCAA CCAGGTGTGG AAAGTGCTCA

2389    GGCTCCCCAG CAGGCAGAAG TATGCAAAGC ATGCATCTCA ATTAGTCAGC AACCATAGTC

2449    CCGCCCCTAA CTCCGCCCAT CCCGCCCCTA ACTCCGCCCA GTTCCGCCCA TTCTCCGCCC

2509    CTAGGCTGAC TAATTTTTTT TATTTATGCA GAGGCCGAGG CCGCCTCTGC CTCTGAGCTA

2569    TTCCAGAAGT AGTGAGGAGG CTTTTTTGGA GGCCTAGGCT TTTGCAAAAA GCTCCCGGGA

2629    GGTCCACAAT GATTGAACAA GATGGATTGC ACGCAGGTTC TCCGGCCGCT TGGGTGGAGA

2689    GGCTATTCGG CTATGACTGG GCACAACAGA CAATCGGCTG CTCTGATGCC GCCGTGTTCC
```

TABLE 4-continued

The annotated DNA sequence of pFTFPI_V1

```
2749  GGCTGTCAGC GCAGGGCGC CCGGTTCTTT TTGTCAAGAC CGACCTGTCC GGTGCCCTGA

2809  ATGAACTCCA GGACGAGGCA GCGCGGCTAT CGTGGCTGGC CACGACGGGC GTTCCTTGCG

2869  CAGCTGTGCT CGACGTTGTC ACTGAAGCGG GAAGGGACTG GCTGCTATTG GGCGAAGTGC

2929  CGGGGCAGGA TCTCCTGTCA TCTCACCTTG CTCCTGCCGA GAAAGTATCC ATCATGGCTG

2989  ATGCAATGCG GCGGCTGCAT ACGCTTGATC CGGCTACCTG CCCATTCGAC CACCAAGCGA

3049  AACATCGCAT CGAGCGAGCA CGTACTCGGA TGGAAGCCGG TCTTGTCGAT CAGGATGATC

3109  TGGACGAAGA GCATCAGGGG CTCGCGCCAG CCGAACTGTT CGCCAGGCTC AAGGCGCGTA

3169  TGCCCGACGG CGAGGATCTC GTCGTGACTC ATGGCGATGC CTGCTTGCCG AATATCATGG

3229  TGGAAAATGG CCGCTTTTCT GGATTCATCG ACTGTGGCCG GCTGGGTGTG GCGGACCGCT

3289  ATCAGGACAT AGCGTTGGCT ACCCGTGATA TTGCTGAAGA GCTTGGCGGC GAATGGGCTG

3349  ACCGCTTCCT CGTGCTTTAC GGTATCGCCG CTCCCGATTC GCAGCGCATC GCCTTCTATC

3409  GCCTTCTTGA CGAGTTCTTC TGAGCGGGAC TCTGGGGTTC GAAATGACCG ACCAAGCGAC

3469  GCCCAACCTG CCATCACGAG ATTTCGATTC CACCGCCGCC TTCTATGAAA GGTTGGGCTT

3529  CGGAATCGTT TTCCGGGACG CCGGCTGGAT GATCCTCCAG CGCGGGGATC TCATGCTGGA

3589  GTTCTTCGCC CACCCCAACT TGTTTATTGC AGCTTATAAT GGTTACAAAT AAAGCAATAG

3649  CATCACAAAT TTCACAAATA AAGCATTTTT TTCACTGCAT TCTAGTTGTG GTTTGTCCAA

3709  ACTCATCAAT GTATCTTATC ATGTCTGTAT ACCGGATCTT TCCGCTTCCT CGCTCACTGA

3769  CTCGCTGCGC TCGGTCGTTC GGCTGCGGCG AGCGGTATCA GCTCACTCAA AGGCGGTAAT

3829  ACGGTTATCC ACAGAATCAG GGGATAACGC AGGAAAGAAC ATGTGAGCAA AAGGCCAGCA

3889  AAAGGCCAGG AACCGTAAAA AGGCCGCGTT GCTGGCGTTT TTCCATAGGC TCCGCCCCCC

3949  TGACGAGCAT CACAAAAATC GACGCTCAAG TCAGAGGTGG CGAAACCCGA CAGGACTATA

4009  AAGATACCAG GCGTTTCCCC CTGGAAGCTC CCTCGTGCGC TCTCCTGTTC CGACCCTGCC

4069  GCTTACCGGA TACCTGTCCG CCTTTCTCCC TTCGGGAAGC GTGGCGCTTT CTCAATGCTC

4129  ACGCTGTAGG TATCTCAGTT CGGTGTAGGT CGTTCGCTCC AAGCTGGGCT GTGTCCACGA

4189  ACCCCCCGTT CAGCCCGACC GCTGCGCCTT ATCCGGTAAC TATCGTCTTG AGTCCAACCC

4249  GGTAAGACAC GACTTATCGC CACTGGCAGC AGCCACTGGT AACAGGATTA GCAGAGCGAG

4309  GTATGTAGGC GGTGCTACAG AGTTCTTGAA GTGGTGGCCT AACTACGGCT ACACTAGAAG

4369  GACAGTATTT GGTATCTGCG CTCTGCTGAA GCCAGTTACC TTCGGAAAAA GAGTTGGTAG

4429  CTCTTGATCC GGCAAACAAA CCACCGCTGG TAGCGGTGGT TTTTTTGTTT GCAAGCAGCA

4489  GATTACGCGC AGAAAAAAAG GATCTCAAGA AGATCCTTTG ATCTTTTCTA CGGGGTCTGA

4549  CGCTCAGTGG AACGAAAACT CACGTTAAGG GATTTTGGTC ATGAGATTAT CAAAAAGGAT

4609  CTTCACCTAG ATCCTTTTAA ATTAAAAATG AAGTTTTAAA TCAATCTAAA GTATATATGA

4669  GTAAACTTGG TCTGACAGTT ACCAATGCTT AATCAGTGAG GCACCTATCT CAGCGATCTG

4729  TCTATTTCGT TCATCCATAG TTGCCTGACT CCCCGTCGTG TAGATAACTA CGATACGGGA
```

TABLE 4-continued

The annotated DNA sequence of pFTFPI_V1

```
4789  GGGCTTACCA TCTGGCCCCA GTGCTGCAAT GATACCGCGA GACCCACGCT CACCGGCTCC
4849  AGATTTATCA GCAATAAACC AGCCAGCCGG AAGGGCCGAG CGCAGAAGTG GTCCTGCAAC
4909  TTTATCCGCC TCCATCCAGT CTATTAATTG TTGCCGGGAA GCTAGAGTAA GTAGTTCGCC
4969  AGTTAATAGT TTGCGCAACG TTGTTGCCAT TGCTACAGGC ATCGTGGTGT CACGCTCGTC
5029  GTTTGGTATG GCTTCATTCA GCTCCGGTTC CCAACGATCA AGGCGAGTTA CATGATCCCC
5089  CATGTTGTGC AAAAAAGCGG TTAGCTCCTT CGGTCCTCCG ATCGTTGTCA GAAGTAAGTT
5149  GGCCGCAGTG TTATCACTCA TGGTTATGGC AGCACTGCAT AATTCTCTTA CTGTCATGCC
5209  ATCCGTAAGA TGCTTTTCTG TGACTGGTGA GTACTCAACC AAGTCATTCT GAGAATAGTG
5269  TATGCGGCGA CCGAGTTGCT CTTGCCCGGC GTCAATACGG GATAATACCG CGCCACATAG
5329  CAGAACTTTA AAAGTGCTCA TCATTGGAAA ACGTTCTTCG GGGCGAAAAC TCTCAAGGAT
5389  CTTACCGCTG TTGAGATCCA GTTCGATGTA ACCCACTCGT GCTCCCAACT GATCTTCAGC
5449  ATCTTTTACT TTCACCAGCG TTTCTGGGTG AGCAAAAACA GGAAGGCAAA ATGCCGCAAA
5509  AAAGGGAATA AGGGCGACAC GGAAATGTTG AATACTCATA CTCTTCCTTT TTCAATATTA
5569  TTGAAGCATT TATCAGGGTT ATTGTCTCAT GAGCGGATAC ATATTTGAAT GTATTTAGAA
5629  AAATAAACAA ATAGGGGTTC CGCGCACATT TCCCCGAAAA GTGCCACCTG ACGTCAGATC
5689  GACGGATCGG GAGATCG (SEQ ID NO: 6)
```

TABLE 5

The AA sequence of DX-88, an inhibitor of human plasma kallikrein.

(SEQ ID NO: 9)
```
         1    1    2    2    3    3    4    4    5    5  5
ab1...5....0....5....0....5....0....5....0....5....0....5..8
EAMHSFCAFKADDGPCRAAHPRWFFNIFTRQCEEFIYGGCEGNQNRFESLEECKKMCTRD
```

TABLE 6

DNA encoding DX-88

(SEQ ID NO: 8)

GAA GCT ATG CAC TCT TTC TGT GCT TTC AAG GCT GAC

GAC GGT CCG TGC AGA GCT GCT CAC CCA AGA TGG TTC

TTC AAC ATC TTC ACG CGA CAA TGC GAG GAG TTC ATC

TAC GGT GGT TGT GAG GGT AAC CAA AAC AGA TTC GAG

TCT CTA GAG GAG TGT AAG AAG ATG TGT ACT AGA GAC

TABLE 7

Comparison of Various BPTI-related KuDoms_SEQ ID NOs: 188, 3, 9, 129, 189, 4, 190, 5, 191, 188, 192, 128, 4, 193, 5, 194, 195, 4, 196, 197, 5 and 198, respectively.

```
           Position
                    1    1    2    2    3    3    4    4    5    5
           1    5   0    5    0    5    0    5    0    5    0    5 8    Type
BPTI       rpdfCleppytGpCkariiryfynakaglCqtFvygGCrakrnnFksaedCmrtCgga   w.t.
           ||   ||||| |||        ||||   ||||| |  |
TFPI-K1    mhsfCafkaddGpCkaimkrfffniftrqCeeFiygGCegnqnrFesleeCkkmCtrd   w.t.
TFPI-K1-lib     xx x xxxxx x           xx xx     x
DX-88    EA """"C"""""G"Cr"ahp"w"""""""""C""F"""GC""""F""""C"""C"""   sel.
DX-1000     """"C"""""G"Cr"rfd"w"""""""""C""F"""GC""""F""""C"""C"""   sel.
TF890       """"C"""""G"CI"FFP"""""""""""C""F"""GCQ"""F""""C"""C"""   des.
TFPI-K2     KPDFCFLEEDPGICRGYITRYFYNNQTKQCERFKYGGCLGNMNNFETLEECKNICEDG   w.t.
TFPI-K2_88  """"C"""""GpC"aahp"w"""""""""C""Fi"Gce"""""""""C"""C"""   des.
TFPI-K3     GPSWCLTPADRGLCRANENRFYYNSVIGKCRPFKYSGCGGNENNFTSKOECLRACKKG   w.t.
TFPI-K3_88  """"C"""""GpC" "ahp"w"""""""""C""Fi" g"Ce"""""""""C"""C"""   des.
TFPI-K2     KPDFCFLEEDPGICRGYITRYFYNNQTKQCERFKYGGCLGNMNNFETLEECKNICEDG   w.t.
TFPI-K2_88  """"C"""""GpC"aahp"w"""""""""C""Fi"Gce"""""""""C"""C"""   des.
TFPI-K3     GPSWCLTPADRGLCRANENRFYYNSVIGKCRPFKYSGCGGNENNFTSKOECLRACKKG   w.t.
TFPI-K3_88  """"C"""""GpC" "ahp"w"""""""""C""Fi" g"ce"""""""""C"""C"""   des.

BPTI        rpdfCleppytGpCkariiryfynakaglCqtFvygGCrakrnnFksaedCmrtCgga   w.t.
            |     ||||        |    |||||     |||||    ||
ITI-K2      tvaaCnlpivrGpCrafiqlwafdavkgkCvlFpygGCqgngnkFysekeCreyCgvp   w.t.
DX-890      --e"C"""""G"Ci"fpr"""""""""C""F"""GC""""F""""C"""C"""      DBT Position
                  1    5    1    1    2    2    3    3    4    4    5    5
                            0    5    0    5    0    5    0    5    0    5 8

TFPI-K2     KPDFCFLEEDPGICRGYITRYFYNNQTKQCERFKYGGCLGNMNNFETLEECKNICEDG   w.t.
TFPI-K2_890 """"C"""""GpCiaffp"w"""""""""C"lFp"Gcq"""""""""C"""C"""   des.
TFPI-K3     GPSWCLTPADRGLCRANENRFYYNSVIGKCRPFKYSGCGGNENNFTSKOECLRACKKG   w.t.
TFPI-K3_890 """"C"""""GpCi"ffp"w"""""""""C"lFp"g"Cq"""""""""C"""C"""   des.
HAI-1-K1    TEDYCLASNKVGRCRGSFPRWYYDPTEQICKSFVYGGCLGNKNNYLREEECILACRGV   w.t.
TFPI-K2     KPDFCFLEEDPGICRGYITRYFYNNQTKQCERFKYGGCLGNMNNFETLEECKNICEDG   w.t.
TFPI-K2matr kpdfcfleedpgicrgyitryfynnqtkqcerfkyggclgnmnnfetleecknicedg   des.
HAI-2-K1    IHDFCLVSKVVGRCRASMPRWWYNVTDGSCQLFVYGGCDGNSNNYLTKEECLKKCATV   w.t.
TFPI-K3     GPSWCLTPADRGLCRANENRFYYNSVIGKCRPFKYSGCGGNENNFTSKOECLRACKKG   w.t.
TFPI-K3hep  gpswcltpadVgRcraSMPrWyynsvigkcrpfVyGgcggnSnnftsEqeclrackkg   des.
                   1    5    1    1    2    2    3    3    4    4    5    5
                             0    5    0    5    0    5    0    5    0    5 8
``` w.t. = wild-type
sel. = selected
des. = designed
DBT = designed, built, and tested

TABLE 8

DX: 88 gene

```
! DX88 gene
!      a b 1 2 3
!      E A M H S
       gag gct atg cac tct
!     |.....mature DX88 ....
!      derived from human LACI-K1
!
!       4   5   6   7   8   9  10  11  12  13  14  15  16  17  18
!       F   C   A   F   K   A   D   D   G   P   C   R   A   A   H
 1224 ttc tgt gct ttc aag gct gac gaC GGT CCG tgc aga gct gct cac
!                                       | RsrII |
!      19  20  21  22  23  24  25  26  27  28  29  30  31  32  33
!       P   R   W   F   F   N   I   F   T   R   Q   C   E   E   F
 1269 cca aga tgg ttc ttc aac atc ttc acg cga caa tgc gag gag ttc
!
!      34  35  36  37  38  39  40  41  42  43  44  45  46  47  48
!       I   Y   G   G   C   E   G   N   Q   N   R   F   E   S   L
 1314 atc tac ggt ggt tgt gag GGT AAC Caa aac aga ttc gag tct cta
!                                | BstEII |
!
!      49  50  51  52  53  54  55  56  57  58
!       E   E   C   K   K   M   C   T   R   D   (SEQ ID NO: 200)
 1359 gag gag tgt aag aag atg tgt act aga gat  (SEQ ID NO: 199)
!LACI domain-------------------------------
!
```

TABLE 9

Gene encoding TF88890 for expression in pFTFPI_V2

```
!Human mature TFPI(1-174) with changes in KuDom1 and KuDom2
!
!         Signal sequence from pFcFuse3..................
!          M   G   W   S   C   I   I   L   F   L   V   A
    1    aTG Gga tgg agc tgt atc atc ctc ttc ttg gtc gcg
!                                                  NruI...
!
!         Signal sequence............
!          T   A   T   G   A   H   S
   37    acg gcc aca ggg gcc cac tcc
!         NruI.. SfiI.............
!                BglI..........
!                     Eco0109I.
!                       ApaI....(Bsp120I)
!
!    Mature modified TFPI
!      1   2   3   4   5   6   7   8   9  10  11  12  13  14  15
!      D   S   E   E   D   E   E   H   T   I   I   T   D   T   E
   58 gat tct gag gaa gat gaa gaa cac aca att atc aca gat acg gag
!
!                              KuDom 1.........................
!     16  17  18  19  20  21  22  23  24  25  26  27  28  29  30
!      L   P   P   L   K   L   M   H   S   F   C   A   F   K   A
  103 ttg cca cca ctg aaa ctt atg cat tca ttt tgt gca ttc aag gcg
!                                        NsiI...
!
!     KuDom 1.... Now like DX-88
!     31  32  33  34  35  36  37  38  39  40  41  42  43  44  45
!      D   D   G   P   C   R   A   A   H   P   R   W   F   F   N
  148 gat gat ggc cca tgt aGa gca GCc CAT CCT aga tGG ttc ttc aat
!
!     46  47  48  49  50  51  52  53  54  55  56  57  58  59  60
!      I   F   T   R   Q   C   E   E   F   I   Y   G   G   C   E
  193 att ttc act cga cag tgc gaa gaa ttt ata tat ggg gga tgt gaa
!
!     61  62  63  64  65  66  67  68  69  70  71  72  73  74  75
!      G   N   Q   N   R   F   E   S   L   E   E   C   K   K   M
  238 gga aat cag aAT CGA Ttt gaa agt ctg gaa gag tgc aaa aaa atg
!                 BspDI...
!
!     End KuDom1.... Linker.......................................
!     76  77  78  79  80  81  82  83  84  85  86  87  88  89  90
!      C   T   R   D   N   A   N   R   I   I   K   T   T   L   Q
  283 TGT ACA aga gat aat gca aac agg att ata aag aca aca ttg caa
!     BsrGI..
```

TABLE 9-continued

Gene encoding TF88890 for expression in pFTFPI_V2

```
        KuDom 2........................................
        91  92  93  94  95  96  97  98  99 100 101 102 103 104 105
        Q   E   K   P   D   F   C5  F   L   E   E   D   P  G12 P13
328     caa gaa aag cca gat ttc tgc ttt ttg gaa gaa gat cct gga CCa KuDom 2.... Now like DX-890......................
        106 107 108 109 110 111 112 113 114 115 116 117 118 119 120
        C14  I   A   F   F   P   R   W   F   Y   N   N   Q   T   K
373     tgt ATC gCt tTt Ttt Ccc agg tGG ttt tat aac aat cag aca aaa 121 122 123 124 125 126 127 128 129 130 131 132 133 134 135
        Q   C   E   L   F   P   Y   G   G   C   Q   G   N   M   N
418     cag tgt gaa cTt ttc CCg tat ggt gga tgc cAg ggc aat atg aac KuDom 2...........................................
        136 137 138 139 140 141 142 143 144 145 146 147 148 149 150
        N   F   E   T   L   E   E   C   K   N   I   C   E   D   G
463     aat ttt gag aca ctg gaa gaa tgc aag aac att tgt gaa gat ggt Linker............................................
        151 152 153 154 155 156 157 158 159 160 161 162 163 164 165
        P   N   G   F   Q   V   D   N   Y   G   T   Q   L   N   A
508     ccg aat ggt ttc cag gtg gat aat tat gga acc cag ctc aat gct Linker.....................
        166 167 168 169 170 171 172 173 174
        V   N   N   S   L   T   P   Q   S   (SEQ ID NO: 11)
553     gtg aat aac tcc ctg act ccg caa tca
                                    |
                          Cleavage site of MMP8
                          Cleavage site of MMP-12
        (Belaaouaj, et al., 2000, J Biol Chem, 275:27123-8)

580                  taa tga tctaga (SEQ ID NO: 10)
                             XbaI...

Peptide Mol. Wt. = 20061
```

TABLE 10

ONs for Remodeling of KuDom 1 and KuDom 2 of mature TFPI(1-174)
(All ONs are writen 5' to 3'.)

| # | Name | Sequence |
|---|------|----------|
| 1 | ON1U23 | GAT TCT GAG GAA GAT GAA GAA CA (SEQ ID NO: 12) |
| 2 | ON718L21 | TGA TTG CGG AGT CAG GGA GTT (SEQ ID NO: 13) |
| 3 | ONK1Bot | GAA AAT ATT GAA GAA ccA TCT agg atg Ggc TGC TcT ACA TGG GCC ATC ATC CGC CTT (SEQ ID NO: 14) |
| 4 | ONK1T | AAG GCG GAT GAT GGC CCA TGT AgA GCA gcC cat cct AGA Tgg TTC TTC AAT ATT TTC (SEQ ID NO: 15) |
| 5 | ONK2B1 | T GTT ATA AAA ccA CCT GGg AAa AaA AgC gat ACA Tgg TCC AGG ATC TTC TT (SEQ ID NO: 16) |
| 6 | ONK2T1 | AA GAA GAT CCT GGA ccA TGT atc GcT TtT cCC AGG Tgg TTT TAT AAC A (SEQ ID NO: 17) |
| 7 | ONK2B2 | CAT ATT GCC CtG GCA TCC ACC ATA Cgg GAA AaG TTC ACA CTG TTT (SEQ ID NO: 18) |
| 8 | ONK2T2 | AAA CAG TGT GAA CtT TTC ccG TAT GGT GGA TGC CaG GGC AAT ATG (SEQ ID NO: 19) |
| 9 | ON_SfiITop | TTAATCTTGCGGCCACAGG GGCCCACTCT <u>GAT TCT GAG GAA GAT GAA GAA CA</u> (SEQ ID NO: 20) |
| 10 | BotAmp | CAAAAAGGCT TCTAGA TCA TTA <u>TGA TTG CGG AGT CAG GGA GTT</u> (SEQ ID NO: 21) |

Mutations are shown lowercase, bold.
Restriction sites are UPPERCASE, BOLD.

TABLE 11

TFPI-2 (SEQ ID NO: 22)

| Codons | Function | AA sequence |
|---|---|---|
| 1-24 | signal | MDPARPLGLSILLLFLTEAALGDA |
| 25-31 | Linker 1 | AQEPTGN |
| 32-89 | KuDom 1 | NAEICLLPL-DYGPCRALLLRYYYDRYTQSCRQFLYGGCEGNA--NNFYTWEACDDACWRI |
| 90-91 | Linker 2 | EK |
| 92-162 | KuDom 2 | VPKVCRLQVSVDDQCEGSTEKYFFNLSSMTCEKFFSGGCHRNRIENRFPDEATCMGFCAPK |
| 163 | Linker 3 | K |
| 164-221 | KuDom 3 | IPSFCYSPK-DEGLCSANVTRYYFNPRYRTCDAFTYTGCGGND--NNFVSREDCKRACAKA |
| 222-245 | Linker 4 | LKKKKKMPKLRFASRIRKIRKKQF |

Positions for KuDom 1: 1, 5, a0, 15, 20, 25, 30, 35, 40, ab, 45, 50, 55, 58

TABLE 12

Library of TFPI2 KuDom2

```
! M13_iii::TFPI-2 K2 for DY3P82
!
!             M13 signal sequence................|   1   2
!                                              S   M   A   D   V   P
!                                              |tCC|ATG|Gct|gat|gtt|cct|
!                                                  NcoI....
!
!                                                      X1  X1  X3      X3  X4
!     3   4   5   6   7   8   9  9a  10  11  12  13  14  15  16
!     K   V   C   R   L   Q   V   S   V   D   D   Q   C   E   G
!    |aag|gtt|tgt|cgt|CTG|CAG|gtt|tct|gtt|gac|gat|caa|tgt|gag|ggt|
!                        PstI...
!
!     X3  X3  X3  X5
!     17  18  19  20  21  22  23  24  25  26  27  28  29  30  31
!     S   T   E   K   Y   F   N   L   S   S   M   T   C   E
!    |tct|act|gaa|aag|tat|ttt|ttc|aac|CtG|AGC|TCt|atg|act|tgc|gaa|
!                                        SacI....
!
!             X3  X7          X3  X8      X9 X10
!     32  33  34  35  36  37  38  39  40  41  42 42a 42b 43  44
!     K   F   S   G   G   C   H   R   N   R   I   E   N   R
!    |aag|ttc|ttt|tct|ggt|ggt|tgc|cat|cgt|aac|cgt|atc|gag|aAC|CGG|
!                                                            AgeI...
!
!     45  46  47  48  49  50  51  52  53  54  55  56  57  58
!     F   P   D   E   A   T   C   M   G   F   C   A   P   K   S
!    |TtT|CCG|GAc|gag|gct|act|tgt|atg|ggt|ttc|tgt|gct|cct|aag|tct|
! AgeI.... BspEI...
!
!         A   D   A   S           (SEQ ID NO: 24)
!        |gct|gac|GCT|AGC|         (SEQ ID NO: 23);
!                    NheI...
modified version: nucleic acid sequence (SEQ ID NO: 143) and amino acid
sequence (SEQ ID NO: 144).
!
! Mixed ON version                          Codon based
! X1 = RRK [DENKSRGG]                       D,E,N,K,S,R,G,V,L,F
! X3 = NNK [FLLLIMVVSSPPITAAY.HQNKDECWRRSRGG]  A,D,E,F,G,H,I,K,L,M,N,P,
(no C)                                       Q,R,S,T,V,W,Y
! X4 = GRt [AG]                             A,G
! X5 = ARG [KR]                             K,R
! X7 = TMT [SY]                             S,Y
! X8 = RRK [DENKSRGG]                       D,E,N,K,S,R,Q,G,V,L,F
! X9 = RRK [DENKSRGG]                       D,E,N,K,S,R,Q,G,V,L,F
! X10 = RNK [IMVVTTAANKDESRGG]              I,M,V,L,A,T,S,Y,G,D,R,F
```

TABLE 13

DNA of a Display Phage displaying TFPI2 KuDom2 (SEQ ID NO: 25)

```
LOCUS       DY3P82_22    8931              CIRCULAR
ORIGIN
    1 AATGCTACTA CTATTAGTAG AATTGATGCC ACCTTTTCAG CTCGCGCCCC AAATGAAAAT
   61 ATAGCTAAAC AGGTTATTGA CCATTTGCGA AATGTATCTA ATGGTCAAAC TAAATCTACT
  121 CGTTCGCAGA ATTGGGAATC AACTGTTATA TGGAATGAAA CTTCCAGACA CCGTACTTTA
  181 GTTGCATATT TAAAACATGT TGAGCTACAG CATTATATTC AGCAATTAAG CTCTAAGCCA
  241 TCCGCAAAAA TGACCTCTTA TCAAAAGGAG CAATTAAAGG TACTCTCTAA TCCTGACCTG
  301 TTGGAGTTTG CTTCCGGTCT GGTTCGCTTT GAAGCTCGAA TTAAAACGCG ATATTTGAAG
  361 TCTTTCGGGC TTCCTCTTAA TCTTTTTGAT GCAATCCGCT TTGCTTCTGA CTATAATAGT
  421 CAGGGTAAAG ACCTGATTTT TGATTTATGG TCATTCTCGT TTTCTGAACT GTTTAAAGCA
  481 TTTGAGGGGG ATTCAATGAA TATTTATGAC GATTCCGCAG TATTGGACGC TATCCAGTCT
  541 AAACATTTTA CTATTACCCC CTCTGGCAAA ACTTCTTTTG CAAAAGCCTC TCGCTATTTT
  601 GGTTTTTATC GTCGTCTGGT AAACGAGGGT TATGATAGTG TTGCTCTTAC TATGCCTCGT
  661 AATTCCTTTT GGCGTTATGT ATCTGCATTA GTTGAATGTG GTATTCCTAA ATCTCAACTG
  721 ATGAATCTTT CTACCTGTAA TAATGTTGTT CCGTTAGTTC GTTTTATTAA CGTAGATTTT
  781 TCTTCCCAAC GTCCTGACTG GTATAATGAG CCAGTTCTTA AAATCGCATA AGGTAATTCA
  841 CAATGATTAA AGTTGAAATT AAACCATCTC AAGCCCAATT TACTACTCGT TCTGGTGTTT
  901 CTCGTCAGGG CAAGCCTTAT TCACTGAATG AGCAGCTTTG TTACGTTGAT TGGGGTAATG
  961 AATATCCGGT TCTTGTCAAG ATTACTCTTG ATGAAGGTCA GCCAGCCTAT GCGCCTGGTC
 1021 TGTACACCGT TCATCTGTCC TCTTTCAAAG TTGGTCAGTT CGGTTCCCTT ATGATTGACC
 1081 GTCTGCGCCT CGTTCCGGCT AAGTAACATG GAGCAGGTCG CGGATTTCGA CACAATTTAT
 1141 CAGGCGATGA TACAAATCTC CGTTGTACTT TGTTTCGCGC TTGGTATAAT CGCTGGGGGT
 1201 CAAAGATGAG TGTTTTAGTG TATTCTTTTG CCTCTTTCGT TTTAGGTTGG TGCCTTCGTA
 1261 GTGGCATTAC GTATTTTACC CGTTTAATGG AAACTTCCTC ATGAAAAAGT CTTTAGTCCT
 1321 CAAAGCCTCT GTAGCCGTTG CTACCCTCGT TCCGATGCTG TCTTTCGCTG CTGAGGGTGA
 1381 CGATCCCGCA AAAGCGGCCT TTAACTCCCT GCAAGCCTCA GCGACCGAAT ATATCGGTTA
 1441 TGCGTGGGCG ATGGTTGTTG TCATTGTCGG CGCAACTATC GGTATCAAGC TGTTTAAGAA
 1501 ATTCACCTCG AAAGCAAGCT GATAAACCGA TACAATTAAA GGCTCCTTTT GGAGCCTTTT
 1561 TTTTTGGAGA TTTTCAACGT GAAAAAATTA TTATTCGCAA TTCCTTTAGT TGTTCCTTTC
 1621 TATTCTCACT CCGCTGAAAC TGTTGAAAGT TGTTTAGCAA ATCCCATAC AGAAAATTCA
 1681 TTTACTAACG TCTGGAAAGA CGACAAAACT TTAGATCGTT ACGCTAACTA TGAGGGCTGT
 1741 CTGTGGAATG CTACAGGCGT TGTAGTTTGT ACTGGTGACG AAACTCAGTG TTACGGTACA
 1801 TGGGTTCCTA TTGGGCTTGC TATCCCTGAA AATGAGGGTG GTGGCTCTGA GGGTGGCGGT
 1861 TCTGAGGGTG GCGGTTCTGA GGGTGGCGGT ACTAAACCTC CTGAGTACGG TGATACACCT
 1921 ATTCCGGGCT ATACTTATAT CAACCCTCTC GACGGCACTT ATCCGCCTGG TACTGAGCAA
 1981 AACCCCGCTA ATCCTAATCC TTCTCTTGAG GAGTCTCAGC CTCTTAATAC TTTCATGTTT
 2041 CAGAATAATA GGTTCCGAAA TAGGCAGGGG GCATTAACTG TTTATACGGG CACTGTTACT
 2101 CAAGGCACTG ACCCCGTTAA AACTTATTAC CAGTACACTC CTGTATCATC AAAAGCCATG
 2161 TATGACGCTT ACTGGAACGG TAAATTCAGA GACTGCGCTT TCCATTCTGG CTTTAATGAG
 2221 GATTTATTTG TTTGTGAATA TCAAGGCCAA TCGTCTGACC TGCCTCAACC TCCTGTCAAT
```

TABLE 13-continued

DNA of a Display Phage displaying TFPI2 KuDom2 (SEQ ID NO: 25)

```
2281  GCTGGCGGCG GCTCTGGTGG TGGTTCTGGT GGCGGCTCTG AGGGTGGTGG CTCTGAGGGT
2341  GGCGGTTCTG AGGGTGGCGG CTCTGAGGGA GGCGGTTCCG GTGGTGGCTC TGGTTCCGGT
2401  GATTTTGATT ATGAAAAGAT GGCAAACGCT AATAAGGGGG CTATGACCGA AAATGCCGAT
2461  GAAAACGCGC TACAGTCTGA CGCTAAAGGC AAACTTGATT CTGTCGCTAC TGATTACGGT
2521  GCTGCTATCG ATGGTTTCAT TGGTGACGTT TCCGGCCTTG CTAATGGTAA TGGTGCTACT
2581  GGTGATTTTG CTGGCTCTAA TTCCCAAATG GCTCAAGTCG GTGACGGTGA TAATTCACCT
2641  TTAATGAATA ATTTCCGTCA ATATTTACCT TCCCTCCCTC AATCGGTTGA ATGTCGCCCT
2701  TTTGTCTTTG GCGCTGGTAA ACCATATGAA TTTTCTATTG ATTGTGACAA AATAAACTTA
2761  TTCCGTGGTG TCTTTGCGTT TCTTTTATAT GTTGCCACCT TTATGTATGT ATTTTCTACG
2821  TTTGCTAACA TACTGCGTAA TAAGGAGTCT TAATCATGCC AGTTCTTTTG GGTATTCCGT
2881  TATTATTGCG TTTCCTCGGT TTCCTTCTGG TAACTTTGTT CGGCTATCTG CTTACTTTTC
2941  TTAAAAAGGG CTTCGGTAAG ATAGCTATTG CTATTTCATT GTTTCTTGCT CTTATTATTG
3001  GGCTTAACTC AATTCTTGTG GGTTATCTCT CTGATATTAG CGCTCAATTA CCCTCTGACT
3061  TTGTTCAGGG TGTTCAGTTA ATTCTCCCGT CTAATGCGCT TCCCTGTTTT TATGTTATTC
3121  TCTCTGTAAA GGCTGCTATT TTCATTTTTG ACGTTAAACA AAAAATCGTT TCTTATTTGG
3181  ATTGGGATAA ATAATATGGC TGTTTATTTT GTAACTGGCA AATTAGGCTC TGGAAAGACG
3241  CTCGTTAGCG TTGGTAAGAT TCAGGATAAA ATTGTAGCTG GGTGCAAAAT AGCAACTAAT
3301  CTTGATTTAA GGCTTCAAAA CCTCCCGCAA GTCGGGAGGT TCGCTAAAAC GCCTCGCGTT
3361  CTTAGAATAC CGGATAAGCC TTCTATATCT GATTTGCTTG CTATTGGGCG CGGTAATGAT
3421  TCCTACGATG AAAATAAAAA CGGCTTGCTT GTTCTCGATG AGTGCGGTAC TTGGTTTAAT
3481  ACCCGTTCTT GGAATGATAA GGAAAGACAG CCGATTATTG ATTGGTTTCT ACATGCTCGT
3541  AAATTAGGAT GGGATATTAT TTTTCTTGTT CAGGACTTAT CTATTGTTGA TAAACAGGCG
3601  CGTTCTGCAT TAGCTGAACA TGTTGTTTAT TGTCGTCGTC TGGACAGAAT TACTTTACCT
3661  TTTGTCGGTA CTTTATATTC TCTTATTACT GGCTCGAAAA TGCCTCTGCC TAAATTACAT
3721  GTTGGCGTTG TTAAATATGG CGATTCTCAA TTAAGCCCTA CTGTTGAGCG TTGGCTTTAT
3781  ACTGGTAAGA ATTTGTATAA CGCATATGAT ACTAAACAGG CTTTTTCTAG TAATTATGAT
3841  TCCGGTGTTT ATTCTTATTT AACGCCTTAT TTATCACACG GTCGGTATTT CAAACCATTA
3901  AATTTAGGTC AGAAGATGAA ATTAACTAAA ATATATTTGA AAAGTTTTC TCGCGTTCTT
3961  TGTCTTGCGA TTGGATTTGC ATCAGCATTT ACATATAGTT ATATAACCCA ACCTAAGCCG
4021  GAGGTTAAAA AGGTAGTCTC TCAGACCTAT GATTTTGATA AATTCACTAT TGACTCTTCT
4081  CAGCGTCTTA ATCTAAGCTA TCGCTATGTT TTCAAGGATT CTAAGGGAAA ATTAATTAAT
4141  AGCGACGATT TACAGAAGCA AGGTTATTCA CTCACATATA TTGATTTATG TACTGTTTCC
4201  ATTAAAAAAG GTAATTCAAA TGAAATTGTT AAATGTAATT AATTTTGTTT TCTTGATGTT
4261  TGTTTCATCA TCTTCTTTTG CTCAGGTAAT TGAAATGAAT AATTCGCCTC TGCGCGATTT
4321  TGTAACTTGG TATTCAAAGC AATCAGGCGA ATCCGTTATT GTTTCTCCCG ATGTAAAAGG
4381  TACTGTTACT GTATATTCAT CTGACGTTAA ACCTGAAAAT CTACGCAATT TCTTTATTTC
4441  TGTTTTACGT GCAAATAATT TTGATATGGT AGGTTCTAAC CCTTCCATAA TTCAGAAGTA
4501  TAATCCAAAC AATCAGGATT ATATTGATGA ATTGCCATCA TCTGATAATC AGGAATATGA
4561  TGATAATTCC GCTCCTTCTG GTGGTTTCTT TGTTCCGCAA AATGATAATG TTACTCAAAC
```

TABLE 13-continued

| DNA of a Display Phage displaying TFPI2 KuDom2 (SEQ ID NO: 25) |
|---|

```
4621  TTTTAAAATT AATAACGTTC GGGCAAAGGA TTTAATACGA GTTGTCGAAT TGTTTGTAAA
4681  GTCTAATACT TCTAAATCCT CAAATGTATT ATCTATTGAC GGCTCTAATC TATTAGTTGT
4741  TAGTGCTCCT AAAGATATTT TAGATAACCT TCCTCAATTC CTTTCAACTG TTGATTTGCC
4801  AACTGACCAG ATATTGATTG AGGGTTTGAT ATTTGAGGTT CAGCAAGGTG ATGCTTTAGA
4861  TTTTTCATTT GCTGCTGGCT CTCAGCGTGG CACTGTTGCA GGCGGTGTTA ATACTGACCG
4921  CCTCACCTCT GTTTTATCTT CTGCTGGTGG TTCGTTCGGT ATTTTTAATG GCGATGTTTT
4981  AGGGCTATCA GTTCGCGCAT TAAAGACTAA TAGCCATTCA AAATATTGT CTGTGCCACG
5041  TATTCTTACG CTTTCAGGTC AGAAGGGTTC TATCTCTGTT GGCCAGAATG TCCCTTTTAT
5101  TACTGGTCGT GTGACTGGTG AATCTGCCAA TGTAAATAAT CCATTTCAGA CGATTGAGCG
5161  TCAAAATGTA GGTATTTCCA TGAGCGTTTT TCCTGTTGCA ATGGCTGGCG GTAATATTGT
5221  TCTGGATATT ACCAGCAAGG CCGATAGTTT GAGTTCTTCT ACTCAGGCAA GTGATGTTAT
5281  TACTAATCAA AGAAGTATTG CTACAACGGT TAATTTGCGT GATGGACAGA CTCTTTTACT
5341  CGGTGGCCTC ACTGATTATA AAAACACTTC TCAGGATTCT GGCGTACCGT TCCTGTCTAA
5401  AATCCCTTTA ATCGGCCTCC TGTTTAGCTC CCGCTCTGAT TCTAACGAGG AAAGCACGTT
5461  ATACGTGCTC GTCAAAGCAA CCATAGTACG CGCCCTGTAG CGGCGCATTA AGCGCGGCGG
5521  GTGTGGTGGT TACGCGCAGC GTGACCGCTA CACTTGCCAG CGCCCTAGCG CCCGCTCCTT
5581  TCGCTTTCTT CCCTTCCTTT CTCGCCACGT TCGCCGGCTT TCCCCGTCAA GCTCTAAATC
5641  GGGGGCTCCC TTTAGGGTTC CGATTTAGTG CTTTACGGCA CCTCGACCCC AAAAAACTTG
5701  ATTTGGGTGA TGGTTGGCCA TCGCCCTGAT AGACGGTTTT TCGCCCTTTG ACGTTGGAGT
5761  CCACGTTCTT TAATAGTGGA CTCTTGTTCC AAACTGGAAC AACACTCAAC CCTATCTCGG
5821  GCTATTCTTT TGATTTATAA GGGATTTTGC CGATTTCGGA ACCACCATCA AACAGGATTT
5881  TCGCCTGCTG GGGCAAACCA GCGTGGACCG CTTGCTGCAA CTCTCTCAGG GCCAGGCGGT
5941  GAAGGGCAAT CAGCTGTTGC CCGTCTCACT GGTGAAAAGA AAACCACCC TGGATCCAAG
6001  CTTGCAGGTG GCACTTTTCG GGGAAATGTG CGCGGAACCC CTATTTGTTT ATTTTTCTAA
6061  ATACATTCAA ATATGTATCC GCTCATGAGA CAATAACCCT GATAAATGCT TCAATAATAT
6121  TGAAAAAGGA AGAGTATGAG TATTCAACAT TTCCGTGTCG CCCTTATTCC CTTTTTTGCG
6181  GCATTTTGCC TTCCTGTTTT TGCTCACCCA GAAACGCTGG TGAAAGTAAA AGATGCTGAA
6241  GATCAGTTGG GCGCACTAGT GGGTTACATC GAACTGGATC TCAACAGCGG TAAGATCCTT
6301  GAGAGTTTTC GCCCCGAAGA ACGTTTTCCA ATGATGAGCA CTTTTAAAGT TCTGCTATGT
6361  GGCGCGGTAT TATCCCGTAT TGACGCCGGG CAAGAGCAAC TCGGTCGCCG CATACACTAT
6421  TCTCAGAATG ACTTGGTTGA GTACTCACCA GTCACAGAAA AGCATCTTAC GGATGGCATG
6481  ACAGTAAGAG AATTATGCAG TGCTGCCATA ACCATGAGTG ATAACACTGC GGCCAACTTA
6541  CTTCTGACAA CGATCGGAGG ACCGAAGGAG CTAACCGCTT TTTTGCACAA CATGGGGGAT
6601  CATGTAACTC GCCTTGATCG TTGGGAACCG GAGCTGAATG AAGCCATACC AAACGACGAG
6661  CGTGACACCA CGATGCCTGT AGCAATGGCA ACAACGTTGC GCAAACTATT AACTGGCGAA
6721  CTACTTACTC TAGCTTCCCG GCAACAATTA ATAGACTGGA TGGAGGCGGA TAAAGTTGCA
6781  GGACCACTTC TGCGCTCGGC CCTTCCGGCT GGCTGGTTTA TTGCTGATAA ATCTGGAGCC
6841  GGTGAGCGTG GGTCTCGCGG TATCATTGCA GCACTGGGGC CAGATGGTAA GCCCTCCCGT
6901  ATCGTAGTTA TCTACACGAC GGGGAGTCAG GCAACTATGG ATGAACGAAA TAGACAGATC
```

TABLE 13-continued

| DNA of a Display Phage displaying TFPI2 KuDom2 (SEQ ID NO: 25) |
|---|

```
6961  GCTGAGATAG GTGCCTCACT GATTAAGCAT TGGTAACTGT CAGACCAAGT TTACTCATAT

7021  ATACTTTAGA TTGATTTAAA ACTTCATTTT TAATTTAAAA GGATCTAGGT GAAGATCCTT

7081  TTTGATAATC TCATGACCAA ATCCCTTAA CGTGAGTTTT CGTTCCACTG TACGTAAGAC

7141  CCCCAAGCTT GTCGACTGAA TGGCGAATGG CGCTTTGCCT GGTTTCCGGC ACCAGAAGCG

7201  GTGCCGGAAA GCTGGCTGGA GTGCGATCTT CCTGACGCTC GAGCGCAACG CAATTAATGT

7261  GAGTTAGCTC ACTCATTAGG CACCCCAGGC TTTACACTTT ATGCTTCCGG CTCGTATGTT

7321  GTGTGGAATT GTGAGCGGAT AACAATTTCA CACAGGAAAC AGCTATGACC ATGATTACGC

7381  CAAGCTTTGG AGCCTTTTTT TTGGAGATTT TCAACGTGAA AAAATTATTA TTCGCAATTC

7441  CTTTAGTTGT TCCTTTCTAT TCCATGGCTG ATGTTCCTAA GGTTTGTCGT CTGCAGGTTT

7501  CTGTTGACGA TCAATGTGAG GGTTCTACTG AAAAGTATTT TTTCAACCTG AGCTCTATGA

7561  CTTGCGAAAA GTTCTTTTCT GGTGGTTGCC ATCGTAACCG TATCGAGAAC CGGTTTCCGG

7621  ACGAGGCTAC TTGTATGGGT TTCTGTGCTC CTAAGCCTGC TGACGCTAGC TCTGCTAGTG

7681  GCGACTTCGA CTACGAGAAA ATGGCTAATG CCAACAAAGG CGCCATGACT GAGAACGCTG

7741  ACGAGAATGC TTTGCAAAGC GATGCCAAGG GTAAGTTAGA CAGCGTCGCG ACCGACTATG

7801  GCGCCGCCAT CGACGGCTTT ATCGGCGATG TCAGTGGTTT GGCCAACGGC AACGGAGCCA

7861  CCGGAGACTT CGCAGGTTCG AATTCTCAGA TGGCCCAGGT TGGAGATGGG ACAACAGTC

7921  CGCTTATGAA CAACTTTAGA CAGTACCTTC CGTCTCTTCC GCAGAGTGTC GAGTGCCGTC

7981  CATTCGTTTT CGGTGCCGGC AAGCCTTACG AGTTCAGCAT CGACTGCGAT AAGATCAATC

8041  TTTTCCGCGG CGTTTTCGCT TTCTTGCTAT ACGTCGCTAC TTTCATGTAC GTTTTCAGCA

8101  CTTTCGCCAA TATTTTACGC AACAAGAAA GCTAGTGATC TCCTAGGAAG CCCGCCTAAT

8161  GAGCGGGCTT TTTTTTTCTG GTATGCATCC TGAGGCCGAT ACTGTCGTCG TCCCCTCAAA

8221  CTGGCAGATG CACGGTTACG ATGCGCCCAT CTACACCAAC GTGACCTATC CCATTACGGT

8281  CAATCCGCCG TTTGTTCCCA CGGAGAATCC GACGGGTTGT TACTCGCTCA CATTTAATGT

8341  TGATGAAAGC TGGCTACAGG AAGGCCAGAC GCGAATTATT TTTGATGGCG TTCCTATTGG

8401  TTAAAAAATG AGCTGATTTA ACAAAAATTT AATGCGAATT TTAACAAAAT ATTAACGTTT

8461  ACAATTTAAA TATTTGCTTA TACAATCTTC CTGTTTTTGG GGCTTTTCTG ATTATCAACC

8521  GGGGTACATA TGATTGACAT GCTAGTTTTA CGATTACCGT TCATCGATTC TCTTGTTTGC

8581  TCCAGACTCT CAGGCAATGA CCTGATAGCC TTTGTAGATC TCTCAAAAAT AGCTACCCTC

8641  TCCGGCATTA ATTTATCAGC TAGAACGGTT GAATATCATA TTGATGGTGA TTTGACTGTC

8701  TCCGGCCTTT CTCACCCTTT TGAATCTTTA CCTACACATT ACTCAGGCAT TGCATTTAAA

8761  ATATATGAGG GTTCTAAAAA TTTTTATCCT TGCGTTGAAA TAAAGGCTTC TCCCGCAAAA

8821  GTATTACAGG GTCATAATGT TTTTGGTACA ACCGATTTAG CTTTATGCTC TGAGGCTTTA

8881  TTGCTTAATT TTGCTAATTC TTTGCCTTGC CTGTATGATT TATTGGATGT T
```

TABLE 14

ONs to make library of TFPI2 KuDom2

1 ON1U21T2 (SEQ ID NO: 26)
5' GGG TCT TCT GTA CGA GTT CTG 3'

2 ON147L21 (SEQ ID NO: 27)
5' CCT CCA GAG TTG ACA GAA TCC 3'

3 ON1U96 (SEQ ID NO: 28)
5' GGG TCT TCT GTA CGA GTT CTG CAG GTT TCT GTT RRK RRK NNK TGT NNK GST NNK NNK NNK ARG TAT TTT TTC AAC CTG AGC TCT ATG ACT TGC GAA 3'

TABLE 14-continued

ONs to make library of TFPI2 KuDom2

4 ON71L97 (SEQ ID NO: 29)
5' CCTCCAGAGTTGACAGAATC CGG AAA CCG GTT CTC MNY MYY GTT MYY MNN GCA ACC ACC AKA MNN GAA CTT TTC GCA AGT CAT AGA GCT CAG GTT GA 3'

$8^4 \times 20^7 \times 2^3 \times 16 = 6.7$ E 14 AA sequences
$8^4 \times 32^7 \times 2^3 \times 16 = 1.8$ E 16 DNA sequences
Fraction without stops = 0.80; only TAG allowed.

TABLE 15

ONs for construction of modified tfpi gene shown in TABLE 4.

| No. | Name | Sequence (5'-to-3') | SEQ ID NO: | U/L | Len |
|---|---|---|---|---|---|
| 1 | ONMatureT | gat tct gag gaa gat gaa gaa ca | 30 | U | 829 |
| 2 | ON1019L27 | aca tat ttt taa caa aaa ttt ctt cat | 31 | L | |
| 3 | ONSfiIT | ttaatcttgcg gcc aca ggg gcc cac tcc gac tct gag gaa gat gaa gaa | 32 | U | 95 |
| 4 | ONSacHinL | cat aag Ctt cag tgg tgg GaG ctc cgt atc | 33 | L | |
| 5 | ONSacHinU | gat acg gag CtC cca cca ctg aaG ctt atg | 34 | U | 120 |
| 6 | ONMluIL | ttc gca ctg Acg Cgt gaa aa | 35 | L | |
| 7 | ONMluIU | tt ttc acG cgT cag tgc gaa | 36 | U | 76 |
| 8 | ONBBBL | tc ttc cag aGA ttc aaa tcg att ctg Gtt Acc ttc aca tcc | 37 | L | |
| 9 | ONBBBU | gga tgt gaa ggT aaC cag aat cga ttt gaa TCt ctg gaa ga | 38 | U | 142 |
| 10 | ONXhoBamL | t tcc agg atc ctc ctc gag aaa gca gaa a | 39 | L | |
| 11 | ONXhoBamU | t ttc tgc ttt CtC gaG gaG gat cct gga a | 40 | U | 142 |
| 12 | ONBsmBIL | ttc ttc cag Cgt ctc aaa a | 41 | L | |
| 13 | ONBsmBIU | t ttt gag acG ctg gaa gaa | 42 | U | 74 |
| 14 | ONApaSalL | c ata att Gtc Gac ctg gaa acc att Ggg Ccc atc ttc a | 43 | L | |
| 15 | ONApaSalU | t gaa gat ggG ccC aat ggt ttc cag gtC gaC aat tat g | 44 | U | 148 |
| 16 | ONSac2L | tcc tct gtc cgc ggg agt gag a | 45 | L | |
| 17 | ONSac2U | t ctc act ccC gcG gac aga gga | 46 | U | 102 |
| 18 | ONBspE2L | cc aca tcc GGA Ata ctt aaa tg | 47 | L | |
| 19 | ONBspE2U | ca ttt aag taT TCC gga tgt ggg g | 48 | U | 74 |
| 20 | ONBssH2L | ttt aca tgc GcG cag aca ttc t | 49 | L | |
| 21 | ONBssH2U | a gaa tgt ctg CgC gca tgt aaa | 50 | U | 147 |
| 22 | ONfinalL | ttgTtTCTaGaTCAtTacatattttt aacaa aaatttcttcat | 51 | L | |

TABLE 15-continued

ONs for construction of modified tfpi gene shown in TABLE 4.

| No. | Name | Sequence (5'-to-3') | SEQ ID NO: | U/L | Len |
|---|---|---|---|---|---|
| 3 | ONSfiI | ttaatcttgcg gcc aca ggg gcc cac tcc gac tct gag gaa gat gaa gaa | 52 | U | 874 |
| 26 | ONfinalL | ttgTtTCTaGaTCAtTacatattttaacaa aaatttcttcat | 53 | L | |

The primers are upper strand (U) or lower strand (L) as indicated in the U/L column.
"Len" indicates the length of the product obtained with human tfpi cDNA as template and the U-L pair of primers.
Uppercase BASES indicate departures from the published cDNA sequence.
Restriction sites are shown bold. Where two restriction sites overlap, one is shown as underscored.

TABLE 16

Modified Human TFPI = PlaKalE101 (SEQ ID NO: 54)

| AAs | Function | AA sequence |
|---|---|---|
| 1-21 | Linker 1 | DSEEDEEHTIITDTELPPLKL |
| 22-79 | KuDom 1 Inhibit plasmin | MHSFCAFKADDGPCRARFDRWFFNIFTRQCEEFIYGGCEGNQNRFESLEECKKMCTRD |
| 80-92 | Linker 2 | NANRIIKTTLQQE |
| 93-150 | KuDom 2 Inhibit h.pKal | KPDFCFLEEDPGPCRAAHPRWFYNnQTKQCERFIYGGCEGNMNNFETLEECKNICEDG |
| 151-184 | Linker 3 | PNGFQVDNYGTQLNAVnNSLTPQSTKVPSLFEFH |
| 185-242 | KuDom 3 Inhibit h.NE | GPSWCLTPADRGPCIAFFPRFYYNSVIGKCRPFPYGGCQGNENnFTSKQECLRACKKG <br> 1  5  1  1  2  2  3  3  4  4  5  5  5 <br> 8  5  0  5  0  5  0  5  0  5  0  5  8 |
| 243-248 | Linker 4 | FIQRIS |

Possible sites of glycosylation are shown as "n".

TABLE 17

ONs for construction of gene encoding PlaKalE101

(SEQ ID NO: 55)
1 Get_TFPI_top
5' ATG ATT TAC ACA ATG AAG AAA GTA CAT 3'

(SEQ ID NO: 56)
2 ON937L24
5' TGA TAT TCT TTG GAT GAA ACC TTT 3'

(SEQ ID NO: 57)
3 MutK1:310U43
5' GAT GGC CCA TGT CGT GCA CGC TTC GAT AGA TGG TTC AAT A 3'

(SEQ ID NO: 58)
4 MutK1:310L43
5' T ATT GAA GAA CCA TCT ATC GAA GCG TGC ACG ACA TGG GCC ATC 3'

(SEQ ID NO: 59)
5 MutK2:517U56
5' GAA GAT CCT GGA CCT TGT CGA GCT GCT CAT CCC AGG TGG TTT TAT AAC AAT CAG AC 3'

(SEQ ID NO: 60)
6 MutK2:517L56
5' GT CTG ATT GTT ATA AAA CCA CCT GGG ATG AGC AGC TCG ACA AGG TCC AGG ATC TTC 3'

(SEQ ID NO: 61)
7 MutK2:577U47
5' CAG TGT GAA CGT TTC ATT TAT GGT GGA TGC GAG GGC AAT ATG AAC AA 3'

(SEQ ID NO: 62)
8 MutK2:577L47
5' TT GTT CAT ATT GCC CTC GCA TCC ACC ATA AAT GAA ACG TTC ACA CTG 3'

(SEQ ID NO: 63)
9 MutK3:792U55
5' A GCA GAC AGA GGA CCT TGT ATT GCC TTT TTT CCC AGA TTC TAC TAC AAT TCA GTC 3'

TABLE 17-continued

ONs for construction of gene encoding PlaKalEl01

(SEQ ID NO: 64)
10  MutK3:792L55
5' GAC TGA ATT GTA GTA GAA TCT GGG AAA AAA GGC AAT
ACA AGG TCC TCT GTC TGC T 3'

(SEQ ID NO: 65)
11  MutK3:867U31
5' T AAG TAC GGT GGA TGT CAG GGA AAT GAA AAC 3'

(SEQ ID NO: 66)
12  MutK3:867L31
5' GTT TTC ATT TCC CTG ACA TCC ACC GTA CTT A 3'

(SEQ ID NO: 67)
13  ONNcoI
5' agattttacttC C atg Gtt tac aca atg aag aaa gt 3'

(SEQ ID NO: 68)
14  ONLowCapPKE
5' ctcttgttttctagatcatta TGA TAT TCT TTG GAT GAA ACC TTT 3'

TABLE 18

| PlaKalEl01::(GGS)₄GG::has (SEQ ID NO: 69) | | |
|---|---|---|
| AAs | Function | AA sequence |
| 1-28 | signal | MIYTMKKVHALWASVCLLLNLAPAPLNA |
| 29-49 | Linker 1 | DSEEDEEHTIITDTELPPLKL |
| 50-107 | KuDom 1 | MHSFCAFKADDGPCRARFDRWFFNIFTRQCEEFIYGGCEGNQNRFESLEECKKMCTRD |
| 108-120 | Linker 2 | NANRIIKTTLQQE |
| 121-178 | KuDom 2 | KPDFCFLEEDPGPCRAAHPRWFYNnQTKQCERFIYGGCEGNMMNFETLEECKNICEDG |
| 179-212 | Linker 3 | PNGFQVDNYGTQLNAVnNSLTPQSTKVPSLFEFH |
| 213-270 | KuDom 3 | GPSWCLTPADRGPCIAFFPRFYYNSVIGKCRPFPYGGCQGNENnFTSKQECLRACKKG |
|   |   |        1      5    10    15    20    25    30    35    40    45    50    55 58 |
| 271-276 | Linker 4 | FIQRIS |
| 277-290 | Linker 5 | GGSGGSGGSGGSGG |
| 291-865 | hSA | DAHKSE VAHRFKDLGE ENFKALVLIA<br>FAQYLQQCPF EDHVKLVNEV TEFAKTCVAD ESAENCDKSL HTLFGDKLCT<br>VATLRETYGE MADCCAKQEP ERNECFLQHK DDNPNLPRLV RPEVDVMCTA<br>FHDNEETFLK KYLYEIARRH PYFYAPELLF FAKRYKAAFT ECCQAADKAA<br>CLLPKLDELR DEGKASSAKQ RLKCASLQKF GERAFKAWAV ARLSQRFPKA<br>EFAEVSKLVT DLTKVHTECC HGDLLECADD RADLAKYICE NQDSISSKLK<br>ECCEKPLLEK SHCIAEVEND EMPADLPSLA ADFVESKDVC KNYAEAKDVF<br>LGMFLYEYAR RHPDYSVVLL LRLAKTYETT LEKCCAAADP HECYAKVFDE<br>FKPLVEEPQN LIKQNCELFE QLGEYKFQNA LLVRYTKKVP QVSTPTLVEV<br>SRNLGKVGSK CCKHPEAKRM PCAEDYLSVV LNQLCVLHEK TPVSDRVTKC<br>CTESLVNRRP CFSALEVDET YVPKEFNAET FTFHADICTL SEKERQIKKQ<br>TALVELVKHK PKATKEQLKA VMDDFAAFVE KCCKADDKET CFAEEGKKLV<br>AASQAALGL |

Possible sites of glycosylation are shown as "n".

TABLE 19

| Modified Human TFPI dimer = PKEPKE02 (SEQ ID NO: 70) | | |
|---|---|---|
| AAs | Function | AA sequence |
| 1-21 | Linker 1 | DSEEDEEHTIITDTELPPLKL |
| 22-79 | KuDom 1 | MHSFCAFKADDGPCRARFDRWFFNIFTRQCEEFIYGGCEGNQNRFESLEECKKMCTRD |
| 80-92 | Linker 2 | NANRIIKTTLQQE |
| 93-150 | KuDom 2 | KPDFCFLEEDPGPCRAAHPRWFYNnQTKQCERFIYGGCEGNMMNFETLEECKNICEDG |
| 151-184 | Linker 3 | PNGFQVDNYGTQLNAVnNSLTPQSTKVPSLFEFH |

TABLE 19-continued

Modified Human TFPI dimer = PKEPKE02 (SEQ ID NO: 70)

| AAs | Function | AA sequence |
|---|---|---|
| 185-242 | KuDom 3 | GPSWCLTPADRGPCIAFFPRFYYNSVIGKCRPFKYGGCQGNENnFTSKQECLRACKKG<br>10 15 20 25 30 35 40 45 50 55 58 |
| 243-248 | Linker 4 | FIQRIS |
| 249-261 | Linker 5 | GGSGSSGGGSSGG |
| 262-282 | Linker 1 | DSEEDEEHTIITDTELPPLKL |
| 283-340 | KuDom 1 | MHSFCAFKADDGPCRARFDRWFFNIFTRQCEEFIYGGCEGNQNRFESLEECKKMCTRD |
| 341-353 | Linker 2 | NANRIIKTTLQQE |
| 354-411 | KuDom 2 | KPDFCFLEEDPGPCRAAHPRWFYNnQTKQCERFIYGGCEGNMNNFETLEECKNICEDG |
| 412-445 | Linker 3 | PNGFQVDNYGTQLNAVnNSLTPQSTKVPSLFEFH |
| 446-503 | KuDom 3 | GPSWCLTPADRGPCIAFFPRFYYNSVIGKCRPFKYGGCQGNENnFTSKQECLRACKKG |
| 504-509 | | FIQRIS |

Possible sites of glycosylation are shown as "n".

TABLE 20

TF88890-2 (SEQ ID NO: 71)

| AA No. | Function | AA sequence |
|---|---|---|
| 1-58 | pKal inhibition | MHSFCAFKADDGPCRAAHPRWFFNIFTRQCEEFIYGGCEGNQNRFESLEECKKMCTRD |
| 59-70 | Linker | GGSGGSSSSSGG |
| 71-128 | h.NE inhibition | MHSFCAFKADDGPCIAFFPRFFFNIFTRQCEEFIYGGCQGNQNRFESLEECKKMCTRD |

TABLE 21

TF88890-3 (SEQ ID NO: 72)

| AA No. | Function | AA sequence |
|---|---|---|
| 1-58 | pKal inhibition | MHSFCAFKADDGPCRAAHPRWFFNIFTRQCEEFIYGGCEGNQNRFESLEECKKMCTRD |
| 59-70 | Linker | GGSGGSSSSSGG |
| 71-128 | h.NE inhibition | MHSFCAFKADDGPCIAFFPRFFFNIFTRQCEEFIYGGCQGNQNRFESLEECKKMCTRD |
| 129-140 | Linker | GGSGGSSSSSGG |
| 141-198 | pKal inhibition | MHSFCAFKADDGPCRAAHPRWFFNIFTRQCEEFIYGGCEGNQNRFESLEECKKMCTRD |

TABLE 22

TF88890-4 (SEQ ID NO: 73)

| AA No. | Function | AA sequence |
|---|---|---|
| 1-58 | pKal inhibition | MHSFCAFKADDGPCRAAHPRWFFNIFTRQCEEFIYGGCEGNQNRFESLEECKKMCTRD |
| 59-70 | Linker | GGSGGSSSSSGG |
| 71-128 | h.NE inhibition | MHSFCAFKADDGPCIAFFPRFFFNIFTRQCEEFIYGGCQGNQNRFESLEECKKMCTRD |
| 129-140 | Linker | GGSGGSSSSSGG |
| 141-198 | pKal inhibition | MHSFCAFKADDGPCRAAHPRWFFNIFTRQCEEFIYGGCEGNQNRFESLEECKKMCTRD |
| 199-210 | Linker | GGSGGSSSSSGG |
| 211-268 | h.NE inhibition | MHSFCAFKADDGPCIAFFPRFFFNIFTRQCEEFIYGGCQGNQNRFESLEECKKMCTRD |

TABLE 23

TF88890-5 (SEQ ID NO: 74)

| AA No. | Function | AA sequence |
|---|---|---|
| 1-58 | pKal inhibition | MHSFCAFKADDGPCRAAHPRWFFNIFTRQCEEFIYGGCEGNQNRFESLEECKKMCTRD |
| 59-75 | Linker | GGSGNGSSSSGGGSGSG |
| 76-133 | h.NE inhibition | MHSFCAFKADDGPCIAFFPRFFFNIFTRQCEEFIYGGCQGNQNRFESLEECKKMCTRD |
| 134-150 | Linker | GGSGNGSSSSGGGSGSG |
| 151-208 | pKal inhibition | MHSFCAFKADDGPCRAAHPRWFFNIFTRQCEEFIYGGCEGNQNRFESLEECKKMCTRD |
| 209-225 | Linker | GGSGNGSSSSGGGSGSG |
| 226-283 | h.NE inhibition | MHSFCAFKADDGPCIAFFPRFFFNIFTRQCEEFIYGGCQGNQNRFESLEECKKMCTRD |

TABLE 24

TF890-6 (SEQ ID NO: 75)

| AA No. | Function | AA sequence |
|---|---|---|
| 1-58 | h.NE inhibition | MHSFCAFKADDGPCIAFFPRFFFNIFTRQCE EFIYGGCQGNQNRFESLEECKKMCTRD |
| 59-70 | Linker | GGSGGSSSSSGG |
| 71-128 | h.NE inhibition | MHSFCAFKADDGPCIAFFPRFFFNIFTRQCE EFIYGGCQGNQNRFESLEECKKMCTRD |
| 129-140 | Linker | GGSGGSSSSSGG |
| 141-198 | h.NE inhibition | MHSFCAFKADDGPCIAFFPRFFFNIFTRQCE EFIYGGCQGNQNRFESLEECKKMCTRD |
| 199-210 | Linker | GGSGGSSSSSGG |
| 211-268 | h.NE inhibition | MHSFCAFKADDGPCIAFFPRFFFNIFTRQCE EFIYGGCQGNQNRFESLEECKKMCTRD |
| 269-280 | Linker | GGSGGSSSSSGG |
| 281-338 | h.NE inhibition | MHSFCAFKADDGPCIAFFPRFFFNIFTRQCE EFIYGGCQGNQNRFESLEECKKMCTRD |
| 339-350 | Linker | GGSGSSSGSSSG |
| 351-408 | h.NE inhibition | MHSFCAFKADDGPCIAFFPRFFFNIFTRQCE EFIYGGCQGNQNRFESLEECKKMCTRD |

TABLE 25

TF890-8 (SEQ ID NO: 76)

| AA No. | Function | AA sequence |
|---|---|---|
| 1-58 | h.NE inhibition | MHSFCAFKADDGPCIAFFPRFFFNIFTRQCE EFIYGGCQGNQNRFESLEECKKMCTRD |
| 59-70 | Linker | GGSGGSSGSSGG |
| 71-128 | h.NE inhibition | MHSFCAFKADDGPCIAFFPRFFFNIFTRQCE EFIYGGCQGNQNRFESLEECKKMCTRD |
| 129-140 | Linker | GGSGGSSSSSGG |
| 141-198 | h.NE inhibition | MHSFCAFKADDGPCIAFFPRFFFNIFTRQCE EFIYGGCQGNQNRFESLEECKKMCTRD |
| 199-210 | Linker | GGSGGSGSSSGG |
| 211-268 | h.NE inhibition | MHSFCAFKADDGPCIAFFPRFFFNIFTRQCE EFIYGGCQGNQNRFESLEECKKMCTRD |
| 269-280 | Linker | GGSGGSSSSGSG |
| 281-338 | h.NE inhibition | MHSFCAFKADDGPCIAFFPRFFFNIFTRQCE EFIYGGCQGNQNRFESLEECKKMCTRD |
| 339-350 | Linker | GGSGSSSGSSSG |
| 351-408 | h.NE inhibition | MHSFCAFKADDGPCIAFFPRFFFNIFTRQCE EFIYGGCQGNQNRFESLEECKKMCTRD |
| 409-420 | Linker | GSGSSSGSGSSG |
| 421-478 | h.NE inhibition | MHSFCAFKADDGPCIAFFPRFFFNIFTRQCE EFIYGGCQGNQNRFESLEECKKMCTRD |
| 479-490 | Linker | GGSSSGSGSGSG |
| 491-548 | h.NE inhibition | MHSFCAFKADDGPCIAFFPRFFFNIFTRQCE EFIYGGCQGNQNRFESLEECKKMCTRD |

TABLE 26

Library for removal of 14-38 disulfide

```
! LACI-D1 display cassette for removal of 14-38 disulfide
!     Signal sequence of M13 iii-------------------------------
!      fM   K   K   L   L   F   A   I   P   L   V   V   P   F   Y
       gtg aaa aaa tta tta ttc gca att cct tta gtt gtt cct ttc tat
!
!              S   M   A                A   E   M   H   S   F
            tCC ATG Gcg             |gcc|gag|ATG|CAT|tcc|ttc
!              NcoI . . .                    NsiI . . .
!
!    C5   F   K   A  D10  D  X12 X13 X14 I15  A   F   F   P  R20  F
     tgc gcc ttc aag gct gac gaC GGT CCG tgt aTT gct TTc TTc CCt cgt ttc
!
!     F   F   N  I25  F   T   R   Q  C30  E   E   F   I   Y   G   G  X38
     ttc ttc aac att ttc ACG CGT cag tgc gag GAA TTC att tac ggt ggt tgt
!                              MluI . . .       EcoRI . . .
!
!    X39 G40  N   Q   N   R  F45  E   S   L  E49
     gaa GGT AAC Cag aAC CGG Ttc gaa tcT CTA Gag
!         BstEII . . . AgeI . . .      XbaI . . .
!                                AsuII . . .
!
!      E   C   K   K   M   C   T   R   D       S   A   S   S   A
                                                         (SEQ ID NO: 78)
     gaa tgt aag aag atg tgt act|cgt|gat|    tct GCT AGC tct gct
                                                         (SEQ ID NO: 77)
!                                              NheI . . .
! an anchor protein such as IIIstump follows.
!
! N = equimolar A,C,G, and T
! H = equimolar A, C, and T
```

TABLE 26-continued

Library for removal of 14-38 disulfide

```
! K = equimolar T and G
! B = equimolar C, G, and T
! V = equimolar A, C, and G
! M = equimolar A and C
! NHK encodes FLSY.PHQIMTNKVADE
! BGG encodes WRG
```

TABLE 27

Oligonucleotides for construction of KuDom Library missing 14-38 disulfide

```
! remove C14-C38 from TF890 20050727
All sequences are 5' to 3'.
1) ONTPrmr, 21 bases                       (SEQ ID NO: 79)
ggcTTcAcTTAccgTgTTccA 2) ONLoPrm, 20 bases                       (SEQ ID NO: 80)
ccAAgtAAccAcAAgTTTcT 3) ONTAAAxC, 113 bases                     (SEQ ID NO: 81)
ggcTTcAcTTAccgTgTTccATggcggccgAgATgcATTccTTcTgcgcc
TTcAAggcTgAcgAcNHKNHKNHKATTgcTTTcTTcccTcgTTTcTTcTT
cAAcATTTTcAcg 4) ONTAABxC, 113 bases                     (SEQ ID NO: 82)
ggcTTcAcTTAccgTgTTccATggcggccgAgATgcATTccTTcTgcgcc
TTcAAggcTgAcgAcNHKNHKBggATTgcTTTcTTcccTcgTTTcTTcTT
cAAcATTTTcAcg 5) ONTABAxC, 113 bases                     (SEQ ID NO: 83)
ggcTTcAcTTAccgTgTTccATggcggccgAgATgcATTccTTcTgcgcc
TTcAAggcTgAcgAcNHKBggNHKATTgcTTTcTTcccTcgTTTcTTcTT
cAAcATTTTcAcg 6) ONTABBxC, 113 bases                     (SEQ ID NO: 84)
ggcTTcAcTTAccgTgTTccATggcggccgAgATgcATTccTTcTgcgcc
TTcAAggcTgAcgAcNHKBggBggATTgcTTTcTTcccTcgTTTcTTcTT
cAAcATTTTcAcg 7) ONTBAAxC, 113 bases                     (SEQ ID NO: 85)
ggcTTcAcTTAccgTgTTccATggcggccgAgATgcATTccTTcTgcgcc
TTcAAggcTgAcgAcBggNHKNHKATTgcTTTcTTcccTcgTTTcTTcTT
cAAcATTTTcAcg 8) ONTBABxC, 113 bases                     (SEQ ID NO: 86)
ggcTTcAcTTAccgTgTTccATggcggccgAgATgcATTccTTcTgcgcc
TTcAAggcTgAcgAcBggNHKBggATTgcTTTcTTcccTcgTTTcTTcTT
cAAcATTTTcAcg 9) ONTBBAxC, 113 bases                     (SEQ ID NO: 87)
ggcTTcAcTTAccgTgTTccATggcggccgAgATgcATTccTTcTgcgcc
TTcAAggcTgAcgAcBggBggNHKATTgcTTTcTTcccTcgTTTcTTcTT
cAAcATTTTcAcg 10) ONTBBBxC, 113 bases                    (SEQ ID NO: 88)
ggcTTcAcTTAccgTgTTccATggcggccgAgATgcATTccTTcTgcgcc
TTcAAggcTgAcgAcBggBggBggATTgcTTTcTTcccTcgTTTcTTcTT
cAAcATTTTcAcg 11) ONLoAAxC, 106 bases                    (SEQ ID NO: 89)
ccAAgtAAccAcAAgTTTcTAgAgATTcgAAccggTTcTggTTAccMDNM
DNAccAccgTAAATgAATTccTcgcAcTgAcgcgcTgAAAATgTTgAAgAA
gAAAcg 12) ONLoABxC, 106 bases                    (SEQ ID NO: 90)
ccAAgtAAccAcAAgTTTcTAgAgATTcgAAccggTTcTggTTAcccVM
DNAccAccgTAAATgAATTccTcgcAcTgAcgcgcTgAAAATgTTgAAgAA
gAAAcg 13) ONLoBAxC, 106 bases                    (SEQ ID NO: 91)
ccAAgtAAccAcAAgTTTcTAgAgATTcgAAccggTTcTggTTAccMDNc
cVAccAccgTAAATgAATTccTcgcAcTgAcgcgcTgAAAATgTTgAAgAA
gAAAcg 14) ONLoBBxC, 106 bases                    (SEQ ID NO: 92)
ccAAgtAAccAcAAgTTTcTAgAgATTcgAAccggTTcTggTTAcccVc
cVAccAccgTAAATgAATTccTcgcAcTgAcgcgcTgAAAATgTTgAAgAA
gAAAcg
```

TABLE 28

Library for genetic diversity but constant AA sequence

```
! Gene encoding a DX-890-like TFPI K1 domain with linker.
! Null Library - Diversity at DNA level, all encode the same AA seq.
!
   1 tgtcctgcacagggtccact
!     scab . . .
!
!     1   2   3   4   5   6   7   8   9   10  11  12  13  14  15
!     G   S   G   M1  H   S   F   C5  A   F   K   A   D10 D   G
   16 |TCC|TCA|GGt|atg|caT|tcN|ttY|tgY|gcN|ttY|aaR|gcN|gaY|gaY|ggN|
!     Bsu36I . . . NsiI . . .
!
!     16  17  18  19  20  21  22  23  24  25  26  27  28  29  30
!     P   C14 I   A   F   F   P   R20 F   F   F   N   I25 F   T
   61 |ccN|tgY|atH|gcN|ttY|ttc|cct|cgt|ttc|ttt|ttc|aac|atH|ttY|ACN|
!
!     31  32  33  34  35  36  37  38  39  40  41  42  43  44  45
!     R   Q   C30 E   E   F   I   Y35 G   G   C38 Q   G40 N   Q
  106 |CGN|caR|tgY|gaR|GAR|TTY|atH|taY|ggN|ggN|tgY|caR|ggN|aaY|caR|
!
!     46  47  48  49  50  51  52  53  54  55  56  57  58  59  60
!     N   R   F45 E   S   L   E   E   C51 K   K   M   C55 T   R
  151 |aaY|cgN|ttt|gag|tct|ctt|gaa|gag|tgY|aaR|aaR|atg|tgY|acN|cgN|
!
```

TABLE 28-continued

Library for genetic diversity but constant AA sequence

```
!     61  62  63  64  65  66  67  68  69  70  71  72  73
!     D58 X_a X_b X_c X_d X_e X_f X_g X_H G_i S_j S_k G_l    (SEQ ID NO: 94)
  196 |gaY|RgY|RgY|RcY|RgY|RgY|Rgy|RgY|RgY|ggc|TCC|TCA|GGT|
!                                         BseRI . . .
!                                              Bsu36I . . .
      Cttctcgttacctggtgggc                                   (SEQ ID NO: 93)
!     scab . . .

1) ONUpPrmr890, 21 bases                                    (SEQ ID NO: 95)
TgTccTgcAcAgggTccAcTT 2) ONLoPrmr890, 21 bases                                    (SEQ ID NO: 96)
gcccAccAggTAAcgAgAAgA 3) UpperA890, 103 bases                                     (SEQ ID NO: 97)
TgTccTgcAcAgggTccAcTTccTcAggTATgcATTcNTTYTgYgcNTTYAARgcNgAYg
AYggNccNTgYATHgcNTTYTTcccTcgTTTcTTTTTcAAcAT 4) LowerB890, 101 bases                                     (SEQ ID NO: 98)
cAcTcTTcAAgAgAcTcAAANcgRTTYTgRTTNccYTgRcANccNccRTADATRAAYTcY
TcRcAYTgNcgNgTRAADATgTTgAAAAAgAAAcgAgggAA 5) TopStC890, 98 bases                                      (SEQ ID NO: 99)
TTTgAgTcTcTTgAAgAgTgYAARAARATgTgYAcNcgNgAYRgYRgYRgYRgYRgYRgY
RgYRgYggcTccTcAggTcTTcTcgTTAccTggTgggc
```

TABLE 29

A phage vector to display TFPI KuDom 1 and derivatives.

```
! DY3P82_TFPI1   8919 bases
!
! Non-cutters
!AatII GACGTc              Acc65I Ggtacc             AflII Cttaag
!ApaI GGGCCc               ApaLI Gtgcac              AscI GGcgcgcc
!BbsI gtcttc               BclI Tgatca               BlpI GCtnagc
!BmgBI CACgtc              BsgI ctgcac               BsiWI Cgtacg
!Bsp120I Gggccc            BspEI Tccgga              BssHII Gcgcgc
!BstXI CCANNNNNntgg  (SEQ ID NO: 164) BstZ17I GTatac   BtrI CACgtg
!DraIII CACNNgtg           Ec1136I GAGctc            EcoNI CCTNNnnnagg
                                                      (SEQ ID NO: 165)
!EcoO109I RGgnccy          EcoRV GATatc              EspI GCtnagc
!FseI GGCCGGcc             HpaI GTTaac               KpnI GGTACc
!MfeI Caattg               NotI GCggccgc             PmeI GTTTaaac
!PmlI CACgtg               PpuMI RGgwccy             PspOMI Gggccc
!PstI CTGCAg               SacI GAGCTc               SapI GCTCTTC
!SbfI CCTGCAgg             SexAI Accwggt             SfiI GGCCNNNNnggcc
                                                      (SEQ ID NO: 173)
!SgfI GCGATcgc             SgrAI CRccggyg            SphI GCATGc
!Sse8387I CCTGCAgg         StuI AGGcct               XmaI Cccggg
!
! cutters
!
! Enzymes that cut more than 3 times.
!
!BsaAI YACgtr                     5
!BspMI Nnnnnnnnngcaggt             4      (SEQ ID NO: 179)
!BsrFI Rccggy                      4
!BtgI Ccrygg                       4
!DsaI Ccrygg                       4
!FauI nNNNNNNGCGGG                 9      (SEQ ID NO: 171)
!
! Enzymes that cut from 1 to 3 times.
!
! $ = DAM site, * = DCM site, & = both
!
!BsrGI Tgtaca              1      1021
!BsaBI GATNNnnatc          2      1149        3974    (SEQ ID NO: 174)
!SnaBI TACgta              2      1268        7131
!BspHI Tcatga              3      1299        6083        7091
!BsmI GAATGCN              2      1746        7733
!-"-NGcattc                1      7477
!BseRI GAGGAGNNNNNNNNNN    1      2008                (SEQ ID NO: 175)
!AlwNI CAGNNNctg           1      2187
!BspDI ATcgat              2      2527        8551
```

TABLE 29-continued

A phage vector to display TFPI KuDom 1 and derivatives.

| | | | | |
|---|---|---|---|---|
| !NdeI CAtatg | 3 | 2723 | 3803 | 8515 |
| !AfeI AGCgct | 1 | 3039 | | |
| !EarI CTCTTCNnnn | 2 | 4074 | 7942 (SEQ ID NO: 170) | |
| !-"- Nnnnngaagag | 1 | 6124 | | |
| !PacI TTAATtaa | 1 | 4132 | | |
| !BsiHKAI GWGCWc | 3 | 4743 | 5465 | 6336 |
| !HgiAI GWGCWc | 3 | 4743 | 5465 | 6336 |
| !BsmFI Nnnnnnnnnnnnnnngtccc | 2 | 5075 | 8183 (SEQ ID No: 184) | |
| !-"- GGGACNNNNNNNNNNnn | 1 | 7897 | (SEQ ID No: 169) | |
| !MscI TGGcca | 3 | 5080 | 5715 | 7828 |
| !PsiI TTAtaa | 2 | 5356 | 5835 | |
| !NaeI GCCggc | 2 | 5613 | 7983 | |
| !NgoMIV Gccggc | 2 | 5613 | 7983 | |
| !BanII GRGCYc | 1 | 5643 | | |
| !DrdI GACNNNNnngtc | 1 | 5750 | (SEQ ID NO: 177) | |
| !AvaI Cycgrg | 2 | 5816 | 7238 | |
| !PvuII CAGctg | 1 | 5951 | | |
| !BsmBI CGTCTCNnnnn | 2 | 5962 | 7939 | |
| !BamHI Ggatcc | 1 | 5992& | | |
| !HindIII Aagctt | 3 | 5998 | 7145 | 7382 |
| !BciVI GTATCCNNNNNN | 1 | 6075 | (SEQ ID NO: 167) | |
| !Eco57I CTGAAG | 1 | 6236$ | | |
| !SpeI Actagt | 1 | 6255 | | |
| !BcgI gcannnnnntcg | 1 | 6396 | (SEQ ID NO: 185) | |
| !ScaI AGTact | 1 | 6440 | | |
| !PvuI CGATcg | 1 | 6551$ | | |
| !FspI TGCgca | 1 | 6698 | | |
| !BglI GCCNNNNnggc | 2 | 6799 | 7491 (SEQ ID NO: 168) | |
| !BpmI CTGGAG | 2 | 6833 | 7216 | |
| !-"- ctccag | 1 | 8568 | | |
| !BsaI GGTCTCNnnnn | 1 | 6851 | (SEQ ID NO: 186) | |
| !AhdI GACNNNnngtc | 1 | 6918 | (SEQ ID NO: 181) | |
| !Eam1105I GACNNNnngtc | 1 | 6918 | (SEQ ID NO: 181) | |
| !AccI GTmkac | 1 | 7151 | | |
| !HincII GTYrac | 1 | 7151 | | |
| !SalI Gtcgac | 1 | 7151 | | |
| !TliI Ctcgag | 1 | 7238 | | |
| !XhoI Ctcgag | 1 | 7238 | | |
| !PflMI CCANNNNntgg | 1 | 7380 | (SEQ ID NO: 172) | |
| !NcoI Ccatgg | 1 | 7462 | | |
| !StyI Ccwwgg | 3 | 7462 | 7753 | 8130 |
| !EagI Cggccg | 1 | 7468 | | |
| !NsiI ATGCAt | 2 | 7476 | 8171 | |
| !PshAI GACNNnngtc | 2 | 7503 | 7899 (SEQ ID NO: 187) | |
| !RsrII CGgwccg | 1 | 7508 | | |
| !MluI Acgcgt | 1 | 7554 | | |
| !EcoRI Gaattc | 2 | 7569 | 7868 | |
| !BstEII Ggtnacc | 1 | 7593 | | |
| !AgeI Accggt | 1 | 7603 | | |
| !BstBI TTcgaa | 2 | 7608 | 7865 | |
| !XbaI Tctaga | 1 | 7616 | | |
| !BsssSI Ctcgtg | 1 | 7642 | | |
| !NheI Gctagc | 1 | 7653 | | |
| !KasI Ggcgcc | 2 | 7707 | 7788 | |
| !Pf1FI GACNnngtc | 1 | 7767 | | |
| !Tth111I GACNnngtc | 1 | 7767 | | |
| !NruI TCGcga | 1 | 7774 | | |
| !XcmI CCANNNNNnnnntgg | 1 | 7883* | (SEQ ID NO: 166) | |
| !BstAPI GCANNNNntgc | 1 | 8005 | (SEQ ID NO: 178) | |
| !SacII CCGCgg | 1 | 8033 | | |
| !AvrII Cctagg | 1 | 8130 | | |
| !Bsu36I CCtnagg | 1 | 8177 | | |
| !SwaI ATTTaaat | 1 | 8452 | | |
| !BglII Agatct | 1 | 8604$ | | |

!------------------------------------------------------------

```
  1    aatgctacta ctattagtag aattgatgcc accttttcag ctcgcgcccc aaatgaaaat 61    atagctaaac aggttattga ccatttgcga aatgtatcta atggtcaaac taaatctact 121    cgttcgcaga attgggaatc aactgttaTa tggaatgaaa cttccagaca ccgtacttta 181    gttgcatatt taaacatgt tgagctacag caTTaTattc agcaattaag ctctaagcca 241    tccgcaaaaa tgacctctta tcaaaaggag caattaaagg tactctctaa tcctgacctg 301    ttggagtttg cttccggtct ggttcgcttt gaagctcgaa ttaaaacgcg atatttgaag 361    tctttcgggc ttcctcttaa tctttttgat gcaatccgct ttgcttctga ctataatagt
```

TABLE 29-continued

A phage vector to display TFPI KuDom 1 and derivatives.

```
 421   cagggtaaag acctgatttt tgatttatgg tcattctcgt tttctgaact gtttaaagca
 481   tttgagggggg attcaatgaa tatttatgac gattccgcag tattggacgc tatccagtct
 541   aaacatttta ctattacccc ctctggcaaa acttcttttg caaaagcctc tcgctatttt
 601   ggttttatc gtcgtctggt aaacgagggt tatgatagtg ttgctcttac tatgcctcgt
 661   aattccttt ggcgttatgt atctgcatta gttgaatgtg gtattcctaa atctcaactg
 721   atgaatcttt ctacctgtaa taatgttgtt ccgttagttc gttttattaa cgtagatttt
 781   tcttcccaac gtcctgactg gtataatgag ccagttctta aaatcgcata aggtaattca
 841   caatgattaa agttgaaatt aaaccatctc aagcccaatt tactactcgt tctggtgttTc
 902   tcgtcagggc aagccttatt cactgaatga gcagctttgt tacgttgatt tgggtaatga
 962   atatccggtt cttgtcaaga ttactcttga tgaaggtcag ccagcctatg cgcctggtcT
1022   GTACAccgtt catctgtcct ctttcaaagt tggtcagttc ggttcccta tgattgaccg
1082   tctgcgcctc gttccggcta agtaacatgg agcaggtcgc ggatttcgac acaatttatc
1142   aggcgatgat acaaatctcc gttgtacttt gtttcgcgct tggtataatc gctgggggtc
1202   aaagatgagt gttttagtgt attctttTgc ctctttcgtt ttaggttggt gccttcgtag
1262   tggcattacg tattttaccc gtttaatgga aacttcctca tgaaaaagtc tttagtcctc
1322   aaagcctctg tagccgttgc taccctcgtt ccgatgctgt ctttcgctgc tgagggtgac
1382   gatcccgcaa aagcggcctt taactccctg caagcctcag cgaccgaata tatccggttat
1442   gcgtgggcga tggttgttgt cattgtcggc gcaactatcg gtatcaagct gtttaagaaa
1502   ttcacctcga aagcaagctg ataaaccgat acaattaaag gctccttttg gagccttttt
1562   ttttggagat tttcaac
!Gene  iii (as in M13mp18)
1579   gtg aaa aaa tta tta ttc gca att cct tta gtt gtt cct ttc tat
1624   tct cac tcc gct gaa act gtt gaa agt tgt tta gca aaa tcc cat
1669   aca gaa aat tca ttt act aac gtc tgg aaa gac gac aaa act tta
1714   gat cgt tac gct aac tat gag ggc tgt ctg tgg aat gct aca ggc
1759   gtt gta gtt tgt act ggt gac gaa act cag tgt tac ggt aca tgg
1804   gtt cct att ggg ctt gct atc cct gaa aat gag ggt ggt ggc tct
1849   gag ggt ggc ggt tct gag ggt ggc ggt tct gag ggt ggc ggt act
1894   aaa cct cct gag tac ggt gat aca cct att ccg ggc tat act tat
1939   atc aac cct ctc gac ggc act tat ccg cct ggt act gag caa aac
1984   ccc gct aat cct aat cct tct ctt GAG GAG tct cag cct ctt aat
2029   act ttc atg ttt cag aat aat agg ttc cga aat agg cag ggg gca
2074   tta act gtt tat acg ggc act gtt act caa ggc act gac ccc gtt
2119   aaa act tat tac cag tac act cct gta tca tca aaa gcc atg tat
2164   gac gct tac tgg aac ggt aaa ttC AGa gaC TGc gct ttc cat tct
2209   ggc ttt aat gag gat tta ttt gtt tgt gaa tat caa ggc caa tcg
2254   tct gac ctg cct caa cct cct gtc aat gct ggc ggc ggc tct ggt
2299   ggt ggt tct ggt ggc ggc tct gag ggt ggt ggc tct gag ggt ggc
2344   ggt tct gag ggt ggc ggc tct gag gga ggc ggt tcc ggt ggt ggc
```

TABLE 29-continued

A phage vector to display TFPI KuDom 1 and derivatives.

```
2389    tct ggt tcc ggt gat ttt gat tat gaa aag atg gca aac gct aat
2434    aag ggg gct atg acc gaa aat gcc gat gaa aac gcg cta cag tct
2479    gac gct aaa ggc aaa ctt gat tct gtc gct act gat tac ggt gct
2524    gct atc gat ggt ttc att ggt gac gtt tcc ggc ctt gct aat ggt
2569    aat ggt gct act ggt gat ttt gct ggc tct aat tcc caa atg gct
2614    caa gtc ggt gac ggt gat aat tca cct tta atg aat aat ttc cgt
2659    caa tat tta cct tcc ctc cct caa tcg gtt gaa tgt cgc cct ttt
2704    gtc ttt Ggc gct ggt aaa cca tat gaa ttt tct att gat tgt gac
2749    aaa ata aac tta ttc cgt ggt gtc ttt gcg ttt ctt tta tat gtt
2794    gcc acc ttt atg tat gta ttt tct acg ttt gct aac ata ctg
2836    cgt aat aag gag tct              t aatcatgcca gttcttttgg gtattccgtt
2882    attattgcgt ttcctcggtt tccttctggt aactttgttc ggctatctgc ttactttcct
2942    taaaagggc ttcggtaaga tagctattgc tatttcattg tttcttgctc ttattattgg
3002    gcttaactca attcttgtgg ttatctctc tgatattAGC GCTcaattac cctctgactt
3062    tgttcagggt gttcagttaa ttctcccgtc taatgcgctt ccctgttttt atgttattct
3122    ctctgtaaag gctgctattt cattttga cgttaaacaa aaaatcgttt cttatttgga
3182    ttgggataaa taatatggct gtttattttg taactggcaa attaggctct ggaaagacgc
3242    tcgttagcgt tggtaagatt caggataaaa ttgtagctgg gtgcaaaata gcaactaatc
3302    ttgatttaag gcttcaaaac ctcccgcaag tcgggaggtt cgctaaaacg cctcgcgttc
3362    ttagaatacc ggataagcct tctatatctg atttgcttgc tattgggcgc ggtaatgatt
3422    cctacgatga aaataaaaac ggcttgcttg ttctcgatga gtgcggtact tggtttaata
3482    cccgttcttg gaatgataag gaaagacagc cgattattga ttggtttcta catgctcgta
3542    aattaggatg ggatattatt tttcttgttc aggacttatc tattgttgat aaacaggcgc
3602    gttctgcatt agctgaacat gttgtttatt gtcgtcgtct ggacagaatt actttacctt
3662    ttgtcggtac tttatattct cttattactg gctcgaaaat gcctctgcct aaattacatg
3722    ttggcgttgt taaatatggc gattctcaat taagccctac tgttgagcgt tggctttata
3782    ctggtaagaa tttgtataac gcatatgata ctaaacaggc ttttctagt aattatgatt
3842    ccggtgttta ttcttattta acgccttatt tatcacacgg tcgtatttc aaaccattaa
3902    atttaggtca agatgaaa ttaactaaaa tatatttgaa aaagtttct cgcgttcttt
3962    gtcttgcgat tggatttgca tcagcattta catatagtta tataacccaa cctaagccgg
4022    aggttaaaaa ggtagtctct cagacctatg attttgataa attcactatt gactcttctc
4082    agcgtcttaa tctaagctat cgctatgttt tcaaggattc taagggaaaa TTAATTAAta
4142    gcgacgattt acagaagcaa ggttattcac tcacatatat tgatttatgt actgtttcca
4202    ttaaaaaagg taattcaaat gaattgtta aatgtaatta attttgtttt cttgatgttt
4262    gtttcatcat cttcttttgc tcaggtaatt gaaatgaata attcgcctct gcgcgatttt
4322    gtaacttggt attcaaagca atcaggcgaa tccgttattg tttctcccga tgtaaaaggt
4382    actgttactg tatattcatc tgacgttaaa cctgaaaatc tacgcaattt ctttatttct
4442    gttttacgtg cAataaattt tgatatggtA ggttcTaACc cttccataat tcagaagtat
4502    aatccaaaca atcaggatta tattgatgaa ttgccatcat ctgataatca ggaatatgat
```

TABLE 29-continued

A phage vector to display TFPI KuDom 1 and derivatives.

```
4562    gataattccg ctccttctgg tggtttvttt gttccgcaaa stgataatgt tactcaaact 4622    tttaaaatta ataacgttcg ggcaaaggat ttaatacgag ttgtcgaatt gtttgtaaag 4682    tctaatactt ctaaatcctc aaatgtatta tctattgacg gctct 4727    aat cta tta gtt gtt aGT GCt Cct aaa gat 4757    att tta gat aac ctt cct caa ttc ctt tcA act gtt gat ttg cca 4802    actgaccaga tattgattga gggtttgata tttgaggttc agcaaggtga tgctttagat 4862    ttttcatttg ctgctggctc tcagcgtggc actgttgcag gcggtgttaa tactgaccgc 4922    ctcacctctg ttttatcttc tgctggtggt tcgttcggta tttttaatgg cgatgtttta 4982    gggctatcag ttcgcgcatt aaagactaat agccattcaa aaatattgtc tgtgccacgt 5042    attcttacgc tttcaggtca aagggttct atctctgttg gccagaatgt ccctttttatt 5102    actggtcgtg tgactggtga atctgccaat gtaaataatc catttcagac gattgagcgt 5162    caaaatgtag gtatttccat gagcgttttt cctgttgcaa tggctggcgg taatattgtt 5222    ctggatatta ccagcaaggc cgatagtttg agttcttcta ctcaggcaag tgatgttatt 5282    actaatcaaa gaagtattgc tacaacggtt aatttgcgtg atggacagac tcttttactc 5342    ggtggcctca ctgattataa aaacacttct caGgattctg cgtaccgtt cctgtctaaa 5402    atcccttttaa tcggcctcct gtttagctcc cgctctgatt cTaacgagga aagcacgtta 5462    tacgtgctcg tcaaagcaac catagtacgc gccctgtagc ggcgcattaa gcgcggcggg 5522    tgtggtggtt acgcgcagcg tgaccgctac acttgccagc gccctagcgc ccgctccttt 5582    cgctttcttc ccttcctttc tcgccacgtt cgccggcttt ccccgtcaag ctctaaatcg 5642    ggggctccct ttagggttcc gatttagtgc tttacggcac ctcgacccca aaaaacttga 5702    tttgggtgat ggtt                          ggcca tcgccctgat agacggtttt 5741    tcgcccttG ACGTTGGAGT Ccacgttctt taatagtgga ctcttgttcc aaactggaac 5801    aacactcaac cctatctcgg gctattcttt tgatttataa gggattttgc cgatttcgga 5861    accaccatca aacaggattt cgcctgctg gggcaaacca gcgtggaccg cttgctgcaa 5921    ctctctcagg gccaggcggt gaagggcaat CAGCTGttgc cCGTCTCact ggtgaaaaga 5981    aaaaccaccc tGGATCC   AAGCTT
!                BamHHI
!                Insert carrying bla gene 6004    gcaggtg gcactttcg gggaaatgtg cgcggaaccc 6041    ctatttgttt attttctaa atacattcaa atatGTATCC gctcatgaga caataacccct
!                                          BciVI 6101    gataaatgct tcaataatat tgaaaaAGGA AGAgt
!       Start bla gene 6136    ATG agt att caa cat ttc cgt gtc gcc ctt att ccc ttt ttt gcg gca ttt 6187    tgc ctt cct gtt ttt gct cac cca gaa acg ctg gtg aaa gta aaa gat gct 6238    gaa gat cag ttg ggC gcA CTA GTg ggt tac atc gaa ctg gat ctc aac agc 6289    ggt aag atc ctt gag agt ttt cgc ccc gaa gaa cgt ttt cca atg atg agc 6340    act ttt aaa gtt ctg cta tgt GGC GcG Gta tta tcc cgt att gac gcc ggg 6391    caa gaG CAA CTC GGT CGc cgC ATA cAC tat tct cag aat gac ttg gtt gAG 6442    TAC Tca cca gtc aca gaa aag cat ctt acg gat ggc atg aca gta aga gaa 6493    tta tgc agt gct gcc ata acc atg agt gat aac act gcg gcc aac tta ctt
```

TABLE 29-continued

A phage vector to display TFPI KuDom 1 and derivatives.

```
6544    ctg aca aCG ATC Gga gga ccg aag gag cta acc gct ttt ttg cac aac atg 6595    ggg gat cat gta act cgc ctt gat cgt tgg gaa ccg gag ctg aat gaa gcc 6646    ata cca aac gac gag cgt gac acc acg atg cct gta gca atg Gca aca acg 6697    tTG CGC Aaa cta tta act ggc gaa cta ctt act cta gct tcc cgg caa caa 6748    tta ata gac tgg atg gag gcg gat aaa gtt gca gga cca ctt ctg cgc tcg 6799    GCC ctt ccG GCt ggc tgg ttt att gct gat aaa tct gga gcc ggt gag cgt 6850    gGG TCT Cgc ggt atc att gca gca ctg ggg cca gat ggt aag ccc tcc cgt 6901    atc gta gtt atc tac acG ACg ggg aGT Cag gca act atg gat gaa cga aat 6952    aga cag atc gct gag ata ggt gcc tca ctg att aag cat tgg TAA ctgt
                                                                    stop 7001    cagaccaagt ttactcatat atactttaga ttgatttaaa acttcatttt taatttaaaa 7061    ggatctaggt gaagatcctt tttgataatc tcatgaccaa aatcccttaa cgtgagtttt 7121    cgttccactg tacgtaagac cccc 7145    AAGCTT    GTCGAC tgaa tggcgaatgg cgctttgcct
                  SalI..
                  HincII 7181    ggtttccggc accagaagcg gtgccggaaa gctggctgga gtgcgatctt 7231    CCTGAcG CTCGAG
                XhoI..

7244                             cgcaacgc aattaatgtg agttagctca 7272    ctcattaggc accccaggct ttacacttta tgcttccggc tcgtatgttg 7322    tgtggaattg tgagcggata acaatttcac acaggaaaca gctatgacca 7372    tgattacg  CCaagctt  TGGa gccttttttt tggagatttt caac
                  Pf1MI. . .

1   2   3   4   5   6   7   8   9  10  11  12  13  14  15

M   K   K   L   L   F   A   I   P   L   V   V   P   F   Y 7416    gtg aaa aaa tta tta ttc gca att cct tta gtt gtt cct ttc tat
        Exact copy of M13 signal, codons 1-15.

S   M   A       A   E   M   H   S   F 7461        tCC ATG Gcg     |gcc|gag|ATG|CAT|tcc|ttc
                  NcoI . . .

C5  A   F   K   A  D10  D  G12  P   C  I15  A   F   F   P  R20  F
7488    tgc gcc ttc aag gct gac gaC GGT CCG tgt aTT gct TTC TTc CCt cgt ttc

F   F   N  I25  F   T   R   Q  C30  E   E   F   I   Y   G   G   C 7539    ttc ttc aac att ttc ACG CGT cag tgc gag GAA TTC att tac ggt ggt tgt
                            MluI . . .

E  G40  N   Q   N   R  F45  E   S   L   E 7590    gaa GGT AAC Cag aAC CGG Ttc gaa tcT CTA Gag
            BstEII . . AgeI . . .    XbaI . . .
                       AsuII . . .

E   C   K   K   M   C   T   R   D       S   A   S
7623    gaa tgt aag aag atg tgt act|cgt|gat|    tct GCT AGC
                                                    NheI . . .

S   A 7659    tct gct

! III'stump
```

TABLE 29-continued

A phage vector to display TFPI KuDom 1 and derivatives.

```
! Domain 3 of III---------------------------------------------------------
!
!           S    G    D    F    D    Y    E    K    M    A    N    A    N    K    G    A
   7665    agt  ggc  gac  ttc  gac  tac  gag  aaa  atg  gct  aat  gcc  aac  aaa  GGC  GCC
!
!           M    T    E    N    A    D    E    N    A    L    Q    S    D    A    K    G
   7713    atG  ACT  GAG  AAC  GCT  GAC  GAG  aat  gct  ttg  caa  agc  gat  gcc  aag  ggt
!
!           K    L    D    S    V    A    T    D    Y    G    A    A    I    D    G    F
   7761    aag  tta  gac  agc  gTC  GCG  Acc  gac  tat  GGC  GCC  gcc  ATC  GAc  ggc  ttt
!                                    NruI . . .
!
!           I    G    D    V    S    G    L    A    N    G    N    G    A    T    G    D
   7809    atc  ggc  gat  gtc  agt  ggt  tTG  GCC  Aac  ggc  aac  gga  gcc  acc  gga  gac
!
!           F    A    G    S    N    S    Q    M    A    Q    V    G    D    G    D    N
   7857    ttc  GCA  GGT  tcG  AAT  TCt  cag  atg  gcC  CAg  gtt  gga  gaT  GGg  gac  aac
!
!           S    P    L    M    N    N    F    R    Q    Y    L    P    S    L    P    Q
   7905    agt  ccg  ctt  atg  aac  aac  ttt  aga  cag  tac  ctt  ccg  tct  ctt  ccg  cag
!
!           S    V    E    C    R    P    F    V    F    G    A    G    K    P    Y    E
   7953    agt  gtc  gag  tgc  cgt  cca  ttc  gtt  ttc  GGt  gcc  ggc  aag  cct  tac  gag
!
!           F    S    I    D    C    D    K    I    N    L    F    R
   8001    ttc  aGC  Atc  gac  TGC  gat  aAg  atc  aat  ctt  ttC  CGC
!                BstAPI . . .                                SacII . . .
!
!                                                            End Domain 3
!
!           G    V    F    A    F    L    L    Y    V    A    T    F    M    Y    V    F
   8037    GGc  gtt  ttc  gct  ttc  ttg  cta  tac  gtc  gct  act  ttc  atg  tac  gtt  ttc
!          start transmembrane segment
!
!           S    T    F    A    N    I    L    R    N    K    E    S    (SEQ ID NO: 101)
   8085    agc  act  ttc  gcc  AAT  ATT  tta  cgc  aac  aaa  gaa  agc
!                                                Intracellular anchor.
!
!                    .    .
   8121             tag  tga  tct  CCT  AGG
!                                 AvrII . . .
!
!                                                                    | M13mp18 >
   8136    aaG  CCC  GCc  taa  tga  GCG  GGC  ttt  ttt  ttt  ct   ggt   ATGCAT CCTGAGG
!          Stem . . . Loop . . . Stem . . . .  MultiT . . .         NsiI   Bsu36I.
!          | Trp terminator                                       |          (2/2)
!
   8184                           ccgat actgtcgtcg tccctcaaa ctggcagatg
!
   8219    cacggttacg atgcgcccat ctacaccaac gtgacctatc ccattacggt caatccgccg
!
   8279    tttgttccca cggagaatcc gacgggttgt tactcgctca catttaatgt tgatgaaagc
!
   8339    tggctacagg aaggccagac gcgaattatt tttgatggcg ttcctattgg ttaaaaaatg
!
   8399    agctgattta acaaaaattt aaTgcgaatt ttaacaaaat attaacgttt acaATTTAAA
!                                                                  SwaI . . .
!
   8459    Tatttgctta tacaatcttc ctgttttgg ggcttttctg attatcaacc GGGGTAcat
!                                                                   RBS?
!
   8518    ATG att gac atg cta gtt tta cga tta ccg ttc atc gat tct ctt gtt tgc
!
!          Start gene II
   8569    tcc aga ctc tca ggc aat gac ctg ata gcc ttt gtA GAT CTc tca aaa ata
!                                                           BglII . . .
!
   8620    gct acc ctc tcc ggc atT aat tta tca gct aga acg gtt gaa tat cat att
!
   8671    gat ggt gat ttg act gtc tcc ggc ctt tct cac cct ttt gaa tct tta cct
```

TABLE 29-continued

A phage vector to display TFPI KuDom 1 and derivatives.

```
8722  aca cat tac tca ggc att gca ttt aaa ata tat gag ggt tct aaa aat ttt 8773  tat cct tgc gtt gaa ata aag gct tct ccc gca aaa gta tta cag ggt cat 8824  aat gtt ttt ggt aca acc gat tta gct tta tgc tct gag gct tta ttg ctt 8875  aat ttt gct aat tct ttg cct tgc ctg tat gat tta ttg gat gtt(SEQ ID NO: 100)
!     gene II continues
```

TABLE 30

Modified Human TFPI = PlaKalEl02 (SEQ ID NO: 102)

| AAs | Function | AA sequence |
|---|---|---|
| 1-21 | Linker 1 | DSEEDEEHTIITDTELPPLKP |
| 22-79 | KuDom 1 Inhibit plasmin | MHSFCAFKADDGPCRARFDRWFFNIFTRQCEEFIYGGCEGNQNRFESLEECKKMCTRD |
| 80-92 | Linker 2 | NANRPIKTTLQQE |
| 93-150 | KuDom 2 Inhibit h.pKal | KPDFCFLEEDPGPCRAAHPRWFYNnQTKQCERFIYGGCEGNMNNFETLEECKNICEDG |
| 151-184 | Linker 3 | PNGFQVDNYGTQLNAVnNSLTPQSPKVPSLFEFH |
| 185-242 | KuDom 3 Inhibit h.NE | GPSWCLTPADRGPCIAFFPRFYYNSVIGKCRPFPYGGCQGNENnFTSKQECLRACKKG<br>1   5   1   1   2   2   3   3   4   4   5   5   5<br>        0   5   0   5   0   5   0   5   0   5   8 |
| 243-248 | Linker 4 | FIQRIS |

Mutations from w.t. are BOLD, UPPERCASE.
Possible glycosylation sites are shown as "n".

TABLE 31

Modified Human TFPI dimer = ELsix (SEQ ID NO: 103)

| Aas | Function | AA sequence |
|---|---|---|
| 1-21 | Linker 1 | DSEEDEEHTIITDTELPPLKL |
| 22-79 | KuDom 1 | MHSFCAFKADDGPCIAFFPRFFFNIFTRQCEEFIYGGCQGNQNRFESLEECKKMCTRD |
| 80-92 | Linker 2 | NANRIIKTTLQQE |
| 93-150 | KuDom 2 | KPDFCFLEEDPGPCIAFFPRFFYNnQTKQCERFIYGGCQGNMNNFETLEECKNICEDG |
| 151-184 | Linker 3 | PNGFQVDNYGTQLNAVnNSLTPQSTKVPSLFEFH |
| 185-242 | KuDom 3 | GPSWCLTPADRGPCIAFFPRFYYNSVIGKCRPFKYGGCQGNENnFTSKQECLRACKKG<br>1   5   1   1   2   2   3   3   4   4   5   5   5<br>        0   5   0   5   0   5   0   5   0   5   8 |
| 243-248 | Linker 4 | FIQRIS |
| 249-261 | Linker 5 | GGSGSGGSGSSGG |
| 262-282 | Linker 1 | DSEEDEEHTIITDTELPPLKL |
| 283-341 | KuDom 1 | MHSFCAFKADDGPCIAFFPRFFFNIFTRQCEEFIYGGCQGNQNRFESLEECKKMCTRD |
| 342-354 | Linker 2 | NANRIIKTTLQQE |
| 355-410 | KuDom 2 | KPDFCFLEEDPGPCIAFFPRFFYNnQTKQCERFIYGGCQGNMNNFETLEECKNICEDG |

TABLE 31-continued

Modified Human TFPI dimer = ELsix (SEQ ID NO: 103)

| Aas | Function | AA sequence |
| --- | --- | --- |
| 411-444 | Linker 3 | PNGFQVDNYGTQLNAVnNSLTPQSTKVPSLFEFH |
| 445-502 | KuDom 3 | GPSWCLTPADRGPCIAFFPRFYYNSVIGKCRPFKYGGCQGNENnFTSKQECLRACKKG |
| 503-507 | | FIQRIS |

Mutations from w.t. are BOLD, UPPERCASE.
Possible glycosylation sites are shown as "n".

TABLE 32

AA Sequence of rabbit TFPI (SEQ ID NO: 104)

| | |
| --- | --- |
| LOCUS | AAB26836    299 aa  linear   MAM 25-AUG-1993 |
| DEFINITION | tissue factor pathway inhibitor; lipoprotein-associated coagulation inhibitor; extrinsic pathway inhibitor; TFPI; LACI; EPI [Oryctolagus cuniculus]. |
| ACCESSION | AAB26836 |
| VERSION | AAB26836.1  GI:386016 |

UPPERCASE BOLD Ns may be glycosylated

| AAs | Function | AA sequence |
| --- | --- | --- |
| 1-24 | signal | mkkehifwtsiclllglvpapvss |
| 25-44 | Linker 1 | aaeedeftNitdikpplqkp |
| 45-102 | KuDom 1 | thsfcamkvddgperayikrfffnilthgceefiyggcegnenrfesleeckekcard |
| 103-115 | Linker 2 | ypkmttkltfqkg |
| 116-173 | KuDom 2 | kpdfcfleedpgicrgyitryfynNgskqcerfkyggclgnlnnfesleeckntceNp |
| 174-207 | Linker 3 | tsdfqvddhrtqlntvNntlinqptkaprrwafh |
| 208-265 | KuDom 3 | gpswclppadrglcqaneirffynaiigkcrpfkysgcggnenNftskkacitackkg |
| 266-299 | Linker 4 | firNlskggliktkrkkkgpvkityvetfvkkt |

TABLE 33 cDNA Sequence of rabbit TFPI

| | |
| --- | --- |
| LOCUS | S61902                900 bp    mRNA    linera  MAM 25-AUG-1993 |
| DEFINITION | tissue factor pathway inhibitor=Kunitz-type protease inhibitor [rabbits, lung, mRNA, 938 nt]. |
| ACCESSION | S61902 REGION: 21..920 |
| VERSION | S61902.1  GI:386015 |
| KEYWORDS | . |
| SOURCE | *Oryctolagus cuniculus*(rabbit) |
|   ORGANISM | *Oryctolagus cuniculus* |
| | Eukaryota; Metazoa; Chordata; Craniata; Vertebrata; Euteleostomi; Mammalia; Eutheria; Euarchontoglires; Glires; Lagomorpha; Leporidae; *Oryctolagus*. |
| REFERENCE | 1 (bases 1 to 900) |
| AUTHORS | Belaaouaj, A., Kuppuswamy, M.N., Birktoft, J.J. and Bajaj, S.P. |
| TITLE | Revised cDNA sequence of rabbit tissue factor pathway inhibitor |
| JOURNAL | Thromb. Res. 69 (6), 547-553(1993) |
| PUBMED | 8503123 |
| REMARK | GenBank staff at the National Library of Medicine created this entry [NCBI gibbsq 133173] from the original journal article. |
| FEATURES | Location/Qualifiers |
|     source | 1 . . . 900 |
| | /organism="*Oryctolagus cuniculus*" |
| | /mol_type="mRNA" |
| | /db_xref="taxon:9986" |
|     gene | <1 . . . >900 |
| | /gene="tissue factor pathway inhibitor, lipoprotein-associated coagulation inhibitor, extrinsic |

TABLE 33-continued cDNA Sequence of rabbit TFPI

```
              pathway inhibitor, TFPI, LACI, EPI"
   CDS        1 . . . 900
              /gene="tissue factor pathway inhibitor,
              lipoprotein-associated coagulation inhibitor, extrinsic
              pathway inhibitor, TFPI, LACI, EPI"
              /note="Kunitz-type protease inhibitor;
              lipoprotein-associated coagulation inhibitor; extrinsic
              pathway inhibitor; TFPI; LACI; EPI"
              /codon_start=1
              /product="tissue factor pathway inhibitor"
              /protein_id="AAB26836.1"
              /db_xref="GI:386016"
              /translation="MKKEHIFWTSICLLLGLVPAPVSSAAEEDEFTNITDIKPPLQKP
              THSFCAMKVDDGPCRAYIKRFFFNILTH-
     QCEEFIYGGCEGNENRFESLEECKEKCARD
              YPKMITKLIFQKGKPDFCFLEEDPGICR-
     GYITRYFYNNQSKQCERFKYGGCLGNLNNF
              ESLEECKNTCENPTSDFQVD-
     DHRTQLNTVNNTLINQPTKAPRRWAFHGPSWCLPPADR
              GLCQANEIRFFYNAIIGKCRPFKYSGCG-
     GNENNFTSKKACITACKKGFIRNLSKGGLI
              KTKRKKKKQPVKITYVETFVKKT" (SEQ ID NO: 104)
ORIGIN
                                                              (SEQ ID NO: 105)
     1  atgaagaaag aacacatctt ttg-
        gacgtct atatgcctgc tgcttggtct tgtccctgcc 61  cctgttagct cagcggccga ggaagat-
        gaa ttcacaaaca ttacagatat taaaccgcca 121  ctacagaagc cgacacactc attttgtg-
        ca atgaaggtag atgatgggcc gtgcagagca 181  tacatcaaga gattttttt caatat-
        tctc acccatcagt gtgaagaatt tatatatgga 241  ggatgtgaag ggaacgagaa tcgattc-
        gag agtctggaag aatgcaaaga aaaatgtgca 301  cgagattatc caaagatgac ta-
        caaagctg acatttcaaa aggaaagcc tgatttctgc 361  tttttggaag aagatcctgg tatttgtc-
        ga ggttatatta ccagatattt ttataacaat 421  caatcaaaac aatgtgaacg tttcaag-
        tac ggtgggtgcc ttggcaatct aaacaacttt 481  gagtcattgg aagaatgcaa aaacacct-
        gt gagaatccaa cgagtgattt ccaggtggat 541  gaccatagaa cccagctcaa tactgt-
        gaat aacactttaa ttaaccagcc gaccaaggct 601  cccagacgtt ggcatttca cggcccct-
        ca tggtgtctgc ccccagcaga cagaggattg 661  tgtcaagcca atgagatcag attcttc-
        tac aatgcaatca tcgggaaatg ccgcccattt 721  aagtacagtg gatgtggggg aaat-
        gaaaat aatttcactt ccaaaaaagc atgtatcaca 781  gcttgtaaaa aaggtttcat ccgaaatc-
        ta tcaaaaggag gactaattaa aaccaaaagg 841  aagaaaaaga agcagccagt-
        gaaaataact tatgtagaaa cttttgttaa aaagacataa
```

TABLE 34

AA sequence of RaTFPKE01, a derivative of rabbit TFPI (SEQ ID NO: 106)

| AAs | Function | AA sequence |
|---|---|---|
| 1-20 | Linker 1 | aaeedeftNitdikpplqkp |
| 21-78 | KuDom 1 | thsfcamkvddgpcraRFDrWffnilthgce efiyggcegnenrfesleeckekcard |
| 79-91 | Linker 2 | Ypkmttkltfqkg |
| 92-149 | KuDom 2 | kpdfcfleedpgPcrAAHPryfynNqskqce rfkyggcEgnlnnfesleeckntceNp |
| 150-183 | Linker 3 | tsdfqvddhrtqlntvNntlinqptkaprrw afh |
| 184-265 | KuDom 3 | gpswclppadrgPcIaFFPrffynaiigkcr pfkyGgcQgnenNftskkacitackkg |
| 266-271 | Linker 4 | firNls |

TABLE 35

AA sequence of RaTFPKE02, a derivative of rabbit TFPI (SEQ ID NO: 107)

| AAs | Function | AA sequence |
|---|---|---|
| 1-20 | Linker 1 | aaeedeftNitdikpplqkp |
| 21-78 | KuDom 1 | thsfcamkvddgperaRFDrWffnilthgce efiyggcegnenrfesleeckekcard |
| 79-91 | Linker 2 | Ypkmttkltfqkg |
| 92-149 | KuDom 2 | kpdfcfleedpgPcrAAHPryfynNqskqce rfkyggcEgnlnnfesleeckntceNp |
| 150-183 | Linker 3 | tsdfqvddhrtqlntvNntlinqptkaprrw afh |
| 184-241 | KuDom 3 | gpswclppadrgPcIaFFPrffynaiigkcr pfkyGgcQgnenNftskkacitackkg |
| 242-247 | Linker 4 | firNls |
| 248-262 | Linker 5 | GGSGSSGSGGSGSSG |
| 263-282 | Linker 1 | aaeedeftNitdikpplqkp |
| 283-340 | KuDom 1 | thsfcamkvddgperaRFDrWffnilthgce efiyggcegnenrfesleeckekcard |
| 341-353 | Linker 2 | Ypkmttkltfqkg |
| 354-411 | KuDom 2 | kpdfcfleedpgPcrAAHPryfynNqskqce rfkyggcEgnlnnfesleeckntceNp |
| 412-445 | Linker 3 | tsdfqvddhrtqlntvNntlinqptkaprrw afh |
| 446-527 | KuDom 3 | gpswclppadrgPcIaFFPrffynaiigkcr pfkyGgcQgnenNftskkacitackkg |
| 528-509 | Linker 4 | firNls |

N may be glycosylated.

TABLE 36

DNA of ratfpke01 (SEQ ID NO: 108)

```
aTG Gga tgg agc tgt atc atc ctc ttc ttg gTC GCG
Acg gcc aca ggg gcc cac tcc gcg gcc gag gaa gat gaa ttc aca aac att aca gat att aaa ccg cca cta cag aag ccg aca cac tca ttt tgt gca atg aag gta gat gat ggg ccg tgc aga gca CGc TTc GaT aga
tGG ttt ttc aat att ctc acc cat cag tgt gaa gaa ttt ata tat gga gga tgt gaa ggg
aac gag aat cga ttc gag agt ctg gaa gaa tgc aaa gaa aaa tgt gca cga gat tat cca aag atg act aca aag ctg aca ttt caa aaa gga aag cct gat ttc tgc ttt ttg gaa gaa gat cct ggt CCt tgt cga gCt GCt CAt CcT aga
tat ttt tat aac aat caa tca aaa caa tgt gaa cgt ttc aag tac ggt ggg tgt GAG ggc
aat cta aac aac ttt gag tca ttg gaa gaa tgc aaa aac acc tgt gag aat cca acg agt gat ttc cag gtg gat gac cat aga acc cag ctc aat act gtg aat aac act tta
att aac cag ccg acc aag gct ccc aga cgt tgg gca ttt cac ggc ccc tca tgg tgt ctg ccc cca gca gac aga gga CCg tgt ATa gcc TTt TTC CCc aga
ttc ttc tac aat gca atc atc ggg aaa tgc cgc cca ttt aag tac Ggt gga tgt CAg gga
aat gaa aat aat ttc act tcc aaa aaa gca tgt atc aca gct tgt aaa aaa gtt ttc atc cga aat cta tca Taa Tga tctaga
```

TABLE 37

Oligonucleotides to produce ratfpke01 from rabbit tfpi
All oligonucleotides are 5'-to-3'

(SEQ ID NO: 109)
1 ONrSfi    TTAATCTTGCGGCCACAGGGGCCCACTCTGCGGCCGAGGAAGATGAA

TABLE 37-continued

Oligonucleotides to produce ratfpke01 from rabbit tfpi
All oligonucleotides are 5'-to-3'

|  |  |  |
|---|---|---|
| 2 | TruncLo | TCATTATGATAGATTTCGGATGAAACCTTTTTTACA (SEQ ID NO: 110) |
| 3 | ONrK1Bot | TATTGAAAAACCATCTATCGAAGCGTGCTCTG (SEQ ID NO: 111) |
| 4 | ONrK1Top | CAGAGCACGCTTCGATAGATGGTTTTTCAATA (SEQ ID NO: 112) |
| 5 | ONrK2Bot1 | AAAAATATCTAGGATGAGCAGCTCGACAAGGACCAGGATCT (SEQ ID NO: 113) |
| 6 | ONrK2To1 | AGATCCTGGTCCTTGTCGAGCTGCTCATCCTAGATATTTTT (SEQ ID NO: 114) |
| 7 | ONrK2B2 | GTTTAGATTGCCCTCGCACCCAC (SEQ ID NO: 115) |
| 8 | ONrK2T2 | GTGGGTGCGAGGGCAATCTAAAC (SEQ ID NO: 116) |
| 9 | ONrK3B1 | GAAGAATCTGGGGAAAAAGGCTATACACGGTCDTCTGTCT (SEQ ID NO: 117) |
| 10 | ONrK3T1 | AGACAGAGGACCGTGTATAGCCTTTTTCCCCAGATTCTTC (SEQ ID NO: 118) |
| 11 | ONrK3B2 | TCATTTCCCTGACATCCACCGTACTTAAATGG (SEQ ID NO: 119) |
| 12 | ONrK3T2 | ATTTAAGTACGGTGGATGTCAGGGAAATGA (SEQ ID NO: 120) |
| 13 | ONrXbaILo | GGATTACTTCTAGATCATTATGATAGATTTCGGATGAAACCTTTTTTACA (SEQ ID NO: 121) |

TABLE 38

TABLE 4B of U.S. Pat. No. 6,583,108
Ki values for the inhibition of various proteases by refolded bikunin(7-64)

| Protease (concentration) | bikunin (7-64) Ki (nM) | Aprotinin Ki (nM) | bikunin (102-159) Ki (nM) |
|---|---|---|---|
| Trypsin (50 pM) | 0.2 | 0.8 | 0.3 |
| Human Plasma Kallikrein (0.2 nM) | 0.7 | 19.0 | 0.7 |
| Human plasmin (50 pM) | 3.7 | 1.3 | 1.8 |
| F.XIIa | Not done | 12,000 | 4,500 |
| F.XIa(100 pM) | 200 | 288 | 15 |
| Human tissue kallikrein | 2.3 | 0.004 | 0.13 |

TABLE 39

AA sequence of bikunin from
U.S. Pat. No. 6,583,108

(SEQ ID NO: 122)
ADRERS
IHDFCLVSKVVGRCRASMPRWWYNVTDGSCQLFVYGGCDGNSNNYLTKEE
CLKKCATVTENATGDLATSRNAADSSVPSAPRRQDSEDHSSDMFN
YEEYCTANAVTGPCRASFPRWYFDVERNSCNNFIYGGCRGNKNSYRSEEA
CMLRCFRQgenpplplgskvvvlagAVS (SEQ ID NO: 123)
AGSFLAWlgslllsgvla

TABLE 39-continued

AA sequence of bikunin from
U.S. Pat. No. 6,583,108

ADRERS
IHDFCLVSKVVGRCRASMPRWWYNVTDGSCQLFVYGGCDGNSNNYLTKEE
CLKKCATVTENATGDLATSRNAADSSVPSAPRRQDSEDHSSDMFN
YEEYCTANAVTGPCRASFPRWYFDVERNSCNNFIYGGCRGNKNSYRSEEA
CMLRCFRQgenpplplgskvvvlagAVS (SEQ ID NO: 124)
MLRAEADGVSRLlgslllsgvla
ADRERS
IHDFCLVSKVVGRCRASMPRWWYNVTDGSCQLFVYGGCDGNSNNYLTKEE
CLKKCATVTENATGDLATSRNAADSSVPSAPRRQDSEDHSSDMFN
YEEYCTANAVTGPCRASFPRWYFDVERNSCNNFIYGGCRGNKNSYRSEEA
CMLRCFRQgenpplplgskvvvlagLFVMVLILFLGASMVYLIRVARRNQ
ERALRTVWSSGDDKEQLVKNTYVL (SEQ ID NO: 125)
MAQLCGLRRSRAFLALlgslllsgvla
ADRERS
IHDFCLVSKVVGRCRASMPRWWYNVTDGSCQLFVYGGCDGNSNNYLTKEE
CLKKCATVTENATGDLATSRNAADSSVPSAPRRQDSEDHSSDMFN
YEEYCTANAVTGPCRASFPRWYFDVERNSCNNFIYGGCRGNKNSYRSEEA
CMLRCFRQgenpplplgskvvvlaglfvmvlilflgasmvylirvarrng
eralrtvwsFGD

TABLE 40

AA sequence of RaTFPKE04, a derivative of rabbit TFPI (SEQ ID NO: 126)

| AAs | Function | AA sequence |
|---|---|---|
| 1-20 | Linker 1 | aaeedeftNitdikpplqkp |
| 21-78 | KuDom 1 | thsfcamkvddgpGraRFDrWffnilthqceefiyggVegnenrfesleeckekcard |
| 79-91 | Linker 2 | Ypkmttkltfqkg |
| 92-149 | KuDom 2 | kpdfcfleedpgPGrAAHPryfynNqskqcerfkyggVEgnlnnfesleeckntceNp |
| 150-183 | Linker 3 | tsdfqvddhrtqlntvNntlinqptkaprrwafh |
| 184-241 | KuDom 3 | gpswclppadrgPGIaFFPrffynaiigkcrpfkyGgVQgnenNftskkacitackkg |
| 242-247 | Linker 4 | firNls |

N may be N-linked gycosylated.

TABLE 41

AA sequence of RaTFPKE05, a derivative of rabbit TFPI (SEQ ID NO: 127)

| AAs | Function | AA sequence |
|---|---|---|
| 1-20 | Linker 1 | aaeedeftNitdikpplqkp |
| 21-78 | KuDom 1 | thsfcamkvddgpGraRFDrWffnilthqceefiyggVegnenrfesleeckekcard |
| 79-91 | Linker 2 | Ypkmttkltfqkg |
| 92-149 | KuDom 2 | kpdfcfleedpgPGrAAHPryfynNqskqcerfkyggVEgnlnnfesleeckntceNp |
| 150-183 | Linker 3 | tsdfqvddhrtqlntvNntlinqptkaprrwafh |
| 184-241 | KuDom 3 | gpswclppadrgPGIaFFPrffynaiigkcrpfkyGgVQgnenNftskkacitackkg |
| 242-247 | Linker 4 | firNls |
| 248-262 | Linker 5 | GGSGSSGSGGSGSSG |
| 263-282 | Linker 1 | aaeedeftNitdikpplqkp |
| 283-340 | KuDom 1 | thsfcamkvddgpGraRFDrWffnilthqceefiyggVegnenrfesleeckekcard |
| 341-353 | Linker 2 | Ypkmttkltfqkg |
| 354-411 | KuDom 2 | kpdfcfleedpgPGrAAHPryfynNqskqcerfkyggVEgnlnnfesleeckntceNp |
| 436-469 | Linker 3 | tsdfqvddhrtqlntvNntlinqptkaprrwafh |
| 470-527 | KuDom 3 | gpswclppadrgPGIaFFPrffynaiigkcrpfkyGgVQgnenNftskkacitackkg |
| 528-533 | Linker 4 | firNls |

TABLE 44

Amino acid sequence of DX-890 (SEQ ID NO: 128)

EACNLPIVRGPCIAFFPRWAFDAVKGKCVLFPYGGCQGNGNKFYSEKECREYCGVP

TABLE 45

Amino acid sequence of DX-1000 (SEQ ID NO: 129)

MHSFCAFKADDGPCRARFDRWFFNIFTRQCEEFIYGGCEGNQNRFESLEECKKMCTRD

TABLE 50 hTFPImC1, an optimized, tagged w.t. TFPI minus Cterminal region.

```
!  1   gccaCC
!          NcoI...
!          Pff1MI...
!
!       Signal seq
!        1   2   3   4   5   6   7   8   9  10  11  12  13  14  15
!        M   G   W   S   C   I   I   L   F   L   V   A   T   A   T
7      ATG Gga TGG agc tgt atc atc ctc ttc ttg gTC GCG AcG GCC aca
! NcoI.....                                     NruI.... SfiI.....
!   PflMI.......
!
!       Signal Mature protein His6 tag
!        16  17  18  19  20  21  22  23  24  25  26  27  28  29  30
!        G   A   H   S   E   G   R   P   G   H   H   H   H   H   H
52     ggG GCC cac tcc gaa ggt cgt ccg GGT CAC Cac cat cat cat cat
! SfiI......                                     BstEII...
!   EcoO109I.
!     ApaI....
!
!                      Thrombin cleavage site      Codon 2 for mature TFPI
!                                          |                  |
```

TABLE 50-continued hTFPImC1, an optimized, tagged w.t. TFPI minus Cterminal region.

```
        31  32  33  34  35  36  37  38  39  40  41  42  43  44  45
         G   G   S   S   L   V   P   R   G   S   E   E   D   E   E
 97     ggc ggt tct agt ctg gtc ccg cgt ggc tct gag gaa gat gaa gaa Start first KuDom
                                                          |
        46  47  48  49  50  51  52  53  54  55  56  57  58  59  60
         H   T   I   I   T   D   T   E   L   P   P   L   K   L   M
142     cac aca att atc aca gat acg gag ttg cca cca ctg aaa ctt ATG
                                                                NsiI...

61  62  63  64  65  66  67  68  69  70  71  72  73  74  75
         H   S   F   C5  A   F   K   A   D   D   G   P   C14 K   A
187     CAT tca ttt tgt gca ttc aag gcg gat gat ggc cca tgt aaa gca
        NsiI..

76  77  78  79  80  81  82  83  84  85  86  87  88  89  90
         I   M   K   R   F   F   F   N   I   F   T   R   Q   C30 E
232     aTC ATG Aaa aga ttt ttc ttc aat att ttc act cga cag tgc gaa
        BspHI...

91  92  93  94  95  96  97  98  99 100 101 102 103 104 105
         E   F   I   Y   G   G   C38 E   G   N   Q   N   R   F   E
277     gaa ttt ata tat ggg gga tgt gaa gga aat cag aAT CGA Ttt gaa
                                                            BspDI...

End First KuDom
                                                          |
       106 107 108 109 110 111 112 113 114 115 116 117 118 119 120
         S   L   E   E   C51 K   K   M   C55 T   R   D   N   A   N
322     agt ctg gaa gag tgc aaa aaa atg TGT ACA aga gat aat gca aac
                                                BsrGI..

Start second KuDom
                                                          |
       121 122 123 124 125 126 127 128 129 130 131 132 133 134 135
         R   I   I   K   T   T   L   Q   Q   E   K   P   D   F   C5
367     agg att ata aag aca aca ttg caa caa gaa aag cca gat ttc tgc 136 137 138 139 140 141 142 143 144 145 146 147 148 149 150
         F   L   E   E   D   P   G   I   C14 R   G   Y   I   T   R
412     ttt ttg gaa gaa gat cct gga ata tgt cga ggt tat att ACC AGG
                                                                SexAI....

*
       151 152 153 154 155 156 157 158 159 160 161 162 163 164 165
         Y   F   Y   N   N   Q   T   K   Q   C30 E   R   F   K   Y
457     Tat ttt tat aac aat cag aca aaa cag tgt gaa cgt ttc aag tat
        SexAI.

166 167 168 169 170 171 172 173 174 175 176 177 178 179 180
         G   G   C38 L   G   N   M   N   N   F   E   T   L   E   E
502     ggt gga tgc ctg ggc aat atg aac aat ttt gag aca ctg gaa gaa End second KuDom
                                                          |
       181 182 183 184 185 186 187 188 189 190 191 192 193 194 195
         C51 K   N   I   C55 E   D   G   P   N   G   F   Q   V   D
547     tgc aag aac att tgt gaa gat ggt ccg aat ggt ttc cag gtg gat

*
       196 197 198 199 200 201 202 203 204 205 206 207 208 209 210
         N   Y   G   T   Q   L   N   A   V   N   N   S   L   T   P
592     aat tat gga acc cag ctc aat gct gtg aat aac tcc ctg act ccg Start third KuDom
                                                          |
       211 212 213 214 215 216 217 218 219 220 221 222 223 224 225
         Q   S   T   K   V   P   S   L   F   E   F   H   G   P   S
637     caa tca acc aag gtt ccc agc ctt ttt gaa ttt cac ggt ccc tca 226 227 228 229 230 231 232 233 234 235 236 237 238 239 240
         W   C5  L   T   P   A   D   R   G   L   C14 R   A   N   E
682     tgg tgt ctc aCT CCA Gca gac aga gga ttg tgt cgt gcc aat gag
                        BpmI....

241 242 243 244 245 246 247 248 249 250 251 252 253 254 255
         N   R   F   Y   Y   N   S   V   I   G   K   C30 R   P   F
```

TABLE 50-continued hTFPImC1, an optimized, tagged w.t. TFPI minus Cterminal region.

```
727  aac aga ttc tac tac aat tca gtc att ggg aaa tgc cgc cca ttt
!
!    256 257 258 259 260 261 262 263 264 265 266 267 268 269 270
!     K   Y   S   G  C38  G   G   N   E   N   N   F   T   S   K
772  aag tac agt gga tgt ggg gga aat gaa aac aat ttt act tcc aaa
!
!    271 272 273 274 275 276 277 278 279 280 281
!     Q   E  C51  L   R   A  C55  K   K   G         (SEQ ID NO: 131).
817  caa gaa tgt ctg agg gca tgt aaa aaa ggt taa
!
850  tga TCTAGA ag    (SEQ ID NO: 130)
!        XbaI..
!
```

TABLE 51 hTFPI[PpKhNE], a TFPI with plasmin, pKal, and hNe inhibition

```
!
!    1  GCCACC
!       NcoI...
!       PflMI...
!
!       Signal sequence............................................
!       1   2   3   4   5   6   7   8   9   10  11  12  13  14  15
!       M   G   W   S   C   I   I   L   F   L   V   A   T   A   T
  7    ATG Gga Tgg agc tgt atc atc ctc ttc ttg gTC GCG AcG GCC aca
!      NcoI...                                   NruI.... SfiI........
!      PflMI..........
!
!Signal................ Cleavage.......... His6 purification tag..
!       16  17  18  19  20  21  22  23  24  25  26  27  28  29  30
!        G   A   H   S   E   G   R   P   G   H   H   H   H   H   H
  52   GGG GCC Cac tcc gaa ggt cgt ccg GGT CAC Cac cat cat cat cat
!      SfiI......                        BstEII...
!      EcoO109I
!      ApaI....
!
!              Thrombin cleavage site   Codon 2 of mature TFPI
!                                  |        |
!       31  32  33  34  35  36  37  38  39  40  41  42  43  44  45
!        G   G   S   S   L   V   P   R   G   S   E   E   D   E   E
  97   ggc ggt tct agt ctg gtc ccg cgt ggt tct gag gaa gat gaa gaa
!
!                                                     Start 1st KuDom
!                                                           |
!       46  47  48  49  50  51  52  53  54  55  56  57  58  59  60
!        H   T   I   I   T   D   T   E   L   P   P   L   K   L   M
  142  cac aca att atc aca gat acg gag ttg cca cca ctg AAG CTT ATG
!                                                      HindIII NsiI...
!
!       61  62  63  64  65  66  67  68  69  70  71  72  73  74  75
!        H   S   F  C5   A   F   K   A   D   D   G   P  C14  R   A
  187  CAT tca ttt tgt gca ttc aag gcg gat gat ggc cca tgt aga gca
!      NsiI.
!
!       76  77  78  79  80  81  82  83  84  85  86  87  88  89  90
!        R   F   D   R   W   F   F   N   I   F   T   R   Q  C30  E
  232  cgc ttc gat aga tgg ttc ttc aat att ttc act cga cag tgc gaa
!
!       91  92  93  94  95  96  97  98  99 100 101 102 103 104 105
!        E   F   I   Y   G   G  C38  E   G   N   Q   N   R   F   E
  277  gaa ttt ata tat ggg gga tgt gaa gga aat cag aAT CGA Ttt gaa
!                                                         BspDI...
!
!                                     End of 1st KuDom
!                                                 |  Linker 2
!       106 107 108 109 110 111 112 113 114 115 116 117 118 119 120
!        S   L   E   E  C51  K   K   M  C55  T   R   D   N   A   N
  322  agt ctg gaa gag tgc aaa aaa atg TGT ACA aga gat aat gca aac
!                                          BsrGI..
!
!       Linker 2................................ Kudom 2..........
!       121 122 123 124 125 126 127 128 129 130 131 132 133 134 135
!        R   I   I   K   T   T   L   Q   Q   E   K   P   D   F  C5
```

TABLE 51-continued hTFPI[PpKhNE], a TFPI with plasmin, pKal, and hNe inhibition

```
367  agg att ata aag aca aca ttg caa caa gaa aag cca gat ttc tgc
!
!    Kudom 2.........................................................
!    136 137 138 139 140 141 142 143 144 145 146 147 148 149 150
!     F   L   E   E   D   P   G   P  C14  R   A   A   H   P   R
412  ttt CTC GAG GAG GAT CCt gga ccg tgt cga gct gct cat ccc agg
!        XhoI...
!            BseRI..
!                BamHI...
!
!                            *
!    151 152 153 154 155 156 157 158 159 160 161 162 163 164 165
!     W   F   Y   N   N   Q   T   K   Q  C30  E   R   F   I   Y
457  tgg ttt tat aac aat cag aca aaa cag tgt gaa cgt ttc atc tat
!
!    166 167 168 169 170 171 172 173 174 175 176 177 178 179 180
!     G   G  C38  E   G   N   M   N   N   F   E   T   L   E   E
502  ggt gga tgc gag ggc aat atg aac aat ttt gag aca ctg gaa gaa
!
!                  End KuDom 2
!                           | Linker 3....................
!    181 182 183 184 185 186 187 188 189 190 191 192 193 194 195
!    C51  K   N   I  C55  E   D   G   P   N   G   F   Q   V   D
547  tgc aag aac att tgt gaa gat ggt ccg aat ggt ttc cag GTC GAC
!                                                         SalI...
!
!                                        *
!    196 197 198 199 200 201 202 203 204 205 206 207 208 209 210
!     N   Y   G   T   Q   L   N   A   V   N   N   S   L   T   P
592  aat tat gga acc cag ctc aat gct gtg aat aac tcc ctg act ccg
!                                                         KuDom 3....
!    211 212 213 214 215 216 217 218 219 220 221 222 223 224 225
!     Q   S   T   K   V   P   S   L   F   E   F   H   G   P   S
637  caa tca acc aag gtt ccc agc ctt ttt gaa ttt cac ggt ccc tca
!
!    226 227 228 229 230 231 232 233 234 235 236 237 238 239 240
!     W   C5  L   T   P   A   D   R   G   P  C14  I   A   F   F
682  tgg tgt ctc act cCC GCG Gac aga gga ccg tgt att gcc ttt ttc
!                           SacII...
!
!    241 242 243 244 245 246 247 248 249 250 251 252 253 254 255
!     P   R   F   Y   Y   N   S   V   I   G   K  C30  R   P   F
727  ccc aga ttc tac tac aat tca gtc att ggg aaa tgc cgc cca ttt
!
!                                                        *
!    256 257 258 259 260 261 262 263 264 265 266 267 268 269 270
!     P   Y   G   G  C38  Q   G   N   E   N   N   F   T   S   K
772  ccg tat ggc gga tgt cag gga aat gaa aac aat ttt act tcc aaa
!
!    271 272 273 274 275 276 277 278 279 280 281
!     Q   E  C51  L   R   A  C55  K   K   G            (SEQ ID NO: 133).
817  caa gaa tgt ctg agg gca tgt aaa aaa ggt taa TGA
!
!
853  TCTAGA AGCTCGCTGATC   (SEQ ID NO: 132)
!    XbaI..
```

TABLE 52

PLA301B

```
  1  ggccaCC
!       NcoI...
!       PflMI....
!
!     1   2   3   4   5   6   7   8   9  10  11  12  13  14  15
!     M   G   W   S   C   I   I   L   F   L   V   A   T   A   T
  8  ATG Gga TGG tcc tgc atc atc ctg ttt ctg gTG GCC Acc gcc aca
!    NcoI...                                      MscI....
!    PflMI........
!
!    16  17  18  19  20  21  22  23  24  25  26  27  28  29  30
!     G   A   H   S   D   S   E   E   D   E   E   H   T   I   I
```

TABLE 52-continued

| | | | | | | | | | | | | | | |
|---|---|---|---|---|---|---|---|---|---|---|---|---|---|---|
| | | | | | | PLA301B | | | | | | | | |

```
 53  GGC GCC cac agc gac agc gag gaa gat gag gaa cac acc atc atc
!KasI...
!
!     31  32  33  34  35  36  37  38  39  40  41  42  43  44  45
!      T   D   T   E   L   P   P   L   K   L   M   H   S   F   C
 98  acc gac acc gag ctg ccc ccc ctg AAG CTT atg cac agc ttc tgc
!                                     HindIII
!
!     46  47  48  49  50  51  52  53  54  55  56  57  58  59  60
!      A   F   K   A   D   D   G   P   C   R   A   R   F   D   R
143  gcc ttc aag gcc gac gac ggc cCC TGC AGG gcc aga ttc gac aga
!                                     SbfI......
!
!     61  62  63  64  65  66  67  68  69  70  71  72  73  74  75
!      W   F   F   N   I   F   T   R   Q   C   E   E   F   I   Y
188  tgg ttc ttc aac atc ttc acc agg cag tgc gag GAA TTC att tat
!                                                 EcoRI..
!
!     76  77  78  79  80  81  82  83  84  85  86  87  88  89  90
!      G   G   C   E   G   N   Q   N   R   F   E   S   L   E   E
233  gga ggc tgt gaa ggc aat cag aac cgg TTC GAA tct ctg gaa gaa
!                                         BstBI..
!
!     91  92  93  94  95  96  97  98  99 100 101 102 103 104 105
!      C   K   K   M   C   T   R   D   N   A   N   R   I   I   K
278  tgc aag aag atG TGC ACc agg gac aac gcc aac agg atc atc aag
!                    ApaLI...
!
!    106 107 108 109 110 111 112 113 114 115 116 117 118 119 120
!      T   T   L   Q   Q   E   K   P   D   F   C   F   L   E   E
323  acc acc ctg cag cag gag aag ccc gac ttc tgc ttc ctg gaa gaG
!                                                             BamHI..
!
!    121 122 123 124 125 126 127 128 129 130 131 132 133 134 135
!      D   P   G   P   C   R   A   R   F   D   R   W   F   Y   N
368  GAT CCt ggc ccc tgc aga gcc cgg ttt gac cgg tgg ttt tac aat
!    BamHI...
!
!              *
!    136 137 138 139 140 141 142 143 144 145 146 147 148 149 150
!      N   Q   T   K   Q   C   E   R   F   I   Y   G   G   C   E
413  aac cag acc aag cag tgt gAG CGC Ttt atc tat ggg gga tgt gaa
!                                AfeI....
!
!    151 152 153 154 155 156 157 158 159 160 161 162 163 164 165
!      G   N   M   N   N   F   E   T   L   E   E   C   K   N   I
458  gga aat atg aat aac ttc gag aca ctg gaa gag tgt aag aac atc
!
!    166 167 168 169 170 171 172 173 174 175 176 177 178 179 180
!      C   E   D   G   P   N   G   F   Q   V   D   N   Y   G   T
503  tgc gag gac ggc ccc aac ggc ttc cag gtg gac aac tac ggc acc
!
!                          *
!    181 182 183 184 185 186 187 188 189 190 191 192 193 194 195
!      Q   L   N   A   V   N   N   S   L   T   P   Q   S   T   K
548  CAA TTG aac gcc gtg aac aac agc ctg acc ccc cag agc acc aag
!    MfeI...
!
!    196 197 198 199 200 201 202 203 204 205 206 207 208 209 210
!      V   P   S   L   F   E   F   H   G   P   S   W   C   L   T
593  gtg ccc agc ctg ttc gag ttc cac ggc ccc agc tgg tgc ctg acc
!
!    211 212 213 214 215 216 217 218 219 220 221 222 223 224 225
!      P   A   D   R   G   P   C   R   A   R   F   D   R   W   Y
638  cca gcc gac agG GGC CCa tgc cgc gcc aga ttt gac agg tgg tac
!                    ApaI....
!
!    226 227 228 229 230 231 232 233 234 235 236 237 238 239 240
!      Y   N   S   V   I   G   K   C   R   P   F   I   Y   G   G
683  tac aac tcc gtg atc ggc aaG TGC AGg ccc ttc atc tac ggc gga
!                                BsgI....
!
!                      *
!    241 242 243 244 245 246 247 248 249 250 251 252 253 254 255
!      C   E   G   N   E   N   N   F   T   S   K   Q   E   C   L
728  tgt gag gga aac gag aac aac ttt ACT AGT aag cag gaa tgC CTG
!                                    SpeI...            Bsu36I..
!
```

TABLE 52-continued

PLA301B

```
!       256 257 258 259 260 261 262 263 264 265 266 267 268
!        R   A   C   K   K   G   F   I   Q   R   I   S       (SEQ ID NO: 135).
773     AGG gcc tgc aag aag ggc ttc atc cag agg atc agc tga tga a
! Bsu36I..
!
816     TCTAGAa     (SEQ ID NO: 134)
!       XbaI..
```

TABLE 53

Vector encodingoptimized, tagged w.t. TFPI minus Cterminal region.

```
LOCUS       pFuse\with 5660 bp    DNA    circular            26 JAN. 2006
BASE COUNT    1376 a    1423 c    1421 g    1440 t
ORIGIN
                                                           (SEQ ID NO: 136)
    1   gtaccgaatt cacattgatt attgagtagt tattaatagt aatcaattac ggggtcatta 61   gttcatagcc catatatgga gttccgcgtt acataactta cggtaaatgg cccgcctggc 121   tgaccgccca acgaccccg cccattgacg tcaataatga cgtatgttcc catagtaacg 181   ccaataggga ctttccattg acgtcaatgg gtggactatt tacggtaaac tgcccacttg 241   gcagtacatc aagtgtatca tatgccaagt acgccccta ttgacgtcaa tgacggtaaa 301   tggcccgcct ggcattatgc ccagtacatg accttatggg actttcctac ttggcagtac 361   atctacgtgt tagtcatcgc tattaccata gtgatgcggt tttggcagta catcaatggg 421   cgtggatagc ggtttgactc acggggattt ccaagtctcc accccattga cgtcaatggg 481   agtttgtttt ggcaccaaaa tcaacgggac tttccaaaat gtcgtaacaa ctccgcccca 541   ttgacgcaaa tgggcggtag gcgtgtacgg tgggaggtct atataagcag agctttctgg 601   ctaactagag aacccactgc ttactggcac gtggaaatta atacgacgtg gccaccatgg 661   gatggagctg tatcatcctc ttcttggtcg cgacggccac aggggcccac tccgaaggtc 721   gtccgggtca ccaccatcat catcatggcg gttctagtct ggtcccgcgt ggctctgagg 781   aagatgaaga acacacaatt atcacagata cggagttgcc accactgaaa cttatgcatt 841   cattttgtgc attcaaggcg gatgatggcc catgtaaagc aatcatgaaa agatttttct 901   tcaatatttt cactcgacag tgcgaagaat ttatatatgg gggatgtgaa ggaaatcaga 961   atcgatttga aagtctggaa gagtgcaaaa aaatgtgtac aagagataat gcaaacagga 1021   ttataaagac aacattgcaa caagaaaagc cagatttctg cttttggaa gaagatcctg 1081   gaatatgtcg aggttatatt accaggtatt tttataacaa tcagacaaaa cagtgtgaac 1141   gtttcaagta tggtggatgc ctgggcaata tgaacaattt tgagacactg gaagaatgca 1201   agaacatttg tgaagatggt ccgaatggtt tccaggtgga taattatgga acccagctca 1261   atgctgtgaa taactccctg actccgcaat caaccaaggt tcccagcctt tttgaatttc 1321   acggtccctc atggtgtctc actccagcag acagaggatt gtgtcgtgcc aatgagaaca 1381   gattctacta caattcagtc attgggaaat gccgcccatt taagtacagt ggatgtgggg 1441   gaaatgaaaa caatttact tccaaacaag aatgtctgag gcatgtaaaa aaggttaat 1501   gatctagaag ctcgctgatc agcctcgact gtgccttcta gttgccagcc atctgttgtt 1561   tgcccctccc ccgtgccttc cttgaccctg gaaggtgcca ctcccactgt cctttcctaa 1621   taaaatgagg aaattgcatc gcattgtctg agtaggtgtc attctattct ggggggtggg 1681   gtggggcagg acagcaaggg ggaggattgg gaagacaata gcaggcatgc tggggatggc 1741   ccgggctcta tggcttctga ggcggaaaga accagctggg gctctagggg gtatccccac
```

TABLE 53-continued

Vector encodingoptimized, tagged w.t. TFPI minus Cterminal region.

```
1801  gcgccctgta gcggcgcatt aagcgcggcg ggtgtggtgg ttacgcgcag cgtgaccgct
1861  acacttgcca gcgccctagc gcccgctcct ttcgctttct tcccttcctt tctcgccacg
1921  ttcgccggct ttccccgtca agctctaaat cggggcatcc ctttagggtt ccgatttagt
1981  gctttacggc acctcgaccc caaaaaactt gattagggtg atggttcacg tagtgggcca
2041  tcgccctgat agacggtttt tcgccctttg acgttggagt ccacgttctt taatagtgga
2101  ctcttgttcc aaactggaac aacactcaac cctatctcgg tctattcttt tgatttataa
2161  gggatttttgg ggatttcggc ctattggtta aaaaatgagc tgatttaaca aaaatttaac
2221  gcgaattaat tctgtggaat gtgtgtcagt tagggtgtgg aaagtcccca ggctccccag
2281  gcaggcagaa gtatgcaaag catgcatctc aattagtcag caaccaggtg tggaaagtcc
2341  ccaggctccc cagcaggcag aagtatgcaa agcatgcatc tcaattagtc agcaaccata
2401  gtcccgcccc taactccgcc catcccgccc ctaactccgc ccagttccgc ccattctccg
2461  cccctaggct gactaattt ttttatttat gcagaggccg aggccgcctc tgcctctgag
2521  ctattccaga gtagtgagg aggcttttt ggaggcctag gcttttgcaa aaagctcccg
2581  ggaggtccac aatgattgaa caagatggat tgcacgcagg ttctccggcc gcttgggtgg
2641  agaggctatt cggctatgac tgggcacaac agacaatcgg ctgctctgat gccgccgtgt
2701  tccggctgtc agcgcagggg cgcccggttc ttttgtcaa gaccgacctg tccggtgccc
2761  tgaatgaact ccaggacgag gcagcgcggc tatcgtggct ggccacgacg ggcgttcctt
2821  gcgcagctgt gctcgacgtt gtcactgaag cgggaaggga ctggctgcta ttgggcgaag
2881  tgccggggca ggatctcctg tcatctcacc ttgctcctgc cgagaaagta tccatcatgg
2941  ctgatgcaat gcggcggctg catacgcttg atccggctac ctgcccattc gaccaccaag
3001  cgaaacatcg catcgagcga gcacgtactc ggatggaagc cggtcttgtc gatcaggatg
3061  atctggacga agagcatcag gggctcgcgc cagccgaact gttcgccagg ctcaaggcgc
3121  gtatgcccga cggcgaggat ctcgtcgtga ctcatggcga tgcctgcttg ccgaatatca
3181  tggtggaaaa tggccgcttt tctggattca tcgactgtgg ccggctgggt gtggcggacc
3241  gctatcagga catagcgttg gctacccgtg atattgctga gagcttggc ggcgaatggg
3301  ctgaccgctt cctcgtgctt tacggtatcg ccgctcccga ttcgcagcgc atcgccttct
3361  atcgccttct tgacgagttc ttctgagcgg gactctgggg ttcgaaatga ccgaccaagc
3421  gacgcccaac ctgccatcac gagatttcga ttccaccgcc gccttctatg aaaggttggg
3481  cttcggaatc gttttccggg acgccggctg atgatcctc cagcgcgggg atctcatgct
3541  ggagttcttc gcccacccca acttgtttat tgcagcttat aatggttaca aataaagcaa
3601  tagcatcaca aatttcacaa ataaagcatt ttttcactg cattctagtt gtggtttgtc
3661  caaactcatc aatgtatctt atcatgtctg tataccggat ctttccgctt cctcgctcac
3721  tgactcgctg cgctcggtcg ttcggctgcg gcgagcggta tcagctcact caaaggcggt
3781  aatacggtta tccacagaat cagggataa cgcaggaaag aacatgtgag caaaaggcca
3841  gcaaaaggcc aggaaccgta aaaaggccgc gttgctggcg ttttccata ggctccgccc
3901  ccctgacgag catcacaaaa atcgacgctc aagtcagagg tggcgaaacc cgacaggact
3961  ataaagatac caggcgtttc ccctggaag ctccctcgtg cgctctcctg ttccgaccct
4021  gccgcttacc ggatacctgt ccgcctttct cccttcggga agcgtggcgc tttctcaatg
4081  ctcacgctgt aggtatctca gttcggtgta ggtcgttcgc tccaagctgg gctgtgtcca
```

TABLE 53-continued

Vector encodingoptimized, tagged w.t. TFPI minus Cterminal region.

```
4141  cgaaccccc  gttcagcccg  accgctgcgc  cttatccggt  aactatcgtc  ttgagtccaa
4201  cccggtaaga  cacgacttat  cgccactggc  agcagccact  ggtaacagga  ttagcagagc
4261  gaggtatgta  ggcggtgcta  cagagttctt  gaagtggtgg  cctaactacg  gctacactag
4321  aaggacagta  tttggtatct  gcgctctgct  gaagccagtt  accttcggaa  aaagagttgg
4381  tagctcttga  tccggcaaac  aaaccaccgc  tggtagcggt  ggtttttttg  tttgcaagca
4441  gcagattacg  cgcagaaaaa  aaggatctca  agaagatcct  ttgatctttt  ctacggggtc
4501  tgacgctcag  tggaacgaaa  actcacgtta  agggattttg  gtcatgagat  tatcaaaaag
4561  gatcttcacc  tagatccttt  taaattaaaa  atgaagtttt  aaatcaatct  aaagtatata
4621  tgagtaaact  tggtctgaca  gttaccaatg  cttaatcagt  gaggcaccta  tctcagcgat
4681  ctgtctattt  cgttcatcca  tagttgcctg  actcccgtc   gtgtagataa  ctacgatacg
4741  ggagggctta  ccatctggcc  ccagtgctgc  aatgatacc  cgagacccac  gctcaccggc
4801  tccagattta  tcagcaataa  accagccagc  cggaagggcc  gagcgcagaa  gtggtcctgc
4861  aactttatcc  gcctccatcc  agtctattaa  ttgttgccgg  gaagctagag  taagtagttc
4921  gccagttaat  agtttgcgca  acgttgttgc  cattgctaca  ggcatcgtgg  tgtcacgctc
4981  gtcgtttggt  atggcttcat  tcagctccgg  ttcccaacga  tcaaggcgag  ttacatgatc
5041  ccccatgttg  tgcaaaaaag  cggttagctc  cttcggtcct  ccgatcgttg  tcagaagtaa
5101  gttggccgca  gtgttatcac  tcatggttat  ggcagcactg  cataattctc  ttactgtcat
5161  gccatccgta  agatgctttt  ctgtgactgg  tgagtactca  accaagtcat  tctgagaata
5221  gtgtatgcgg  cgaccgagtt  gctcttgccc  ggcgtcaata  cgggataata  ccgcgccaca
5281  tagcagaact  ttaaaagtgc  tcatcattgg  aaaacgttct  tcggggcgaa  aactctcaag
5341  gatcttaccg  ctgttgagat  ccagttcgat  gtaacccact  cgtgctccca  actgatcttc
5401  agcatctttt  actttcacca  gcgtttctgg  gtgagcaaaa  acaggaaggc  aaaatgccgc
5461  aaaaaaggga  ataagggcga  cacggaaatg  ttgaatactc  atactcttcc  tttttcaata
5521  ttattgaagc  atttatcagg  gttattgtct  catgagcgga  tacatatttg  aatgtattta
5581  gaaaaataaa  caaatagggg  ttccgcgcac  atttccccga  aaagtgccac  ctgacgtcag
5641  atcgacggat  cgggagatcg
```

TABLE 54

Vector for TFPI with plasmin, pKal, and hNe inhibition

```
LOCUS       TriKun\no\  5660 bp    DNA    circular         19 DEC. 2005
BASE COUNT    1355 a    1442 c       1426 g      1437 t
ORIGIN
                                                         (SEQ ID NO: 137)
    1  gtaccgaatt  cacattgatt  attgagtagt  tattaatagt  aatcaattac  ggggtcatta
   61  gttcatagcc  catatatgga  gttccgcgtt  acataactta  cggtaaatgg  cccgcctggc
  121  tgaccgccca  acgacccccg  cccattgacg  tcaataatga  cgtatgttcc  catagtaacg
  181  ccaatagga   ctttccattg  acgtcaatgg  gtggactatt  tacggtaaac  tgcccacttg
  241  gcagtacatc  aagtgtatca  tatgccaagt  acgccccta   ttgacgtcaa  tgacggtaaa
  301  tggcccgcct  ggcattatgc  ccagtacatg  accttatggg  actttcctac  ttggcagtac
  361  atctacgtgt  tagtcatcgc  tattaccata  gtgatgcggt  tttggcagta  catcaatggg
```

TABLE 54-continued

Vector for TFPI with plasmin, pKal, and hNe inhibition

```
 421  cgtggatagc ggtttgactc acggggattt ccaagtctcc accccattga cgtcaatggg
 481  agtttgtttt ggcaccaaaa tcaacgggac tttccaaaat gtcgtaacaa ctccgcccca
 541  ttgacgcaaa tgggcggtag gcgtgtacgg tgggaggtct atataagcag agctttctgg
 601  ctaactagag aacccactgc ttactggcac gtggaaatta atacgacgtg gccaccatgg
 661  gatggagctg tatcatcctc ttcttggtcg cgacggccac aggggcccac tccgaaggtc
 721  gtccgggtca ccaccatcat catcatggcg gttctagtct ggtcccgcgt ggttctgagg
 781  aagatgaaga acacacaatt atcacagata cggagttgcc accactgaag cttatgcatt
 841  cattttgtgc attcaaggcg gatgatggcc catgtagagc acgcttcgat agatggttct
 901  tcaatatttt cactcgacag tgcgaagaat ttatatatgg gggatgtgaa ggaaatcaga
 961  atcgatttga aagtctggaa gagtgcaaaa aaatgtgtac aagagataat gcaaacagga
1021  ttataaagac aacattgcaa caagaaaagc cagatttctg ctttctcgag gaggatcctg
1081  gaccgtgtcg agctgctcat cccaggtggt tttataacaa tcagacaaaa cagtgtgaac
1141  gtttcatcta tggtggatgc gagggcaata tgaacaattt tgagacactg gaagaatgca
1201  agaacatttg tgaagatggt ccgaatggtt tccaggtcga caattatgga acccagctca
1261  atgctgtgaa taactccctg actccgcaat caaccaaggt tcccagcctt tttgaatttc
1321  acggtccctc atggtgtctc actcccgcgg acagaggacc gtgtattgcc ttttcccca
1381  gattctacta caattcagtc attgggaaat gccgcccatt tccgtatggc ggatgtcagg
1441  gaaatgaaaa caatttttact tccaaacaag aatgtctgag ggcatgtaaa aaaggttaat
1501  gatctagaag ctcgctgatc agcctcgact gtgccttcta gttgccagcc atctgttgtt
1561  tgccctcccc ccgtgccttc cttgaccctg gaaggtgcca ctcccactgt cctttcctaa
1621  taaaatgagg aaattgcatc gcattgtctg agtaggtgtc attctattct gggggtggg
1681  gtggggcagg acagcaaggg ggaggattgg gaagacaata gcaggcatgc tggggatggc
1741  ccgggctcta tggcttctga gcggaaaga accagctggg gctctagggg gtatccccac
1801  gcgccctgta gcggcgcatt aagcgcggcg ggtgtggtgg ttacgcgcag cgtgaccgct
1861  acacttgcca gcgccctagc gcccgctcct ttcgctttct tcccttcctt tctcgccacg
1921  ttcgccggct tccccgtca agctctaaat cggggcatcc ctttagggtt ccgatttagt
1981  gctttacggc acctcgaccc caaaaaactt gattagggtg atggttcacg tagtgggcca
2041  tcgccctgat agacggtttt tcgcccttg acgttggagt ccacgttctt taatagtgga
2101  ctcttgttcc aaactggaac aacactcaac cctatctcgg tctattcttt tgatttataa
2161  gggattttgg ggatttcggc ctattggtta aaaaatgagc tgatttaaca aaaatttaac
2221  gcgaattaat tctgtggaat gtgtgtcagt tagggtgtgg aaagtcccca ggctccccag
2281  gcaggcagaa gtatgcaaag catgcatctc aattagtcag caaccaggtg tggaaagtcc
2341  ccaggctccc cagcaggcag aagtatgcaa agcatgcatc tcaattagtc agcaaccata
2401  gtcccgcccc taactccgcc catcccgccc ctaactccgc ccagttccgc ccattctccg
2461  cccctaggct gactaatttt ttttatttat gcagaggccg aggccgcctc tgcctctgag
2521  ctattccaga agtagtgagg aggcttttt ggaggcctag gcttttgcaa aaagctcccg
2581  ggaggtccac aatgattgaa caagatggat tgcacgcagg ttctccggcc gcttgggtgg
2641  agaggctatt cggctatgac tgggcacaac agacaatcgg ctgctctgat gccgccgtgt
2701  tccggctgtc agcgcagggg cgcccggttc ttttttgtcaa gaccgacctg tccggtgccc
```

TABLE 54-continued

Vector for TFPI with plasmin, pKal, and hNe inhibition

```
2761  tgaatgaact ccaggacgag gcagcgcggc tatcgtggct ggccacgacg ggcgttcctt
2821  gcgcagctgt gctcgacgtt gtcactgaag cgggaaggga ctggctgcta ttgggcgaag
2881  tgccggggca ggatctcctg tcatctcacc ttgctcctgc cgagaaagta tccatcatgg
2941  ctgatgcaat gcggcggctg catacgcttg atccggctac ctgcccattc gaccaccaag
3001  cgaaacatcg catcgagcga gcacgtactc ggatggaagc cggtcttgtc gatcaggatg
3061  atctggacga agagcatcag gggctcgcgc cagccgaact gttcgccagg ctcaaggcgc
3121  gtatgcccga cggcgaggat ctcgtcgtga ctcatggcga tgcctgcttg ccgaatatca
3181  tggtggaaaa tggccgcttt tctggattca tcgactgtgg ccggctgggt gtggcggacc
3241  gctatcagga catagcgttg gctacccgtg atattgctga agagcttggc ggcgaatggg
3301  ctgaccgctt cctcgtgctt tacggtatcg ccgctcccga ttcgcagcgc atcgccttct
3361  atcgccttct tgacgagttc ttctgagcgg gactctgggg ttcgaaatga ccaccaagc
3421  gacgcccaac ctgccatcac gagatttcga ttccaccgcc gccttctatg aaaggttggg
3481  cttcggaatc gttttccggg acgccggctg gatgatcctc cagcgcgggg atctcatgct
3541  ggagttcttc gcccaccccca acttgtttat tgcagcttat aatggttaca ataaagcaa
3601  tagcatcaca aatttcacaa ataaagcatt ttttcactg cattctagtt gtggtttgtc
3661  caaactcatc aatgtatctt atcatgtctg tataccggat cttccgctt cctcgctcac
3721  tgactcgctg cgctcggtcg ttcggctgcg gcgagcggta tcagctcact caaaggcggt
3781  aatacggtta tccacagaat caggggataa cgcaggaaag aacatgtgag caaaaggcca
3841  gcaaaaggcc aggaaccgta aaaaggccgc gttgctggcg tttttccata ggctccgccc
3901  ccctgacgag catcacaaaa atcgacgctc aagtcagagg tggcgaaacc cgacaggact
3961  ataaagatac caggcgtttc ccctggaag ctccctcgtg cgctctcctg ttccgaccct
4021  gccgcttacc ggatacctgt ccgcctttct cccttcggga agcgtggcgc tttctcaatg
4081  ctcacgctgt aggtatctca gttcggtgta ggtcgttcgc tccaagctgg gctgtgtcca
4141  cgaacccccc gttcagcccg accgctgcgc cttatccggt aactatcgtc ttgagtccaa
4201  cccggtaaga cacgacttat cgccactggc agcagccact ggtaacagga ttagcagagc
4261  gaggtatgta ggcggtgcta cagagttctt gaagtggtgg cctaactacg gctacactag
4321  aaggacagta tttggtatct gcgctctgct gaagccagtt accttcggaa aaagagttgg
4381  tagctcttga tccggcaaac aaaccaccgc tggtagcggt ggttttttg tttgcaagca
4441  gcagattacg cgcagaaaaa aaggatctca agaagatcct ttgatctttt ctacggggtc
4501  tgacgctcag tggaacgaaa actcacgtta agggattttg gtcatgagat tatcaaaaag
4561  gatcttcacc tagatccttt taaattaaaa atgaagtttt aaatcaatct aaagtatata
4621  tgagtaaact tggtctgaca gttaccaatg cttaatcagt gaggcaccta tctcagcgat
4681  ctgtctattt cgttcatcca tagttgcctg actccccgtc gtgtagataa ctacgatacg
4741  ggagggctta ccatctggcc ccagtgctgc aatgataccg cgagacccac gctcaccggc
4801  tccagattta tcagcaataa accagccagc cggaagggcc gagcgcagaa gtggtcctgc
4861  aactttatcc gcctccatcc agtctattaa ttgttgccgg gaagctagag taagtagttc
4921  gccagttaat agtttgcgca acgttgttgc cattgctaca ggcatcgtgg tgtcacgctc
4981  gtcgtttggt atggcttcat tcagctccgg ttcccaacga tcaaggcgag ttacatgatc
5041  ccccatgttg tgcaaaaaag cggttagctc cttcggtcct ccgatcgttg tcagaagtaa
```

TABLE 54-continued

Vector for TFPI with plasmin, pKal, and hNe inhibition

```
5101  gttggccgca gtgttatcac tcatggttat ggcagcactg cataattctc ttactgtcat
5161  gccatccgta agatgctttt ctgtgactgg tgagtactca accaagtcat tctgagaata
5221  gtgtatgcgg cgaccgagtt gctcttgccc ggcgtcaata cgggataata ccgcgccaca
5281  tagcagaact ttaaaagtgc tcatcattgg aaaacgttct cggggcgaa aactctcaag
5341  gatcttaccg ctgttgagat ccagttcgat gtaacccact cgtgctccca actgatcttc
5401  agcatctttt actttcacca gcgtttctgg gtgagcaaaa acaggaaggc aaaatgccgc
5461  aaaaaaggga ataagggcga cacggaaatg ttgaatactc atactcttcc ttttcaata
5521  ttattgaagc atttatcagg gttattgtct catgagcgga tacatatttg aatgtattta
5581  gaaaaataaa caatagggg ttccgcgcac atttccccga aaagtgccac ctgacgtcag
5641  atcgacggat cgggagatcg
```

TABLE 55

Vector containing DXMMM

```
LOCUS      pFuse-dxmmm  5622 bp    DNA    circular         19 JUL. 2006
BASE COUNT   1321 a    1491 c    1446 g      1364 t
ORIGIN
                                                          (SEQ ID NO: 138)
   1  gtaccgaatt cacattgatt attgagtagt tattaatagt aatcaattac ggggtcatta
  61  gttcatagcc catatatgga gttccgcgtt acataactta cggtaaatgg cccgcctggc
 121  tgaccgccca acgacccccg cccattgacg tcaataatga cgtatgttcc catagtaacg
 181  ccaataggga ctttccattg acgtcaatgg gtggactatt tacggtaaac tgcccacttg
 241  gcagtacatc aagtgtatca tatgccaagt acgcccccta ttgacgtcaa tgacggtaaa
 301  tggcccgcct ggcattatgc ccagtacatg accttatggg actttcctac ttggcagtac
 361  atctacgtgt tagtcatcgc tattaccata gtgatgcggt tttggcagta catcaatggg
 421  cgtggatagc ggtttgactc acggggattt ccaagtctcc accccattga cgtcaatggg
 481  agtttgtttt ggcaccaaaa tcaacgggac tttccaaaat gtcgtaacaa ctccgcccca
 541  ttgacgcaaa tgggcggtag gcgtgtacgg tgggaggtct atataagcag agctttctgg
 601  ctaactagag aacccactgc ttactggcac gtggaaatta atacgacgtg ccaccatgg
 661  gatggtcctg catcatcctg tttctggtgg ccaccgccac aggcgcccac agcgacagcg
 721  aggaagatga ggaacacacc atcatcaccg acaccgagct gcccccctg aagcttatgc
 781  acagcttctg cgccttcaag gccgacgacg gcccctgcag ggccagattc gacagatggt
 841  tcttcaacat cttcaccagg cagtgcgagg aattcattta tggaggctgt gaaggcaatc
 901  agaaccggtt cgaatctctg gaagaatgca gaagatgtg caccagggac aacgccaaca
 961  ggatcatcaa gaccaccctg cagcaggaga gcccgactt ctgcttcctg gaagaggatc
1021  ctggcccctg cagagcccgg tttgaccggt ggttttacaa taaccagacc aagcagtgtg
1081  agcgctttat ctatgggggga tgtgaaggaa atatgaataa cttcgagaca ctggaagagt
1141  gtaagaacat ctgcgaggac ggccccaacg gcttccaggt ggacaactac ggcacccaat
1201  tgaacgccgt gaacaacagc ctgacccccc agagcaccaa ggtgcccagc ctgttcgagt
1261  tccacggccc cagctggtgc ctgacccag ccgacagggg cccatgccgc gccagatttg
1321  acaggtggta ctacaactcc gtgatcggca gtgcaggcc cttcatctac ggcggatgtg
1381  agggaaacga gaacaacttt actagtaagc aggaatgcct gaggcctgc aagaagggct
```

TABLE 55-continued

Vector containing DXMMM

```
1441  tcatccagag gatcagctga tgaatctaga agctcgctga tcagcctcga ctgtgccttc
1501  tagttgccag ccatctgttg tttgcccctc ccccgtgcct tccttgaccc tggaaggtgc
1561  cactcccact gtcctttcct aataaaatga ggaaattgca tcgcattgtc tgagtaggtg
1621  tcattctatt ctgggggggtg gggtggggca ggacagcaag ggggaggatt gggaagacaa
1681  tagcaggcat gctggggatg gcccgggctc tatggcttct gaggcggaaa gaaccagctg
1741  gggctctagg gggtatcccc acgcgccctg tagcggcgca ttaagcgcgg cgggtgtggt
1801  ggttacgcgc agcgtgaccg ctacacttgc cagcgcccta gcgcccgctc ctttcgcttt
1861  cttcccttcc tttctcgcca cgttcgccgg ctttccccgt caagctctaa atcggggcat
1921  ccctttaggg ttccgattta gtgctttacg gcacctcgac cccaaaaaac ttgattaggg
1981  tgatggttca cgtagtgggc catcgccctg atagacggtt tttcgccctt tgacgttgga
2041  gtccacgttc tttaatagtg gactcttgtt ccaaactgga acaacactca accctatctc
2101  ggtctattct tttgatttat aagggatttt ggggatttcg gcctattggt taaaaaatga
2161  gctgatttaa caaaaattta acgcgaatta attctgtgga atgtgtgtca gttagggtgt
2221  ggaaagtccc caggctcccc aggcaggcag aagtatgcaa agcatgcatc tcaattagtc
2281  agcaaccagg tgtggaaagt ccccaggctc cccagcaggc agaagtatgc aaagcatgca
2341  tctcaattag tcagcaacca tagtcccgcc cctaactccg cccatcccgc ccctaactcc
2401  gcccagtcc gcccattctc cgcccctagg ctgactaatt ttttttattt atgcagaggc
2461  cgaggccgcc tctgcctctg agctattcca gaagtagtga ggaggctttt ttggaggcct
2521  aggcttttgc aaaaagctcc cggagggtcc acaatgattg aacaagatgg attgcacgca
2581  ggttctccgg ccgcttgggt ggagaggcta ttcggctatg actgggcaca acagacaatc
2641  ggctgctctg atgccgccgt gttccggctg tcagcgcagg ggcgcccggt tctttttgtc
2701  aagaccgacc tgtccggtgc cctgaatgaa ctccaggacg aggcagcgcg gctatcgtgg
2761  ctggccacga cgggcgttcc ttgcgcagct gtgctcgacg ttgtcactga agcgggaagg
2821  gactggctgc tattgggcga agtgccgggg caggatctcc tgtcatctca ccttgctcct
2881  gccgagaaag tatccatcat ggctgatgca atgcggcggc tgcatacgct tgatccggct
2941  acctgcccat tcgaccacca agcgaaacat cgcatcgagc gagcacgtac tcggatggaa
3001  gccggtcttg tcgatcagga tgatctggac gaagagcatc aggggctcgc gccagccgaa
3061  ctgttcgcca ggctcaaggc gcgtatgccc gacggcgagg atctcgtcgt gactcatggc
3121  gatgcctgct tgccgaatat catggtggaa aatggccgct tttctggatt catcgactgt
3181  ggccggctgg gtgtggcgga ccgctatcag gacatagcgt tggctacccg tgatattgct
3241  gaagagcttg gcggcgaatg ggctgaccgc ttcctcgtgc tttacggtat cgccgctccc
3301  gattcgcagc gcatcgcctt ctatcgcctt cttgacgagt tcttctgagc gggactctgg
3361  ggttcgaaat gaccgaccaa gcgacgccca acctgccatc acgagatttc gattccaccg
3421  ccgccttcta tgaaaggttg ggcttcggaa tcgttttccg gacgccggc tggatgatcc
3481  tccagcgcgg ggatctcatg ctggagttct cgcccacccc aacttgttt attgcagctt
3541  ataatggtta caaataaagc aatagcatca caaatttcac aaataaagca tttttttcac
3601  tgcattctag ttgtggtttg tccaaactca tcaatgtatc ttatcatgtc tgtataccgg
3661  atctttccgc ttcctcgctc actgactcgc tgcgctcggt cgttcggctg cggcgagcgg
3721  tatcagctca ctcaaaggcg gtaatacggt tatccacaga atcaggggat aacgcaggaa
```

TABLE 55-continued

Vector containing DXMMM

```
3781  agaacatgtg agcaaaaggc cagcaaaagg ccaggaaccg taaaaaggcc gcgttgctgg
3841  cgttttttcca taggctccgc cccccctgacg agcatcacaa aaatcgacgc tcaagtcaga
3901  ggtggcgaaa cccgacagga ctataaagat accaggcgtt tccccctgga agctccctcg
3961  tgcgctctcc tgttccgacc ctgccgctta ccggatacct gtccgccttt ctcccttcgg
4021  gaagcgtggc gctttctcaa tgctcacgct gtaggtatct cagttcggtg taggtcgttc
4081  gctccaagct gggctgtgtc cacgaacccc cgttcagcc cgaccgctgc gccttatccg
4141  gtaactatcg tcttgagtcc aacccggtaa gacacgactt atcgccactg gcagcagcca
4201  ctggtaacag gattagcaga gcgaggtatg taggcggtgc tacagagttc ttgaagtggt
4261  ggcctaacta cggctacact agaaggacag tatttggtat ctgcgctctg ctgaagccag
4321  ttaccttcgg aaaaagagtt ggtagctctt gatccggcaa acaaaccacc gctggtagcg
4381  gtggtttttt tgtttgcaag cagcagatta cgcgcagaaa aaaaggatct caagaagatc
4441  ctttgatctt ttctacgggg tctgacgctc agtggaacga aaactcacgt taagggattt
4501  tggtcatgag attatcaaaa aggatcttca cctagatcct tttaaattaa aaatgaagtt
4561  ttaaatcaat ctaaagtata tatgagtaaa cttggtctga cagttaccaa tgcttaatca
4621  gtgaggcacc tatctcagcg atctgtctat ttcgttcatc catagttgcc tgactccccg
4681  tcgtgtagat aactacgata cgggagggct taccatctgg ccccagtgct gcaatgatac
4741  cgcgagaccc acgctcaccg gctccagatt tatcagcaat aaaccagcca gccggaaggg
4801  ccgagcgcag aagtggtcct gcaactttat ccgcctccat ccagtctatt aattgttgcc
4861  gggaagctag agtaagtagt tcgccagtta atagtttgcg caacgttgtt gccattgcta
4921  caggcatcgt ggtgtcacgc tcgtcgtttg gtatggcttc attcagctcc ggttcccaac
4981  gatcaaggcg agttacatga tcccccatgt tgtgcaaaaa agcggttagc tccttcggtc
5041  ctccgatcgt tgtcagaagt aagttggccg cagtgttatc actcatggtt atggcagcac
5101  tgcataattc tcttactgtc atgccatccg taagatgctt ttctgtgact ggtgagtact
5161  caaccaagtc attctgagaa tagtgtatgc ggcgaccgag ttgctcttgc ccggcgtcaa
5221  tacgggataa taccgcgcca catagcagaa ctttaaaagt gctcatcatt ggaaaacgtt
5281  cttcggggcg aaaactctca aggatcttac cgctgttgag atccagttcg atgtaaccca
5341  ctcgtgctcc caactgatct tcagcatctt ttactttcac cagcgtttct gggtgagcaa
5401  aaacaggaag gcaaaatgcc gcaaaaaagg gaataagggc gacacggaaa tgttgaatac
5461  tcatactctt cctttttcaa tattattgaa gcatttatca gggttattgt ctcatgagcg
5521  gatacatatt tgaatgtatt tagaaaaata aacaaatagg ggttccgcgc acatttcccc
5581  gaaaagtgcc acctgacgtc agatcgacgg atcgggagat cg
```

55

TABLE 56

AA sequence of hTFPImC1 (SEQ ID NO: 139)

| Item | Extent | AA sequence |
|---|---|---|
| Signal | 1-19 | MGWSCIILFLVATATGAHS |
| Cleaveage | 20-24 | EGRPG |
| His tag | 25-30 | HHHHHH |

TABLE 56-continued

AA sequence of hTFPImC1 (SEQ ID NO: 139)

| Item | Extent | AA sequence |
| --- | --- | --- |
| Thrombin | 31-39 | GGSSLVPRG |
| Linker 1 | 40-59 | SEEDEEHTIITDTELPPLKL |
| KuDom 1 | 60-117 | MHSFCAFKADDGPCKAIMKRFFFNIFTRQCEEFIYGGCEGNQNRFESLEECKKMCTRD |
| Linker 2 | 118-130 | NANRIIKTTLQQE |
| KuDom 2 | 131-188 | KPDFCFLEEDPGICRGYITRYFYNNQTKQCERFKYGGCLGNMNNFETLEECKNICEDG (*) |
| Linker 3 | 189-222 | PNGFQVDNYGTQLNAVNNSLTPQSTKVPSLFEFH (*) |
| KuDom 3 | 223-280 | GPSWCLTPADRGLCRANENRFYYNSVIGKCRPFKYSGCGGNENNFTSKQECLRACKKG (*) |

TABLE 57

AA sequence of hTFPI[PpKhNE] (SEQ ID NO: 140)

| Function | Limits | AA sequence |
| --- | --- | --- |
| Signal | 1-19 | MGWSCIILFLVATATGAHS |
| Cleavage | 20-24 | EGRPG |
| His6 | 25-30 | HHHHHH |
| Thrombin | 31-39 | GGSSLVPRG |
| Linker 1 | 40-59 | SEEDEEHTIITDTELPPLKL |
| KuDom 1 | 60-117 | MHSFCAFKADDGPCRARFDRWFFNIFTRQCEEFIYGGCEGNQNRFESLEECKKMCTRD<br>              K IMK F  <- wild type |
| Linker 2 | 118-130 | NANRIIKTTLQQE |
| KuDom 2 | 131-188 | KPDFCFLEEDPGPCRAAHPRWFYNNQTKQCERFIYGGCEGNMNNFETLEECKNICEDG (*)<br>           I   GYIT  Y         K     L    <- wild type |
| Linker 3 | 189-222 | PNGFQVDNYGTQLNAVNNSLTPQSTKVPSLFEFH |
| KuDom 4 | 223-280 | GPSNCLTPADRGPCIAFFPRFYYNSVIGKCRPFPYGGCQGNENNFTSKQECLRACKKG (*)<br>         L    R NEN           K S  G      <- wild type |

TABLE 58

Amino-acid sequence of PLA301B (SEQ ID NO: 141)

| Function | Limits | AA sequence |
| --- | --- | --- |
| Signal | 1-19 | MGWSCIILFLVATATGAHS |
| Linker 1 | 20-40 | DSEEDEEHTIITDTELPPLKL |
| KuDom 1 | 41-98 | MHSFCAFKADDGPCRARFDRWFFNIFTRQCEEFIYGGCEGNQNRFESLEECKKMCTRD<br>              K IMK F  <- wild type |
| Linker 2 | 99-111 | NANRIIKTTLQQE |
| KuDom 2 | 112-169 | KPDFCFLEEDPGPCRARFDRWFYNNQTKQCERFIYGGCEGNMNNFETLEECKNICEDG (*)<br>           I   GYIT Y         K    <- wild type |

TABLE 58-continued

Amino-acid sequence of PLA301B (SEQ ID NO: 141)

| Function | Limits | AA sequence |
|---|---|---|
| Linker 3 | 170-203 | PNGFQVDNYGTQLNAVNNSLTPQSTKVPSLFEFH |
| KuDom 3 | 204-261 | GPSWCLTPADRGPCRARFDRWYYNSVIGKCRPFIYGGCEGNENNFTSKQECLRACKKG |
|  |  |             L    NEN F          K S  G   <- wild type |
| Linker 4 | 262-267 | FIQRIS |

TABLE 60

Distributions of AA types in 103 KuDoms, including 19 human KuDoms

| Res. Id. | Different AA types | Contents |
|---|---|---|
| -5 | 12 | -58 21 T4 E4 S4 Q3 R3 P2 L D A K |
| -4 | 14 | -56 21 A4 P3 D3 L3 F2 V2 W2 E2 N2 Q S G |
| -3 | 15 | -52 20 Q5 K5 P5 E4 T2 F2 L2 A R D V M G |
| -2 | 16 | -33 19 Q7 E7 K7 P5 A5 R4 F3 T3 H2 W2 G2 L2 S Y |
| -1 | 17 | -24 19 R11 D7 Q6 T5 K5 P5 N4 V4 G3 E3 H2 L2 Z C S |
| 1 | 18 | R31 K15 T12 V6 -6 G5 D4 I3 S3 A3 L3 P3 H2 Y2 M2 F N E |
| 2 | 18 | P40 E11 R8 H7 V7 A6 K5 Q4 N3 D2 I2 -2 L M S T G F |
| 3 | 15 | D37 S11 K9 E9 A8 T7 P6 R5 G4 Y2 L Q W N — |
| 4 | 13 | F37 A12 I12 V8 S7 L6 Y6 D5 W3 P3 H2 M K |
| 5 | 3 | C101 A S |
| 6 | 16 | L25 N12 E11 S10 Q7 K7 AS I4 R4 F4 Y4 T3 D3 G2 V M |
| 7 | 13 | L53 E23 Q7 K4 M3 A3 D2 F2 S2 H P T V |
| 8 | 13 | P66 G6 A6 E5 Q5 H3 K3 D2 L2 S2 N I W |
| 9 | 16 | P30 A17 K10 I8 V8 L6 Y6 E4 R4 F3 M2 Q H S N D |
| 9a | 6 | -96 G3 P Q S D |
| 10 | 13 | D23 E19 V15 Y15 R7 S7 N6 A5 K2 I Q W M |
| 11 | 14 | T31 Q12 P12 V8 R7 S6 E5 I4 K4 D4 A4 Y3 G2 H |
| 12 | 6 | G97 D2 E I K T |
| 13 | 11 | P60 R11 L9 I5 S5 N4 T3 Q2 D2 E V |
| 14 | 1 | C103 |
| 15 | 14 | K33 R32 L8 F5 T5 N3 Y3 -3 D2 S2 M2 E2 Q2 G |
| 16 | 12 | A60 G24 D4 K4 E2 Q2 R2 L H F S T |
| 17 | 18 | R17 Y15 F13 S10 M10 K7 N6 H6 G4 L3 A2 P2 T2 Q2 D I V E |
| 18 | 12 | I48 F17 M12 V8 T4 E4 L3 A3 P D K Y |
| 19 | 14 | P23 I16 K13 R12 L8 S8 T7 Q6 E4 V2 H N F G |

TABLE 60-continued

Distributions of AA types in 103 KuDoms, including 19 human KuDoms

| Res. Id. | Different AA types | Contents |
|---|---|---|
| 20 | 10 | R60 L12 A10 S9 K4 G2 Q2 V2 H I |
| 21 | 8 | Y43 F29 W24 I2 L2 R K E |
| 22 | 8 | Y41 F35 A12 W5 H4 S4 R N |
| 23 | 4 | Y75 F24 H2 A2 |
| 24 | 7 | N65 D26 K4 Y3 S2 R2 F |
| 25 | 16 | A31 P10 S10 G7 Q6 L6 N5 V5 W5 F4 T4 K3 R3 I2 D M |
| 26 | 16 | K27 A13 T13 V9 E8 R7 S7 Q5 D3 N2 I2 F2 Y2 H L G |
| 26a | 3 | -101 T N |
| 26b | 2 | -101 G2 |
| 26c | 4 | -100 V Y S |
| 27 | 12 | A25 S24 T23 K9 Q5 L4 E4 I3 D3 N R Y |
| 28 | 10 | G39 K23 N11 M9 H5 Q5 R5 E3 S2 Y |
| 29 | 14 | K31 Q19 L14 A11 R6 S6 T6 E2 F2 G2 H I M N |
| 30 | 3 | C101 A V |
| 31 | 16 | E32 Q20 V11 K7 L6 R5 A5 T4 H3 I2 N2 D2 M S Y Z |
| 32 | 13 | P21 T18 R11 L10 Q10 S8 E8 K6 A3 N2 G2 M2 V2 |
| 33 | 2 | F102 Y |
| 34 | 17 | I24 V22 T10 K9 F6 N5 Q5 H4 L4 D3 W3 E2 P2 A R S Y |
| 35 | 7 | Y94 W3 F2 S D G - |
| 36 | 5 | G83 S11 T5 R3 - |
| 37 | 2 | G101 I2 |
| 38 | 1 | C103 |
| 39 | 12 | G32 R21 Q12 K8 E7 L7 M6 D5 P2 N H Y |
| 40 | 5 | G85 A15 E K R |
| 41 | 3 | N84 K15 D4 |
| 42 | 12 | A23 R17 G16 S10 E7 D7 N6 K5 H4 Q4 L2 M2 |
| 42a | 4 | -100 N T I |
| 42b | 3 | -101 G E |
| 42c | 2 | -102 A |
| 43 | 5 | N96 G4 D R Y |

TABLE 60-continued

Distributions of AA types in 103 KuDoms, including 19 human KuDoms

| Res. Id. | Different AA types | Contents |
|---|---|---|
| 44 | 8 | N61 R27 K8 Q3 F S V Y |
| 45 | 5 | P95 Y5 E A D |
| 46 | 17 | K31 E17 Y11 D7 V6 L6 S4 G4 R4 T3 Q2 N2 P2 I A H M |
| 47 | 8 | S47 T46 N3 D2 R2 K L E |
| 48 | 13 | E21 I16 L16 A13 Q11 K8 R7 D3 W3 T2 V S Y |
| 49 | 13 | E45 K18 D12 A8 Q7 H4 P2 R2 G M N T V |
| 50 | 11 | E55 D21 A8 K4 Q4 Y4 L3 N C T M |
| 51 | 3 | C100 A2 K |
| 52 | 13 | R26 M22 L15 K13 E11 Q5 N3 I2 F H D S V |
| 53 | 15 | R34 Q13 E13 K9 N8 A6 H4 C3 T3 G2 L2 D2 W2 M S |
| 54 | 13 | T45 A13 Y10 V7 K6 I5 F5 R5 E3 S L Q C |
| 55 | 4 | C100 A T - |
| 56 | 16 | G32 R15 V12 I9 E7 K7 A6 S3 L3 P2 M2 H F D W — |
| 57 | 16 | G30 V11 T9 P8 A7 K6 -6 N5 D4 R4 S4 L3 I3 Q Y F |
| 58 | 18 | -23 A18 P13 V11 K7 G6 I4 R3 Y3 S3 N2 E2 Q2 D2 T M F C |
| 59 | 17 | -43 G11 A9 9 S4 E4 I4 V3 Y3 F2 K2 P2 Q2 R2 N T L |
| 60 | 16 | -45 I1 A6 D6 P5 I5 K5 G4 E4 N3 V3 S2 T Q R C |
| 61 | 13 | -53 I1 G8 E5 P5 Q4 K4 A4 S2 T2 D2 R2 V |
| 62 | 19 | -53 I2 D8 P4 R3 S3 K3 G3 Y2 E2 T2 A L M V W N I Q |
| 63 | 13 | -49 22 E10 Q3 R3 S3 G3 K3 I2 T2 V L P |
| 64 | 12 | -50 27 E6 S3 V3 K3 N3 I2 R2 L2 T D |

TABLE 61

PlaMatHep, a Modified Human TFPI inhibiting Plasmin, Matriptase, and Hepsin (SEQ ID NO: 142)

| AAs | Function | AA sequence |
|---|---|---|
| 1-21 | Linker 1 | DSEEDEEHTIITDTELPPLKL |
| 22-79 | KuDom 1 Inhibit plasmin | MHSFCAFKADDGPCRARFDRWFFNIFTRQCEEFIYGGCEGNQNRFESLEECKKMCTRD |
| 80-92 | Linker 2 | NANRIIKTTLQQE |
| 93-150 | KuDom 2 Inhibit matriptase | kpdfcfleedpgRcrgSFPrWfynnqtkqcKSfVyggclgnmnnfetleecknicedg |
| 151-184 | Linker 3 | PNGFQVDNYGTQLNAVnNSLTPQSTKVPSLFEFH |

TABLE 61-continued

PlaMatHep, a Modified Human TFPI inhibiting Plasmin, Matriptase, and Hepsin (SEQ ID NO: 142)

| AAs | Function | AA sequence |
|---|---|---|
| 185-242 | KuDom 3 Inhibit hepsin | gpswcltpadVgRcraSMPrWyynsvigkcrpfVyGgcggnSnnftsEqeclrackkg<br>1 5 1 1 2 2 3 3 4 4 5 5 5<br>0 5 0 5 0 5 0 5 0 5 8 |
| 243-248 | Linker 4 | FIQRIS |

Possible sites of glycosylation are shown as "n".

Other embodiments are within the following claims.

What is claimed is:

1. An isolated protein comprising two to six engineered Kunitz domain sequences, wherein the protein comprises the amino acid sequence of SEQ ID NO:11, 54, 70, 71, 72, 73, 74, 102, 106, 107 or 127.

2. The isolated protein of claim 1, wherein the protein does not include a serum albumin moiety.

3. The protein of claim 1, wherein the protein comprises three Kunitz domains.

4. The protein of claim 1, wherein the protein comprises four Kunitz domains.

5. The protein of claim 1, wherein the protein comprises five Kunitz domains.

6. The protein of claim 1, wherein the protein comprises six Kunitz domains.

7. The protein of claim 1, wherein the protein is modified with two or more PEG moieties.

* * * * *

SEQUENCE LISTING

<160> NUMBER OF SEQ ID NOS: 203

<210> SEQ ID NO 1
<211> LENGTH: 304
<212> TYPE: PRT
<213> ORGANISM: Homo sapiens

<400> SEQUENCE: 1

```
Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
            20                  25                  30

Asp Glu Glu His Thr Ile Ile Thr Asp Thr Glu Leu Pro Pro Leu Lys
        35                  40                  45

Leu Met His Ser Phe Cys Ala Phe Lys Ala Asp Asp Gly Pro Cys Lys
50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
            100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
            180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                245                 250                 255

Phe Thr Ser Lys Gln Glu Cys Leu Arg Ala Cys Lys Lys Gly Phe Ile
            260                 265                 270
```

Gln Arg Ile Ser Lys Gly Gly Leu Ile Lys Thr Lys Arg Arg Lys
        275                 280                 285

Lys Gln Arg Val Lys Ile Ala Tyr Glu Glu Ile Phe Val Lys Asn Met
        290                 295                 300

<210> SEQ ID NO 2
<211> LENGTH: 1431
<212> TYPE: DNA
<213> ORGANISM: Homo sapiens

<400> SEQUENCE: 2

```
ggcgggtctg cttctaaaag aagaagtaga gaagataaat cctgtcttca atacctggaa    60
ggaaaaacaa aataacctca actccgtttt gaaaaaaaca ttccaagaac tttcatcaga   120
gattttactt agatgattta cacaatgaag aaagtacatg cactttgggc ttctgtatgc   180
ctgctgctta atcttgcccc tgcccctctt aatgctgatt ctgaggaaga tgaagaacac   240
acaattatca cagatacgga gttgccacca ctgaaactta tgcattcatt tgtgcattc   300
aaggcggatg atggcccatg taagcaatc atgaaaagat ttttcttcaa tattttcact   360
cgacagtgcg aagaatttat atatggggga tgtgaaggaa atcagaatcg atttgaaagt   420
ctggaagagt gcaaaaaaat gtgtacaaga gataatgcaa acaggattat aagacaaca   480
ttgcaacaag aaaagccaga tttctgcttt ttggaagaag atcctggaat atgtcgaggt   540
tatattacca ggtatttta taacaatcag acaaacagt gtgaacgttt caagtatggt   600
ggatgcctgg gcaatatgaa caattttgag acactggaag aatgcaagaa catttgtgaa   660
gatggtccga atggtttcca ggtggataat tatggaaccc agctcaatgc tgtgaataac   720
tccctgactc cgcaatcaac caaggttccc agccttttttg aatttcacgg tccctcatgg   780
tgtctcactc cagcagacag aggattgtgt cgtgccaatg agaacagatt ctactacaat   840
tcagtcattg ggaaatgccg cccatttaag tacagtggat gtgggggaaa tgaaaacaat   900
tttacttcca acaagaatg tctgagggca tgtaaaaaag gtttcatcca agaatatca   960
aaaggaggcc taattaaaac caaaagaaaa agaaagaagc agagagtgaa aatagcatat  1020
gaagaaattt ttgttaaaaa tatgtgaatt tgttatagca atgtaacatt aattctacta  1080
aatattttat atgaaatgtt tcactatgat tttctattt tcttctaaaa tcgttttaat  1140
taatatgttc attaaatttt ctatgcttat tgtacttgtt atcaacacgt ttgtatcaga  1200
gttgcttttc taatcttgtt aaattgctta ttctaggtct gtaatttatt aactggctac  1260
tgggaaatta cttattttct ggatctatct gtattttcat ttaactacaa attatcatac  1320
taccggctac atcaaatcag tcctttgatt ccatttggtg accatctgtt tgagaatatg  1380
atcatgtaaa tgattatctc ctttatagcc tgtaaccaga ttaagccccc c           1431
```

<210> SEQ ID NO 3
<211> LENGTH: 58
<212> TYPE: PRT
<213> ORGANISM: Homo sapiens

<400> SEQUENCE: 3

Met His Ser Phe Cys Ala Phe Lys Ala Asp Asp Gly Pro Cys Lys Ala
  1               5                  10                  15

Ile Met Lys Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
        50                  55

<210> SEQ ID NO 4
<211> LENGTH: 58
<212> TYPE: PRT
<213> ORGANISM: Homo sapiens

<400> SEQUENCE: 4

Lys Pro Asp Phe Cys Phe Leu Glu Glu Asp Pro Gly Ile Cys Arg Gly
  1               5                  10                  15

Tyr Ile Thr Arg Tyr Phe Tyr Asn Asn Gln Thr Lys Gln Cys Glu Arg
             20                  25                  30

Phe Lys Tyr Gly Gly Cys Leu Gly Asn Met Asn Asn Phe Glu Thr Leu
         35                  40                  45

Glu Glu Cys Lys Asn Ile Cys Glu Asp Gly
        50                  55

<210> SEQ ID NO 5
<211> LENGTH: 58
<212> TYPE: PRT
<213> ORGANISM: Homo sapiens

<400> SEQUENCE: 5

Gly Pro Ser Trp Cys Leu Thr Pro Ala Asp Arg Gly Leu Cys Arg Ala
  1               5                  10                  15

Asn Glu Asn Arg Phe Tyr Tyr Asn Ser Val Ile Gly Lys Cys Arg Pro
             20                  25                  30

Phe Lys Tyr Ser Gly Cys Gly Gly Asn Glu Asn Asn Phe Thr Ser Lys
         35                  40                  45

Gln Glu Cys Leu Arg Ala Cys Lys Lys Gly
        50                  55

<210> SEQ ID NO 6
<211> LENGTH: 5705
<212> TYPE: DNA
<213> ORGANISM: Homo sapiens
<220> FEATURE:
<220> FEATURE:
<221> NAME/KEY: CDS
<222> LOCATION: (657)..(1542)

<400> SEQUENCE: 6

| | | |
|---|---|---|
| gtaccgaatt cacattgatt attgagtagt tattaatagt aatcaattac ggggtcatta | 60 |
| gttcatagcc catatatgga gttccgcgtt acataactta cggtaaatgg cccgcctggc | 120 |
| tgaccgccca acgaccccg cccattgacg tcaataatga cgtatgttcc catagtaacg | 180 |
| ccaatagga ctttccattg acgtcaatgg gtggactatt tacggtaaac tgcccacttg | 240 |
| gcagtacatc aagtgtatca tatgccaagt acgccccta ttgacgtcaa tgacggtaaa | 300 |
| tggcccgcct ggcattatgc ccagtacatg accttatggg actttcctac ttggcagtac | 360 |
| atctacgtgt tagtcatcgc tattaccata gtgatgcggt tttggcagta catcaatggg | 420 |
| cgtggatagc ggtttgactc acggggattt ccaagtctcc accccattga cgtcaatggg | 480 |
| agtttgtttt ggcaccaaaa tcaacgggac tttccaaaat gtcgtaacaa ctccgcccca | 540 |
| ttgacgcaaa tgggcggtag gcgtgtacgg tgggaggtct atataagcag agctttctgg | 600 |
| ctaactagag aacccactgc ttactggcac gtggaaatta atacgacgtg gccacc atg | 659 |
|  |  | Met |
|  |  | 1 |

```
gga tgg agc tgt atc atc ctc ttc ttg gtc gcg acg gcc aca ggg gcc       707
Gly Trp Ser Cys Ile Ile Leu Phe Leu Val Ala Thr Ala Thr Gly Ala
          5                  10                 15 cac tcc gac tct gag gaa gat gaa gaa cac aca att atc aca gat acg       755
His Ser Asp Ser Glu Glu Asp Glu Glu His Thr Ile Ile Thr Asp Thr
             20                  25                 30 gag ctc cca cca ctg aag ctt atg cat tca ttt tgt gca ttc aag gcg       803
Glu Leu Pro Pro Leu Lys Leu Met His Ser Phe Cys Ala Phe Lys Ala
         35                  40                  45 gat gat ggc cca tgt aaa gca atc atg aaa aga ttt ttc ttc aat att       851
Asp Asp Gly Pro Cys Lys Ala Ile Met Lys Arg Phe Phe Phe Asn Ile
 50                  55                  60                  65 ttc acg cgt cag tgc gaa gaa ttt ata tat ggg gga tgt gaa ggt aac       899
Phe Thr Arg Gln Cys Glu Glu Phe Ile Tyr Gly Gly Cys Glu Gly Asn
                 70                  75                  80 cag aat cga ttt gaa tct ctg gaa gag tgc aaa aaa atg tgt aca aga       947
Gln Asn Arg Phe Glu Ser Leu Glu Glu Cys Lys Lys Met Cys Thr Arg
             85                  90                  95 gat aat gca aac agg att ata aag aca aca ttg caa caa gaa aag cca       995
Asp Asn Ala Asn Arg Ile Ile Lys Thr Thr Leu Gln Gln Glu Lys Pro
        100                 105                 110 gat ttc tgc ttt ctc gag gag gat cct gga ata tgt cga ggt tat att      1043
Asp Phe Cys Phe Leu Glu Glu Asp Pro Gly Ile Cys Arg Gly Tyr Ile
    115                 120                 125 acc agg tat ttt tat aac aat cag aca aaa cag tgt gaa cgt ttc aag      1091
Thr Arg Tyr Phe Tyr Asn Asn Gln Thr Lys Gln Cys Glu Arg Phe Lys
130                 135                 140                 145 tat ggt gga tgc ctg ggc aat atg aac aat ttt gag acg ctg gaa gaa      1139
Tyr Gly Gly Cys Leu Gly Asn Met Asn Asn Phe Glu Thr Leu Glu Glu
                150                 155                 160 tgc aag aac att tgt gaa gat ggg ccc aat ggt ttc cag gtc gac aat      1187
Cys Lys Asn Ile Cys Glu Asp Gly Pro Asn Gly Phe Gln Val Asp Asn
            165                 170                 175 tat gga acc cag ctc aat gct gtg aat aac tcc ctg act ccg caa tca      1235
Tyr Gly Thr Gln Leu Asn Ala Val Asn Asn Ser Leu Thr Pro Gln Ser
        180                 185                 190 acc aag gtt ccc agc ctt ttt gaa ttt cac ggt ccc tca tgg tgt ctc      1283
Thr Lys Val Pro Ser Leu Phe Glu Phe His Gly Pro Ser Trp Cys Leu
    195                 200                 205 act ccc gcg gac aga gga ttg tgt cgt gcc aat gag aac aga ttc tac      1331
Thr Pro Ala Asp Arg Gly Leu Cys Arg Ala Asn Glu Asn Arg Phe Tyr
210                 215                 220                 225 tac aat tca gtc att ggg aaa tgc cgc cca ttt aag tat tcc gga tgt      1379
Tyr Asn Ser Val Ile Gly Lys Cys Arg Pro Phe Lys Tyr Ser Gly Cys
                230                 235                 240 ggg gga aat gaa aac aat ttt act tcc aaa caa gaa tgt ctg cgc gca      1427
Gly Gly Asn Glu Asn Asn Phe Thr Ser Lys Gln Glu Cys Leu Arg Ala
            245                 250                 255 tgt aaa aaa ggt ttc atc caa aga ata tca aaa gga ggc cta att aaa      1475
Cys Lys Lys Gly Phe Ile Gln Arg Ile Ser Lys Gly Gly Leu Ile Lys
        260                 265                 270 acc aaa aga aaa aga aag aag cag aga gtg aaa ata gca tat gaa gaa      1523
Thr Lys Arg Lys Arg Lys Lys Gln Arg Val Lys Ile Ala Tyr Glu Glu
    275                 280                 285 att ttt gtt aaa aat atg t aatgatctag aagctcgctg atcagcctcg           1572
Ile Phe Val Lys Asn Met
290                 295 actgtgcctt ctagttgcca gccatctgtt gtttgcccct cccccgtgcc ttccttgacc    1632
```

```
ctggaaggtg ccactcccac tgtcctttcc taataaaatg aggaaattgc atcgcattgt   1692
ctgagtaggt gtcattctat tctgggggt ggggtggggc aggacagcaa ggggaggat    1752
tgggaagaca atagcaggca tgctggggat ggcccgggct ctatggcttc tgaggcggaa   1812
agaaccagct ggggctctag ggggtatccc cacgcgccct gtagcggcgc attaagcgcg   1872
gcgggtgtgg tggttacgcg cagcgtgacc gctacacttg ccagcgccct agcgcccgct   1932
cctttcgctt tcttcccttc ctttctcgcc acgttcgccg gctttccccg tcaagctcta   1992
aatcggggca tccctttagg gttccgattt agtgctttac ggcacctcga ccccaaaaaa   2052
cttgattagg gtgatggttc acgtagtggg ccatcgccct gatagacggt ttttcgccct   2112
ttgacgttgg agtccacgtt ctttaatagt ggactcttgt tccaaactgg aacaacactc   2172
aaccctatct cggtctattc ttttgattta taagggattt tggggatttc ggcctattgg   2232
ttaaaaatg agctgattta acaaaaattt aacgcgaatt aattctgtgg aatgtgtgtc    2292
agttagggtg tggaaagtcc ccaggctccc caggcaggca gaagtatgca aagcatgcat   2352
ctcaattagt cagcaaccag gtgtggaaag tccccaggct cccagcagg cagaagtatg    2412
caaagcatgc atctcaatta gtcagcaacc atagtcccgc ccctaactcc gcccatcccg   2472
cccctaactc cgcccagttc cgcccattct ccgcccctag gctgactaat ttttttatt    2532
tatgcagagg ccgaggccgc ctctgcctct gagctattcc agaagtagtg aggaggcttt   2592
tttggaggcc taggcttttg caaaaagctc ccggaggtc cacaatgatt gaacaagatg    2652
gattgcacgc aggttctccg gccgcttggg tggagaggct attcggctat gactgggcac   2712
aacagacaat cggctgctct gatgccgccg tgttccggct gtcagcgcag gggcgcccgg   2772
ttcttttgt caagaccgac ctgtccggtg ccctgaatga actccaggac gaggcagcgc    2832
ggctatcgtg gctggccacg acgggcgttc cttgcgcagc tgtgctcgac gttgtcactg   2892
aagcgggaag ggactggctg ctattgggcg aagtgccggg gcaggatctc ctgtcatctc   2952
accttgctcc tgccgagaaa gtatccatca ggctgatgc aatgcggcgg ctgcatacgc    3012
ttgatccggc tacctgccca ttcgaccacc aagcgaaaca tcgcatcgag cgagcacgta   3072
ctcggatgga agccggtctt gtcgatcagg atgatctgga cgaagagcat caggggctcg   3132
cgccagccga actgttcgcc aggctcaagg cgcgtatgcc cgacggcgag gatctcgtcg   3192
tgactcatgg cgatgcctgc ttgccgaata tcatggtgga aaatggccgc ttttctggat   3252
tcatcgactg tggccggctg ggtgtggcgg accgctatca ggacatagcg ttggctaccc   3312
gtgatattgc tgaagagctt ggcggcgaat gggctgaccg cttcctcgtg ctttacggta   3372
tcgccgctcc cgattcgcag cgcatcgcct tctatcgcct tcttgacgag ttcttctgag   3432
cgggactctg gggttcgaaa tgaccgacca agcgacgccc aacctgccat cacgagattt   3492
cgattccacc gccgccttct atgaaaggtt gggcttcgga atcgttttcc gggacgccgg   3552
ctggatgatc ctccagcgcg ggatctcat gctggagttc ttcgcccacc ccaacttgtt    3612
tattgcagct tataatggtt acaaataaag caatagcatc acaaatttca caaataaagc   3672
attttttca ctgcattcta gttgtggttt gtccaaactc atcaatgtat cttatcatgt    3732
ctgtataccg gatctttccg cttcctcgct cactgactcg ctgcgctcgg tcgttcggct   3792
gcggcgagcg gtatcagctc actcaaaggc ggtaatacgg ttatccacag aatcagggga   3852
taacgcagga aagaacatgt gagcaaaagg ccagcaaaag gccaggaacc gtaaaaaggc   3912
cgcgttgctg gcgtttttcc ataggctccg cccccctgac gagcatcaca aaaatcgacg   3972
ctcaagtcag aggtggcgaa acccgacagg actataaaga taccaggcgt ttcccctgg    4032
```

```
aagctccctc gtgcgctctc ctgttccgac cctgccgctt accggatacc tgtccgcctt    4092
tctcccttcg ggaagcgtgg cgctttctca atgctcacgc tgtaggtatc tcagttcggt    4152
gtaggtcgtt cgctccaagc tgggctgtgt ccacgaaccc cccgttcagc ccgaccgctg    4212
cgccttatcc ggtaactatc gtcttgagtc aacccggta agacacgact tatcgccact     4272
ggcagcagcc actggtaaca ggattagcag agcgaggtat gtaggcggtg ctacagagtt    4332
cttgaagtgg tggcctaact acggctacac tagaaggaca gtatttggta tctgcgctct    4392
gctgaagcca gttaccttcg gaaaagagt tggtagctct tgatccggca aacaaaccac    4452
cgctggtagc ggtggttttt ttgtttgcaa gcagcagatt acgcgcagaa aaaaggatc    4512
tcaagaagat cctttgatct tttctacggg gtctgacgct cagtggaacg aaaactcacg    4572
ttaagggatt ttggtcatga gattatcaaa aaggatcttc acctagatcc ttttaaatta    4632
aaaatgaagt tttaaatcaa tctaaagtat atatgagtaa acttggtctg acagttacca    4692
atgcttaatc agtgaggcac ctatctcagc gatctgtcta tttcgttcat ccatagttgc    4752
ctgactcccc gtcgtgtaga taactacgat acgggagggc ttaccatctg gccccagtgc    4812
tgcaatgata ccgcgagacc cacgctcacc ggctccagat ttatcagcaa taaaccagcc    4872
agccggaagg gccgagcgca gaagtggtcc tgcaacttta tccgcctcca tccagtctat    4932
taattgttgc cgggaagcta gagtaagtag ttcgccagtt aatagtttgc gcaacgttgt    4992
tgccattgct acaggcatcg tggtgtcacg ctcgtcgttt ggtatggctt cattcagctc    5052
cggttcccaa cgatcaaggc gagttacatg atcccccatg ttgtgcaaaa aagcggttag    5112
ctccttcggt cctccgatcg ttgtcagaag taagttggcc gcagtgttat cactcatggt    5172
tatggcagca ctgcataatt ctcttactgt catgccatcc gtaagatgct tttctgtgac    5232
tggtgagtac tcaaccaagt cattctgaga atagtgtatg cggcgaccga gttgctcttg    5292
cccggcgtca atacgggata ataccgcgcc acatagcaga actttaaaag tgctcatcat    5352
tggaaaacgt tcttcggggc gaaaactctc aaggatctta ccgctgttga tccagttc    5412
gatgtaaccc actcgtgctc ccaactgatc ttcagcatct tttactttca ccagcgtttc    5472
tgggtgagca aaaacaggaa ggcaaaatgc cgcaaaaaag gaataagggc gacacggaa    5532
atgttgaata ctcatactct tcctttttca atattattga agcatttatc agggttattg    5592
tctcatgagc ggatacatat ttgaatgtat ttagaaaaat aaacaaatag ggttccgcg    5652
cacatttccc cgaaaagtgc cacctgacgt cagatcgacg gatcgggaga tcg           5705
```

<210> SEQ ID NO 7
<211> LENGTH: 295
<212> TYPE: PRT
<213> ORGANISM: Homo sapiens

<400> SEQUENCE: 7

```
Met Gly Trp Ser Cys Ile Ile Leu Phe Leu Val Ala Thr Ala Thr Gly
 1               5                  10                  15

Ala His Ser Asp Ser Glu Glu Asp Glu Glu His Thr Ile Ile Thr Asp
                20                  25                  30

Thr Glu Leu Pro Pro Leu Lys Leu Met His Ser Phe Cys Ala Phe Lys
            35                  40                  45

Ala Asp Asp Gly Pro Cys Lys Ala Ile Met Lys Arg Phe Phe Phe Asn
        50                  55                  60

Ile Phe Thr Arg Gln Cys Glu Glu Phe Ile Tyr Gly Gly Cys Glu Gly
 65                  70                  75                  80
```

```
Asn Gln Asn Arg Phe Glu Ser Leu Glu Glu Cys Lys Lys Met Cys Thr
                85                  90                  95

Arg Asp Asn Ala Asn Arg Ile Ile Lys Thr Thr Leu Gln Gln Glu Lys
            100                 105                 110

Pro Asp Phe Cys Phe Leu Glu Glu Asp Pro Gly Ile Cys Arg Gly Tyr
        115                 120                 125

Ile Thr Arg Tyr Phe Tyr Asn Asn Gln Thr Lys Gln Cys Glu Arg Phe
130                 135                 140

Lys Tyr Gly Gly Cys Leu Gly Asn Met Asn Asn Phe Glu Thr Leu Glu
145                 150                 155                 160

Glu Cys Lys Asn Ile Cys Glu Asp Gly Pro Asn Gly Phe Gln Val Asp
                165                 170                 175

Asn Tyr Gly Thr Gln Leu Asn Ala Val Asn Asn Ser Leu Thr Pro Gln
            180                 185                 190

Ser Thr Lys Val Pro Ser Leu Phe Glu Phe His Gly Pro Ser Trp Cys
        195                 200                 205

Leu Thr Pro Ala Asp Arg Gly Leu Cys Arg Ala Asn Glu Asn Arg Phe
210                 215                 220

Tyr Tyr Asn Ser Val Ile Gly Lys Cys Arg Pro Phe Lys Tyr Ser Gly
225                 230                 235                 240

Cys Gly Gly Asn Glu Asn Asn Phe Thr Ser Lys Gln Glu Cys Leu Arg
                245                 250                 255

Ala Cys Lys Lys Gly Phe Ile Gln Arg Ile Ser Lys Gly Gly Leu Ile
            260                 265                 270

Lys Thr Lys Arg Lys Arg Lys Lys Gln Arg Val Lys Ile Ala Tyr Glu
        275                 280                 285

Glu Ile Phe Val Lys Asn Met
290                 295

<210> SEQ ID NO 8
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gaagctatgc actctttctg tgctttcaag gctgacgacg gtccgtgcag agctgctcac     60
ccaagatggt tcttcaacat cttcacgcga caatgcgagg agttcatcta cggtggttgt    120
gagggtaacc aaaacagatt cgagtctcta gaggagtgta agaagatgtg tactagagac    180

<210> SEQ ID NO 9
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ala Met His Ser Phe Cys Ala Phe Lys Ala Asp Asp Gly Pro Cys
1               5                   10                  15

Arg Ala Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
        35                  40                  45
```

```
Ser Leu Glu Glu Cys Lys Lys Met Cys Thr Arg Asp
 50                  55                  60

<210> SEQ ID NO 10
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(579)

<400> SEQUENCE: 10 atg gga tgg agc tgt atc atc ctc ttc ttg gtc gcg acg gcc aca ggg      48
Met Gly Trp Ser Cys Ile Ile Leu Phe Leu Val Ala Thr Ala Thr Gly
  1               5                  10                  15 gcc cac tcc gat tct gag gaa gat gaa gaa cac aca att atc aca gat      96
Ala His Ser Asp Ser Glu Glu Asp Glu Glu His Thr Ile Ile Thr Asp
             20                  25                  30 acg gag ttg cca cca ctg aaa ctt atg cat tca ttt tgt gca ttc aag     144
Thr Glu Leu Pro Pro Leu Lys Leu Met His Ser Phe Cys Ala Phe Lys
         35                  40                  45 gcg gat gat ggc cca tgt aga gca gcc cat cct aga tgg ttc ttc aat     192
Ala Asp Asp Gly Pro Cys Arg Ala Ala His Pro Arg Trp Phe Phe Asn
     50                  55                  60 att ttc act cga cag tgc gaa gaa ttt ata tat ggg gga tgt gaa gga     240
Ile Phe Thr Arg Gln Cys Glu Glu Phe Ile Tyr Gly Gly Cys Glu Gly
 65                  70                  75                  80 aat cag aat cga ttt gaa agt ctg gaa gag tgc aaa aaa atg tgt aca     288
Asn Gln Asn Arg Phe Glu Ser Leu Glu Glu Cys Lys Lys Met Cys Thr
                 85                  90                  95 aga gat aat gca aac agg att ata aag aca aca ttg caa caa gaa aag     336
Arg Asp Asn Ala Asn Arg Ile Ile Lys Thr Thr Leu Gln Gln Glu Lys
            100                 105                 110 cca gat ttc tgc ttt ttg gaa gaa gat cct gga cca tgt atc gct ttt     384
Pro Asp Phe Cys Phe Leu Glu Glu Asp Pro Gly Pro Cys Ile Ala Phe
        115                 120                 125 ttt ccc agg tgg ttt tat aac aat cag aca aaa cag tgt gaa ctt ttc     432
Phe Pro Arg Trp Phe Tyr Asn Asn Gln Thr Lys Gln Cys Glu Leu Phe
    130                 135                 140 ccg tat ggt gga tgc cag ggc aat atg aac aat ttt gag aca ctg gaa     480
Pro Tyr Gly Gly Cys Gln Gly Asn Met Asn Asn Phe Glu Thr Leu Glu
145                 150                 155                 160 gaa tgc aag aac att tgt gaa gat ggt ccg aat ggt ttc cag gtg gat     528
Glu Cys Lys Asn Ile Cys Glu Asp Gly Pro Asn Gly Phe Gln Val Asp
                165                 170                 175 aat tat gga acc cag ctc aat gct gtg aat aac tcc ctg act ccg caa     576
Asn Tyr Gly Thr Gln Leu Asn Ala Val Asn Asn Ser Leu Thr Pro Gln
            180                 185                 190 tca taatgatcta ga                                                   591
Ser

<210> SEQ ID NO 11
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

```
Met Gly Trp Ser Cys Ile Ile Leu Phe Leu Val Ala Thr Ala Thr Gly
 1               5                  10                  15

Ala His Ser Asp Ser Glu Glu Asp Glu His Thr Ile Ile Thr Asp
             20                  25                  30

Thr Glu Leu Pro Pro Leu Lys Leu Met His Ser Phe Cys Ala Phe Lys
             35                  40                  45

Ala Asp Asp Gly Pro Cys Arg Ala Ala His Pro Arg Trp Phe Phe Asn
 50                  55                  60

Ile Phe Thr Arg Gln Cys Glu Phe Ile Tyr Gly Gly Cys Glu Gly
 65                  70                  75                  80

Asn Gln Asn Arg Phe Glu Ser Leu Glu Glu Cys Lys Lys Met Cys Thr
                 85                  90                  95

Arg Asp Asn Ala Asn Arg Ile Ile Lys Thr Thr Leu Gln Gln Glu Lys
                100                 105                 110

Pro Asp Phe Cys Phe Leu Glu Glu Asp Pro Gly Pro Cys Ile Ala Phe
            115                 120                 125

Phe Pro Arg Trp Phe Tyr Asn Asn Gln Thr Lys Gln Cys Glu Leu Phe
130                 135                 140

Pro Tyr Gly Gly Cys Gln Gly Asn Met Asn Asn Phe Glu Thr Leu Glu
145                 150                 155                 160

Glu Cys Lys Asn Ile Cys Glu Asp Gly Pro Asn Gly Phe Gln Val Asp
                165                 170                 175

Asn Tyr Gly Thr Gln Leu Asn Ala Val Asn Asn Ser Leu Thr Pro Gln
                180                 185                 190

Ser

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gattctgagg aagatgaaga aca                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgattgcgga gtcagggagt t                                              21

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gaaaatattg aagaaccatc taggatgggc tgctctacat gggccatcat ccgcctt       57
```

```
<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaggcggatg atggcccatg tagagcagcc catcctagat ggttcttcaa tattttc      57

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgttataaaa ccacctggga aaaaagcga tacatggtcc aggatcttct t             51

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagaagatcc tggaccatgt atcgcttttt ttcccaggtg gttttataac a             51

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catattgccc tggcatccac catacgggaa aagttcacac tgttt                    45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaacagtgtg aactttccc gtatggtgga tgccagggca atatg                     45

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttaatcttgc ggccacaggg gcccactctg attctgagga agatgaagaa ca            52

<210> SEQ ID NO 21
```

-continued

<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caaaaaggct tctagatcat tatgattgcg gagtcaggga gtt                43

<210> SEQ ID NO 22
<211> LENGTH: 235
<212> TYPE: PRT
<213> ORGANISM: Homo sapiens

<400> SEQUENCE: 22

Met Asp Pro Ala Arg Pro Leu Gly Leu Ser Ile Leu Leu Leu Phe Leu
1               5                   10                  15

Thr Glu Ala Ala Leu Gly Asp Ala Ala Gln Glu Pro Thr Gly Asn Asn
            20                  25                  30

Ala Glu Ile Cys Leu Leu Pro Leu Asp Tyr Gly Pro Cys Arg Ala Leu
        35                  40                  45

Leu Leu Arg Tyr Tyr Asp Arg Tyr Thr Gln Ser Cys Arg Gln Phe
    50                  55                  60

Leu Tyr Gly Gly Cys Glu Gly Asn Ala Asn Asn Phe Tyr Thr Trp Glu
65                  70                  75                  80

Ala Cys Asp Asp Ala Cys Trp Arg Ile Glu Lys Val Pro Lys Val Cys
                85                  90                  95

Arg Leu Gln Val Ser Val Asp Asp Gln Cys Glu Gly Ser Thr Glu Lys
            100                 105                 110

Tyr Phe Phe Asn Leu Ser Ser Met Thr Cys Glu Lys Phe Phe Ser Gly
        115                 120                 125

Gly Cys His Arg Asn Arg Ile Glu Asn Arg Phe Pro Asp Glu Ala Thr
    130                 135                 140

Cys Met Gly Phe Cys Ala Pro Lys Lys Ile Pro Ser Phe Cys Tyr Ser
145                 150                 155                 160

Pro Lys Asp Glu Gly Leu Cys Ser Ala Asn Val Thr Arg Tyr Tyr Phe
                165                 170                 175

Asn Pro Arg Tyr Arg Thr Cys Asp Ala Phe Thr Tyr Thr Gly Cys Gly
            180                 185                 190

Gly Asn Asp Asn Asn Phe Val Ser Arg Glu Asp Cys Lys Arg Ala Cys
        195                 200                 205

Ala Lys Ala Leu Lys Lys Lys Lys Met Pro Lys Leu Arg Phe Ala
    210                 215                 220

Ser Arg Ile Arg Lys Ile Arg Lys Lys Gln Phe
225                 230                 235

<210> SEQ ID NO 23
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(210)

<400> SEQUENCE: 23 tcc atg gct gat gtt cct aag gtt tgt cgt ctg cag gtt tct gtt gac    48

```
Ser Met Ala Asp Val Pro Lys Val Cys Arg Leu Gln Val Ser Val Asp
 1               5                  10                  15 gat caa tgt gag ggt tct act gaa aag tat ttt ttc aac ctg agc tct      96
Asp Gln Cys Glu Gly Ser Thr Glu Lys Tyr Phe Phe Asn Leu Ser Ser
             20                  25                  30 atg act tgc gaa aag ttc ttt tct ggt ggt tgc cat cgt aac cgt atc     144
Met Thr Cys Glu Lys Phe Phe Ser Gly Gly Cys His Arg Asn Arg Ile
         35                  40                  45 gag aac cgg ttt ccg gac gag gct act tgt atg ggt ttc tgt gct cct     192
Glu Asn Arg Phe Pro Asp Glu Ala Thr Cys Met Gly Phe Cys Ala Pro
     50                  55                  60 aag tct gct gac gct agc                                             210
Lys Ser Ala Asp Ala Ser
 65                  70
```

<210> SEQ ID NO 24
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ser Met Ala Asp Val Pro Lys Val Cys Arg Leu Gln Val Ser Val Asp
 1               5                  10                  15

Asp Gln Cys Glu Gly Ser Thr Glu Lys Tyr Phe Phe Asn Leu Ser Ser
             20                  25                  30

Met Thr Cys Glu Lys Phe Phe Ser Gly Gly Cys His Arg Asn Arg Ile
         35                  40                  45

Glu Asn Arg Phe Pro Asp Glu Ala Thr Cys Met Gly Phe Cys Ala Pro
     50                  55                  60

Lys Ser Ala Asp Ala Ser
 65                  70
```

<210> SEQ ID NO 25
<211> LENGTH: 8931
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
aatgctacta ctattagtag aattgatgcc acctttcag ctcgcgcccc aaatgaaaat        60
atagctaaac aggttattga ccatttgcga aatgtatcta atggtcaaac taaatctact      120
cgttcgcaga attgggaatc aactgttata tggaatgaaa cttccagaca ccgtacttta      180
gttgcatatt taaaacatgt tgagctacag cattatattc agcaattaag ctctaagcca      240
tccgcaaaaa tgacctctta tcaaaaggag caattaaagg tactctctaa tcctgacctg      300
ttggagtttg cttccggtct ggttcgcttt gaagctcgaa ttaaaacgcg atatttgaag      360
tctttcgggc ttcctcttaa tcttttttgat gcaatccgct ttgcttctga ctataatagt      420
cagggtaaag acctgatttt tgatttatgg tcattctcgt tttctgaact gtttaaagca      480
tttgaggggg attcaatgaa tatttatgac gattccgcag tattggacgc tatccagtct      540
aaacatttta ctattacccc ctctggcaaa acttcttttg caaaagcctc tcgctatttt      600 ggttttatc gtcgtctggt aaacgagggt tatgatagtg ttgctcttac tatgcctcgt      660
aattcctttt ggcgttatgt atctgcatta gttgaatgtg gtattcctaa atctcaactg      720
```

```
atgaatctttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattctttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
tttttggaga ttttcaacgt gaaaaaatta ttattcgcaa ttcctttagt tgttcctttc   1620
tattctcact ccgctgaaac tgttgaaagt tgtttagcaa atcccatac agaaaattca    1680 tttactaacg tctggaaaga cgacaaaact ttagatcgtt acgctaacta tgagggctgt   1740
ctgtggaatg ctacaggcgt tgtagtttgt actggtgacg aaactcagtg ttacggtaca   1800
tgggttccta ttgggcttgc tatccctgaa atgagggtg gtggctctga gggtggcggt   1860 tctgaggggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg accccgttaa aacttattac cagtacactc ctgtatcatc aaaagccatg   2160
tatgacgctt actggaacgg taaattcaga gactgcgctt tccattctgg ctttaatgag   2220
gatttatttg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataagggg ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtctttg cgctggtaa accatatgaa ttttctattg attgtgacaa ataaactta    2760 ttccgtggtg tctttgcgtt tctttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttacttttc   2940
ttaaaaaggg cttcggtaag atagctattg ctatttcatt gtttcttgct cttattattg   3000
ggcttaactc aattcttgtg ggttatctct ctgatattag cgctcaatta ccctctgact   3060
```

```
ttgttcaggg tgttcagtta attctcccgt ctaatgcgct tccctgtttt tatgttattc    3120
tctctgtaaa ggctgctatt ttcattttg acgttaaaca aaaaatcgtt tcttatttgg     3180
attgggataa ataatatggc tgtttatttt gtaactggca aattaggctc tggaaagacg    3240
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
gttggcgttg ttaaatatgg cgattctcaa ttaagcccta ctgttgagcg ttggctttat    3780
actggtaaga atttgtataa cgcatatgat actaaacagg cttttttctag taattatgat   3840
tccggtgttt attcttattt aacgccttat ttatcacacg gtcggtattt caaaccatta    3900
aatttaggtc agaagatgaa attaactaaa atatatttga aaagttttc tcgcgttctt     3960
tgtcttgcga ttggatttgc atcagcattt acatatagtt ataaccca acctaagccg      4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt cttgatgtt     4260
tgtttcatca tcttctttg ctcaggtaat tgaaatgaat aattcgcctc tgcgcgattt     4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gcaaataatt ttgatatggt aggttctaac ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgttttgtaaa   4680
gtctaatact tctaaatcct caaatgtatt atctattgac ggctctaatc tattagttgt    4740
tagtgctcct aaagatattt tagataacct tcctcaattc ctttcaactg ttgatttgcc    4800
aactgaccag atattgattg agggtttgat atttgaggtt cagcaaggtg atgctttaga    4860
ttttcatttt gctgctggct ctcagcgtgg cactgttgca ggcggtgtta atactgaccg    4920
cctcacctct gttttatctt ctgctggtgg ttcgttcggt atttttaatg gcgatgtttt    4980
agggctatca gttcgcgcat taaagactaa tagccattca aaaatattgt ctgtgccacg    5040
tattcttacg ctttcaggtc agaagggttc tatctctgtt ggccagaatg tcccttttat    5100
tactggtcgt gtgactggtg aatctgccaa tgtaaataat ccatttcaga cgattgagcg    5160
tcaaaatgta ggtattttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctcttttact   5340
cggtggcctc actgattata aaaacacttc tcaggattct ggcgtaccgt tcctgtctaa    5400
aatcccttta atcggcctcc tgtttagctc ccgctctgat tctaacgagg aaagcacgtt    5460
```

```
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgcttcctt cccttccttt ctcgccacgt tcgccggctt tccccgtcaa gctctaaatc    5640
gggggctccc tttagggttc cgatttagtg ctttacggca cctcgacccc aaaaaacttg    5700
atttgggtga tggttggcca tcgccctgat agacggtttt cgcccttttg acgttggagt    5760
ccacgttctt taatagtgga ctcttgttcc aaactggaac aacactcaac cctatctcgg    5820
gctattcttt tgatttataa gggattttgc cgatttcgga accaccatca aacaggattt    5880
tcgcctgctg gggcaaacca gcgtggaccg cttgctgcaa ctctctcagg gccaggcggt    5940
gaagggcaat cagctgttgc ccgtctcact ggtgaaaaga aaaccaccc tggatccaag     6000 cttgcaggtg gcacttttcg gggaaatgtg cgcggaaccc ctatttgttt attttctaa     6060 atacattcaa atatgtatcc gctcatgaga caataaccct gataaatgct tcaataatat    6120
tgaaaaagga agagtatgag tattcaacat ttccgtgtcg cccttattcc cttttttgcg    6180 gcatttttgcc ttcctgtttt tgctcaccca gaaacgctgg tgaaagtaaa agatgctgaa   6240
gatcagttgg gcgcactagt gggttacatc gaactggatc tcaacagcgg taagatcctt    6300
gagagttttc gccccgaaga acgttttcca atgatgagca cttttaaagt tctgctatgt    6360
ggcgcggtat tatcccgtat tgacgccggg caagagcaac tcggtcgccg catacactat    6420
tctcagaatg acttggttga gtactcacca gtcacagaaa agcatcttac ggatggcatg    6480
acagtaagag aattatgcag tgctgccata accatgagtg ataacactgc ggccaactta    6540
cttctgacaa cgatcggagg accgaaggag ctaaccgctt ttttgcacaa catgggggat    6600
catgtaactc gccttgatcg ttgggaaccg gagctgaatg aagccatacc aaacgacgag    6660
cgtgacacca cgatgcctgt agcaatggca acaacgttgc gcaaactatt aactggcgaa    6720
ctacttactc tagcttcccg gcaacaatta atagactgga tggaggcgga taaagttgca    6780
ggaccacttc tgcgctcggc ccttccggct ggctggttta ttgctgataa atctggagcc    6840
ggtgagcgtg ggtctcgcgg tatcattgca gcactggggc cagatggtaa gccctcccgt    6900
atcgtagtta tctacacgac ggggagtcag gcaactatgg atgaacgaaa tagacagatc    6960
gctgagatag gtgcctcact gattaagcat tggtaactgt cagaccaagt ttactcatat    7020
atactttaga ttgatttaaa acttcatttt taatttaaaa ggatctaggt gaagatcctt    7080
tttgataatc tcatgaccaa aatcccttaa cgtgagtttt cgttccactg tacgtaagac    7140
ccccaagctt gtcgactgaa tggcgaatgg cgctttgcct ggtttccggc accagaagcg    7200
gtgccggaaa gctggctgga gtgcgatctt cctgacgctc gagcgcaacg caattaatgt    7260
gagttagctc actcattagg caccccaggc tttacacttt atgcttccgg ctcgtatgtt    7320
gtgtggaatt gtgagcggat aacaatttca cacaggaaac agctatgacc atgattacgc    7380
caagctttgg agcctttttt ttggagattt tcaacgtgaa aaaattatta ttcgcaattc    7440
ctttagttgt tcctttctat tccatggctg atgttcctaa ggtttgtcgt ctgcaggttt    7500
ctgttgacga tcaatgtgag ggttctactg aaaagtattt tttcaacctg agctctatga    7560
cttgcgaaaa gttcttttct ggtggttgcc atcgtaaccg tatcgagaac cggtttccgg    7620
acgaggctac ttgtatgggt ttctgtgctc ctaagcctgc tgacgctagc tctgctagtg    7680
gcgacttcga ctacgagaaa atggctaatg ccaacaaagg cgccatgact gagaacgctg    7740
acgagaatgc tttgcaaagc gatgccaagg gtaagttaga cagcgtcgcg accgactatg    7800
```

-continued

```
gcgccgccat cgacggcttt atcggcgatg tcagtggttt ggccaacggc aacggagcca    7860
ccggagactt cgcaggttcg aattctcaga tgcccaggt tggagatggg gacaacagtc     7920
cgcttatgaa caactttaga cagtaccttc cgtctcttcc gcagagtgtc gagtgccgtc    7980
cattcgtttt cggtgccggc aagccttacg agttcagcat cgactgcgat aagatcaatc    8040
ttttccgcgg cgttttcgct tcttgctat acgtcgctac tttcatgtac gttttcagca     8100
ctttcgccaa tatttacgc aacaaagaaa gctagtgatc tcctaggaag cccgcctaat     8160
gagcgggctt ttttttcctg gtatgcatcc tgaggccgat actgtcgtcg tcccctcaaa    8220
ctggcagatg cacggttacg atgcgcccat ctacaccaac gtgacctatc ccattacggt    8280
caatccgccg tttgttccca cggagaatcc gacgggttgt tactcgctca catttaatgt    8340
tgatgaaagc tggctacagg aaggccgac gcgaattatt tttgatggcg ttcctattgg     8400
ttaaaaaatg agctgattta acaaaaattt aatgcgaatt ttaacaaaat attaacgttt    8460
acaatttaaa tatttgctta tacaatcttc ctgttttttgg ggcttttctg attatcaacc   8520
ggggtacata tgattgacat gctagtttta cgattaccgt tcatcgattc tcttgtttgc    8580
tccagactct caggcaatga cctgatagcc tttgtagatc tctcaaaaat agctaccctc    8640
tccggcatta atttatcagc tagaacggtt gaatatcata ttgatggtga tttgactgtc   8700
tccggccttt ctcacccttt tgaatcttta cctacacatt actcaggcat tgcatttaaa    8760
atatatgagg gttctaaaaa tttttatcct tgcgttgaaa taaaggcttc tcccgcaaaa    8820
gtattacagg gtcataatgt ttttggtaca accgatttag ctttatgctc tgaggcttta    8880
ttgcttaatt ttgctaattc tttgccttgc ctgtatgatt tattggatgt t             8931
```

```
<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggtcttctg tacgagttct g                                               21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctccagagt tgacagaatc c                                               21

<210> SEQ ID NO 28
<211> LENGTH: 96
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (40)..(41)
<223> OTHER INFORMATION: a, c, g, t, unknown or other
<220> FEATURE:
<221> NAME/KEY: modified_base
<222> LOCATION: (46)..(47)
```

```
<223> OTHER INFORMATION: a, c, g, t, unknown or other
<220> FEATURE:
<221> NAME/KEY: modified_base
<222> LOCATION: (52)..(53)
<223> OTHER INFORMATION: a, c, g, t, unknown or other
<220> FEATURE:
<221> NAME/KEY: modified_base
<222> LOCATION: (55)..(56)
<223> OTHER INFORMATION: a, c, g, t, unknown or other
<220> FEATURE:
<221> NAME/KEY: modified_base
<222> LOCATION: (58)..(59)
<223> OTHER INFORMATION: a, c, g, t, unknown or other

<400> SEQUENCE: 28
gggtcttctg tacgagttct gcaggttct gttrrkrrkn nktgtnnkgs tnnknnknnk      60
argtattttt tcaacctgag ctctatgact tgcgaa                              96

<210> SEQ ID NO 29
<211> LENGTH: 97
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (37)
<223> OTHER INFORMATION: a, c, g, t, unknown or other
<220> FEATURE:
<221> NAME/KEY: modified_base
<222> LOCATION: (49)..(50)
<223> OTHER INFORMATION: a, c, g, t, unknown or other
<220> FEATURE:
<221> NAME/KEY: modified_base
<222> LOCATION: (64)..(65)
<223> OTHER INFORMATION: a, c, g, t, unknown or other

<400> SEQUENCE: 29
cctccagagt tgacagaatc cggaaaccgg ttctcmnymy ygttmyymnn gcaaccaca      60 kamnngaact tttcgcaagt catagagctc aggttga                             97

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gattctgagg aagatgaaga aca                                            23

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acatattttt aacaaaaatt tcttcat                                        27

<210> SEQ ID NO 32
<211> LENGTH: 50
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 32
ttaatcttgc ggccacaggg gcccactccg actctgagga agatgaagaa                 50

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cataagcttc agtggtggga gctccgtatc                                       30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gatacggagc tcccaccact gaagcttatg                                       30

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttcgcactga cgcgtgaaaa                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttttcacgcg tcagtgcgaa                                                  20

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcttccagag attcaaatcg attctggtta ccttcacatc c                          41

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 38
ggatgtgaag gtaaccagaa tcgatttgaa tctctggaag a                41

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttccaggatc ctcctcgaga aagcagaaa                              29

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tttctgcttt ctcgaggagg atcctggaa                              29

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttcttccagc gtctcaaaa                                         19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttttgagacg ctggaagaa                                         19

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cataattgtc gacctggaaa ccattgggcc catcttca                    38

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgaagatggg cccaatggtt tccaggtcga caattatg            38

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tcctctgtcc gcgggagtga ga            22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctcactccc gcggacagag ga            22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccacatccgg aatacttaaa tg            22

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
catttaagta ttccggatgt gggg            24

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tttacatgcg cgcagacatt ct            22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 50
agaatgtctg cgcgcatgta aa                                              22

<210> SEQ ID NO 51
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttgtttctag atcattacat atttttaaca aaatttctt cat                        43

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttaatcttgc ggccacaggg gcccactccg actctgagga agatgaagaa                50

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttgtttctag atcattacat atttttaaca aaatttctt cat                        43

<210> SEQ ID NO 54
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

Asp Ser Glu Glu Asp Glu His Thr Ile Ile Thr Asp Thr Glu Leu
 1               5                  10                  15

Pro Pro Leu Lys Leu Met His Ser Phe Cys Ala Phe Lys Ala Asp Asp
            20                  25                  30

Gly Pro Cys Arg Ala Arg Phe Asp Arg Trp Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Pro Cys Arg Ala Ala His Pro Arg
            100                 105                 110

Trp Phe Tyr Asn Gln Thr Lys Gln Cys Glu Arg Phe Ile Tyr Gly Gly
        115                 120                 125

Cys Glu Gly Asn Met Asn Asn Phe Glu Thr Leu Glu Glu Cys Lys Asn

```
                130             135             140
Ile Cys Glu Asp Gly Pro Asn Gly Phe Gln Val Asp Asn Tyr Gly Thr
145                 150                 155                 160

Gln Leu Asn Ala Val Asn Ser Leu Thr Pro Gln Ser Thr Lys Val Pro
                165                 170                 175

Ser Leu Phe Glu Phe His Gly Pro Ser Trp Cys Leu Thr Pro Ala Asp
            180                 185                 190

Arg Gly Pro Cys Ile Ala Phe Phe Pro Arg Phe Tyr Tyr Asn Ser Val
        195                 200                 205

Ile Gly Lys Cys Arg Pro Phe Pro Tyr Gly Gly Cys Gln Gly Asn Glu
    210                 215                 220

Asn Phe Thr Ser Lys Gln Glu Cys Leu Arg Ala Cys Lys Lys Gly Phe
225                 230                 235                 240

Ile Gln Arg Ile Ser
            245
```

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
atgatttaca caatgaagaa agtacat                                         27

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgatattctt tggatgaaac cttt                                            24

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gatggcccat gtcgtgcacg cttcgataga tggttcttca ata                      43

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tattgaagaa ccatctatcg aagcgtgcac gacatgggcc atc                      43

<210> SEQ ID NO 59
<211> LENGTH: 56
<212> TYPE: DNA

<213> ORGANISM: Artificial Sequence
<220> FEATURE:
<223> OTHER INFORMATION: Description of Artificial Sequence: Synthetic primer

<400> SEQUENCE: 59
gaagatcctg gaccttgtcg agctgctcat cccaggtggt tttataacaa tcagac     56

<210> SEQ ID NO 60
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gtctgattgt tataaaacca cctgggatga gcagctcgac aaggtccagg atcttc     56

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
cagtgtgaac gtttcattta tggtggatgc gagggcaata tgaacaa     47

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ttgttcatat tgccctcgca tccaccataa atgaaacgtt cacactg     47

<210> SEQ ID NO 63
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
agcagacaga ggaccttgta ttgccttttt tcccagattc tactacaatt cagtc     55

<210> SEQ ID NO 64
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gactgaattg tagtagaatc tgggaaaaaa ggcaatacaa ggtcctctgt ctgct     55

<210> SEQ ID NO 65
<211> LENGTH: 31
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 65
taagtacggt ggatgtcagg gaaatgaaaa c                                      31

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gttttcattt ccctgacatc caccgtactt a                                      31

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agattttact tccatggttt acacaatgaa gaaagt                                 36

<210> SEQ ID NO 68
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctcttgtttc tagatcatta tgatattctt tggatgaaac cttt                        44

<210> SEQ ID NO 69
<211> LENGTH: 872
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69
```

Met Ile Tyr Thr Met Lys Lys Val His Ala Leu Trp Ala Ser Val Cys
 1               5                  10                  15

Leu Leu Leu Asn Leu Ala Pro Ala Pro Leu Asn Ala Asp Ser Glu Glu
             20                  25                  30

Asp Glu Glu His Thr Ile Ile Thr Asp Thr Glu Leu Pro Pro Leu Lys
         35                  40                  45

Leu Met His Ser Phe Cys Ala Phe Lys Ala Asp Asp Gly Pro Cys Arg
     50                  55                  60

Ala Arg Phe Asp Arg Trp Phe Phe Asn Ile Phe Thr Arg Gln Cys Glu
 65                  70                  75                  80

Glu Phe Ile Tyr Gly Gly Cys Glu Gly Asn Gln Asn Arg Phe Glu Ser
                 85                  90                  95

Leu Glu Glu Cys Lys Lys Met Cys Thr Arg Asp Asn Ala Asn Arg Ile
            100                 105                 110

-continued

```
Ile Lys Thr Thr Leu Gln Gln Glu Lys Pro Asp Phe Cys Phe Leu Glu
        115                 120                 125

Glu Asp Pro Gly Pro Cys Arg Ala Ala His Pro Arg Trp Phe Tyr Asn
130                 135                 140

Gln Thr Lys Gln Cys Glu Arg Phe Ile Tyr Gly Gly Cys Glu Gly Asn
145                 150                 155                 160

Met Asn Asn Phe Glu Thr Leu Glu Glu Cys Lys Asn Ile Cys Glu Asp
            165                 170                 175

Gly Pro Asn Gly Phe Gln Val Asp Asn Tyr Gly Thr Gln Leu Asn Ala
                180                 185                 190

Val Asn Ser Leu Thr Pro Gln Ser Thr Lys Val Pro Ser Leu Phe Glu
            195                 200                 205

Phe His Gly Pro Ser Trp Cys Leu Thr Pro Ala Asp Arg Gly Pro Cys
        210                 215                 220

Ile Ala Phe Phe Pro Arg Phe Tyr Tyr Asn Ser Val Ile Gly Lys Cys
225                 230                 235                 240

Arg Pro Phe Pro Tyr Gly Gly Cys Gln Gly Asn Glu Asn Phe Thr Ser
                245                 250                 255

Lys Gln Glu Cys Leu Arg Ala Cys Lys Lys Gly Phe Ile Gln Arg Ile
            260                 265                 270

Ser Gly Gly Ser Gly Gly Ser Gly Gly Ser Gly Gly Ser Gly Gly Asp
        275                 280                 285

Ala His Lys Ser Glu Val Ala His Arg Phe Lys Asp Leu Gly Glu Glu
        290                 295                 300

Asn Phe Lys Ala Leu Val Leu Ile Ala Phe Ala Gln Tyr Leu Gln Gln
305                 310                 315                 320

Cys Pro Phe Glu Asp His Val Lys Leu Val Asn Glu Val Thr Glu Phe
                325                 330                 335

Ala Lys Thr Cys Val Ala Asp Glu Ser Ala Glu Asn Cys Asp Lys Ser
            340                 345                 350

Leu His Thr Leu Phe Gly Asp Lys Leu Cys Thr Val Ala Thr Leu Arg
        355                 360                 365

Glu Thr Tyr Gly Glu Met Ala Asp Cys Cys Ala Lys Gln Glu Pro Glu
370                 375                 380

Arg Asn Glu Cys Phe Leu Gln His Lys Asp Asp Asn Pro Asn Leu Pro
385                 390                 395                 400

Arg Leu Val Arg Pro Glu Val Asp Val Met Cys Thr Ala Phe His Asp
                405                 410                 415

Asn Glu Glu Thr Phe Leu Lys Lys Tyr Leu Tyr Glu Ile Ala Arg Arg
            420                 425                 430

His Pro Tyr Phe Tyr Ala Pro Glu Leu Leu Phe Phe Ala Lys Arg Tyr
        435                 440                 445

Lys Ala Ala Phe Thr Glu Cys Cys Gln Ala Ala Asp Lys Ala Ala Cys
    450                 455                 460

Leu Leu Pro Lys Leu Asp Glu Leu Arg Asp Glu Gly Lys Ala Ser Ser
465                 470                 475                 480

Ala Lys Gln Arg Leu Lys Cys Ala Ser Leu Gln Lys Phe Gly Glu Arg
                485                 490                 495

Ala Phe Lys Ala Trp Ala Val Ala Arg Leu Ser Gln Arg Phe Pro Lys
            500                 505                 510

Ala Glu Phe Ala Glu Val Ser Lys Leu Val Thr Asp Leu Thr Lys Val
        515                 520                 525

His Thr Glu Cys Cys His Gly Asp Leu Leu Glu Cys Ala Asp Asp Arg
```

```
                530                 535                 540
Ala Asp Leu Ala Lys Tyr Ile Cys Glu Asn Gln Asp Ser Ile Ser Ser
545                 550                 555                 560

Lys Leu Lys Glu Cys Cys Glu Lys Pro Leu Leu Glu Lys Ser His Cys
                565                 570                 575

Ile Ala Glu Val Glu Asn Asp Glu Met Pro Ala Asp Leu Pro Ser Leu
                580                 585                 590

Ala Ala Asp Phe Val Glu Ser Lys Asp Val Cys Lys Asn Tyr Ala Glu
                595                 600                 605

Ala Lys Asp Val Phe Leu Gly Met Phe Leu Tyr Glu Tyr Ala Arg Arg
                610                 615                 620

His Pro Asp Tyr Ser Val Val Leu Leu Leu Arg Leu Ala Lys Thr Tyr
625                 630                 635                 640

Glu Thr Thr Leu Glu Lys Cys Cys Ala Ala Ala Asp Pro His Glu Cys
                645                 650                 655

Tyr Ala Lys Val Phe Asp Glu Phe Lys Pro Leu Val Glu Glu Pro Gln
                660                 665                 670

Asn Leu Ile Lys Gln Asn Cys Glu Leu Phe Glu Gln Leu Gly Glu Tyr
                675                 680                 685

Lys Phe Gln Asn Ala Leu Leu Val Arg Tyr Thr Lys Lys Val Pro Gln
                690                 695                 700

Val Ser Thr Pro Thr Leu Val Glu Val Ser Arg Asn Leu Gly Lys Val
705                 710                 715                 720

Gly Ser Lys Cys Cys Lys His Pro Glu Ala Lys Arg Met Pro Cys Ala
                725                 730                 735

Glu Asp Tyr Leu Ser Val Val Leu Asn Gln Leu Cys Val Leu His Glu
                740                 745                 750

Lys Thr Pro Val Ser Asp Arg Val Thr Lys Cys Cys Thr Glu Ser Leu
                755                 760                 765

Val Asn Arg Arg Pro Cys Phe Ser Ala Leu Glu Val Asp Glu Thr Tyr
770                 775                 780

Val Pro Lys Glu Phe Asn Ala Glu Thr Phe Thr Phe His Ala Asp Ile
785                 790                 795                 800

Cys Thr Leu Ser Glu Lys Glu Arg Gln Ile Lys Lys Gln Thr Ala Leu
                805                 810                 815

Val Glu Leu Val Lys His Lys Pro Lys Ala Thr Lys Glu Gln Leu Lys
                820                 825                 830

Ala Val Met Asp Asp Phe Ala Ala Phe Val Glu Lys Cys Cys Lys Ala
                835                 840                 845

Asp Asp Lys Glu Thr Cys Phe Ala Glu Glu Gly Lys Lys Leu Val Ala
                850                 855                 860

Ala Ser Gln Ala Ala Leu Gly Leu
865                 870

<210> SEQ ID NO 70
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ser Glu Glu Asp Glu Glu His Thr Ile Ile Thr Asp Thr Glu Leu
1               5                   10                  15
```

-continued

```
Pro Pro Leu Lys Leu Met His Ser Phe Cys Ala Phe Lys Ala Asp Asp
            20                  25                  30

Gly Pro Cys Arg Ala Arg Phe Asp Arg Trp Phe Phe Asn Ile Phe Thr
        35                  40                  45

Arg Gln Cys Glu Glu Phe Ile Tyr Gly Gly Cys Glu Gly Asn Gln Asn
50                      55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Pro Cys Arg Ala Ala His Pro Arg
            100                 105                 110

Trp Phe Tyr Asn Gln Thr Lys Gln Cys Glu Arg Phe Ile Tyr Gly Gly
        115                 120                 125

Cys Glu Gly Asn Met Asn Asn Phe Glu Thr Leu Glu Glu Cys Lys Asn
        130                 135                 140

Ile Cys Glu Asp Gly Pro Asn Gly Phe Gln Val Asp Asn Tyr Gly Thr
145                 150                 155                 160

Gln Leu Asn Ala Val Asn Ser Leu Thr Pro Gln Ser Thr Lys Val Pro
                165                 170                 175

Ser Leu Phe Glu Phe His Gly Pro Ser Trp Cys Leu Thr Pro Ala Asp
            180                 185                 190

Arg Gly Pro Cys Ile Ala Phe Phe Pro Arg Phe Tyr Tyr Asn Ser Val
        195                 200                 205

Ile Gly Lys Cys Arg Pro Phe Lys Tyr Gly Gly Cys Gln Gly Asn Glu
        210                 215                 220

Asn Phe Thr Ser Lys Gln Glu Cys Leu Arg Ala Cys Lys Lys Gly Phe
225                 230                 235                 240

Ile Gln Arg Ile Ser Gly Ser Gly Ser Ser Gly Gly Ser Ser Gly Ser Ser
                245                 250                 255

Gly Gly Asp Ser Glu Glu Asp Glu Glu His Thr Ile Ile Thr Asp Thr
            260                 265                 270

Glu Leu Pro Pro Leu Lys Leu Met His Ser Phe Cys Ala Phe Lys Ala
        275                 280                 285

Asp Asp Gly Pro Cys Arg Ala Arg Phe Asp Arg Trp Phe Phe Asn Ile
290                 295                 300

Phe Thr Arg Gln Cys Glu Glu Phe Ile Tyr Gly Gly Cys Glu Gly Asn
305                 310                 315                 320

Gln Asn Arg Phe Glu Ser Leu Glu Glu Cys Lys Lys Met Cys Thr Arg
                325                 330                 335

Asp Asn Ala Asn Arg Ile Ile Lys Thr Thr Leu Gln Gln Glu Lys Pro
            340                 345                 350

Asp Phe Cys Phe Leu Glu Glu Asp Pro Gly Pro Cys Arg Ala Ala His
        355                 360                 365

Pro Arg Trp Phe Tyr Asn Gln Thr Lys Gln Cys Glu Arg Phe Ile Tyr
        370                 375                 380

Gly Gly Cys Glu Gly Asn Met Asn Asn Phe Glu Thr Leu Glu Glu Cys
385                 390                 395                 400

Lys Asn Ile Cys Glu Asp Gly Pro Asn Gly Phe Gln Val Asp Asn Tyr
                405                 410                 415

Gly Thr Gln Leu Asn Ala Val Asn Ser Leu Thr Pro Gln Ser Thr Lys
            420                 425                 430

Val Pro Ser Leu Phe Glu Phe His Gly Pro Ser Trp Cys Leu Thr Pro
```

```
                    435                 440                 445
Ala Asp Arg Gly Pro Cys Ile Ala Phe Phe Pro Arg Phe Tyr Tyr Asn
            450                 455                 460

Ser Val Ile Gly Lys Cys Arg Pro Lys Tyr Gly Gly Cys Gln Gly
465                 470                 475                 480

Asn Glu Asn Phe Thr Ser Lys Gln Glu Cys Leu Arg Ala Cys Lys Lys
                485                 490                 495

Gly Phe Ile Gln Arg Ile Ser
                500

<210> SEQ ID NO 71
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp Gly Gly Ser Gly Gly Ser
    50                  55                  60

Ser Ser Ser Ser Gly Gly Met His Ser Phe Cys Ala Phe Lys Ala Asp
65                  70                  75                  80

Asp Gly Pro Cys Ile Ala Phe Phe Pro Arg Phe Phe Asn Ile Phe
                85                  90                  95

Thr Arg Gln Cys Glu Glu Phe Ile Tyr Gly Gly Cys Gln Gly Asn Gln
            100                 105                 110

Asn Arg Phe Glu Ser Leu Glu Glu Cys Lys Lys Met Cys Thr Arg Asp
        115                 120                 125

<210> SEQ ID NO 72
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp Gly Gly Ser Gly Gly Ser
    50                  55                  60

Ser Ser Ser Ser Gly Gly Met His Ser Phe Cys Ala Phe Lys Ala Asp
65                  70                  75                  80

Asp Gly Pro Cys Ile Ala Phe Phe Pro Arg Phe Phe Asn Ile Phe
                85                  90                  95

Thr Arg Gln Cys Glu Glu Phe Ile Tyr Gly Gly Cys Gln Gly Asn Gln
```

```
                100                 105                 110
Asn Arg Phe Glu Ser Leu Glu Glu Cys Lys Lys Met Cys Thr Arg Asp
        115                 120                 125

Gly Gly Ser Gly Gly Ser Ser Ser Ser Gly Gly Met His Ser Phe
    130                 135                 140

Cys Ala Phe Lys Ala Asp Asp Gly Pro Cys Arg Ala Ala His Pro Arg
145                 150                 155                 160

Trp Phe Phe Asn Ile Phe Thr Arg Gln Cys Glu Glu Phe Ile Tyr Gly
                165                 170                 175

Gly Cys Glu Gly Asn Gln Asn Arg Phe Glu Ser Leu Glu Glu Cys Lys
            180                 185                 190

Lys Met Cys Thr Arg Asp
        195

<210> SEQ ID NO 73
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp Gly Gly Ser Gly Gly Ser
50                  55                  60

Ser Ser Ser Ser Gly Gly Met His Ser Phe Cys Ala Phe Lys Ala Asp
65                  70                  75                  80

Asp Gly Pro Cys Ile Ala Phe Phe Pro Arg Phe Phe Phe Asn Ile Phe
                85                  90                  95

Thr Arg Gln Cys Glu Glu Phe Ile Tyr Gly Gly Cys Gly Asn Gln
            100                 105                 110

Asn Arg Phe Glu Ser Leu Glu Glu Cys Lys Lys Met Cys Thr Arg Asp
        115                 120                 125

Gly Gly Ser Gly Gly Ser Ser Ser Ser Gly Gly Met His Ser Phe
    130                 135                 140

Cys Ala Phe Lys Ala Asp Asp Gly Pro Cys Arg Ala Ala His Pro Arg
145                 150                 155                 160

Trp Phe Phe Asn Ile Phe Thr Arg Gln Cys Glu Glu Phe Ile Tyr Gly
                165                 170                 175

Gly Cys Glu Gly Asn Gln Asn Arg Phe Glu Ser Leu Glu Glu Cys Lys
            180                 185                 190

Lys Met Cys Thr Arg Asp Gly Gly Ser Gly Gly Ser Ser Ser Ser Ser
        195                 200                 205

Gly Gly Met His Ser Phe Cys Ala Phe Lys Ala Asp Asp Gly Pro Cys
    210                 215                 220

Ile Ala Phe Phe Pro Arg Phe Phe Asn Ile Phe Thr Arg Gln Cys
225                 230                 235                 240

Glu Glu Phe Ile Tyr Gly Gly Cys Gln Gly Asn Gln Asn Arg Phe Glu
                245                 250                 255
```

```
Ser Leu Glu Glu Cys Lys Lys Met Cys Thr Arg Asp
        260                 265
```

<210> SEQ ID NO 74
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Met His Ser Phe Cys Ala Phe Lys Ala Asp Asp Gly Pro Cys Arg Ala
 1               5                  10                  15

Ala His Pro Arg Trp Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
         35                  40                  45

Glu Glu Cys Lys Lys Met Cys Thr Arg Asp Gly Gly Ser Gly Asn Gly
 50                  55                  60

Ser Ser Ser Ser Gly Gly Gly Ser Gly Ser Gly Met His Ser Phe Cys
65                  70                  75                  80

Ala Phe Lys Ala Asp Asp Gly Pro Cys Ile Ala Phe Phe Pro Arg Phe
                 85                  90                  95

Phe Phe Asn Ile Phe Thr Arg Gln Cys Glu Glu Phe Ile Tyr Gly Gly
            100                 105                 110

Cys Gln Asn Gln Asn Arg Phe Glu Ser Leu Glu Glu Cys Lys Lys Met
        115                 120                 125

Cys Thr Arg Asp Gly Gly Ser Gly Asn Gly Ser Ser Ser Ser Gly Gly
    130                 135                 140

Gly Ser Gly Ser Gly Met His Ser Phe Cys Ala Phe Lys Ala Asp Asp
145                 150                 155                 160

Gly Pro Cys Arg Ala Ala His Pro Arg Trp Phe Phe Asn Ile Phe Thr
                165                 170                 175

Arg Gln Cys Glu Glu Phe Ile Tyr Gly Gly Cys Glu Gly Asn Gln Asn
            180                 185                 190

Arg Phe Glu Ser Leu Glu Glu Cys Lys Lys Met Cys Thr Arg Asp Gly
        195                 200                 205

Gly Ser Gly Asn Gly Ser Ser Ser Ser Gly Gly Gly Ser Gly Ser Gly
    210                 215                 220

Met His Ser Phe Cys Ala Phe Lys Ala Asp Asp Gly Pro Cys Ile Ala
225                 230                 235                 240

Phe Phe Pro Arg Phe Phe Phe Asn Ile Phe Thr Arg Gln Cys Glu Glu
                245                 250                 255

Phe Ile Tyr Gly Gly Cys Gln Asn Gln Asn Arg Phe Glu Ser Leu
            260                 265                 270

Glu Glu Cys Lys Lys Met Cys Thr Arg Asp
        275                 280
```

<210> SEQ ID NO 75
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

```
Met His Ser Phe Cys Ala Phe Lys Ala Asp Asp Gly Pro Cys Ile Ala
1               5                   10                  15

Phe Phe Pro Arg Phe Phe Asn Ile Phe Thr Arg Gln Cys Glu Glu
        20                  25                  30

Phe Ile Tyr Gly Gly Cys Gln Gly Asn Gln Asn Arg Phe Glu Ser Leu
            35                  40                  45

Glu Glu Cys Lys Lys Met Cys Thr Arg Asp Gly Gly Ser Gly Gly Ser
50                  55                  60

Ser Ser Ser Ser Gly Gly Met His Ser Phe Cys Ala Phe Lys Ala Asp
65              70                  75                  80

Asp Gly Pro Cys Ile Ala Phe Phe Pro Arg Phe Phe Asn Ile Phe
                85                  90                  95

Thr Arg Gln Cys Glu Glu Phe Ile Tyr Gly Gly Cys Gln Gly Asn Gln
        100                 105                 110

Asn Arg Phe Glu Ser Leu Glu Glu Cys Lys Lys Met Cys Thr Arg Asp
            115                 120                 125

Gly Gly Ser Gly Gly Ser Ser Ser Ser Gly Gly Met His Ser Phe
    130                 135                 140

Cys Ala Phe Lys Ala Asp Asp Gly Pro Cys Ile Ala Phe Phe Pro Arg
145                 150                 155                 160

Phe Phe Phe Asn Ile Phe Thr Arg Gln Cys Glu Glu Phe Ile Tyr Gly
                165                 170                 175

Gly Cys Gln Gly Asn Gln Asn Arg Phe Glu Ser Leu Glu Glu Cys Lys
        180                 185                 190

Lys Met Cys Thr Arg Asp Gly Gly Ser Gly Gly Ser Ser Ser Ser
        195                 200                 205

Gly Gly Met His Ser Phe Cys Ala Phe Lys Ala Asp Asp Gly Pro Cys
    210                 215                 220

Ile Ala Phe Phe Pro Arg Phe Phe Phe Asn Ile Phe Thr Arg Gln Cys
225                 230                 235                 240

Glu Glu Phe Ile Tyr Gly Gly Cys Gln Gly Asn Gln Asn Arg Phe Glu
                245                 250                 255

Ser Leu Glu Glu Cys Lys Lys Met Cys Thr Arg Asp Gly Gly Ser Gly
            260                 265                 270

Gly Ser Ser Ser Ser Gly Gly Met His Ser Phe Cys Ala Phe Lys
    275                 280                 285

Ala Asp Asp Gly Pro Cys Ile Ala Phe Phe Pro Arg Phe Phe Phe Asn
    290                 295                 300

Ile Phe Thr Arg Gln Cys Glu Glu Phe Ile Tyr Gly Gly Cys Gln Gly
305                 310                 315                 320

Asn Gln Asn Arg Phe Glu Ser Leu Glu Glu Cys Lys Lys Met Cys Thr
            325                 330                 335

Arg Asp Gly Gly Ser Gly Ser Ser Ser Gly Ser Ser Ser Gly Met His
        340                 345                 350

Ser Phe Cys Ala Phe Lys Ala Asp Asp Gly Pro Cys Ile Ala Phe Phe
        355                 360                 365

Pro Arg Phe Phe Phe Asn Ile Phe Thr Arg Gln Cys Glu Glu Phe Ile
    370                 375                 380

Tyr Gly Gly Cys Gln Gly Asn Gln Asn Arg Phe Glu Ser Leu Glu Glu
385                 390                 395                 400

Cys Lys Lys Met Cys Thr Arg Asp
                405
```

<210> SEQ ID NO 76
<211> LENGTH: 548
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Met His Ser Phe Cys Ala Phe Lys Ala Asp Asp Gly Pro Cys Ile Ala
 1               5                  10                  15

Phe Phe Pro Arg Phe Phe Phe Asn Ile Phe Thr Arg Gln Cys Glu Glu
                20                  25                  30

Phe Ile Tyr Gly Gly Cys Gln Gly Asn Gln Asn Arg Phe Glu Ser Leu
            35                  40                  45

Glu Glu Cys Lys Lys Met Cys Thr Arg Asp Gly Gly Ser Gly Gly Ser
 50                  55                  60

Ser Gly Ser Ser Gly Gly Met His Ser Phe Cys Ala Phe Lys Ala Asp
 65                  70                  75                  80

Asp Gly Pro Cys Ile Ala Phe Phe Pro Arg Phe Phe Phe Asn Ile Phe
                85                  90                  95

Thr Arg Gln Cys Glu Glu Phe Ile Tyr Gly Gly Cys Gln Gly Asn Gln
            100                 105                 110

Asn Arg Phe Glu Ser Leu Glu Glu Cys Lys Lys Met Cys Thr Arg Asp
        115                 120                 125

Gly Gly Ser Gly Gly Ser Ser Ser Ser Gly Gly Met His Ser Phe
    130                 135                 140

Cys Ala Phe Lys Ala Asp Asp Gly Pro Cys Ile Ala Phe Phe Pro Arg
145                 150                 155                 160

Phe Phe Phe Asn Ile Phe Thr Arg Gln Cys Glu Glu Phe Ile Tyr Gly
                165                 170                 175

Gly Cys Gln Gly Asn Gln Asn Arg Phe Glu Ser Leu Glu Glu Cys Lys
            180                 185                 190

Lys Met Cys Thr Arg Asp Gly Gly Ser Gly Gly Ser Ser Ser
        195                 200                 205

Gly Gly Met His Ser Phe Cys Ala Phe Lys Ala Asp Asp Gly Pro Cys
    210                 215                 220

Ile Ala Phe Phe Pro Arg Phe Phe Phe Asn Ile Phe Thr Arg Gln Cys
225                 230                 235                 240

Glu Glu Phe Ile Tyr Gly Gly Cys Gln Gly Asn Gln Asn Arg Phe Glu
                245                 250                 255

Ser Leu Glu Glu Cys Lys Lys Met Cys Thr Arg Asp Gly Gly Ser Gly
            260                 265                 270

Gly Ser Ser Ser Gly Ser Gly Met His Ser Phe Cys Ala Phe Lys
        275                 280                 285

Ala Asp Asp Gly Pro Cys Ile Ala Phe Phe Pro Arg Phe Phe Phe Asn
    290                 295                 300

Ile Phe Thr Arg Gln Cys Glu Glu Phe Ile Tyr Gly Gly Cys Gln Gly
305                 310                 315                 320

Asn Gln Asn Arg Phe Glu Ser Leu Glu Glu Cys Lys Lys Met Cys Thr
                325                 330                 335

Arg Asp Gly Gly Ser Gly Ser Ser Ser Gly Ser Ser Ser Gly Met His
            340                 345                 350

Ser Phe Cys Ala Phe Lys Ala Asp Asp Gly Pro Cys Ile Ala Phe Phe
        355                 360                 365
```

```
Pro Arg Phe Phe Asn Ile Phe Thr Arg Gln Cys Glu Glu Phe Ile
    370                 375                 380

Tyr Gly Gly Cys Gln Gly Asn Gln Asn Arg Phe Glu Ser Leu Glu Glu
385                 390                 395                 400

Cys Lys Lys Met Cys Thr Arg Asp Gly Ser Gly Ser Ser Gly Ser Ser
                405                 410                 415

Gly Ser Ser Gly Met His Ser Phe Cys Ala Phe Lys Ala Asp Asp Gly
                420                 425                 430

Pro Cys Ile Ala Phe Phe Pro Arg Phe Phe Phe Asn Ile Phe Thr Arg
            435                 440                 445

Gln Cys Glu Glu Phe Ile Tyr Gly Gly Cys Gln Gly Asn Gln Asn Arg
    450                 455                 460

Phe Glu Ser Leu Glu Glu Cys Lys Lys Met Cys Thr Arg Asp Gly Gly
465                 470                 475                 480

Ser Ser Ser Gly Ser Gly Ser Gly Met His Ser Phe Cys Ala
                485                 490                 495

Phe Lys Ala Asp Asp Gly Pro Cys Ile Ala Phe Pro Arg Phe Phe
                500                 505                 510

Phe Asn Ile Phe Thr Arg Gln Cys Glu Glu Phe Ile Tyr Gly Gly Cys
            515                 520                 525

Gln Gly Asn Gln Asn Arg Phe Glu Ser Leu Glu Glu Cys Lys Lys Met
    530                 535                 540

Cys Thr Arg Asp
545

<210> SEQ ID NO 77
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(249)

<400> SEQUENCE: 77 gtg aaa aaa tta tta ttc gca att cct tta gtt gtt cct ttc tat tcc      48
Met Lys Lys Leu Leu Phe Ala Ile Pro Leu Val Val Pro Phe Tyr Ser
1               5                   10                  15 atg gcg gcc gag atg cat tcc ttc tgc gcc ttc aag gct gac gac ggt      96
Met Ala Ala Glu Met His Ser Phe Cys Ala Phe Lys Ala Asp Asp Xaa
                20                  25                  30 ccg tgt att gct ttc ttc cct cgt ttc ttc ttc aac att ttc acg cgt     144
Xaa Xaa Ile Ala Phe Phe Pro Arg Phe Phe Phe Asn Ile Phe Thr Arg
            35                  40                  45 cag tgc gag gaa ttc att tac ggt ggt tgt gaa ggt aac cag aac cgg     192
Gln Cys Glu Glu Phe Ile Tyr Gly Gly Xaa Xaa Gly Asn Gln Asn Arg
    50                  55                  60 ttc gaa tct cta gag gaa tgt aag aag atg tgt act cgt gat tct gct     240
Phe Glu Ser Leu Glu Glu Cys Lys Lys Met Cys Thr Arg Asp Ser Ala
65                  70                  75                  80 agc tct gct                                                         249
Ser Ser Ala <210> SEQ ID NO 78
<211> LENGTH: 83
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (32)..(33)
<223> OTHER INFORMATION: variable amino acid
<220> FEATURE:
<221> NAME/KEY: MOD_RES
<222> LOCATION: (34)
<223> OTHER INFORMATION: any amino acid except Cys if Xaa in position 58
      is a Cys
<220> FEATURE:
<221> NAME/KEY: MOD_RES
<222> LOCATION: (58)
<223> OTHER INFORMATION: any amino acid except Cys if Xaa in position 34
      is a Cys
<220> FEATURE:
<221> NAME/KEY: MOD_RES
<222> LOCATION: (59)
<223> OTHER INFORMATION: variable amino acid

<400> SEQUENCE: 78

Met Lys Lys Leu Leu Phe Ala Ile Pro Leu Val Val Pro Phe Tyr Ser
 1               5                  10                  15

Met Ala Ala Glu Met His Ser Phe Cys Ala Phe Lys Ala Asp Asp Xaa
            20                  25                  30

Xaa Xaa Ile Ala Phe Phe Pro Arg Phe Phe Phe Asn Ile Phe Thr Arg
        35                  40                  45

Gln Cys Glu Glu Phe Ile Tyr Gly Gly Xaa Xaa Gly Asn Gln Asn Arg
 50                  55                  60

Phe Glu Ser Leu Glu Glu Cys Lys Lys Met Cys Thr Arg Asp Ser Ala
 65                  70                  75                  80

Ser Ser Ala

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggcttcactt accgtgttcc a                                            21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ccaagtaacc acaagtttct                                              20

<210> SEQ ID NO 81
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: 66, 69, 72
<223> OTHER INFORMATION: a, c, g, t, unknown or other
<220> FEATURE:
```

```
<221> NAME/KEY: modified_base
<222> LOCATION: (66)
<223> OTHER INFORMATION: a, c, g, t, unknown or other
<220> FEATURE:
<221> NAME/KEY: modified_base
<222> LOCATION: (69)
<223> OTHER INFORMATION: a, c, g, t, unknown or other
<220> FEATURE:
<221> NAME/KEY: modified_base
<222> LOCATION: (72)
<223> OTHER INFORMATION: a, c, g, t, unknown or other

<400> SEQUENCE: 81
ggcttcactt accgtgttcc atggcggccg agatgcattc cttctgcgcc ttcaaggctg    60
acgacnhknh knhkattgct ttcttccctc gtttcttctt caacattttc acg          113

<210> SEQ ID NO 82
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (66)
<223> OTHER INFORMATION: a, c, g, t, unknown or other
<220> FEATURE:
<221> NAME/KEY: modified_base
<222> LOCATION: (69)
<223> OTHER INFORMATION: a, c, g, t, unknown or other

<400> SEQUENCE: 82
ggcttcactt accgtgttcc atggcggccg agatgcattc cttctgcgcc ttcaaggctg    60
acgacnhknh kbggattgct ttcttccctc gtttcttctt caacattttc acg          113

<210> SEQ ID NO 83
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (66)
<223> OTHER INFORMATION: a, c, g, t, unknown or other
<220> FEATURE:
<221> NAME/KEY: modified_base
<222> LOCATION: (72)
<223> OTHER INFORMATION: a, c, g, t, unknown or other

<400> SEQUENCE: 83
ggcttcactt accgtgttcc atggcggccg agatgcattc cttctgcgcc ttcaaggctg    60
acgacnhkbg gnhkattgct ttcttccctc gtttcttctt caacattttc acg          113

<210> SEQ ID NO 84
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (66)
<223> OTHER INFORMATION: a, c, g, t, unknown or other

<400> SEQUENCE: 84
```

```
ggcttcactt accgtgttcc atggcggccg agatgcattc cttctgcgcc ttcaaggctg    60
acgacnhkbg gbggattgct ttcttccctc gtttcttctt caacattttc acg          113
```

<210> SEQ ID NO 85
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (69)
<223> OTHER INFORMATION: a, c, g, t, unknown or other
<220> FEATURE:
<221> NAME/KEY: modified_base
<222> LOCATION: (72)
<223> OTHER INFORMATION: a, c, g, t, unknown or other

<400> SEQUENCE: 85

```
ggcttcactt accgtgttcc atggcggccg agatgcattc cttctgcgcc ttcaaggctg    60
acgacbggnh knhkattgct ttcttccctc gtttcttctt caacattttc acg          113
```

<210> SEQ ID NO 86
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (69)
<223> OTHER INFORMATION: a, c, g, t, unknown or other

<400> SEQUENCE: 86

```
ggcttcactt accgtgttcc atggcggccg agatgcattc cttctgcgcc ttcaaggctg    60
acgacbggnh kbggattgct ttcttccctc gtttcttctt caacattttc acg          113
```

<210> SEQ ID NO 87
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (72)
<223> OTHER INFORMATION: a, c, g, t, unknown or other

<400> SEQUENCE: 87

```
ggcttcactt accgtgttcc atggcggccg agatgcattc cttctgcgcc ttcaaggctg    60
acgacbggbg gnhkattgct ttcttccctc gtttcttctt caacattttc acg          113
```

<210> SEQ ID NO 88
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
ggcttcactt accgtgttcc atggcggccg agatgcattc cttctgcgcc ttcaaggctg    60
acgacbggbg gbggattgct ttcttccctc gtttcttctt caacattttc acg          113
```

```
<210> SEQ ID NO 89
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)
<223> OTHER INFORMATION: a, c, g, t, unknown or other
<220> FEATURE:
<221> NAME/KEY: modified_base
<222> LOCATION: (52)
<223> OTHER INFORMATION: a, c, g, t, unknown or other

<400> SEQUENCE: 89
ccaagtaacc acaagtttct agagattcga accggttctg gttaccmdnm dnaccaccgt      60
aaatgaattc ctcgcactga cgcgtgaaaa tgttgaagaa gaaacg                    106

<210> SEQ ID NO 90
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (52)
<223> OTHER INFORMATION: a, c, g, t, unknown or other

<400> SEQUENCE: 90
ccaagtaacc acaagtttct agagattcga accggttctg gttaccccvm dnaccaccgt      60
aaatgaattc ctcgcactga cgcgtgaaaa tgttgaagaa gaaacg                    106

<210> SEQ ID NO 91
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)
<223> OTHER INFORMATION: a, c, g, t, unknown or other

<400> SEQUENCE: 91
ccaagtaacc acaagtttct agagattcga accggttctg gttaccmdnc cvaccaccgt      60
aaatgaattc ctcgcactga cgcgtgaaaa tgttgaagaa gaaacg                    106

<210> SEQ ID NO 92
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
ccaagtaacc acaagtttct agagattcga accggttctg gttaccccvc cvaccaccgt      60
aaatgaattc ctcgcactga cgcgtgaaaa tgttgaagaa gaaacg                    106

<210> SEQ ID NO 93
```

-continued

```
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (21)..(239)
<220> FEATURE:
<221> NAME/KEY: modified_base
<222> LOCATION: (38)
<223> OTHER INFORMATION: a, c, g, t, unknown or other
<220> FEATURE:
<221> NAME/KEY: modified_base
<222> LOCATION: (47)
<223> OTHER INFORMATION: a, c, g, t, unknown or other
<220> FEATURE:
<221> NAME/KEY: modified_base
<222> LOCATION: (56)
<223> OTHER INFORMATION: a, c, g, t, unknown or other
<220> FEATURE:
<221> NAME/KEY: modified_base
<222> LOCATION: (65)
<223> OTHER INFORMATION: a, c, g, t, unknown or other
<220> FEATURE:
<221> NAME/KEY: modified_base
<222> LOCATION: (68)
<223> OTHER INFORMATION: a, c, g, t, unknown or other
<220> FEATURE:
<221> NAME/KEY: modified_base
<222> LOCATION: (77)
<223> OTHER INFORMATION: a, c, g, t, unknown or other
<220> FEATURE:
<221> NAME/KEY: modified_base
<222> LOCATION: (110)
<223> OTHER INFORMATION: a, c, g, t, unknown or other
<220> FEATURE:
<221> NAME/KEY: modified_base
<222> LOCATION: (113)
<223> OTHER INFORMATION: a, c, g, t, unknown or other
<220> FEATURE:
<221> NAME/KEY: modified_base
<222> LOCATION: (137)
<223> OTHER INFORMATION: a, c, g, t, unknown or other
<220> FEATURE:
<221> NAME/KEY: modified_base
<222> LOCATION: (140)
<223> OTHER INFORMATION: a, c, g, t, unknown or other
<220> FEATURE:
<221> NAME/KEY: modified_base
<222> LOCATION: (149)
<223> OTHER INFORMATION: a, c, g, t, unknown or other
<220> FEATURE:
<221> NAME/KEY: modified_base
<222> LOCATION: (161)
<223> OTHER INFORMATION: a, c, g, t, unknown or other
<220> FEATURE:
<221> NAME/KEY: modified_base
<222> LOCATION: (197)
<223> OTHER INFORMATION: a, c, g, t, unknown or other
<220> FEATURE:
<221> NAME/KEY: modified_base
<222> LOCATION: (200)
<223> OTHER INFORMATION: a, c, g, t, unknown or other

<400> SEQUENCE: 93
tgtcctgcac agggtccact tcc tca ggt atg cat tcn tty tgy gcn tty aar      53
                     Ser Ser Gly Met His Ser Phe Cys Ala Phe Lys
                      1               5                  10 gcn gay gay ggn ccn tgy ath gcn tty ttc cct cgt ttc ttt ttc aac      101
Ala Asp Asp Gly Pro Cys Ile Ala Phe Phe Pro Arg Phe Phe Phe Asn
             15                  20                  25 ath tty acn cgn car tgy gar gar tty ath tay ggn ggn tgy car ggn      149
Ile Phe Thr Arg Gln Cys Glu Glu Phe Ile Tyr Gly Gly Cys Gln Gly
         30                  35                  40
```

```
aay car aay cgn ttt gag tct ctt gaa gag tgy aar aar atg tgy acn    197
Asn Gln Asn Arg Phe Glu Ser Leu Glu Glu Cys Lys Lys Met Cys Thr
         45                  50                  55 cgn gay rgy rgy rcy rgy rgy rgy rgy ggc tcc tca ggt                239
Arg Asp Xaa Xaa Xaa Xaa Xaa Xaa Xaa Gly Ser Ser Gly
 60                  65                  70 cttctcgtta cctggtgggc                                              259
```

<210> SEQ ID NO 94
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(63)
<223> OTHER INFORMATION: Gly or Ser
<220> FEATURE:
<221> NAME/KEY: MOD_RES
<222> LOCATION: (64)
<223> OTHER INFORMATION: Thr or Ala
<220> FEATURE:
<221> NAME/KEY: MOD_RES
<222> LOCATION: (65)..(69)
<223> OTHER INFORMATION: Gly or Ser

<400> SEQUENCE: 94

```
Gly Ser Gly Met His Ser Phe Cys Ala Phe Lys Ala Asp Asp Gly Pro
 1               5                  10                  15

Cys Ile Ala Phe Phe Pro Arg Phe Phe Asn Ile Phe Thr Arg Gln
             20                  25                  30

Cys Glu Glu Phe Ile Tyr Gly Gly Cys Gln Gly Asn Gln Asn Arg Phe
         35                  40                  45

Glu Ser Leu Glu Glu Cys Lys Lys Met Cys Thr Arg Asp Xaa Xaa Xaa
     50                  55                  60

Xaa Xaa Xaa Xaa Xaa Gly Ser Ser Gly
 65                  70
```

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tgtcctgcac agggtccact t                                            21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcccaccagg taacgagaag a                                            21

<210> SEQ ID NO 97
<211> LENGTH: 103
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: 38, 47, 56, 65, 68, 77
<223> OTHER INFORMATION: a, c, g, t, unknown or other
<220> FEATURE:
<221> NAME/KEY: modified_base
<222> LOCATION: (38)
<223> OTHER INFORMATION: a, c, g, t, unknown or other
<220> FEATURE:
<221> NAME/KEY: modified_base
<222> LOCATION: (47)
<223> OTHER INFORMATION: a, c, g, t, unknown or other
<220> FEATURE:
<221> NAME/KEY: modified_base
<222> LOCATION: (56)
<223> OTHER INFORMATION: a, c, g, t, unknown or other
<220> FEATURE:
<221> NAME/KEY: modified_base
<222> LOCATION: (65)
<223> OTHER INFORMATION: a, c, g, t, unknown or other
<220> FEATURE:
<221> NAME/KEY: modified_base
<222> LOCATION: (68)
<223> OTHER INFORMATION: a, c, g, t, unknown or other
<220> FEATURE:
<221> NAME/KEY: modified_base
<222> LOCATION: (77)
<223> OTHER INFORMATION: a, c, g, t, unknown or other

<400> SEQUENCE: 97
tgtcctgcac agggtccact tcctcaggta tgcattcntt ytgygcntty aargcngayg    60
ayggnccntg yathgcntty ttccctcgtt tcttttttcaa cat                   103

<210> SEQ ID NO 98
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: 21, 33, 42, 45, 69, 72
<223> OTHER INFORMATION: a, c, g, t, unknown or other
<220> FEATURE:
<221> NAME/KEY: modified_base
<222> LOCATION: (21)
<223> OTHER INFORMATION: a, c, g, t, unknown or other
<220> FEATURE:
<221> NAME/KEY: modified_base
<222> LOCATION: (33)
<223> OTHER INFORMATION: a, c, g, t, unknown or other
<220> FEATURE:
<221> NAME/KEY: modified_base
<222> LOCATION: (42)
<223> OTHER INFORMATION: a, c, g, t, unknown or other
<220> FEATURE:
<221> NAME/KEY: modified_base
<222> LOCATION: (45)
<223> OTHER INFORMATION: a, c, g, t, unknown or other
<220> FEATURE:
<221> NAME/KEY: modified_base
<222> LOCATION: (69)
<223> OTHER INFORMATION: a, c, g, t, unknown or other
<220> FEATURE:
<221> NAME/KEY: modified_base
<222> LOCATION: (72)
<223> OTHER INFORMATION: a, c, g, t, unknown or other

<400> SEQUENCE: 98
cactcttcaa gagactcaaa ncgrttytgr ttnccytgrc anccnccrta datraaytcy    60

```
tcrcaytgnc gngtraadat gttgaaaaag aaacgaggga a                    101
```

```
<210> SEQ ID NO 99
<211> LENGTH: 98
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (36)
<223> OTHER INFORMATION: a, c, g, t, unknown or other
<220> FEATURE:
<221> NAME/KEY: modified_base
<222> LOCATION: (39)
<223> OTHER INFORMATION: a, c, g, t, unknown or other

<400> SEQUENCE: 99
tttgagtctc ttgaagagtg yaaraaratg tgyacncgng ayrgyrgyrg yrgyrgyrgy   60
rgyrgyggct cctcaggtct tctcgttacc tggtgggc                          98
```

```
<210> SEQ ID NO 100
<211> LENGTH: 8919
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (7416)..(8120)

<400> SEQUENCE: 100
aatgctacta ctattagtag aattgatgcc acctttcag ctcgcgcccc aaatgaaaat    60
atagctaaac aggttattga ccatttgcga aatgtatcta atggtcaaac taaatctact  120
cgttcgcaga attgggaatc aactgttata tggaatgaaa cttccagaca ccgtacttta  180
gttgcatatt taaaacatgt tgagctacag cattatattc agcaattaag ctctaagcca  240
tccgcaaaaa tgacctctta tcaaaaggag caattaaagg tactctctaa tcctgacctg  300
ttggagtttg cttccggtct ggttcgcttt gaagctcgaa ttaaaacgcg atatttgaag  360
tctttcgggc ttcctcttaa tctttttgat gcaatccgct ttgcttctga ctataatagt  420
cagggtaaag acctgatttt tgatttatgg tcattctcgt tttctgaact gtttaaagca  480
tttgaggggg attcaatgaa tatttatgac gattccgcag tattggacgc tatccagtct  540
aaacatttta ctattacccc ctctggcaaa acttcttttg caaaagcctc tcgctatttt  600 ggttttatc gtcgtctggt aaacgagggt tatgatagtg ttgctcttac tatgcctcgt  660
aattcctttt ggcgttatgt atctgcatta gttgaatgtg gtattcctaa atctcaactg  720
atgaatcttt ctacctgtaa taatgttgtt ccgttagttc gttttattaa cgtagatttt  780
tcttcccaac gtcctgactg gtataatgag ccagttctta aaatcgcata aggtaattca  840
caatgattaa agttgaaatt aaaccatctc aagcccaatt tactactcgt tctggtgttt  900
ctcgtcaggg caagccttat tcactgaatg agcagctttg ttacgttgat ttgggtaatg  960
aatatccggt tcttgtcaag attactcttg atgaaggtca gccagcctat gcgcctggtc 1020
tgtacaccgt tcatctgtcc tctttcaaag ttggtcagtt cggttccctt atgattgacc 1080
gtctgcgcct cgttccggct aagtaacatg gagcaggtcg cggatttcga cacaatttat 1140
caggcgatga tacaaatctc cgttgtactt tgtttcgcgc ttggtataat cgctggggt  1200
```

| | |
|---|---|
| caaagatgag tgttttagtg tattcttttg cctctttcgt tttaggttgg tgccttcgta | 1260 |
| gtggcattac gtattttacc cgtttaatgg aaacttcctc atgaaaaagt ctttagtcct | 1320 |
| caaagcctct gtagccgttg ctaccctcgt tccgatgctg tctttcgctg ctgagggtga | 1380 |
| cgatcccgca aaagcggcct ttaactccct gcaagcctca gcgaccgaat atatcggtta | 1440 |
| tgcgtgggcg atggttgttg tcattgtcgg cgcaactatc ggtatcaagc tgtttaagaa | 1500 |
| attcacctcg aaagcaagct gataaaccga tacaattaaa ggctccttt ggagccttt | 1560 |
| tttttggaga ttttcaacgt gaaaaaatta ttattcgcaa ttcctttagt gttcctttc | 1620 |
| tattctcact ccgctgaaac tgttgaaagt tgtttagcaa aatcccatac agaaaattca | 1680 |
| tttactaacg tctggaaaga cgacaaaact ttagatcgtt acgctaacta tgagggctgt | 1740 |
| ctgtggaatg ctacaggcgt tgtagtttgt actggtgacg aaactcagtg ttacggtaca | 1800 |
| tgggttccta ttgggcttgc tatccctgaa aatgagggtg gtggctctga gggtggcggt | 1860 |
| tctgagggtg gcggttctga gggtggcggt actaaacctc ctgagtacgg tgatacacct | 1920 |
| attccgggct atacttatat caaccctctc gacggcactt atccgcctgg tactgagcaa | 1980 |
| aaccccgcta atcctaatcc ttctcttgag gagtctcagc ctcttaatac tttcatgttt | 2040 |
| cagaataata ggttccgaaa taggcagggg gcattaactg tttatacggg cactgttact | 2100 |
| caaggcactg accccgttaa aactattac cagtacactc ctgtatcatc aaaagccatg | 2160 |
| tatgacgctt actggaacgg taaattcaga gactgcgctt tccattctgg ctttaatgag | 2220 |
| gatttatttg tttgtgaata tcaaggccaa tcgtctgacc tgcctcaacc tcctgtcaat | 2280 |
| gctggcggcg gctctggtgg tggttctggt ggcggctctg agggtggtgg ctctgagggt | 2340 |
| ggcggttctg agggtggcgg ctctgaggga ggcggttccg gtggtggctc tggttccggt | 2400 |
| gattttgatt atgaaaagat ggcaaacgct aataagggg ctatgaccga aaatgccgat | 2460 |
| gaaaacgcgc tacagtctga cgctaaaggc aaacttgatt ctgtcgctac tgattacggt | 2520 |
| gctgctatcg atggtttcat tggtgacgtt tccggccttg ctaatggtaa tggtgctact | 2580 |
| ggtgattttg ctggctctaa ttcccaaatg gctcaagtcg tgacggtga taattcacct | 2640 |
| ttaatgaata atttccgtca atatttacct tccctccctc aatcggttga atgtcgccct | 2700 |
| tttgtctttg cgctggtaa accatatgaa ttttctattg attgtgacaa aataaactta | 2760 |
| ttccgtggtg tctttgcgtt tcttttatat gttgccacct ttatgtatgt attttctacg | 2820 |
| tttgctaaca tactgcgtaa taaggagtct taatcatgcc agttcttttg ggtattccgt | 2880 |
| tattattgcg tttcctcggt ttccttctgg taactttgtt cggctatctg cttacttttc | 2940 |
| ttaaaaaggg cttcggtaag atagctattg ctatttcatt gtttcttgct cttattattg | 3000 |
| ggcttaactc aattcttgtg ggttatctct ctgatattag cgctcaatta ccctctgact | 3060 |
| ttgttcaggg tgttcagtta attctcccgt ctaatgcgct tccctgtttt tatgttattc | 3120 |
| tctctgtaaa ggctgctatt ttcattttg acgttaaaca aaaaatcgtt tcttatttgg | 3180 |
| attgggataa ataatatggc tgtttatttt gtaactggca aattaggctc tggaaagacg | 3240 |
| ctcgttagcg ttggtaagat tcaggataaa attgtagctg ggtgcaaaat agcaactaat | 3300 |
| cttgatttaa ggcttcaaaa cctcccgcaa gtcgggaggt tcgctaaaac gcctcgcgtt | 3360 |
| cttagaatac cggataagcc ttctatatct gatttgcttg ctattgggcg cggtaatgat | 3420 |
| tcctacgatg aaaataaaaa cggcttgctt gttctcgatg agtgcggtac ttggtttaat | 3480 |
| acccgttctt ggaatgataa ggaaagacag ccgattattg attggtttct acatgctcgt | 3540 |

```
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
gttggcgttg ttaaatatgg cgattctcaa ttaagcccta ctgttgagcg ttggctttat    3780
actggtaaga atttgtataa cgcatatgat actaaacagg cttttttctag taattatgat    3840
tccggtgttt attcttattt aacgccttat ttatcacacg gtcggtattt caaaccatta    3900
aatttaggtc agaagatgaa attaactaaa atatatttga aaagttttc tcgcgttctt    3960
tgtcttgcga ttggatttgc atcagcattt acatatagtt ataacccca acctaagccg    4020
gaggttaaaa aggtagtctc tcagacctat gatttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttcttttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gcaaataatt ttgatatggt aggttctaac ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atctattgac ggctctaatc tattagttgt    4740
tagtgctcct aaagatattt tagataacct tcctcaattc ctttcaactg ttgatttgcc    4800
aactgaccag atattgattg agggtttgat atttgaggtt cagcaaggtg atgctttaga    4860
ttttttcattt gctgctggct ctcagcgtgg cactgttgca ggcggtgtta atactgaccg    4920
cctcacctct gttttatctt ctgctggtgg ttcgttcggt attttttaatg gcgatgtttt    4980
agggctatca gttcgcgcat taagactaa tagccattca aaaatattgt ctgtgccacg    5040
tattcttacg ctttcaggtc agaagggttc tatctctgtt ggccagaatg tccctttta    5100
tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctcttttact    5340
cggtggcctc actgattata aaaacacttc tcaggattct ggcgtaccgt tcctgtctaa    5400
aatcccttta atcggcctcc tgtttagctc ccgctctgat tctaacgagg aaagcacgtt    5460
atacgtgctc gtcaaagcaa ccatagtacg cgccctgtag cggcgcatta agcgcggcgg    5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
gggggctccc tttagggttc cgatttagtg ctttacggca cctcgacccc aaaaaacttg    5700
atttgggtga tggttggcca tcgccctgat agacggtttt tcgccctttg acgttggagt    5760
ccacgttctt taatagtgga ctcttgttcc aaactggaac aacactcaac cctatctcgg    5820
gctattcttt tgatttataa gggattttgc cgatttcgga accaccatca aacaggattt    5880
tcgcctgctg gggcaaacca gcgtggaccg cttgctgcaa ctctctcagg gccaggcggt    5940
```

```
gaagggcaat cagctgttgc ccgtctcact ggtgaaaaga aaaccaccc tggatccaag      6000
cttgcaggtg gcacttttcg gggaaatgtg cgcggaaccc ctatttgttt attttttctaa   6060
atacattcaa atatgtatcc gctcatgaga caataaccct gataaatgct tcaataatat    6120
tgaaaaagga agagtatgag tattcaacat ttccgtgtcg cccttattcc cttttttgcg    6180
gcattttgcc ttcctgtttt tgctcaccca gaaacgctgg tgaaagtaaa agatgctgaa    6240
gatcagttgg gcgcactagt gggttacatc gaactggatc tcaacagcgg taagatcctt   6300
gagagttttc gccccgaaga acgttttcca atgatgagca cttttaaagt tctgctatgt   6360
ggcgcggtat tatcccgtat tgacgccggg caagagcaac tcggtcgccg catacactat   6420
tctcagaatg acttggttga gtactcacca gtcacagaaa agcatcttac ggatggcatg   6480
acagtaagag aattatgcag tgctgccata accatgagtg ataacactgc ggccaactta   6540
cttctgacaa cgatcggagg accgaaggag ctaaccgctt ttttgcacaa catgggggat   6600
catgtaactc gccttgatcg ttgggaaccg gagctgaatg aagccatacc aaacgacgag   6660
cgtgacacca cgatgcctgt agcaatggca acaacgttgc gcaaactatt aactggcgaa   6720
ctacttactc tagcttcccg gcaacaatta atagactgga tggaggcgga taaagttgca   6780
ggaccacttc tgcgctcggc ccttccggct ggctggttta ttgctgataa atctggagcc   6840
ggtgagcgtg ggtctcgcgg tatcattgca gcactggggc cagatggtaa gccctcccgt   6900
atcgtagtta tctacacgac ggggagtcag gcaactatgg atgaacgaaa tagacagatc   6960
gctgagatag gtgcctcact gattaagcat tggtaactgt cagaccaagt ttactcatat   7020
atactttaga ttgatttaaa acttcatttt taatttaaaa ggatctaggt gaagatcctt   7080
tttgataatc tcatgaccaa aatcccttaa cgtgagtttt cgttccactg tacgtaagac   7140
ccccaagctt gtcgactgaa tggcgaatgg cgctttgcct ggtttccggc accagaagcg   7200
gtgccggaaa gctggctgga gtgcgatctt cctgacgctc gagcgcaacg caattaatgt   7260
gagttagctc actcattagg cacccaggc tttacacttt atgcttccgg ctcgtatgtt   7320
gtgtggaatt gtgagcggat aacaatttca cacaggaaac agctatgacc atgattacgc   7380
caagctttgg agcctttttt ttggagattt tcaac gtg aaa aaa tta tta ttc       7433
                                      Val Lys Lys Leu Leu Phe
                                       1                5
gca att cct tta gtt gtt cct ttc tat tcc atg gcg gcc gag atg cat      7481
Ala Ile Pro Leu Val Val Pro Phe Tyr Ser Met Ala Ala Glu Met His
         10                  15                  20
tcc ttc tgc gcc ttc aag gct gac gac ggt ccg tgt att gct ttc ttc      7529
Ser Phe Cys Ala Phe Lys Ala Asp Asp Gly Pro Cys Ile Ala Phe Phe
     25                  30                  35
cct cgt ttc ttc ttc aac att ttc acg cgt cag tgc gag gaa ttc att      7577
Pro Arg Phe Phe Phe Asn Ile Phe Thr Arg Gln Cys Glu Glu Phe Ile
 40                  45                  50
tac ggt ggt tgt gaa ggt aac cag aac cgg ttc gaa tct cta gag gaa      7625
Tyr Gly Gly Cys Glu Gly Asn Gln Asn Arg Phe Glu Ser Leu Glu Glu
 55                  60                  65                  70
tgt aag aag atg tgt act cgt gat tct gct agc tct gct agt ggc gac      7673
Cys Lys Lys Met Cys Thr Arg Asp Ser Ala Ser Ser Ala Ser Gly Asp
             75                  80                  85
ttc gac tac gag aaa atg gct aat gcc aac aaa ggc gcc atg act gag      7721
Phe Asp Tyr Glu Lys Met Ala Asn Ala Asn Lys Gly Ala Met Thr Glu
         90                  95                  100
aac gct gac gag aat gct ttg caa agc gat gcc aag ggt aag tta gac      7769
Asn Ala Asp Glu Asn Ala Leu Gln Ser Asp Ala Lys Gly Lys Leu Asp
```

| | | | | | | | | | | | | | | | |
|---|---|---|---|---|---|---|---|---|---|---|---|---|---|---|---|
| | | 105 | | | | 110 | | | | | 115 | | | | |
| agc | gtc | gcg | acc | gac | tat | ggc | gcc | gcc | atc | gac | ggc | ttt | atc | ggc gat | 7817 |
| Ser | Val | Ala | Thr | Asp | Tyr | Gly | Ala | Ala | Ile | Asp | Gly | Phe | Ile | Gly Asp | |
| | 120 | | | | | 125 | | | | | 130 | | | | |
| gtc | agt | ggt | ttg | gcc | aac | ggc | aac | gga | gcc | acc | gga | gac | ttc | gca ggt | 7865 |
| Val | Ser | Gly | Leu | Ala | Asn | Gly | Asn | Gly | Ala | Thr | Gly | Asp | Phe | Ala Gly | |
| 135 | | | | | 140 | | | | | 145 | | | | 150 | |
| tcg | aat | tct | cag | atg | gcc | cag | gtt | gga | gat | ggg | gac | aac | agt | ccg ctt | 7913 |
| Ser | Asn | Ser | Gln | Met | Ala | Gln | Val | Gly | Asp | Gly | Asp | Asn | Ser | Pro Leu | |
| | | | | 155 | | | | | 160 | | | | | 165 | |
| atg | aac | aac | ttt | aga | cag | tac | ctt | ccg | tct | ctt | ccg | cag | agt | gtc gag | 7961 |
| Met | Asn | Asn | Phe | Arg | Gln | Tyr | Leu | Pro | Ser | Leu | Pro | Gln | Ser | Val Glu | |
| | | | 170 | | | | | 175 | | | | | 180 | | |
| tgc | cgt | cca | ttc | gtt | ttc | ggt | gcc | ggc | aag | cct | tac | gag | ttc | agc atc | 8009 |
| Cys | Arg | Pro | Phe | Val | Phe | Gly | Ala | Gly | Lys | Pro | Tyr | Glu | Phe | Ser Ile | |
| | | | | 185 | | | | | 190 | | | | | 195 | |
| gac | tgc | gat | aag | atc | aat | ctt | ttc | cgc | ggc | gtt | ttc | gct | ttc | ttg cta | 8057 |
| Asp | Cys | Asp | Lys | Ile | Asn | Leu | Phe | Arg | Gly | Val | Phe | Ala | Phe | Leu Leu | |
| | | | 200 | | | | | 205 | | | | | 210 | | |
| tac | gtc | gct | act | ttc | atg | tac | gtt | ttc | agc | act | ttc | gcc | aat | att tta | 8105 |
| Tyr | Val | Ala | Thr | Phe | Met | Tyr | Val | Phe | Ser | Thr | Phe | Ala | Asn | Ile Leu | |
| 215 | | | | | 220 | | | | | 225 | | | | 230 | |
| cgc | aac | aaa | gaa | agc | tagtgatctc ctaggaagcc cgcctaatga gcgggctttt | | | | | | | | | | 8160 |
| Arg | Asn | Lys | Glu | Ser | | | | | | | | | | | |
| | | | | 235 | | | | | | | | | | | |

```
tttttctggt atgcatcctg aggccgatac tgtcgtcgtc ccctcaaact ggcagatgca      8220
cggttacgat gcgcccatct acaccaacgt gacctatccc attacggtca atccgccgtt      8280
tgttcccacg gagaatccga cgggttgtta ctcgctcaca tttaatgttg atgaaagctg      8340
gctacaggaa ggccagacgc gaattatttt tgatggcgtt cctattggtt aaaaaatgag      8400
ctgatttaac aaaaatttaa tgcgaatttt aacaaaatat taacgtttac aatttaaata      8460
tttgcttata caatcttcct gttttgggg cttttctgat tatcaaccgg ggtacatatg      8520
attgacatgc tagttttacg attaccgttc atcgattctc ttgtttgctc cagactctca      8580
ggcaatgacc tgatagcctt tgtagatctc tcaaaaatag ctaccctctc cggcattaat      8640
ttatcagcta gaacggttga atatcatatt gatggtgatt tgactgtctc cggcctttct      8700 caccctttttg aatctttacc tacacattac tcaggcattg catttaaaat atatgagggt      8760
tctaaaaatt tttatccttg cgttgaaata aaggcttctc ccgcaaaagt attacagggt      8820
cataatgttt ttggtacaac cgatttagct ttatgctctg aggctttatt gcttaatttt      8880
gctaattctt tgccttgcct gtatgattta ttggatgtt                             8919
```

<210> SEQ ID NO 101
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Met Lys Lys Leu Leu Phe Ala Ile Pro Leu Val Val Pro Phe Tyr Ser
1               5                   10                  15

Met Ala Ala Glu Met His Ser Phe Cys Ala Phe Lys Ala Asp Asp Gly
            20                  25                  30

Pro Cys Ile Ala Phe Phe Pro Arg Phe Phe Asn Ile Phe Thr Arg
        35                  40                  45

Gln Cys Glu Glu Phe Ile Tyr Gly Gly Cys Glu Gly Asn Gln Asn Arg
 50                  55                  60

Phe Glu Ser Leu Glu Glu Cys Lys Lys Met Cys Thr Arg Asp Ser Ala
65                  70                  75                  80

Ser Ser Ala Ser Gly Asp Phe Asp Tyr Glu Lys Met Ala Asn Ala Asn
                85                  90                  95

Lys Gly Ala Met Thr Glu Asn Ala Asp Glu Asn Ala Leu Gln Ser Asp
            100                 105                 110

Ala Lys Gly Lys Leu Asp Ser Val Ala Thr Asp Tyr Gly Ala Ala Ile
        115                 120                 125

Asp Gly Phe Ile Gly Asp Val Ser Gly Leu Ala Asn Gly Asn Gly Ala
    130                 135                 140

Thr Gly Asp Phe Ala Gly Ser Asn Ser Gln Met Ala Gln Val Gly Asp
145                 150                 155                 160

Gly Asp Asn Ser Pro Leu Met Asn Asn Phe Arg Gln Tyr Leu Pro Ser
                165                 170                 175

Leu Pro Gln Ser Val Glu Cys Arg Pro Phe Val Phe Gly Ala Gly Lys
            180                 185                 190

Pro Tyr Glu Phe Ser Ile Asp Cys Asp Lys Ile Asn Leu Phe Arg Gly
        195                 200                 205

Val Phe Ala Phe Leu Leu Tyr Val Ala Thr Phe Met Tyr Val Phe Ser
    210                 215                 220

Thr Phe Ala Asn Ile Leu Arg Asn Lys Glu Ser
225                 230                 235

<210> SEQ ID NO 102
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ser Glu Glu Asp Glu Glu His Thr Ile Ile Thr Asp Thr Glu Leu
 1               5                  10                  15

Pro Pro Leu Lys Pro Met His Ser Phe Cys Ala Phe Lys Ala Asp Asp
                20                  25                  30

Gly Pro Cys Arg Ala Arg Phe Asp Arg Trp Phe Phe Asn Ile Phe Thr
            35                  40                  45

Arg Gln Cys Glu Glu Phe Ile Tyr Gly Gly Cys Glu Gly Asn Gln Asn
 50                  55                  60

Arg Phe Glu Ser Leu Glu Glu Cys Lys Lys Met Cys Thr Arg Asp Asn
65                  70                  75                  80

Ala Asn Arg Pro Ile Lys Thr Thr Leu Gln Gln Glu Lys Pro Asp Phe
                85                  90                  95

Cys Phe Leu Glu Glu Asp Pro Gly Pro Cys Arg Ala Ala His Pro Arg
            100                 105                 110

Trp Phe Tyr Asn Gln Thr Lys Gln Cys Glu Arg Phe Ile Tyr Gly Gly
        115                 120                 125

Cys Glu Gly Asn Met Asn Asn Phe Glu Thr Leu Glu Glu Cys Lys Asn
    130                 135                 140

Ile Cys Glu Asp Gly Pro Asn Gly Phe Gln Val Asp Asn Tyr Gly Thr
145                 150                 155                 160

Gln Leu Asn Ala Val Asn Ser Leu Thr Pro Gln Ser Pro Lys Val Pro

```
            165                 170                 175
Ser Leu Phe Glu Phe His Gly Pro Ser Trp Cys Leu Thr Pro Ala Asp
            180                 185                 190

Arg Gly Pro Cys Ile Ala Phe Phe Pro Arg Phe Tyr Tyr Asn Ser Val
            195                 200                 205

Ile Gly Lys Cys Arg Pro Phe Pro Tyr Gly Gly Cys Gln Gly Asn Glu
    210                 215                 220

Asn Phe Thr Ser Lys Gln Glu Cys Leu Arg Ala Cys Lys Lys Gly
225                 230                 235

<210> SEQ ID NO 103
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Ile Ala Phe Phe Pro Arg Phe Phe Phe Asn Ile Phe Thr
        35                  40                  45

Arg Gln Cys Glu Glu Phe Ile Tyr Gly Gly Cys Gln Gly Asn Gln Asn
    50                  55                  60

Arg Phe Glu Ser Leu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Pro Cys Ile Ala Phe Phe Pro Arg
            100                 105                 110

Phe Phe Tyr Asn Gln Thr Lys Gln Cys Glu Arg Phe Ile Tyr Gly Gly
            115                 120                 125

Cys Gln Gly Asn Met Asn Asn Phe Glu Thr Leu Glu Glu Cys Lys Asn
        130                 135                 140

Ile Cys Glu Asp Gly Pro Asn Gly Phe Gln Val Asp Asn Tyr Gly Thr
145                 150                 155                 160

Gln Leu Asn Ala Val Asn Ser Leu Thr Pro Gln Ser Thr Lys Val Pro
                165                 170                 175

Ser Leu Phe Glu Phe His Gly Pro Ser Trp Cys Leu Thr Pro Ala Asp
            180                 185                 190

Arg Gly Pro Cys Ile Ala Phe Phe Pro Arg Phe Tyr Tyr Asn Ser Val
            195                 200                 205

Ile Gly Lys Cys Arg Pro Phe Lys Tyr Gly Gly Cys Gln Gly Asn Glu
        210                 215                 220

Asn Phe Thr Ser Lys Gln Glu Cys Leu Arg Ala Cys Lys Lys Gly Phe
225                 230                 235                 240

Ile Gln Arg Ile Ser Gly Gly Ser Gly Ser Gly Gly Ser Gly Ser Ser
                245                 250                 255

Gly Gly Asp Ser Glu Glu Asp Glu Glu His Thr Ile Ile Thr Asp Thr
            260                 265                 270

Glu Leu Pro Pro Leu Lys Leu Met His Ser Phe Cys Ala Phe Lys Ala
        275                 280                 285
```

Asp Asp Gly Pro Cys Ile Ala Phe Phe Pro Arg Phe Phe Asn Ile
    290                 295                 300

Phe Thr Arg Gln Cys Glu Glu Phe Ile Tyr Gly Gly Cys Gln Gly Asn
305                 310                 315                 320

Gln Asn Arg Phe Glu Ser Leu Glu Glu Cys Lys Lys Met Cys Thr Arg
                325                 330                 335

Asp Asn Ala Asn Arg Ile Ile Lys Thr Thr Leu Gln Gln Glu Lys Pro
                340                 345                 350

Asp Phe Cys Phe Leu Glu Glu Asp Pro Gly Pro Cys Ile Ala Phe Phe
            355                 360                 365

Pro Arg Phe Phe Tyr Asn Gln Thr Lys Gln Cys Glu Arg Phe Ile Tyr
370                 375                 380

Gly Gly Cys Gln Gly Asn Met Asn Asn Phe Glu Thr Leu Glu Glu Cys
385                 390                 395                 400

Lys Asn Ile Cys Glu Asp Gly Pro Asn Gly Phe Gln Val Asp Asn Tyr
                405                 410                 415

Gly Thr Gln Leu Asn Ala Val Asn Ser Leu Thr Pro Gln Ser Thr Lys
            420                 425                 430

Val Pro Ser Leu Phe Glu Phe His Gly Pro Ser Trp Cys Leu Thr Pro
        435                 440                 445

Ala Asp Arg Gly Pro Cys Ile Ala Phe Phe Pro Arg Phe Tyr Tyr Asn
450                 455                 460

Ser Val Ile Gly Lys Cys Arg Pro Phe Lys Tyr Gly Gly Cys Gln Gly
465                 470                 475                 480

Asn Glu Asn Phe Thr Ser Lys Gln Glu Cys Leu Arg Ala Cys Lys Lys
                485                 490                 495

Gly Phe Ile Gln Arg Ile Ser
            500

<210> SEQ ID NO 104
<211> LENGTH: 299
<212> TYPE: PRT
<213> ORGANISM: Oryctolagus cuniculus

<400> SEQUENCE: 104

Met Lys Lys Glu His Ile Phe Trp Thr Ser Ile Cys Leu Leu Leu Gly
1               5                   10                  15

Leu Val Pro Ala Pro Val Ser Ser Ala Ala Glu Glu Asp Glu Phe Thr
            20                  25                  30

Asn Ile Thr Asp Ile Lys Pro Pro Leu Gln Lys Pro Thr His Ser Phe
        35                  40                  45

Cys Ala Met Lys Val Asp Asp Gly Pro Cys Arg Ala Tyr Ile Lys Arg
    50                  55                  60

Phe Phe Phe Asn Ile Leu Thr His Gln Cys Glu Glu Phe Ile Tyr Gly
65                  70                  75                  80

Gly Cys Glu Gly Asn Glu Asn Arg Phe Glu Ser Leu Glu Glu Cys Lys
                85                  90                  95

Glu Lys Cys Ala Arg Asp Tyr Pro Lys Met Thr Thr Lys Leu Thr Phe
                100                 105                 110

Gln Lys Gly Lys Pro Asp Phe Cys Phe Leu Glu Glu Asp Pro Gly Ile
            115                 120                 125

Cys Arg Gly Tyr Ile Thr Arg Tyr Phe Tyr Asn Asn Gln Ser Lys Gln
        130                 135                 140

Cys Glu Arg Phe Lys Tyr Gly Gly Cys Leu Gly Asn Leu Asn Asn Phe
145                 150                 155                 160

Glu Ser Leu Glu Glu Cys Lys Asn Thr Cys Glu Asn Pro Thr Ser Asp
                165                 170                 175

Phe Gln Val Asp Asp His Arg Thr Gln Leu Asn Thr Val Asn Asn Thr
            180                 185                 190

Leu Ile Asn Gln Pro Thr Lys Ala Pro Arg Arg Trp Ala Phe His Gly
        195                 200                 205

Pro Ser Trp Cys Leu Pro Pro Ala Asp Arg Gly Leu Cys Gln Ala Asn
    210                 215                 220

Glu Ile Arg Phe Phe Tyr Asn Ala Ile Ile Gly Lys Cys Arg Pro Phe
225                 230                 235                 240

Lys Tyr Ser Gly Cys Gly Gly Asn Glu Asn Asn Phe Thr Ser Lys Lys
                245                 250                 255

Ala Cys Ile Thr Ala Cys Lys Lys Gly Phe Ile Arg Asn Leu Ser Lys
            260                 265                 270

Gly Gly Leu Ile Lys Thr Lys Arg Lys Lys Lys Gln Pro Val Lys
        275                 280                 285

Ile Thr Tyr Val Glu Thr Phe Val Lys Lys Thr
    290                 295

<210> SEQ ID NO 105
<211> LENGTH: 900
<212> TYPE: DNA
<213> ORGANISM: Oryctolagus cuniculus

<400> SEQUENCE: 105
atgaagaaag aacacatctt ttggacgtct atatgcctgc tgcttggtct tgtccctgcc     60
cctgttagct cagcggccga ggaagatgaa ttcacaaaca ttacagatat taaaccgcca    120
ctacagaagc cgacacactc attttgtgca atgaaggtag atgatgggcc gtgcagagca    180
tacatcaaga gattttttt caatattctc acccatcagt gtgaagaatt tatatatgga    240
ggatgtgaag gaacgagaa tcgattcgag agtctggaag aatgcaaaga aaatgtgca    300 cgagattatc caagatgac tacaaagctg acatttcaaa aaggaaagcc tgatttctgc    360
tttttggaag aagatcctgg tatttgtcga ggttatatta ccagatattt ttataacaat    420
caatcaaaac aatgtgaacg tttcaagtac ggtgggtgcc ttggcaatct aaacaacttt    480
gagtcattgg aagaatgcaa aaacacctgt gagaatccaa cgagtgattt ccaggtggat    540
gaccatagaa cccagctcaa tactgtgaat aacactttaa ttaaccagcc gaccaaggct    600
cccagacgtt gggcatttca cggcccctca tggtgtctgc ccccagcaga cagaggattg    660
tgtcaagcca atgagatcag attcttctac aatgcaatca tcgggaaatg ccgcccattt    720
aagtacagtg gatgtggggg aaatgaaaat aatttcactt ccaaaaaagc atgtatcaca    780
gcttgtaaaa aaggtttcat ccgaaatcta tcaaaaggag gactaattaa aaccaaaagg    840
aagaaaaaga agcagccagt gaaaataact tatgtagaaa cttttgttaa aaagacataa    900

<210> SEQ ID NO 106
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Ala Glu Glu Asp Glu Phe Thr Asn Ile Thr Asp Ile Lys Pro Pro
1               5                   10                  15

Leu Gln Lys Pro Thr His Ser Phe Cys Ala Met Lys Val Asp Asp Gly
            20                  25                  30

Pro Cys Arg Ala Arg Phe Asp Arg Trp Phe Phe Asn Ile Leu Thr His
        35                  40                  45

Gln Cys Glu Glu Phe Ile Tyr Gly Gly Cys Gly Asn Glu Asn Arg
 50                  55                  60

Phe Glu Ser Leu Glu Glu Cys Lys Glu Lys Cys Ala Arg Asp Tyr Pro
65                  70                  75                  80

Lys Met Thr Thr Lys Leu Thr Phe Gln Lys Gly Lys Pro Asp Phe Cys
                85                  90                  95

Phe Leu Glu Glu Asp Pro Gly Pro Cys Arg Ala Ala His Pro Arg Tyr
            100                 105                 110

Phe Tyr Asn Asn Gln Ser Lys Gln Cys Glu Arg Phe Lys Tyr Gly Gly
        115                 120                 125

Cys Glu Gly Asn Leu Asn Asn Phe Glu Ser Leu Glu Glu Cys Lys Asn
130                 135                 140

Thr Cys Glu Asn Pro Thr Ser Asp Phe Gln Val Asp Asp His Arg Thr
145                 150                 155                 160

Gln Leu Asn Thr Val Asn Asn Thr Leu Ile Asn Gln Pro Thr Lys Ala
                165                 170                 175

Pro Arg Arg Trp Ala Phe His Gly Pro Ser Trp Cys Leu Pro Pro Ala
            180                 185                 190

Asp Arg Gly Pro Cys Ile Ala Phe Phe Pro Arg Phe Phe Tyr Asn Ala
        195                 200                 205

Ile Ile Gly Lys Cys Arg Pro Phe Lys Tyr Gly Gly Cys Gln Gly Asn
    210                 215                 220

Glu Asn Asn Phe Thr Ser Lys Lys Ala Cys Ile Thr Ala Cys Lys Lys
225                 230                 235                 240

Gly Phe Ile Arg Asn Leu Ser
                245

<210> SEQ ID NO 107
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Ala Glu Glu Asp Glu Phe Thr Asn Ile Thr Asp Ile Lys Pro Pro
 1               5                  10                  15

Leu Gln Lys Pro Thr His Ser Phe Cys Ala Met Lys Val Asp Asp Gly
            20                  25                  30

Pro Cys Arg Ala Arg Phe Asp Arg Trp Phe Phe Asn Ile Leu Thr His
        35                  40                  45

Gln Cys Glu Glu Phe Ile Tyr Gly Gly Cys Gly Asn Glu Asn Arg
 50                  55                  60

Phe Glu Ser Leu Glu Glu Cys Lys Glu Lys Cys Ala Arg Asp Tyr Pro
65                  70                  75                  80

Lys Met Thr Thr Lys Leu Thr Phe Gln Lys Gly Lys Pro Asp Phe Cys
                85                  90                  95

Phe Leu Glu Glu Asp Pro Gly Pro Cys Arg Ala Ala His Pro Arg Tyr
            100                 105                 110

Phe Tyr Asn Asn Gln Ser Lys Gln Cys Glu Arg Phe Lys Tyr Gly Gly

```
                115                 120                 125
Cys Glu Gly Asn Leu Asn Asn Phe Glu Ser Leu Glu Glu Cys Lys Asn
        130                 135                 140

Thr Cys Glu Asn Pro Thr Ser Asp Phe Gln Val Asp Asp His Arg Thr
145                 150                 155                 160

Gln Leu Asn Thr Val Asn Asn Thr Leu Ile Asn Gln Pro Thr Lys Ala
                165                 170                 175

Pro Arg Arg Trp Ala Phe His Gly Pro Ser Trp Cys Leu Pro Pro Ala
            180                 185                 190

Asp Arg Gly Pro Cys Ile Ala Phe Phe Pro Arg Phe Tyr Asn Ala
            195                 200                 205

Ile Ile Gly Lys Cys Arg Pro Phe Lys Tyr Gly Gly Cys Gln Gly Asn
        210                 215                 220

Glu Asn Asn Phe Thr Ser Lys Lys Ala Cys Ile Thr Ala Cys Lys Lys
225                 230                 235                 240

Gly Phe Ile Arg Asn Leu Ser Gly Gly Ser Gly Ser Ser Gly Ser Gly
                245                 250                 255

Gly Ser Gly Ser Ser Gly Ala Ala Glu Glu Asp Glu Phe Thr Asn Ile
            260                 265                 270

Thr Asp Ile Lys Pro Pro Leu Gln Lys Pro Thr His Ser Phe Cys Ala
        275                 280                 285

Met Lys Val Asp Asp Gly Pro Cys Arg Ala Arg Phe Asp Arg Trp Phe
    290                 295                 300

Phe Asn Ile Leu Thr His Gln Cys Glu Glu Phe Ile Tyr Gly Gly Cys
305                 310                 315                 320

Glu Gly Asn Glu Asn Arg Phe Glu Ser Leu Glu Glu Cys Lys Glu Lys
                325                 330                 335

Cys Ala Arg Asp Tyr Pro Lys Met Thr Thr Lys Leu Thr Phe Gln Lys
            340                 345                 350

Gly Lys Pro Asp Phe Cys Phe Leu Glu Glu Asp Pro Gly Pro Cys Arg
        355                 360                 365

Ala Ala His Pro Arg Tyr Phe Tyr Asn Asn Gln Ser Lys Gln Cys Glu
    370                 375                 380

Arg Phe Lys Tyr Gly Gly Cys Glu Gly Asn Leu Asn Phe Glu Ser
385                 390                 395                 400

Leu Glu Glu Cys Lys Asn Thr Cys Glu Asn Pro Thr Ser Asp Phe Gln
                405                 410                 415

Val Asp Asp His Arg Thr Gln Leu Asn Thr Val Asn Asn Thr Leu Ile
            420                 425                 430

Asn Gln Pro Thr Lys Ala Pro Arg Arg Trp Ala Phe His Gly Pro Ser
        435                 440                 445

Trp Cys Leu Pro Pro Ala Asp Arg Gly Pro Cys Ile Ala Phe Phe Pro
    450                 455                 460

Arg Phe Phe Tyr Asn Ala Ile Ile Gly Lys Cys Arg Pro Phe Lys Tyr
465                 470                 475                 480

Gly Gly Cys Gln Gly Asn Glu Asn Asn Phe Thr Ser Lys Lys Ala Cys
                485                 490                 495

Ile Thr Ala Cys Lys Lys Gly Phe Ile Arg Asn Leu Ser
            500                 505

<210> SEQ ID NO 108
<211> LENGTH: 810
<212> TYPE: DNA
<213> ORGANISM: Artificial Sequence
```

-continued

```
<220> FEATURE:
<223> OTHER INFORMATION: Description of Artificial Sequence: Synthetic
      polynucleotide

<400> SEQUENCE: 108
atgggatgga gctgtatcat cctcttcttg gtcgcgacgg ccacaggggc ccactccgcg      60
gccgaggaag atgaattcac aaacattaca gatattaaac cgccactaca gaagccgaca     120
cactcatttt gtgcaatgaa ggtagatgat gggccgtgca gagcacgctt cgatagatgg     180
tttttcaata ttctcaccca tcagtgtgaa gaatttatat atggaggatg tgaagggaac     240
gagaatcgat tcgagagtct ggaagaatgc aaagaaaaat gtgcacgaga ttatccaaag     300
atgactacaa agctgacatt tcaaaaagga aagcctgatt tctgcttttt ggaagaagat     360
cctggtcctt gtcgagctgc tcatcctaga tattttata caatcaatc aaaacaatgt      420 gaacgtttca agtacggtgg gtgcgagggc aatctaaaca actttgagtc attggaagaa     480
tgcaaaaaca cctgtgagaa tccaacgagt gatttccagg tggatgacca tagaacccag     540
ctcaatactg tgaataacac tttaattaac cagccgacca aggctcccag acgttgggca     600
tttcacggcc cctcatggtg tctgccccca gcagacagag gaccgtgtat agccttttc      660 cccagattct tctacaatgc aatcatcggg aaatgccgcc catttaagta cggtggatgt     720
cagggaaatg aaaataattt cacttccaaa aaagcatgta tcacagcttg taaaaaggt      780 ttcatccgaa atctatcata atgatctaga                                     810

<210> SEQ ID NO 109
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttaatcttgc ggccacaggg gcccactctg cggccgagga agatgaa                    47

<210> SEQ ID NO 110
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tcattatgat agatttcgga tgaaaccttt tttaca                                36

<210> SEQ ID NO 111
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tattgaaaaa ccatctatcg aagcgtgctc tg                                    32

<210> SEQ ID NO 112
<211> LENGTH: 32
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 112
cagagcacgc ttcgatagat ggttttcaa ta                                    32

<210> SEQ ID NO 113
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aaaaatatct aggatgagca gctcgacaag gaccaggatc t                         41

<210> SEQ ID NO 114
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
agatcctggt ccttgtcgag ctgctcatcc tagatatttt t                         41

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gtttagattg ccctcgcacc cac                                             23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gtgggtgcga gggcaatcta aac                                             23

<210> SEQ ID NO 117
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gaagaatctg gggaaaaagg ctatacacgg tcdtctgtct                           40

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic

```
                              primer

<400> SEQUENCE: 118
agacagagga ccgtgtatag ccttttccc cagattcttc                              40

<210> SEQ ID NO 119
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tcatttccct gacatccacc gtacttaaat gg                                     32

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
atttaagtac ggtggatgtc agggaaatga                                        30

<210> SEQ ID NO 121
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ggattacttc tagatcatta tgatagattt cggatgaaac cttttttaca                  50

<210> SEQ ID NO 122
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Asp Arg Glu Arg Ser Ile His Asp Phe Cys Leu Val Ser Lys Val
  1               5                  10                  15

Val Gly Arg Cys Arg Ala Ser Met Pro Arg Trp Trp Tyr Asn Val Thr
                 20                  25                  30

Asp Gly Ser Cys Gln Leu Phe Val Tyr Gly Gly Cys Asp Gly Asn Ser
             35                  40                  45

Asn Asn Tyr Leu Thr Lys Glu Glu Cys Leu Lys Lys Cys Ala Thr Val
         50                  55                  60

Thr Glu Asn Ala Thr Gly Asp Leu Ala Thr Ser Arg Asn Ala Ala Asp
 65                  70                  75                  80

Ser Ser Val Pro Ser Ala Pro Arg Arg Gln Asp Ser Glu Asp His Ser
                 85                  90                  95

Ser Asp Met Phe Asn Tyr Glu Glu Tyr Cys Thr Ala Asn Ala Val Thr
                100                 105                 110

Gly Pro Cys Arg Ala Ser Phe Pro Arg Trp Tyr Phe Asp Val Glu Arg
            115                 120                 125
```

```
Asn Ser Cys Asn Asn Phe Ile Tyr Gly Gly Cys Arg Gly Asn Lys Asn
            130                 135                 140
Ser Tyr Arg Ser Glu Glu Ala Cys Met Leu Arg Cys Phe Arg Gln Gln
145                 150                 155                 160
Glu Asn Pro Pro Leu Pro Leu Gly Ser Lys Val Val Val Leu Ala Gly
                165                 170                 175
Ala Val Ser

<210> SEQ ID NO 123
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ala Gly Ser Phe Leu Ala Trp Leu Gly Ser Leu Leu Ser Gly Val
1               5                   10                  15
Leu Ala Ala Asp Arg Glu Arg Ser Ile His Asp Phe Cys Leu Val Ser
                20                  25                  30
Lys Val Gly Arg Cys Arg Ala Ser Met Pro Arg Trp Trp Tyr Asn
            35                  40                  45
Val Thr Asp Gly Ser Cys Gln Leu Phe Val Tyr Gly Gly Cys Asp Gly
 50                 55                  60
Asn Ser Asn Asn Tyr Leu Thr Lys Glu Glu Cys Leu Lys Lys Cys Ala
65                  70                  75                  80
Thr Val Thr Glu Asn Ala Thr Gly Asp Leu Ala Thr Ser Arg Asn Ala
                85                  90                  95
Ala Asp Ser Ser Val Pro Ser Ala Pro Arg Arg Gln Asp Ser Glu Asp
            100                 105                 110
His Ser Ser Asp Met Phe Asn Tyr Glu Glu Tyr Cys Thr Ala Asn Ala
        115                 120                 125
Val Thr Gly Pro Cys Arg Ala Ser Phe Pro Arg Trp Tyr Phe Asp Val
    130                 135                 140
Glu Arg Asn Ser Cys Asn Asn Phe Ile Tyr Gly Gly Cys Arg Gly Asn
145                 150                 155                 160
Lys Asn Ser Tyr Arg Ser Glu Glu Ala Cys Met Leu Arg Cys Phe Arg
                165                 170                 175
Gln Gln Glu Asn Pro Pro Leu Pro Leu Gly Ser Lys Val Val Val Leu
            180                 185                 190
Ala Gly Ala Val Ser
        195

<210> SEQ ID NO 124
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Leu Arg Ala Glu Ala Asp Gly Val Ser Arg Leu Leu Gly Ser Leu
1               5                   10                  15
Leu Leu Ser Gly Val Leu Ala Ala Asp Arg Glu Arg Ser Ile His Asp
                20                  25                  30
```

```
Phe Cys Leu Val Ser Lys Val Gly Arg Cys Arg Ala Ser Met Pro
         35                  40                  45

Arg Trp Trp Tyr Asn Val Thr Asp Gly Ser Cys Gln Leu Phe Val Tyr
 50                  55                  60

Gly Gly Cys Asp Gly Asn Ser Asn Asn Tyr Leu Thr Lys Glu Glu Cys
 65                  70                  75                  80

Leu Lys Lys Cys Ala Thr Val Thr Glu Asn Ala Thr Gly Asp Leu Ala
                 85                  90                  95

Thr Ser Arg Asn Ala Ala Asp Ser Ser Val Pro Ser Ala Pro Arg Arg
                100                 105                 110

Gln Asp Ser Glu Asp His Ser Ser Asp Met Phe Asn Tyr Glu Glu Tyr
                115                 120                 125

Cys Thr Ala Asn Ala Val Thr Gly Pro Cys Arg Ala Ser Phe Pro Arg
130                 135                 140

Trp Tyr Phe Asp Val Glu Arg Asn Ser Cys Asn Asn Phe Ile Tyr Gly
145                 150                 155                 160

Gly Cys Arg Gly Asn Lys Asn Ser Tyr Arg Ser Glu Glu Ala Cys Met
                165                 170                 175

Leu Arg Cys Phe Arg Gln Gln Glu Asn Pro Pro Leu Pro Leu Gly Ser
                180                 185                 190

Lys Val Val Leu Ala Gly Leu Phe Val Met Val Leu Ile Leu Phe
                195                 200                 205

Leu Gly Ala Ser Met Val Tyr Leu Ile Arg Val Ala Arg Arg Asn Gln
                210                 215                 220

Glu Arg Ala Leu Arg Thr Val Trp Ser Ser Gly Asp Asp Lys Glu Gln
225                 230                 235                 240

Leu Val Lys Asn Thr Tyr Val Leu
                245

<210> SEQ ID NO 125
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Ala Gln Leu Cys Gly Leu Arg Arg Ser Arg Ala Phe Leu Ala Leu
 1               5                  10                  15

Leu Gly Ser Leu Leu Leu Ser Gly Val Leu Ala Ala Asp Arg Glu Arg
                 20                  25                  30

Ser Ile His Asp Phe Cys Leu Val Ser Lys Val Val Gly Arg Cys Arg
                 35                  40                  45

Ala Ser Met Pro Arg Trp Trp Tyr Asn Val Thr Asp Gly Ser Cys Gln
 50                  55                  60

Leu Phe Val Tyr Gly Gly Cys Asp Gly Asn Ser Asn Asn Tyr Leu Thr
 65                  70                  75                  80

Lys Glu Glu Cys Leu Lys Lys Cys Ala Thr Val Thr Glu Asn Ala Thr
                 85                  90                  95

Gly Asp Leu Ala Thr Ser Arg Asn Ala Ala Asp Ser Ser Val Pro Ser
                100                 105                 110

Ala Pro Arg Arg Gln Asp Ser Glu Asp His Ser Ser Asp Met Phe Asn
                115                 120                 125

Tyr Glu Glu Tyr Cys Thr Ala Asn Ala Val Thr Gly Pro Cys Arg Ala
130                 135                 140
```

Ser Phe Pro Arg Trp Tyr Phe Asp Val Glu Arg Asn Ser Cys Asn Asn
145                 150                 155                 160

Phe Ile Tyr Gly Gly Cys Arg Gly Asn Lys Asn Ser Tyr Arg Ser Glu
            165                 170                 175

Glu Ala Cys Met Leu Arg Cys Phe Arg Gln Gln Glu Asn Pro Pro Leu
        180                 185                 190

Pro Leu Gly Ser Lys Val Val Val Leu Ala Gly Leu Phe Val Met Val
            195                 200                 205

Leu Ile Leu Phe Leu Gly Ala Ser Met Val Tyr Leu Ile Arg Val Ala
        210                 215                 220

Arg Arg Asn Gln Glu Arg Ala Leu Arg Thr Val Trp Ser Phe Gly Asp
225                 230                 235                 240

<210> SEQ ID NO 126
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Ala Glu Glu Asp Glu Phe Thr Asn Ile Thr Asp Ile Lys Pro Pro
1               5                   10                  15

Leu Gln Lys Pro Thr His Ser Phe Cys Ala Met Lys Val Asp Asp Gly
            20                  25                  30

Pro Gly Arg Ala Arg Phe Asp Arg Trp Phe Phe Asn Ile Leu Thr His
        35                  40                  45

Gln Cys Glu Glu Phe Ile Tyr Gly Gly Val Glu Gly Asn Glu Asn Arg
    50                  55                  60

Phe Glu Ser Leu Glu Glu Cys Lys Glu Lys Cys Ala Arg Asp Tyr Pro
65                  70                  75                  80

Lys Met Thr Thr Lys Leu Thr Phe Gln Lys Gly Lys Pro Asp Phe Cys
                85                  90                  95

Phe Leu Glu Glu Asp Pro Gly Pro Gly Arg Ala Ala His Pro Arg Tyr
            100                 105                 110

Phe Tyr Asn Asn Gln Ser Lys Gln Cys Glu Arg Phe Lys Tyr Gly Gly
        115                 120                 125

Val Glu Gly Asn Leu Asn Asn Phe Glu Ser Leu Glu Glu Cys Lys Asn
130                 135                 140

Thr Cys Glu Asn Pro Thr Ser Asp Phe Gln Val Asp Asp His Arg Thr
145                 150                 155                 160

Gln Leu Asn Thr Val Asn Asn Thr Leu Ile Asn Gln Pro Thr Lys Ala
            165                 170                 175

Pro Arg Arg Trp Ala Phe His Gly Pro Ser Trp Cys Leu Pro Pro Ala
        180                 185                 190

Asp Arg Gly Pro Gly Ile Ala Phe Phe Pro Arg Phe Tyr Asn Ala
        195                 200                 205

Ile Ile Gly Lys Cys Arg Pro Phe Lys Tyr Gly Gly Val Gln Gly Asn
        210                 215                 220

Glu Asn Asn Phe Thr Ser Lys Lys Ala Cys Ile Thr Ala Cys Lys Lys
225                 230                 235                 240

Gly Phe Ile Arg Asn Leu Ser
            245

```
<210> SEQ ID NO 127
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Ala Glu Glu Asp Glu Phe Thr Asn Ile Thr Asp Ile Lys Pro Pro
 1               5                  10                  15

Leu Gln Lys Pro Thr His Ser Phe Cys Ala Met Lys Val Asp Asp Gly
            20                  25                  30

Pro Gly Arg Ala Arg Phe Asp Arg Trp Phe Phe Asn Ile Leu Thr His
        35                  40                  45

Gln Cys Glu Glu Phe Ile Tyr Gly Gly Val Glu Gly Asn Glu Asn Arg
50                  55                  60

Phe Glu Ser Leu Glu Glu Cys Lys Glu Lys Cys Ala Arg Asp Tyr Pro
65                  70                  75                  80

Lys Met Thr Thr Lys Leu Thr Phe Gln Lys Gly Lys Pro Asp Phe Cys
                85                  90                  95

Phe Leu Glu Glu Asp Pro Gly Pro Gly Arg Ala Ala His Pro Arg Tyr
            100                 105                 110

Phe Tyr Asn Asn Gln Ser Lys Gln Cys Glu Arg Phe Lys Tyr Gly Gly
        115                 120                 125

Val Glu Gly Asn Leu Asn Asn Phe Glu Ser Leu Glu Glu Cys Lys Asn
130                 135                 140

Thr Cys Glu Asn Pro Thr Ser Asp Phe Gln Val Asp Asp His Arg Thr
145                 150                 155                 160

Gln Leu Asn Thr Val Asn Asn Thr Leu Ile Asn Gln Pro Thr Lys Ala
                165                 170                 175

Pro Arg Arg Trp Ala Phe His Gly Pro Ser Trp Cys Leu Pro Pro Ala
            180                 185                 190

Asp Arg Gly Pro Gly Ile Ala Phe Phe Pro Arg Phe Phe Tyr Asn Ala
        195                 200                 205

Ile Ile Gly Lys Cys Arg Pro Phe Lys Tyr Gly Gly Val Gln Gly Asn
210                 215                 220

Glu Asn Asn Phe Thr Ser Lys Lys Ala Cys Ile Thr Ala Cys Lys Lys
225                 230                 235                 240

Gly Phe Ile Arg Asn Leu Ser Gly Gly Ser Gly Ser Ser Gly Ser Gly
                245                 250                 255

Gly Ser Gly Ser Ser Gly Ala Ala Glu Glu Asp Glu Phe Thr Asn Ile
            260                 265                 270

Thr Asp Ile Lys Pro Pro Leu Gln Lys Pro Thr His Ser Phe Cys Ala
        275                 280                 285

Met Lys Val Asp Asp Gly Pro Gly Arg Ala Arg Phe Asp Arg Trp Phe
290                 295                 300

Phe Asn Ile Leu Thr His Gln Cys Glu Glu Phe Ile Tyr Gly Gly Val
305                 310                 315                 320

Glu Gly Asn Glu Asn Arg Phe Glu Ser Leu Glu Glu Cys Lys Glu Lys
                325                 330                 335

Cys Ala Arg Asp Tyr Pro Lys Met Thr Thr Lys Leu Thr Phe Gln Lys
            340                 345                 350

Gly Lys Pro Asp Phe Cys Phe Leu Glu Glu Asp Pro Gly Pro Gly Arg
        355                 360                 365
```

```
Ala Ala His Pro Arg Tyr Phe Tyr Asn Asn Gln Ser Lys Gln Cys Glu
        370                 375                 380

Arg Phe Lys Tyr Gly Gly Val Glu Gly Asn Leu Asn Asn Phe Glu Ser
385                 390                 395                 400

Leu Glu Glu Cys Lys Asn Thr Cys Glu Asn Pro Thr Ser Asp Phe Gln
                405                 410                 415

Val Asp Asp His Arg Thr Gln Leu Asn Thr Val Asn Asn Thr Leu Ile
            420                 425                 430

Asn Gln Pro Thr Lys Ala Pro Arg Arg Trp Ala Phe His Gly Pro Ser
        435                 440                 445

Trp Cys Leu Pro Pro Ala Asp Arg Gly Pro Gly Ile Ala Phe Phe Pro
    450                 455                 460

Arg Phe Phe Tyr Asn Ala Ile Ile Gly Lys Cys Arg Pro Phe Lys Tyr
465                 470                 475                 480

Gly Gly Val Gln Gly Asn Glu Asn Asn Phe Thr Ser Lys Lys Ala Cys
                485                 490                 495

Ile Thr Ala Cys Lys Lys Gly Phe Ile Arg Asn Leu Ser
            500                 505

<210> SEQ ID NO 128
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 129
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met His Ser Phe Cys Ala Phe Lys Ala Asp Asp Gly Pro Cys Arg Ala
1               5                   10                  15

Arg Phe Asp Arg Trp Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 130
<211> LENGTH: 860
<212> TYPE: DNA
<213> ORGANISM: Artificial Sequence
<220> FEATURE:
```

<223> OTHER INFORMATION: Description of Artificial Sequence: Synthetic
polynucleotide
<220> FEATURE:
<221> NAME/KEY: CDS
<222> LOCATION: (7)..(846)

<400> SEQUENCE: 130

```
gccacc atg gga tgg agc tgt atc atc ctc ttc ttg gtc gcg acg gcc        48
       Met Gly Trp Ser Cys Ile Ile Leu Phe Leu Val Ala Thr Ala
         1               5                  10 aca ggg gcc cac tcc gaa ggt cgt ccg ggt cac cac cat cat cat cat       96
Thr Gly Ala His Ser Glu Gly Arg Pro Gly His His His His His His
 15              20                  25                  30 ggc ggt tct agt ctg gtc ccg cgt ggc tct gag gaa gat gaa gaa cac      144
Gly Gly Ser Ser Leu Val Pro Arg Gly Ser Glu Glu Asp Glu Glu His
             35                  40                  45 aca att atc aca gat acg gag ttg cca cca ctg aaa ctt atg cat tca      192
Thr Ile Ile Thr Asp Thr Glu Leu Pro Pro Leu Lys Leu Met His Ser
         50                  55                  60 ttt tgt gca ttc aag gcg gat gat ggc cca tgt aaa gca atc atg aaa      240
Phe Cys Ala Phe Lys Ala Asp Asp Gly Pro Cys Lys Ala Ile Met Lys
 65                  70                  75 aga ttt ttc ttc aat att ttc act cga cag tgc gaa gaa ttt ata tat      288
Arg Phe Phe Phe Asn Ile Phe Thr Arg Gln Cys Glu Glu Phe Ile Tyr
         80                  85                  90 ggg gga tgt gaa gga aat cag aat cga ttt gaa agt ctg gaa gag tgc      336
Gly Gly Cys Glu Gly Asn Gln Asn Arg Phe Glu Ser Leu Glu Glu Cys
 95                 100                 105                 110 aaa aaa atg tgt aca aga gat aat gca aac agg att ata aag aca aca      384
Lys Lys Met Cys Thr Arg Asp Asn Ala Asn Arg Ile Ile Lys Thr Thr
                115                 120                 125 ttg caa caa gaa aag cca gat ttc tgc ttt ttg gaa gaa gat cct gga      432
Leu Gln Gln Glu Lys Pro Asp Phe Cys Phe Leu Glu Glu Asp Pro Gly
            130                 135                 140 ata tgt cga ggt tat att acc agg tat ttt tat aac aat cag aca aaa      480
Ile Cys Arg Gly Tyr Ile Thr Arg Tyr Phe Tyr Asn Asn Gln Thr Lys
145                 150                 155 cag tgt gaa cgt ttc aag tat ggt gga tgc ctg ggc aat atg aac aat      528
Gln Cys Glu Arg Phe Lys Tyr Gly Gly Cys Leu Gly Asn Met Asn Asn
            160                 165                 170 ttt gag aca ctg gaa gaa tgc aag aac att tgt gaa gat ggt ccg aat      576
Phe Glu Thr Leu Glu Glu Cys Lys Asn Ile Cys Glu Asp Gly Pro Asn
175                 180                 185                 190 ggt ttc cag gtg gat aat tat gga acc cag ctc aat gct gtg aat aac      624
Gly Phe Gln Val Asp Asn Tyr Gly Thr Gln Leu Asn Ala Val Asn Asn
                195                 200                 205 tcc ctg act ccg caa tca acc aag gtt ccc agc ctt ttt gaa ttt cac      672
Ser Leu Thr Pro Gln Ser Thr Lys Val Pro Ser Leu Phe Glu Phe His
            210                 215                 220 ggt ccc tca tgg tgt ctc act cca gca gac aga gga ttg tgt cgt gcc      720
Gly Pro Ser Trp Cys Leu Thr Pro Ala Asp Arg Gly Leu Cys Arg Ala
            225                 230                 235 aat gag aac aga ttc tac tac aat tca gtc att ggg aaa tgc cgc cca      768
Asn Glu Asn Arg Phe Tyr Tyr Asn Ser Val Ile Gly Lys Cys Arg Pro
240                 245                 250 ttt aag tac agt gga tgt ggg gga aat gaa aac aat ttt act tcc aaa      816
Phe Lys Tyr Ser Gly Cys Gly Gly Asn Glu Asn Asn Phe Thr Ser Lys
            255                 260                 265                 270 caa gaa tgt ctg agg gca tgt aaa aaa ggt taatgatcta gaag               860
Gln Glu Cys Leu Arg Ala Cys Lys Lys Gly
                275                 280
```

<210> SEQ ID NO 131
<211> LENGTH: 280
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Met Gly Trp Ser Cys Ile Ile Leu Phe Leu Val Ala Thr Ala Thr Gly
 1               5                  10                  15
Ala His Ser Glu Gly Arg Pro Gly His His His His His Gly Gly
                20                  25                  30
Ser Ser Leu Val Pro Arg Gly Ser Glu Glu Asp Glu Glu His Thr Ile
            35                  40                  45
Ile Thr Asp Thr Glu Leu Pro Pro Leu Lys Leu Met His Ser Phe Cys
        50                  55                  60
Ala Phe Lys Ala Asp Asp Gly Pro Cys Lys Ala Ile Met Lys Arg Phe
65                  70                  75                  80
Phe Phe Asn Ile Phe Thr Arg Gln Cys Glu Glu Phe Ile Tyr Gly Gly
                85                  90                  95
Cys Glu Gly Asn Gln Asn Arg Phe Glu Ser Leu Glu Glu Cys Lys Lys
            100                 105                 110
Met Cys Thr Arg Asp Asn Ala Asn Arg Ile Ile Lys Thr Thr Leu Gln
        115                 120                 125
Gln Glu Lys Pro Asp Phe Cys Phe Leu Glu Glu Asp Pro Gly Ile Cys
    130                 135                 140
Arg Gly Tyr Ile Thr Arg Tyr Phe Tyr Asn Asn Gln Thr Lys Gln Cys
145                 150                 155                 160
Glu Arg Phe Lys Tyr Gly Gly Cys Leu Gly Asn Met Asn Asn Phe Glu
                165                 170                 175
Thr Leu Glu Glu Cys Lys Asn Ile Cys Glu Asp Gly Pro Asn Gly Phe
            180                 185                 190
Gln Val Asp Asn Tyr Gly Thr Gln Leu Asn Ala Val Asn Asn Ser Leu
        195                 200                 205
Thr Pro Gln Ser Thr Lys Val Pro Ser Leu Phe Glu Phe His Gly Pro
    210                 215                 220
Ser Trp Cys Leu Thr Pro Ala Asp Arg Gly Leu Cys Arg Ala Asn Glu
225                 230                 235                 240
Asn Arg Phe Tyr Tyr Asn Ser Val Ile Gly Lys Cys Arg Pro Phe Lys
                245                 250                 255
Tyr Ser Gly Cys Gly Gly Asn Glu Asn Asn Phe Thr Ser Lys Gln Glu
            260                 265                 270
Cys Leu Arg Ala Cys Lys Lys Gly
        275                 280
```

<210> SEQ ID NO 132
<211> LENGTH: 870
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (7)..(846)

<400> SEQUENCE: 132

```
gccacc atg gga tgg agc tgt atc atc ctc ttc ttg gtc gcg acg gcc          48
       Met Gly Trp Ser Cys Ile Ile Leu Phe Leu Val Ala Thr Ala
        1               5                  10 aca ggg gcc cac tcc gaa ggt cgt ccg ggt cac cac cat cat cat              96
Thr Gly Ala His Ser Glu Gly Arg Pro Gly His His His His His
 15              20                  25                  30 ggc ggt tct agt ctg gtc ccg cgt ggt tct gag gaa gat gaa gaa cac         144
Gly Gly Ser Ser Leu Val Pro Arg Gly Ser Glu Glu Asp Glu Glu His
                 35                  40                  45 aca att atc aca gat acg gag ttg cca cca ctg aag ctt atg cat tca         192
Thr Ile Ile Thr Asp Thr Glu Leu Pro Pro Leu Lys Leu Met His Ser
             50                  55                  60 ttt tgt gca ttc aag gcg gat gat ggc cca tgt aga gca cgc ttc gat         240
Phe Cys Ala Phe Lys Ala Asp Asp Gly Pro Cys Arg Ala Arg Phe Asp
         65                  70                  75 aga tgg ttc ttc aat att ttc act cga cag tgc gaa gaa ttt ata tat         288
Arg Trp Phe Phe Asn Ile Phe Thr Arg Gln Cys Glu Glu Phe Ile Tyr
     80                  85                  90 ggg gga tgt gaa gga aat cag aat cga ttt gaa agt ctg gaa gag tgc         336
Gly Gly Cys Glu Gly Asn Gln Asn Arg Phe Glu Ser Leu Glu Glu Cys
 95                 100                 105                 110 aaa aaa atg tgt aca aga gat aat gca aac agg att ata aag aca aca         384
Lys Lys Met Cys Thr Arg Asp Asn Ala Asn Arg Ile Ile Lys Thr Thr
                115                 120                 125 ttg caa caa gaa aag cca gat ttc tgc ttt ctc gag gag gat cct gga         432
Leu Gln Gln Glu Lys Pro Asp Phe Cys Phe Leu Glu Glu Asp Pro Gly
            130                 135                 140 ccg tgt cga gct gct cat ccc agg tgg ttt tat aac aat cag aca aaa         480
Pro Cys Arg Ala Ala His Pro Arg Trp Phe Tyr Asn Asn Gln Thr Lys
        145                 150                 155 cag tgt gaa cgt ttc atc tat ggt gga tgc gag ggc aat atg aac aat         528
Gln Cys Glu Arg Phe Ile Tyr Gly Gly Cys Glu Gly Asn Met Asn Asn
    160                 165                 170 ttt gag aca ctg gaa gaa tgc aag aac att tgt gaa gat ggt ccg aat         576
Phe Glu Thr Leu Glu Glu Cys Lys Asn Ile Cys Glu Asp Gly Pro Asn
175                 180                 185                 190 ggt ttc cag gtc gac aat tat gga acc cag ctc aat gct gtg aat aac         624
Gly Phe Gln Val Asp Asn Tyr Gly Thr Gln Leu Asn Ala Val Asn Asn
                195                 200                 205 tcc ctg act ccg caa tca acc aag gtt ccc agc ctt ttt gaa ttt cac         672
Ser Leu Thr Pro Gln Ser Thr Lys Val Pro Ser Leu Phe Glu Phe His
            210                 215                 220 ggt ccc tca tgg tgt ctc act ccc gcg gac aga gga ccg tgt att gcc         720
Gly Pro Ser Trp Cys Leu Thr Pro Ala Asp Arg Gly Pro Cys Ile Ala
        225                 230                 235 ttt ttc ccc aga ttc tac tac aat tca gtc att ggg aaa tgc cgc cca         768
Phe Phe Pro Arg Phe Tyr Tyr Asn Ser Val Ile Gly Lys Cys Arg Pro
    240                 245                 250 ttt ccg tat ggc gga tgt cag gga aat gaa aac aat ttt act tcc aaa         816
Phe Pro Tyr Gly Gly Cys Gln Gly Asn Glu Asn Asn Phe Thr Ser Lys
255                 260                 265                 270 caa gaa tgt ctg agg gca tgt aaa aaa ggt taatgatcta gaagctcgct          866
Gln Glu Cys Leu Arg Ala Cys Lys Lys Gly
                275                 280 gatc                                                                    870

<210> SEQ ID NO 133
<211> LENGTH: 280
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 133

```
Met Gly Trp Ser Cys Ile Ile Leu Phe Leu Val Ala Thr Ala Thr Gly
  1               5                  10                  15

Ala His Ser Glu Gly Arg Pro Gly His His His His His His Gly Gly
             20                  25                  30

Ser Ser Leu Val Pro Arg Gly Ser Glu Glu Asp Glu Glu His Thr Ile
         35                  40                  45

Ile Thr Asp Thr Glu Leu Pro Pro Leu Lys Leu Met His Ser Phe Cys
 50                  55                  60

Ala Phe Lys Ala Asp Asp Gly Pro Cys Arg Ala Arg Phe Asp Arg Trp
65                  70                  75                  80

Phe Phe Asn Ile Phe Thr Arg Gln Cys Glu Glu Phe Ile Tyr Gly Gly
                 85                  90                  95

Cys Glu Gly Asn Gln Asn Arg Phe Glu Ser Leu Glu Glu Cys Lys Lys
            100                 105                 110

Met Cys Thr Arg Asp Asn Ala Asn Arg Ile Ile Lys Thr Thr Leu Gln
            115                 120                 125

Gln Glu Lys Pro Asp Phe Cys Phe Leu Glu Glu Asp Pro Gly Pro Cys
        130                 135                 140

Arg Ala Ala His Pro Arg Trp Phe Tyr Asn Asn Gln Thr Lys Gln Cys
145                 150                 155                 160

Glu Arg Phe Ile Tyr Gly Gly Cys Glu Gly Asn Met Asn Asn Phe Glu
                165                 170                 175

Thr Leu Glu Glu Cys Lys Asn Ile Cys Glu Asp Gly Pro Asn Gly Phe
            180                 185                 190

Gln Val Asp Asn Tyr Gly Thr Gln Leu Asn Ala Val Asn Asn Ser Leu
        195                 200                 205

Thr Pro Gln Ser Thr Lys Val Pro Ser Leu Phe Glu Phe His Gly Pro
    210                 215                 220

Ser Trp Cys Leu Thr Pro Ala Asp Arg Gly Pro Cys Ile Ala Phe Phe
225                 230                 235                 240

Pro Arg Phe Tyr Tyr Asn Ser Val Ile Gly Lys Cys Arg Pro Phe Pro
                245                 250                 255

Tyr Gly Gly Cys Gln Gly Asn Glu Asn Asn Phe Thr Ser Lys Gln Glu
            260                 265                 270

Cys Leu Arg Ala Cys Lys Lys Gly
            275                 280
```

<210> SEQ ID NO 134
<211> LENGTH: 822
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (8)..(808)

<400> SEQUENCE: 134

```
ggccacc atg gga tgg tcc tgc atc atc ctg ttt ctg gtg gcc acc gcc      49
        Met Gly Trp Ser Cys Ile Ile Leu Phe Leu Val Ala Thr Ala
          1               5                  10
```

| | | |
|---|---|---|
| aca ggc gcc cac agc gac agc gag gaa gat gag gaa cac acc atc atc<br>Thr Gly Ala His Ser Asp Ser Glu Glu Asp Glu Glu His Thr Ile Ile<br>15                    20                    25                    30 | | 97 |
| acc gac acc gag ctg ccc ccc ctg aag ctt atg cac agc ttc tgc gcc<br>Thr Asp Thr Glu Leu Pro Pro Leu Lys Leu Met His Ser Phe Cys Ala<br>                    35                    40                    45 | | 145 |
| ttc aag gcc gac gac ggc ccc tgc agg gcc aga ttc gac aga tgg ttc<br>Phe Lys Ala Asp Asp Gly Pro Cys Arg Ala Arg Phe Asp Arg Trp Phe<br>            50                    55                    60 | | 193 |
| ttc aac atc ttc acc agg cag tgc gag gaa ttc att tat gga ggc tgt<br>Phe Asn Ile Phe Thr Arg Gln Cys Glu Glu Phe Ile Tyr Gly Gly Cys<br>65                    70                    75 | | 241 |
| gaa ggc aat cag aac cgg ttc gaa tct ctg gaa gaa tgc aag aag atg<br>Glu Gly Asn Gln Asn Arg Phe Glu Ser Leu Glu Glu Cys Lys Lys Met<br>        80                    85                    90 | | 289 |
| tgc acc agg gac aac gcc aac agg atc atc aag acc acc ctg cag cag<br>Cys Thr Arg Asp Asn Ala Asn Arg Ile Ile Lys Thr Thr Leu Gln Gln<br>95                  100                105              110 | | 337 |
| gag aag ccc gac ttc tgc ttc ctg gaa gag gat cct ggc ccc tgc aga<br>Glu Lys Pro Asp Phe Cys Phe Leu Glu Glu Asp Pro Gly Pro Cys Arg<br>                115                120              125 | | 385 |
| gcc cgg ttt gac cgg tgg ttt tac aat aac cag acc aag cag tgt gag<br>Ala Arg Phe Asp Arg Trp Phe Tyr Asn Asn Gln Thr Lys Gln Cys Glu<br>            130                135              140 | | 433 |
| cgc ttt atc tat ggg gga tgt gaa gga aat atg aat aac ttc gag aca<br>Arg Phe Ile Tyr Gly Gly Cys Glu Gly Asn Met Asn Asn Phe Glu Thr<br>            145                150              155 | | 481 |
| ctg gaa gag tgt aag aac atc tgc gag gac ggc ccc aac ggc ttc cag<br>Leu Glu Glu Cys Lys Asn Ile Cys Glu Asp Gly Pro Asn Gly Phe Gln<br>160                    165                170 | | 529 |
| gtg gac aac tac ggc acc caa ttg aac gcc gtg aac aac agc ctg acc<br>Val Asp Asn Tyr Gly Thr Gln Leu Asn Ala Val Asn Asn Ser Leu Thr<br>175                    180                185              190 | | 577 |
| ccc cag agc acc aag gtg ccc agc ctg ttc gag ttc cac ggc ccc agc<br>Pro Gln Ser Thr Lys Val Pro Ser Leu Phe Glu Phe His Gly Pro Ser<br>              195                200              205 | | 625 |
| tgg tgc ctg acc cca gcc gac agg ggc cca tgc cgc gcc aga ttt gac<br>Trp Cys Leu Thr Pro Ala Asp Arg Gly Pro Cys Arg Ala Arg Phe Asp<br>            210                215              220 | | 673 |
| agg tgg tac tac aac tcc gtg atc ggc aag tgc agg ccc ttc atc tac<br>Arg Trp Tyr Tyr Asn Ser Val Ile Gly Lys Cys Arg Pro Phe Ile Tyr<br>            225                230              235 | | 721 |
| ggc gga tgt gag gga aac gag aac aac ttt act agt aag cag gaa tgc<br>Gly Gly Cys Glu Gly Asn Glu Asn Asn Phe Thr Ser Lys Gln Glu Cys<br>240                    245                250 | | 769 |
| ctg agg gcc tgc aag aag ggc ttc atc cag agg atc agc tgatgaatct<br>Leu Arg Ala Cys Lys Lys Gly Phe Ile Gln Arg Ile Ser<br>255                    260                265 | | 818 |
| agaa | | 822 |

<210> SEQ ID NO 135
<211> LENGTH: 267
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 135

Met Gly Trp Ser Cys Ile Ile Leu Phe Leu Val Ala Thr Ala Thr Gly
1                   5                    10                    15

Ala His Ser Asp Ser Glu Glu Asp Glu Glu His Thr Ile Ile Thr Asp
            20                  25                  30

Thr Glu Leu Pro Pro Leu Lys Leu Met His Ser Phe Cys Ala Phe Lys
        35                  40                  45

Ala Asp Asp Gly Pro Cys Arg Ala Arg Phe Asp Arg Trp Phe Phe Asn
 50                  55                  60

Ile Phe Thr Arg Gln Cys Glu Glu Phe Ile Tyr Gly Gly Cys Glu Gly
 65                  70                  75                  80

Asn Gln Asn Arg Phe Glu Ser Leu Glu Glu Cys Lys Lys Met Cys Thr
                85                  90                  95

Arg Asp Asn Ala Asn Arg Ile Ile Lys Thr Thr Leu Gln Gln Glu Lys
            100                 105                 110

Pro Asp Phe Cys Phe Leu Glu Glu Asp Pro Gly Pro Cys Arg Ala Arg
        115                 120                 125

Phe Asp Arg Trp Phe Tyr Asn Asn Gln Thr Lys Gln Cys Glu Arg Phe
130                 135                 140

Ile Tyr Gly Gly Cys Glu Gly Asn Met Asn Asn Phe Glu Thr Leu Glu
145                 150                 155                 160

Glu Cys Lys Asn Ile Cys Glu Asp Gly Pro Asn Gly Phe Gln Val Asp
                165                 170                 175

Asn Tyr Gly Thr Gln Leu Asn Ala Val Asn Asn Ser Leu Thr Pro Gln
            180                 185                 190

Ser Thr Lys Val Pro Ser Leu Phe Glu Phe His Gly Pro Ser Trp Cys
        195                 200                 205

Leu Thr Pro Ala Asp Arg Gly Pro Cys Arg Ala Arg Phe Asp Arg Trp
210                 215                 220

Tyr Tyr Asn Ser Val Ile Gly Lys Cys Arg Pro Phe Ile Tyr Gly Gly
225                 230                 235                 240

Cys Glu Gly Asn Glu Asn Asn Phe Thr Ser Lys Gln Glu Cys Leu Arg
                245                 250                 255

Ala Cys Lys Lys Gly Phe Ile Gln Arg Ile Ser
            260                 265

<210> SEQ ID NO 136
<211> LENGTH: 5660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
gtaccgaatt cacattgatt attgagtagt tattaatagt aatcaattac ggggtcatta      60
gttcatagcc catatatgga gttccgcgtt acataactta cggtaaatgg cccgcctggc     120
tgaccgccca acgaccccg cccattgacg tcaataatga cgtatgttcc catagtaacg      180
ccaataggga ctttccattg acgtcaatgg gtggactatt tacggtaaac tgcccacttg     240
gcagtacatc aagtgtatca tatgccaagt acgccccta ttgacgtcaa tgacggtaaa      300
tggcccgcct ggcattatgc ccagtacatg accttatggg actttcctac ttggcagtac     360
atctacgtgt tagtcatcgc tattaccata gtgatgcggt tttggcagta catcaatggg     420
cgtggatagc ggtttgactc acggggattt ccaagtctcc accccattga cgtcaatggg     480
agtttgtttt ggcaccaaaa tcaacgggac tttccaaaat gtcgtaacaa ctccgcccca     540
ttgacgcaaa tgggcggtag gcgtgtacgg tgggaggtct atataagcag agctttctgg     600

```
ctaactagag aacccactgc ttactggcac gtggaaatta atacgacgtg gccaccatgg    660
gatggagctg tatcatcctc ttcttggtcg cgacggccac aggggcccac tccgaaggtc    720
gtccgggtca ccaccatcat catcatggcg gttctagtct ggtcccgcgt ggctctgagg    780
aagatgaaga acacacaatt atcacagata cggagttgcc accactgaaa cttatgcatt    840
cattttgtgc attcaaggcg gatgatggcc catgtaaagc aatcatgaaa agattttct    900 tcaatatttt cactcgacag tgcgaagaat ttatatatgg gggatgtgaa ggaaatcaga    960
atcgatttga aagtctggaa gagtgcaaaa aaatgtgtac aagagataat gcaaacagga   1020
ttataaagac aacattgcaa caagaaaagc cagatttctg cttttttggaa gaagatcctg   1080 gaatatgtcg aggttatatt accaggtatt tttataacaa tcagacaaaa cagtgtgaac   1140
gtttcaagta tggtggatgc ctgggcaata tgaacaattt tgagacactg gaagaatgca   1200
agaacatttg tgaagatggt ccgaatggtt tccaggtgga taattatgga acccagctca   1260
atgctgtgaa taactccctg actccgcaat caaccaaggt tcccagcctt tttgaatttc   1320
acggtccctc atggtgtctc actccagcag acagaggatt gtgtcgtgcc aatgagaaca   1380
gattctacta caattcagtc attgggaaat gccgcccatt taagtacagt ggatgtgggg   1440
gaaatgaaaa caattttact tccaaacaag aatgtctgag ggcatgtaaa aaaggttaat   1500
gatctagaag ctcgctgatc agcctcgact gtgccttcta gttgccagcc atctgttgtt   1560
tgcccctccc ccgtgccttc cttgaccctg aaggtgcca ctcccactgt cctttcctaa    1620
taaaatgagg aaattgcatc gcattgtctg agtaggtgtc attctattct ggggggtggg   1680
gtggggcagg acagcaaggg ggaggattgg gaagacaata gcaggcatgc tggggatggc   1740
ccgggctcta tggcttctga ggcggaaaga accagctggg gctctagggg gtatccccac   1800
gcgccctgta gcggcgcatt aagcgcggcg ggtgtggtgg ttacgcgcag cgtgaccgct   1860
acacttgcca gcgccctagc gcccgctcct ttcgctttct tcccttcctt tctcgccacg   1920
ttcgccggct ttccccgtca agctctaaat cggggcatcc ctttagggtt ccgatttagt   1980
gctttacggc acctcgaccc caaaaaactt gattagggtg atggttcacg tagtgggcca   2040
tcgccctgat agacggtttt tcgccctttg acgttggagt ccacgttctt taatagtgga   2100
ctcttgttcc aaactggaac aacactcaac cctatctcgg tctattcttt tgatttataa   2160
gggattttgg ggatttcggc ctattggtta aaaaatgagc tgatttaaca aaaatttaac   2220
gcgaattaat tctgtggaat gtgtgtcagt tagggtgtgg aaagtcccca ggctccccag   2280
gcaggcagaa gtatgcaaag catgcatctc aattagtcag caaccaggtg tggaaagtcc   2340
ccaggctccc cagcaggcag aagtatgcaa agcatgcatc tcaattagtc agcaaccata   2400
gtcccgcccc taactccgcc catccccgcc ctaactccgc ccagttccgc ccattctccg   2460
cccctaggct gactaatttt ttttatttat gcagaggccg aggccgcctc tgcctctgag   2520
ctattccaga agtagtgagg aggcttttt ggaggcctag gcttttgcaa aaagctcccg    2580
ggaggtccac aatgattgaa caagatggat tgcacgcagg ttctccggcc gcttgggtgg   2640
agaggctatt cggctatgac tgggcacaac agacaatcgg ctgctctgat gccgccgtgt   2700
tccggctgtc agcgcagggg cgcccggttc ttttttgtcaa gaccgacctg tccggtgccc   2760
tgaatgaact ccaggacgag gcagcgcggc tatcgtggct ggccacgacg ggcgttcctt   2820
gcgcagctgt gctcgacgtt gtcactgaag cggaagggga ctggctgcta ttgggcgaag   2880
tgccggggca ggatctcctg tcatctcacc ttgctcctgc cgagaaagta tccatcatgg   2940
```

-continued

```
ctgatgcaat gcggcggctg catacgcttg atccggctac ctgcccattc gaccaccaag    3000
cgaaacatcg catcgagcga gcacgtactc ggatggaagc cggtcttgtc gatcaggatg    3060
atctggacga agagcatcag gggctcgcgc cagccgaact gttcgccagg ctcaaggcgc    3120
gtatgcccga cggcgaggat ctcgtcgtga ctcatggcga tgcctgcttg ccgaatatca    3180
tggtggaaaa tggccgcttt tctggattca tcgactgtgg ccggctgggt gtggcggacc    3240
gctatcagga catagcgttg ctacccgtg atattgctga agagcttggc ggcgaatggg     3300
ctgaccgctt cctcgtgctt tacggtatcg ccgctcccga ttcgcagcgc atcgccttct    3360
atcgccttct tgacgagttc ttctgagcgg gactctgggg ttcgaaatga ccgaccaagc    3420
gacgcccaac ctgccatcac gagatttcga ttccaccgcc gccttctatg aaaggttggg    3480
cttcggaatc gttttccggg acgccggctg atgatcctc cagcgcgggg atctcatgct     3540
ggagttcttc gcccacccca acttgtttat tgcagcttat aatggttaca aataaagcaa    3600
tagcatcaca aatttcacaa ataaagcatt ttttcactg cattctagtt gtggtttgtc     3660
caaactcatc aatgtatctt atcatgtctg tataccggat cttccgcttc ctcgctcac    3720
tgactcgctg cgctcggtcg ttcggctgcg gcgagcggta tcagctcact caaaggcggt    3780
aatacggtta tccacagaat caggggataa cgcaggaaag aacatgtgag caaaaggcca    3840
gcaaaaggcc aggaaccgta aaaaggccgc gttgctggcg ttttccata ggctccgccc     3900
ccctgacgag catcacaaaa atcgacgctc aagtcagagg tggcgaaacc cgacaggact    3960
ataaagatac caggcgtttc ccctggaag ctccctcgtg cgctctcctg ttccgaccct     4020
gccgcttacc ggatacctgt ccgcctttct cccttcggga agcgtggcgc tttctcaatg    4080
ctcacgctgt aggtatctca gttcggtgta ggtcgttcgc tccaagctgg gctgtgtcca    4140
cgaaccccc gttcagcccg accgctgcgc cttatccggt aactatcgtc ttgagtccaa     4200
cccggtaaga cacgacttat cgccactggc agcagccact ggtaacagga ttagcagagc    4260
gaggtatgta ggcggtgcta cagagttctt gaagtggtgg cctaactacg gctacactag    4320
aaggacagta tttggtatct gcgctctgct gaagccagtt accttcggaa aaagagttgg    4380
tagctcttga tccggcaaac aaaccaccgc tggtagcggt ggtttttttg tttgcaagca    4440
gcagattacg cgcagaaaaa aaggatctca agaagatcct ttgatctttt ctacggggtc    4500
tgacgctcag tggaacgaaa actcacgtta agggattttg gtcatgagat tatcaaaaag    4560
gatcttcacc tagatccttt taaattaaaa atgaagtttt aaatcaatct aaagtatata    4620
tgagtaaact tggtctgaca gttaccaatg cttaatcagt gaggcaccta tctcagcgat    4680
ctgtctattt cgttcatcca tagttgcctg actccccgtc gtgtagataa ctacgatacg    4740
ggagggctta ccatctggcc ccagtgctgc aatgataccg cgagacccac gctcaccggc    4800
tccagattta tcagcaataa accagccagc cggaagggcc gagcgcagaa gtggtcctgc    4860
aactttatcc gcctccatcc agtctattaa ttgttgccgg gaagctagag taagtagttc    4920
gccagttaat agtttgcgca acgttgttgc cattgctaca ggcatcgtgg tgtcacgctc    4980
gtcgtttggt atggcttcat tcagctccgg ttcccaacga tcaaggcgag ttacatgatc    5040
ccccatgttg tgcaaaaaag cggttagctc cttcggtcct ccgatcgttg tcagaagtaa    5100
gttggccgca gtgttatcac tcatggttat ggcagcactg cataattctc ttactgtcat    5160
gccatccgta agatgctttt ctgtgactgg tgagtactca accaagtcat tctgagaata    5220
gtgtatgcgg cgaccgagtt gctcttgccc ggcgtcaata cggataata ccgcgccaca     5280
tagcagaact ttaaaagtgc tcatcattgg aaaacgttct tcggggcgaa aactctcaag    5340
```

```
gatcttaccg ctgttgagat ccagttcgat gtaacccact cgtgctccca actgatcttc    5400
agcatctttt actttcacca gcgtttctgg gtgagcaaaa acaggaaggc aaaatgccgc    5460
aaaaaaggga ataagggcga cacggaaatg ttgaatactc atactcttcc tttttcaata    5520
ttattgaagc atttatcagg gttattgtct catgagcgga tacatatttg aatgtattta    5580
gaaaaataaa caaatagggg ttccgcgcac atttccccga aaagtgccac ctgacgtcag    5640
atcgacggat cgggagatcg                                                5660

<210> SEQ ID NO 137
<211> LENGTH: 5660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gtaccgaatt cacattgatt attgagtagt tattaatagt aatcaattac ggggtcatta      60
gttcatagcc catatatgga gttccgcgtt acataactta cggtaaatgg cccgcctggc     120
tgaccgccca acgaccccg cccattgacg tcaataatga cgtatgttcc catagtaacg     180
ccaataggga ctttccattg acgtcaatgg gtggactatt tacggtaaac tgcccacttg     240
gcagtacatc aagtgtatca tatgccaagt acgccccta ttgacgtcaa tgacggtaaa     300
tggcccgcct ggcattatgc ccagtacatg accttatggg actttcctac ttggcagtac     360
atctacgtgt tagtcatcgc tattaccata gtgatgcggt tttggcagta catcaatggg     420
cgtggatagc ggtttgactc acggggattt ccaagtctcc accccattga cgtcaatggg     480
agtttgtttt ggcaccaaaa tcaacgggac tttccaaaat gtcgtaacaa ctccgcccca     540
ttgacgcaaa tgggcggtag gcgtgtacgg tgggaggtct atataagcag agctttctgg     600
ctaactagag aacccactgc ttactggcac gtggaaatta atacgacgtg gccaccatgg     660
gatggagctg tatcatcctc ttcttggtcg cgacggccac aggggcccac tccgaaggtc     720
gtccgggtca ccaccatcat catcatggcg gttctagtct ggtcccgcgt ggttctgagg     780
aagatgaaga acacacaatt atcacagata cggagttgcc accactgaag cttatgcatt     840
cattttgtgc attcaaggcg gatgatggcc catgtagagc acgcttcgat agatggttct     900
tcaatatttt cactcgacag tgcgaagaat ttatatatgg gggatgtgaa ggaaatcaga     960
atcgatttga aagtctggaa gagtgcaaaa aaatgtgtac aagagataat gcaaacagga    1020
ttataaagac aacattgcaa caagaaaagc cagatttctg ctttctcgag gaggatcctg    1080
gaccgtgtcg agctgctcat cccaggtggt tttataacaa tcagacaaaa cagtgtgaac    1140
gtttcatcta tggtggatgc gagggcaata tgaacaattt tgagacactg aagaatgca    1200 agaacatttg tgaagatggt ccgaatggtt tccaggtcga caattatgga acccagctca    1260
atgctgtgaa taactccctg actccgcaat caaccaaggt tcccagcctt tttgaatttc    1320
acggtccctc atggtgtctc actcccgcgg acagaggacc gtgtattgcc tttttcccca    1380
gattctacta caattcagtc attgggaaat gccgcccatt tccgtatggc ggatgtcagg    1440
gaaatgaaaa caatttact tccaaacaag aatgtctgag ggcatgtaaa aaaggttaat    1500
gatctagaag ctcgctgatc agcctcgact gtgccttcta gttgccagcc atctgttgtt    1560
tgcccctccc ccgtgccttc cttgaccctg gaaggtgcca ctcccactgt cctttcctaa    1620
taaaatgagg aaattgcatc gcattgtctg agtaggtgtc attctattct gggggtgggg    1680
```

```
gtggggcagg acagcaaggg ggaggattgg gaagacaata gcaggcatgc tggggatggc    1740
ccgggctcta tggcttctga ggcggaaaga accagctggg gctctagggg gtatccccac    1800
gcgccctgta gcggcgcatt aagcgcggcg ggtgtggtgg ttacgcgcag cgtgaccgct    1860
acacttgcca gcgccctagc gcccgctcct ttcgctttct tcccttcctt tctcgccacg    1920
ttcgccggct ttccccgtca agctctaaat cggggcatcc ctttagggtt ccgatttagt    1980
gctttacggc acctcgaccc caaaaaactt gattagggtg atggttcacg tagtgggcca    2040
tcgccctgat agacggtttt tcgccctttg acgttggagt ccacgttctt taatagtgga    2100
ctcttgttcc aaactggaac aacactcaac cctatctcgg tctattcttt tgatttataa    2160
gggattttgg ggatttcggc ctattggtta aaaaatgagc tgatttaaca aaaatttaac    2220
gcgaattaat tctgtggaat gtgtgtcagt tagggtgtgg aaagtccccca ggctccccag    2280 gcaggcagaa gtatgcaaag catgcatctc aattagtcag caaccaggtg tggaaagtcc    2340
ccaggctccc cagcaggcag aagtatgcaa agcatgcatc tcaattagtc agcaaccata    2400
gtcccgcccc taactccgcc catcccgccc ctaactccgc ccagttccgc ccattctccg    2460
cccctaggct gactaatttt ttttatttat gcagaggccg aggccgcctc tgcctctgag    2520
ctattccaga agtagtgagg aggcttttt ggaggcctag gcttttgcaa aaagctcccg    2580
ggaggtccac aatgattgaa caagatggat tgcacgcagg ttctccggcc gcttgggtgg    2640
agaggctatt cggctatgac tgggcacaac agacaatcgg ctgctctgat gccgccgtgt    2700
tccggctgtc agcgcagggg cgcccggttc tttttgtcaa gaccgacctg tccggtgccc    2760
tgaatgaact ccaggacgag gcagcgcggc tatcgtggct ggccacgacg ggcgttcctt    2820
gcgcagctgt gctcgacgtt gtcactgaag cgggaaggga ctggctgcta ttgggcgaag    2880
tgccggggca ggatctcctg tcatctcacc ttgctcctgc cgagaaagta tccatcatgg    2940
ctgatgcaat gcggcggctg catacgcttg atccggctac ctgcccattc gaccaccaag    3000
cgaaacatcg catcgagcga gcacgtactc ggatggaagc cggtcttgtc gatcaggatg    3060
atctggacga agagcatcag gggctcgcgc cagccgaact gttcgccagg ctcaaggcgc    3120
gtatgcccga cggcgaggat ctcgtcgtga ctcatggcga tgcctgcttg ccgaatatca    3180
tggtggaaaa tggccgcttt tctggattca tcgactgtgg ccggctgggt gtggcggacc    3240
gctatcagga catagcgttg gctacccgtg atattgctga agagcttggc ggcgaatggg    3300
ctgaccgctt cctcgtgctt tacggtatcg ccgctcccga ttcgcagcgc atcgccttct    3360
atcgccttct tgacgagttc ttctgagcgg gactctgggg ttcgaaatga ccgaccaagc    3420
gacgcccaac ctgccatcac gagatttcga ttccaccgcc gccttctatg aaaggttggg    3480
cttcggaatc gttttccggg acgccggctg atgatcctc cagcgcgggg atctcatgct    3540
ggagttcttc gcccacccca acttgtttat tgcagcttat aatggttaca aataaagcaa    3600
tagcatcaca aatttcacaa ataaagcatt ttttcactg cattctagtt gtggtttgtc    3660
caaactcatc aatgtatctt atcatgtctg tataccggat cttccgcttc ctcgctcac    3720 tgactcgctg cgctcggtcg ttcggctgcg gcgagcggta tcagctcact caaaggcggt    3780
aatacggtta tccacagaat caggggataa cgcaggaaaa acatgtgag caaaaggcca    3840 gcaaaaggcc aggaaccgta aaaaggccgc gttgctggcg ttttccata ggctccgccc    3900 ccctgacgag catcacaaaa atcgacgctc aagtcagagg tggcgaaacc cgacaggact    3960
ataaagatac caggcgtttc cccctggaag ctccctcgtg cgctctcctg ttccgaccct    4020
```

```
gccgcttacc ggatacctgt ccgcctttct cccttcggga agcgtggcgc tttctcaatg    4080
ctcacgctgt aggtatctca gttcggtgta ggtcgttcgc tccaagctgg gctgtgtcca    4140 cgaaccccc  gttcagcccg accgctgcgc cttatccggt aactatcgtc ttgagtccaa    4200
cccggtaaga cacgacttat cgccactggc agcagccact ggtaacagga ttagcagagc    4260
gaggtatgta ggcggtgcta cagagttctt gaagtggtgg cctaactacg gctacactag    4320
aaggacagta tttggtatct gcgctctgct gaagccagtt accttcggaa aaagagttgg    4380
tagctcttga tccggcaaac aaaccaccgc tggtagcggt ggtttttttg tttgcaagca    4440
gcagattacg cgcagaaaaa aaggatctca agaagatcct ttgatctttt ctacggggtc    4500
tgacgctcag tggaacgaaa actcacgtta agggattttg gtcatgagat tatcaaaaag    4560
gatcttcacc tagatccttt taaattaaaa atgaagtttt aaatcaatct aaagtatata    4620
tgagtaaact tggtctgaca gttaccaatg cttaatcagt gaggcaccta tctcagcgat    4680
ctgtctattt cgttcatcca tagttgcctg actccccgtc gtgtagataa ctacgatacg    4740
ggagggctta ccatctggcc ccagtgctgc aatgataccg cgagacccac gctcaccggc    4800
tccagattta tcagcaataa accagccagc cggaagggcc gagcgcagaa gtggtcctgc    4860
aactttatcc gcctccatcc agtctattaa ttgttgccgg gaagctagag taagtagttc    4920
gccagttaat agtttgcgca acgttgttgc cattgctaca ggcatcgtgg tgtcacgctc    4980
gtcgtttggt atggcttcat tcagctccgg ttcccaacga tcaaggcgag ttacatgatc    5040
ccccatgttg tgcaaaaaag cggttagctc cttcggtcct ccgatcgttg tcagaagtaa    5100
gttggccgca gtgttatcac tcatggttat ggcagcactg cataattctc ttactgtcat    5160
gccatccgta agatgctttt ctgtgactgg tgagtactca accaagtcat tctgagaata    5220
gtgtatgcgg cgaccgagtt gctcttgccc ggcgtcaata cgggataata ccgcgccaca    5280
tagcagaact ttaaaagtgc tcatcattgg aaaacgttct cggggcgaaa actctcaag    5340 gatcttaccg ctgttgagat ccagttcgat gtaacccact cgtgctccca actgatcttc    5400
agcatctttt actttcacca gcgtttctgg gtgagcaaaa acaggaaggc aaaatgccgc    5460
aaaaaaggga ataagggcga cacggaaatg ttgaatactc atactcttcc ttttcaata    5520 ttattgaagc atttatcagg gttattgtct catgagcgga tacatatttg aatgtattta    5580
gaaaaataaa caaatagggg ttccgcgcac atttccccga aaagtgccac ctgacgtcag    5640
atcgacggat cgggagatcg                                                5660

<210> SEQ ID NO 138
<211> LENGTH: 5622
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gtaccgaatt cacattgatt attgagtagt tattaatagt aatcaattac ggggtcatta      60
gttcatagcc catatatgga gttccgcgtt acataactta cggtaaatgg cccgcctggc     120
tgaccgccca acgacccccg cccattgacg tcaataatga cgtatgttcc catagtaacg     180 ccaatagggga ctttccattg acgtcaatgg gtggactatt tacggtaaac tgcccacttg    240
gcagtacatc aagtgtatca tatgccaagt acgccccta ttgacgtcaa tgacggtaaa     300
tggcccgcct ggcattatgc ccagtacatg accttatggg actttcctac ttggcagtac    360
```

-continued

| | |
|---|---|
| atctacgtgt tagtcatcgc tattaccata gtgatgcggt tttggcagta catcaatggg | 420 |
| cgtggatagc ggtttgactc acggggattt ccaagtctcc accccattga cgtcaatggg | 480 |
| agtttgtttt ggcaccaaaa tcaacgggac tttccaaaat gtcgtaacaa ctccgcccca | 540 |
| ttgacgcaaa tgggcggtag gcgtgtacgg tgggaggtct atataagcag agctttctgg | 600 |
| ctaactagag aacccactgc ttactggcac gtggaaatta atacgacgtg gccaccatgg | 660 |
| gatggtcctg catcatcctg tttctggtgg ccaccgccac aggcgcccac agcgacagcg | 720 |
| aggaagatga ggaacacacc atcatcaccg acaccgagct gccccccctg aagcttatgc | 780 |
| acagcttctg cgccttcaag gccgacacg ggccctgcag ggccagattc gacagatggt | 840 |
| tcttcaacat cttcaccagg cagtgcgagg aattcattta tggaggctgt gaaggcaatc | 900 |
| agaaccggtt cgaatctctg gaagaatgca agaagatgtg caccagggac aacgccaaca | 960 |
| ggatcatcaa gaccaccctg cagcaggaga agcccgactt ctgcttcctg gaagaggatc | 1020 |
| ctggcccctg cagagcccgg tttgaccggt ggttttacaa taaccagacc aagcagtgtg | 1080 |
| agcgctttat ctatggggga tgtgaaggaa atatgaataa cttcgagaca ctggaagagt | 1140 |
| gtaagaacat ctgcgaggac ggccccaacg gcttccaggt ggacaactac ggcacccaat | 1200 |
| tgaacgccgt gaacaacagc ctgacccccc agagcaccaa ggtgcccagc ctgttcgagt | 1260 |
| tccacggccc cagctggtgc ctgacccag ccgacagggg cccatgccgc gccagatttg | 1320 |
| acaggtggta ctacaactcc gtgatcggca agtgcaggcc cttcatctac ggcggatgtg | 1380 |
| agggaaacga gaacaacttt actagtaagc aggaatgcct gagggcctgc aagaagggct | 1440 |
| tcatccagag gatcagctga tgaatctaga agctcgctga tcagcctcga ctgtgccttc | 1500 |
| tagttgccag ccatctgttg tttgcccctc ccccgtgcct tccttgaccc tggaaggtgc | 1560 |
| cactcccact gtccttctcc aataaaatga ggaaattgca tcgcattgtc tgagtaggtg | 1620 |
| tcattctatt ctggggggtg gggtggggca ggacagcaag ggggaggatt gggaagacaa | 1680 |
| tagcaggcat gctgggatg gcccgggctc tatggcttct gaggcggaaa gaaccagctg | 1740 |
| gggctctagg gggtatcccc acgcgccctg tagcggcgca ttaagcgcgg cgggtgtggt | 1800 |
| ggttacgcgc agcgtgaccg ctacacttgc cagcgcccta gcgcccgctc ctttcgcttt | 1860 |
| cttcccttcc tttctcgcca cgttcgccgg ctttccccgt caagctctaa atcggggcat | 1920 |
| ccctttaggg ttccgattta gtgctttacg gcacctcgac cccaaaaaac ttgattaggg | 1980 |
| tgatggttca cgtagtgggc catcgccctg atagacggtt tttcgccctt tgacgttgga | 2040 |
| gtccacgttc tttaatagtg gactcttgtt ccaaactgga acaacactca accctatctc | 2100 |
| ggtctattct tttgatttat aagggatttt ggggatttcg gcctattggt taaaaaatga | 2160 |
| gctgatttaa caaaaattta acgcgaatta attctgtgga atgtgtgtca gttagggtgt | 2220 |
| ggaaagtccc caggctcccc aggcaggcag aagtatgcaa agcatgcatc tcaattagtc | 2280 |
| agcaaccagg tgtggaaagt ccccaggctc cccagcaggc agaagtatgc aaagcatgca | 2340 |
| tctcaattag tcagcaacca tagtcccgcc cctaactccg cccatcccgc ccctaactcc | 2400 |
| gcccagttcc gcccattctc cgccctaggg ctgactaatt tttttatttt atgcagaggc | 2460 |
| cgaggccgcc tctgcctctg agctattcca gaagtagtga ggaggctttt ttggaggcct | 2520 |
| aggcttttgc aaaaagctcc cgggaggtcc acaatgattg aacaagatgg attgcacgca | 2580 |
| ggttctccgg ccgcttgggt ggagaggcta ttcggctatg actgggcaca acagacaatc | 2640 |
| ggctgctctg atgccgccgt gttccggctg tcagcgcagg ggcgcccggt tctttttgtc | 2700 |
| aagaccgacc tgtccggtgc cctgaatgaa ctccaggacg aggcagcgcg gctatcgtgg | 2760 |

```
ctggccacga cgggcgttcc ttgcgcagct gtgctcgacg ttgtcactga agcgggaagg   2820
gactggctgc tattgggcga agtgccgggg caggatctcc tgtcatctca ccttgctcct   2880
gccgagaaag tatccatcat ggctgatgca atgcggcggc tgcatacgct tgatccggct   2940
acctgcccat tcgaccacca agcgaaacat cgcatcgagc gagcacgtac tcggatggaa   3000
gccggtcttg tcgatcagga tgatctggac gaagagcatc aggggctcgc gccagccgaa   3060
ctgttcgcca ggctcaaggc gcgtatgccc gacggcgagg atctcgtcgt gactcatggc   3120
gatgcctgct tgccgaatat catggtggaa aatggccgct tttctggatt catcgactgt   3180
ggccggctgg gtgtggcgga ccgctatcag gacatagcgt tggctacccg tgatattgct   3240
gaagagcttg gcggcgaatg ggctgaccgc ttcctcgtgc tttacggtat cgccgctccc   3300
gattcgcagc gcatcgcctt ctatcgcctt cttgacgagt tcttctgagc gggactctgg   3360
ggttcgaaat gaccgaccaa gcgacgccca acctgccatc acgagatttc gattccaccg   3420
ccgccttcta tgaaaggttg gcttcggaat cgttttccg ggacgccggc tggatgatcc   3480
tccagcgcgg ggatctcatg ctggagttct tcgcccaccc caacttgttt attgcagctt   3540
ataatggtta caaataaagc aatagcatca caaatttcac aaataaagca ttttttcac   3600
tgcattctag ttgtggtttg tccaaactca tcaatgtatc ttatcatgtc tgtataccgg   3660
atctttccgc ttcctcgctc actgactcgc tgcgctcggt cgttcggctg cggcgagcgg   3720
tatcagctca ctcaaaggcg gtaatacggt tatccacaga atcaggggat aacgcaggaa   3780
agaacatgtg agcaaaaggc cagcaaaagg ccaggaaccg taaaaaggcc gcgttgctgg   3840
cgttttccca taggctccgc cccctgacg agcatcacaa aaatcgacgc tcaagtcaga   3900
ggtggcgaaa cccgacagga ctataaagat accaggcgtt tccccctgga agctccctcg   3960
tgcgctctcc tgttccgacc ctgccgctta ccggatacct gtccgccttt ctcccttcgg   4020
gaagcgtggc gctttctcaa tgctcacgct gtaggtatct cagttcggtg taggtcgttc   4080
gctccaagct gggctgtgtc cacgaacccc cgttcagcc cgaccgctgc gccttatccg   4140
gtaactatcg tcttgagtcc aacccggtaa gacacgactt atcgccactg gcagcagcca   4200
ctggtaacag gattagcaga gcgaggtatg taggcggtgc tacagagttc ttgaagtggt   4260
ggcctaacta cggctacact agaaggacag tatttggtat ctgcgctctg ctgaagccag   4320
ttaccttcgg aaaaagagtt ggtagctctt gatccggcaa acaaaccacc gctggtagcg   4380
gtggtttttt tgtttgcaag cagcagatta cgcgcagaaa aaaaggatct caagaagatc   4440
ctttgatctt ttctacgggg tctgacgctc agtggaacga aaactcacgt taagggattt   4500
tggtcatgag attatcaaaa aggatcttca cctagatcct tttaaattaa aaatgaagtt   4560
ttaaatcaat ctaaagtata tatgagtaaa cttggtctga cagttaccaa tgcttaatca   4620
gtgaggcacc tatctcagcg atctgtctat ttcgttcatc catagttgcc tgactccccg   4680
tcgtgtagat aactacgata cgggagggct taccatctgg ccccagtgct gcaatgatac   4740
cgcgagaccc acgctcaccg gctccagatt tatcagcaat aaaccagcca gccggaaggg   4800
ccgagcgcag aagtggtcct gcaactttat ccgcctccat ccagtctatt aattgttgcc   4860
gggaagctag agtaagtagt tcgccagtta atagtttgcg caacgttgtt gccattgcta   4920
caggcatcgt ggtgtcacgc tcgtcgtttg gtatggcttc attcagctcc ggttcccaac   4980
gatcaaggcg agttacatga tcccccatgt tgtgcaaaaa agcggttagc tccttcggtc   5040
ctccgatcgt tgtcagaagt aagttggccg cagtgttatc actcatggtt atggcagcac   5100
```

-continued

```
tgcataattc tcttactgtc atgccatccg taagatgctt ttctgtgact ggtgagtact    5160
caaccaagtc attctgagaa tagtgtatgc ggcgaccgag ttgctcttgc ccggcgtcaa    5220
tacgggataa taccgcgcca catagcagaa ctttaaaagt gctcatcatt ggaaaacgtt    5280
cttcggggcg aaaactctca aggatcttac cgctgttgag atccagttcg atgtaaccca    5340
ctcgtgctcc caactgatct tcagcatctt ttactttcac cagcgtttct gggtgagcaa    5400
aaacaggaag gcaaaatgcc gcaaaaaagg gaataagggc gacacggaaa tgttgaatac    5460
tcatactctt cctttttcaa tattattgaa gcatttatca gggttattgt ctcatgagcg    5520
gatacatatt tgaatgtatt tagaaaaata aacaataggg gttccgcgc acatttcccc     5580 gaaaagtgcc acctgacgtc agatcgacgg atcgggagat cg                       5622
```

<210> SEQ ID NO 139
<211> LENGTH: 280
<212> TYPE: PRT
<213> ORGANISM: Artificial Sequence
<220> FEATURE:
<223> OTHER INFORMATION: Description of Artificial Sequence: Synthetic
  polypeptide

<400> SEQUENCE: 139

```
Met Gly Trp Ser Cys Ile Ile Leu Phe Leu Val Ala Thr Ala Thr Gly
1               5                   10                  15

Ala His Ser Glu Gly Arg Pro Gly His His His His His Gly Gly
            20                  25                  30

Ser Ser Leu Val Pro Arg Gly Ser Glu Glu Asp Glu Glu His Thr Ile
        35                  40                  45

Ile Thr Asp Thr Glu Leu Pro Pro Leu Lys Leu Met His Ser Phe Cys
    50                  55                  60

Ala Phe Lys Ala Asp Asp Gly Pro Cys Lys Ala Ile Met Lys Arg Phe
65                  70                  75                  80

Phe Phe Asn Ile Phe Thr Arg Gln Cys Glu Glu Phe Ile Tyr Gly Gly
                85                  90                  95

Cys Glu Gly Asn Gln Asn Arg Phe Glu Ser Leu Glu Glu Cys Lys Lys
            100                 105                 110

Met Cys Thr Arg Asp Asn Ala Asn Arg Ile Ile Lys Thr Thr Leu Gln
        115                 120                 125

Gln Glu Lys Pro Asp Phe Cys Phe Leu Glu Glu Asp Pro Gly Ile Cys
    130                 135                 140

Arg Gly Tyr Ile Thr Arg Tyr Phe Tyr Asn Asn Gln Thr Lys Gln Cys
145                 150                 155                 160

Glu Arg Phe Lys Tyr Gly Gly Cys Leu Gly Asn Met Asn Asn Phe Glu
                165                 170                 175

Thr Leu Glu Glu Cys Lys Asn Ile Cys Glu Asp Gly Pro Asn Gly Phe
            180                 185                 190

Gln Val Asp Asn Tyr Gly Thr Gln Leu Asn Ala Val Asn Asn Ser Leu
        195                 200                 205

Thr Pro Gln Ser Thr Lys Val Pro Ser Leu Phe Glu Phe His Gly Pro
    210                 215                 220

Ser Trp Cys Leu Thr Pro Ala Asp Arg Gly Leu Cys Arg Ala Asn Glu
225                 230                 235                 240

Asn Arg Phe Tyr Tyr Asn Ser Val Ile Gly Lys Cys Arg Pro Phe Lys
                245                 250                 255

Tyr Ser Gly Cys Gly Gly Asn Glu Asn Asn Phe Thr Ser Lys Gln Glu
            260                 265                 270
```

```
Cys Leu Arg Ala Cys Lys Lys Gly
        275                 280

<210> SEQ ID NO 140
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Gly Trp Ser Cys Ile Ile Leu Phe Leu Val Ala Thr Ala Thr Gly
 1               5                  10                  15

Ala His Ser Glu Gly Arg Pro Gly His His His His His Gly Gly
            20                  25                  30

Ser Ser Leu Val Pro Arg Gly Ser Glu Glu Asp Glu His Thr Ile
        35                  40                  45

Ile Thr Asp Thr Glu Leu Pro Pro Leu Lys Leu Met His Ser Phe Cys
 50                  55                  60

Ala Phe Lys Ala Asp Asp Gly Pro Cys Arg Ala Arg Phe Asp Arg Trp
65                   70                  75                  80

Phe Phe Asn Ile Phe Thr Arg Gln Cys Glu Glu Phe Ile Tyr Gly Gly
                85                  90                  95

Cys Glu Gly Asn Gln Asn Arg Phe Glu Ser Leu Glu Glu Cys Lys Lys
            100                 105                 110

Met Cys Thr Arg Asp Asn Ala Asn Arg Ile Ile Lys Thr Thr Leu Gln
            115                 120                 125

Gln Glu Lys Pro Asp Phe Cys Phe Leu Glu Glu Asp Pro Gly Pro Cys
        130                 135                 140

Arg Ala Ala His Pro Arg Trp Phe Tyr Asn Asn Gln Thr Lys Gln Cys
145                 150                 155                 160

Glu Arg Phe Ile Tyr Gly Gly Cys Glu Gly Asn Met Asn Asn Phe Glu
                165                 170                 175

Thr Leu Glu Glu Cys Lys Asn Ile Cys Glu Asp Gly Pro Asn Gly Phe
            180                 185                 190

Gln Val Asp Asn Tyr Gly Thr Gln Leu Asn Ala Val Asn Asn Ser Leu
        195                 200                 205

Thr Pro Gln Ser Thr Lys Val Pro Ser Leu Phe Glu Phe His Gly Pro
210                 215                 220

Ser Trp Cys Leu Thr Pro Ala Asp Arg Gly Pro Cys Ile Ala Phe Phe
225                 230                 235                 240

Pro Arg Phe Tyr Tyr Asn Ser Val Ile Gly Lys Cys Arg Pro Phe Pro
                245                 250                 255

Tyr Gly Gly Cys Gln Gly Asn Glu Asn Asn Phe Thr Ser Lys Gln Glu
            260                 265                 270

Cys Leu Arg Ala Cys Lys Lys Gly
        275                 280

<210> SEQ ID NO 141
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141
```

Met Gly Trp Ser Cys Ile Ile Leu Phe Leu Val Ala Thr Ala Thr Gly
1               5                   10                  15

Ala His Ser Asp Ser Glu Asp Glu His Thr Ile Ile Thr Asp
            20                  25                  30

Thr Glu Leu Pro Pro Leu Lys Leu Met His Ser Phe Cys Ala Phe Lys
        35                  40                  45

Ala Asp Asp Gly Pro Cys Arg Ala Arg Phe Asp Arg Trp Phe Phe Asn
50                      55                  60

Ile Phe Thr Arg Gln Cys Glu Glu Phe Ile Tyr Gly Gly Cys Glu Gly
65                  70                  75                  80

Asn Gln Asn Arg Phe Glu Ser Leu Glu Glu Cys Lys Lys Met Cys Thr
                85                  90                  95

Arg Asp Asn Ala Asn Arg Ile Ile Lys Thr Thr Leu Gln Gln Glu Lys
            100                 105                 110

Pro Asp Phe Cys Phe Leu Glu Glu Asp Pro Gly Pro Cys Arg Ala Arg
        115                 120                 125

Phe Asp Arg Trp Phe Tyr Asn Asn Gln Thr Lys Gln Cys Glu Arg Phe
    130                 135                 140

Ile Tyr Gly Gly Cys Glu Gly Asn Met Asn Asn Phe Glu Thr Leu Glu
145                 150                 155                 160

Glu Cys Lys Asn Ile Cys Glu Asp Gly Pro Asn Gly Phe Gln Val Asp
                165                 170                 175

Asn Tyr Gly Thr Gln Leu Asn Ala Val Asn Asn Ser Leu Thr Pro Gln
            180                 185                 190

Ser Thr Lys Val Pro Ser Leu Phe Glu Phe His Gly Pro Ser Trp Cys
        195                 200                 205

Leu Thr Pro Ala Asp Arg Gly Pro Cys Arg Ala Arg Phe Asp Arg Trp
    210                 215                 220

Tyr Tyr Asn Ser Val Ile Gly Lys Cys Arg Pro Phe Ile Tyr Gly Gly
225                 230                 235                 240

Cys Glu Gly Asn Glu Asn Asn Phe Thr Ser Lys Gln Glu Cys Leu Arg
                245                 250                 255

Ala Cys Lys Lys Gly Phe Ile Gln Arg Ile Ser
            260                 265

<210> SEQ ID NO 142
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30

Gly Pro Cys Arg Ala Arg Phe Asp Arg Trp Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Arg Ser Phe Pro

```
                        85                  90                  95
Trp Lys Ser Val Pro Asn Gly Phe Gln Val Asp Asn Tyr Gly Thr Gln
            100                 105                 110

Leu Asn Ala Val Asn Ser Leu Thr Pro Gln Ser Thr Lys Val Pro Ser
        115                 120                 125

Leu Phe Glu Phe His Gly Pro Ser Trp Cys Leu Thr Pro Ala Asp Val
    130                 135                 140

Gly Arg Cys Arg Ala Ser Met Pro Arg Trp Tyr Tyr Asn Ser Val Ile
145                 150                 155                 160

Gly Lys Cys Arg Pro Phe Val Tyr Gly Gly Cys Gly Gly Asn Ser Asn
                165                 170                 175

Asn Phe Thr Ser Glu Gln Glu Cys Leu Arg Ala Cys Lys Lys Gly
            180                 185                 190

<210> SEQ ID NO 143
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(210)
<220> FEATURE:
<221> NAME/KEY: modified_base
<222> LOCATION: (52)..(53)
<223> OTHER INFORMATION: a, c, g, t, unknown or other
<220> FEATURE:
<221> NAME/KEY: modified_base
<222> LOCATION: (58)..(59)
<223> OTHER INFORMATION: a, c, g, t, unknown or other
<220> FEATURE:
<221> NAME/KEY: modified_base
<222> LOCATION: (64)..(65)
<223> OTHER INFORMATION: a, c, g, t, unknown or other
<220> FEATURE:
<221> NAME/KEY: modified_base
<222> LOCATION: (67)..(68)
<223> OTHER INFORMATION: a, c, g, t, unknown or other
<220> FEATURE:
<221> NAME/KEY: modified_base
<222> LOCATION: (70)..(71)
<223> OTHER INFORMATION: a, c, g, t, unknown or other
<220> FEATURE:
<221> NAME/KEY: modified_base
<222> LOCATION: (115)..(116)
<223> OTHER INFORMATION: a, c, g, t, unknown or other
<220> FEATURE:
<221> NAME/KEY: modified_base
<222> LOCATION: (130)..(131)
<223> OTHER INFORMATION: a, c, g, t, unknown or other
<220> FEATURE:
<221> NAME/KEY: modified_base
<222> LOCATION: (143)
<223> OTHER INFORMATION: a, c, g, t, unknown or other

<400> SEQUENCE: 143 tcc atg gct gat gtt cct aag gtt tgt cgt ctg cag gtt tct gtt rrk       48
Ser Met Ala Asp Val Pro Lys Val Cys Arg Leu Gln Val Ser Val Xaa
 1               5                  10                  15 rrk nnk tgt nnk grt nnk nnk nnk arg tat ttt ttc aac ctg agc tct       96
Xaa Xaa Cys Xaa Xaa Xaa Xaa Xaa Tyr Phe Phe Asn Leu Ser Ser
            20                  25                  30 atg act tgc gaa aag ttc nnk tmt ggt ggt tgc nnk rrk aac rrk rnk      144
Met Thr Cys Glu Lys Phe Xaa Xaa Gly Gly Cys Xaa Xaa Asn Xaa Xaa
        35                  40                  45 gag aac cgg ttt ccg gac gag gct act tgt atg ggt ttc tgt gct cct      192
```

```
Glu Asn Arg Phe Pro Asp Glu Ala Thr Cys Met Gly Phe Cys Ala Pro
 50                  55                  60 aag tct gct gac gct agc                                      210
Lys Ser Ala Asp Ala Ser
 65              70
```

<210> SEQ ID NO 144
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(17)
<223> OTHER INFORMATION: Asp, Glu, Asn, Lys, Ser, Arg or Gly
<220> FEATURE:
<221> NAME/KEY: MOD_RES
<222> LOCATION: (18)
<223> OTHER INFORMATION: any amino acid other than Cys
<220> FEATURE:
<221> NAME/KEY: MOD_RES
<222> LOCATION: (20)
<223> OTHER INFORMATION: any amino acid other than Cys
<220> FEATURE:
<221> NAME/KEY: MOD_RES
<222> LOCATION: (21)
<223> OTHER INFORMATION: Ala or Gly
<220> FEATURE:
<221> NAME/KEY: MOD_RES
<222> LOCATION: (22)..(24)
<223> OTHER INFORMATION: any amino acid other than Cys
<220> FEATURE:
<221> NAME/KEY: MOD_RES
<222> LOCATION: (25)
<223> OTHER INFORMATION: Lys or Arg
<220> FEATURE:
<221> NAME/KEY: MOD_RES
<222> LOCATION: (39)
<223> OTHER INFORMATION: any amino acid other than Cys
<220> FEATURE:
<221> NAME/KEY: MOD_RES
<222> LOCATION: (40)
<223> OTHER INFORMATION: Ser or Tyr
<220> FEATURE:
<221> NAME/KEY: MOD_RES
<222> LOCATION: (44)
<223> OTHER INFORMATION: any amino acid other than Cys
<220> FEATURE:
<221> NAME/KEY: MOD_RES
<222> LOCATION: (45)
<223> OTHER INFORMATION: Asp, Glu, Asn, Lys, Ser, Arg or Gly
<220> FEATURE:
<221> NAME/KEY: MOD_RES
<222> LOCATION: (47)
<223> OTHER INFORMATION: Asp, Glu, Asn, Lys, Ser, Arg or Gly
<220> FEATURE:
<221> NAME/KEY: MOD_RES
<222> LOCATION: (48)
<223> OTHER INFORMATION: Ile, Met, Val, Leu, Ala, Thr, Ser, Tyr, Gly,
      Asp, Arg or Phe

<400> SEQUENCE: 144

```
Ser Met Ala Asp Val Pro Lys Val Cys Arg Leu Gln Val Ser Val Xaa
 1               5                  10                  15

Xaa Xaa Cys Xaa Xaa Xaa Xaa Xaa Xaa Tyr Phe Phe Asn Leu Ser Ser
             20                  25                  30

Met Thr Cys Glu Lys Phe Xaa Xaa Gly Gly Cys Xaa Xaa Asn Xaa Xaa
         35                  40                  45

Glu Asn Arg Phe Pro Asp Glu Ala Thr Cys Met Gly Phe Cys Ala Pro
 50                  55                  60
```

-continued

Lys Ser Ala Asp Ala Ser
 65                  70

<210> SEQ ID NO 145
<211> LENGTH: 27
<212> TYPE: PRT
<213> ORGANISM: Homo sapiens

<400> SEQUENCE: 145

Gly Gly Leu Ile Lys Thr Lys Arg Lys Arg Lys Lys Gln Arg Val Lys
  1               5                  10                  15

Ile Ala Tyr Glu Glu Ile Phe Val Lys Asn Met
             20                  25

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Phe Leu Ser Tyr
  1

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Ser Gly Gly Ser Ser Ser Ser Ser Gly
  1               5                  10

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Val Ile Leu Met Phe Trp Tyr
  1               5

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Glu Asp Arg Lys His
  1               5

<210> SEQ ID NO 150
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 150

Gly Gly Ser Gly Asn Gly Ser Ser Ser Gly Gly Ser Gly Ser Gly
1               5                   10                  15

<210> SEQ ID NO 151
<211> LENGTH: 28
<212> TYPE: PRT
<213> ORGANISM: Homo sapiens

<400> SEQUENCE: 151

Lys Gly Gly Leu Ile Lys Thr Lys Arg Lys Arg Lys Lys Gln Arg Val
1               5                   10                  15

Lys Ile Ala Tyr Glu Glu Ile Phe Val Lys Asn Met
            20                  25

<210> SEQ ID NO 152
<211> LENGTH: 8
<212> TYPE: PRT
<213> ORGANISM: Homo sapiens

<400> SEQUENCE: 152

Gly Pro Gln Gly Ile Ala Gly Gln
1               5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dpn-Pro

<400> SEQUENCE: 153

Pro Gln Gly Ile Gln Gly
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dpn-Pro
<220> FEATURE:
<221> NAME/KEY: MOD_RES
<222> LOCATION: (7)
<223> OTHER INFORMATION: D-Arg

<400> SEQUENCE: 154

Pro Leu Gly Leu Trp Ala Arg
1               5

<210> SEQ ID NO 155
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 155

Gly Pro Gln Gly Ile Trp Gly Gln
 1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Mca-Pro
<220> FEATURE:
<221> NAME/KEY: MOD_RES
<222> LOCATION: (5)
<223> OTHER INFORMATION: Dpa

<400> SEQUENCE: 156

Pro Leu Gly Leu Xaa Ala Arg
 1               5

<210> SEQ ID NO 157
<211> LENGTH: 8
<212> TYPE: PRT
<213> ORGANISM: Homo sapiens

<400> SEQUENCE: 157

Arg Pro Phe Gln Val Lys Asp Thr
 1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ala Met Phe Leu Glu Ala Ile
 1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Glu Ala Ile Pro Met Ser Ile Pro
 1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Leu Val Glu Ala Leu Tyr Leu Val
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Glu Ala Leu Tyr Leu Val Cys Gly
1               5

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Gly Ser Gly Gly Ser Gly Gly Ser Gly Gly Ser Gly Gly
1               5                   10

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Gly Ser Gly Ser Ser Gly Ser Gly Gly Ser Gly Ser Ser Gly
1               5                   10                  15

<210> SEQ ID NO 164
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 164
ccannnnnnt gg                                                            12

<210> SEQ ID NO 165
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 165
cctnnnnnag g                                                             11

```
<210> SEQ ID NO 166
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(12)
<223> OTHER INFORMATION: a, c, g, t, unknown or other

<400> SEQUENCE: 166
ccannnnnnn nntgg                                               15

<210> SEQ ID NO 167
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 167
gtatccnnnn nn                                                  12

<210> SEQ ID NO 168
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 168
gccnnnnngg c                                                   11

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(17)
<223> OTHER INFORMATION: a, c, g, t, unknown or other

<400> SEQUENCE: 169
gggacnnnnn nnnnnnn                                             17

<210> SEQ ID NO 170
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (7)..(10)
<223> OTHER INFORMATION: a, c, g, t, unknown or other

<400> SEQUENCE: 170 ctcttcnnnn                                                                10

<210> SEQ ID NO 171
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, g, t, unknown or other

<400> SEQUENCE: 171
nnnnnnngcg gg                                                             12

<210> SEQ ID NO 172
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 172
ccannnnntg g                                                              11

<210> SEQ ID NO 173
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, g, t, unknown or other

<400> SEQUENCE: 173
ggccnnnnng gcc                                                            13

<210> SEQ ID NO 174
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 174 gatnnnnatc                                                                10

<210> SEQ ID NO 175
<211> LENGTH: 16
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(16)
<223> OTHER INFORMATION: a, c, g, t, unknown or other

<400> SEQUENCE: 175
gaggagnnnn nnnnnn                                                       16

<210> SEQ ID NO 176
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, g, t, unknown or other

<400> SEQUENCE: 176
nnnnnngaga cg                                                           12

<210> SEQ ID NO 177
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 177
gacnnnnnng tc                                                           12

<210> SEQ ID NO 178
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 178
gcannnnntg c                                                            11

<210> SEQ ID NO 179
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, c, g, t, unknown or other

<400> SEQUENCE: 179
nnnnnnnnng caggt                                                  15

<210> SEQ ID NO 180
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 180
acctgcnnnn n                                                      11

<210> SEQ ID NO 181
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 181
gacnnnnngt c                                                      11

<210> SEQ ID NO 182
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, g, t, unknown or other

<400> SEQUENCE: 182
nnnnngagac c                                                      11

<210> SEQ ID NO 183
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 183
cgannnnnnt gc                                                     12

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (1)..(16)
<223> OTHER INFORMATION: a, c, g, t, unknown or other

<400> SEQUENCE: 184
nnnnnnnnnn nnnnngtccc                                               20

<210> SEQ ID NO 185
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 185
gcannnnnnt cg                                                       12

<210> SEQ ID NO 186
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 186
ggtctcnnnn n                                                        11

<210> SEQ ID NO 187
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 187 gacnnnngtc                                                          10

<210> SEQ ID NO 188
<211> LENGTH: 58
<212> TYPE: PRT
<213> ORGANISM: Bos taurus

<400> SEQUENCE: 188

Arg Pro Asp Phe Cys Leu Glu Pro Pro Tyr Thr Gly Pro Cys Lys Ala
  1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
     50                  55
```

-continued

<210> SEQ ID NO 189
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met His Ser Phe Cys Ala Phe Lys Ala Asp Asp Gly Pro Cys Ile Ala
1               5                   10                  15

Phe Phe Pro Arg Phe Phe Asn Ile Phe Thr Arg Gln Cys Glu Glu
            20                  25                  30

Phe Ile Tyr Gly Gly Cys Gly Asn Gly Asn Gln Asn Arg Phe Glu Ser
        35                  40                  45

Leu Glu Glu Cys Lys Lys Met Cys Thr Arg Asp
    50                  55

<210> SEQ ID NO 190
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Lys Pro Asp Phe Cys Phe Leu Glu Glu Asp Pro Gly Pro Cys Arg Ala
1               5                   10                  15

Ala His Pro Arg Trp Phe Tyr Asn Asn Gln Thr Lys Gln Cys Glu Arg
            20                  25                  30

Phe Ile Tyr Gly Gly Cys Glu Gly Asn Met Asn Asn Phe Glu Thr Leu
        35                  40                  45

Glu Glu Cys Lys Asn Ile Cys Glu Asp Gly
    50                  55

<210> SEQ ID NO 191
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Pro Ser Trp Cys Leu Thr Pro Ala Asp Arg Gly Pro Cys Arg Ala
1               5                   10                  15

Ala His Pro Arg Trp Tyr Tyr Asn Ser Val Ile Gly Lys Cys Arg Pro
            20                  25                  30

Phe Ile Tyr Gly Gly Cys Glu Gly Asn Glu Asn Asn Phe Thr Ser Lys
        35                  40                  45

Gln Glu Cys Leu Arg Ala Cys Lys Lys Gly
    50                  55

<210> SEQ ID NO 192
<211> LENGTH: 58
<212> TYPE: PRT
<213> ORGANISM: Homo sapiens

<400> SEQUENCE: 192

Thr Val Ala Ala Cys Asn Leu Pro Ile Val Arg Gly Pro Cys Arg Ala
1               5                   10                  15

-continued

```
Phe Ile Gln Leu Trp Ala Phe Asp Ala Val Lys Gly Lys Cys Val Leu
                 20                  25                  30

Phe Pro Tyr Gly Gly Cys Gln Gly Asn Gly Asn Lys Phe Tyr Ser Glu
             35                  40                  45

Lys Glu Cys Arg Glu Tyr Cys Gly Val Pro
 50                  55

<210> SEQ ID NO 193
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Lys Pro Asp Phe Cys Phe Leu Glu Glu Asp Pro Gly Pro Cys Ile Ala
 1               5                  10                  15

Phe Phe Pro Arg Trp Phe Tyr Asn Asn Gln Thr Lys Gln Cys Glu Leu
                 20                  25                  30

Phe Pro Tyr Gly Gly Cys Gln Gly Asn Met Asn Asn Phe Glu Thr Leu
             35                  40                  45

Glu Glu Cys Lys Asn Ile Cys Glu Asp Gly
 50                  55

<210> SEQ ID NO 194
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Pro Ser Trp Cys Leu Thr Pro Ala Asp Arg Gly Pro Cys Ile Ala
 1               5                  10                  15

Phe Phe Pro Arg Trp Tyr Tyr Asn Ser Val Ile Gly Lys Cys Arg Leu
                 20                  25                  30

Phe Pro Tyr Gly Gly Cys Gln Gly Asn Glu Asn Asn Phe Thr Ser Lys
             35                  40                  45

Gln Glu Cys Leu Arg Ala Cys Lys Lys Gly
 50                  55

<210> SEQ ID NO 195
<211> LENGTH: 58
<212> TYPE: PRT
<213> ORGANISM: Homo sapiens

<400> SEQUENCE: 195

Thr Glu Asp Tyr Cys Leu Ala Ser Asn Lys Val Gly Arg Cys Arg Gly
 1               5                  10                  15

Ser Phe Pro Arg Trp Tyr Tyr Asp Pro Thr Glu Gln Ile Cys Lys Ser
                 20                  25                  30

Phe Val Tyr Gly Gly Cys Leu Gly Asn Lys Asn Asn Tyr Leu Arg Glu
             35                  40                  45

Glu Glu Cys Ile Leu Ala Cys Arg Gly Val
 50                  55

<210> SEQ ID NO 196
<211> LENGTH: 58
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Lys Pro Asp Phe Cys Phe Leu Glu Glu Asp Pro Gly Arg Cys Arg Gly
  1               5                  10                  15

Ser Phe Pro Arg Trp Phe Tyr Asn Asn Gln Thr Lys Gln Cys Lys Ser
             20                  25                  30

Phe Val Tyr Gly Gly Cys Leu Gly Asn Met Asn Asn Phe Glu Thr Leu
         35                  40                  45

Glu Glu Cys Lys Asn Ile Cys Glu Asp Gly
     50                  55

<210> SEQ ID NO 197
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ile His Asp Phe Cys Leu Val Ser Lys Val Val Gly Arg Cys Arg Ala
  1               5                  10                  15

Ser Met Pro Arg Trp Trp Tyr Asn Val Thr Asp Gly Ser Cys Gln Leu
             20                  25                  30

Phe Val Tyr Gly Gly Cys Asp Gly Asn Ser Asn Asn Tyr Leu Thr Lys
         35                  40                  45

Glu Glu Cys Leu Lys Lys Cys Ala Thr Val
     50                  55

<210> SEQ ID NO 198
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Pro Ser Trp Cys Leu Thr Pro Ala Asp Val Gly Arg Cys Arg Ala
  1               5                  10                  15

Ser Met Pro Arg Trp Tyr Tyr Asn Ser Val Ile Gly Lys Cys Arg Pro
             20                  25                  30

Phe Val Tyr Gly Gly Cys Gly Gly Asn Ser Asn Asn Phe Thr Ser Glu
         35                  40                  45

Gln Glu Cys Leu Arg Ala Cys Lys Lys Gly
     50                  55

<210> SEQ ID NO 199
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(180)

<400> SEQUENCE: 199
```

```
gag gct atg cac tct ttc tgt gct ttc aag gct gac gac ggt ccg tgc      48
Glu Ala Met His Ser Phe Cys Ala Phe Lys Ala Asp Asp Gly Pro Cys
 1               5                  10                  15 aga gct gct cac cca aga tgg ttc ttc aac atc ttc acg cga caa tgc      96
Arg Ala Ala His Pro Arg Trp Phe Phe Asn Ile Phe Thr Arg Gln Cys
             20                  25                  30 gag gag ttc atc tac ggt ggt tgt gag ggt aac caa aac aga ttc gag    144
Glu Glu Phe Ile Tyr Gly Gly Cys Glu Gly Asn Gln Asn Arg Phe Glu
         35                  40                  45 tct cta gag gag tgt aag aag atg tgt act aga gat                    180
Ser Leu Glu Glu Cys Lys Lys Met Cys Thr Arg Asp
     50                  55                  60

<210> SEQ ID NO 200
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Glu Ala Met His Ser Phe Cys Ala Phe Lys Ala Asp Asp Gly Pro Cys
 1               5                  10                  15

Arg Ala Ala His Pro Arg Trp Phe Phe Asn Ile Phe Thr Arg Gln Cys
             20                  25                  30

Glu Glu Phe Ile Tyr Gly Gly Cys Glu Gly Asn Gln Asn Arg Phe Glu
         35                  40                  45

Ser Leu Glu Glu Cys Lys Lys Met Cys Thr Arg Asp
     50                  55                  60

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dnp-Pro
<220> FEATURE:
<221> NAME/KEY: MOD_RES
<222> LOCATION: (8)
<223> OTHER INFORMATION: D-Arg

<400> SEQUENCE: 201

Pro Gln Gly Ile Ala Gly Gln Arg
 1               5

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Pro His Gln Ile Met Thr Asn Lys Val Ala Asp Glu
 1               5                  10

<210> SEQ ID NO 203
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Asn Ala Asn Asn Phe
 1               5
```